US007705053B2

(12) United States Patent
Koyano et al.

(10) Patent No.: US 7,705,053 B2
(45) Date of Patent: Apr. 27, 2010

(54) BENZAMIDE DERIVATIVE

(75) Inventors: Hiroshi Koyano, Kamakura (JP); Atsushi Suda, Kamakura (JP); Kousuke Aso, Kamakura (JP); Kihito Hada, Kamakura (JP); Miyuki Asai, Kamakura (JP); Masami Hasegawa, Kamakura (JP); Yasuko Sato, Kamakura (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 733 days.

(21) Appl. No.: 10/584,233

(22) PCT Filed: Dec. 27, 2004

(86) PCT No.: PCT/JP2004/019574

§ 371 (c)(1), (2), (4) Date: Jun. 26, 2006

(87) PCT Pub. No.: WO2005/063689

PCT Pub. Date: Jul. 14, 2005

(65) Prior Publication Data

US 2007/0123493 A1 May 31, 2007

(30) Foreign Application Priority Data

| | | | |
|---|---|---|---|
| Dec. 26, 2003 | (JP) | ............................ | 2003-434565 |
| Mar. 5, 2004 | (JP) | ............................ | 2004-063266 |
| Oct. 5, 2004 | (JP) | ............................ | 2004-292580 |

(51) Int. Cl.
*A61K 31/166* (2006.01)
*C07C 233/12* (2006.01)

(52) U.S. Cl. ...................................... 514/617; 564/129

(58) Field of Classification Search ................. 514/617; 564/129

See application file for complete search history.

(56) References Cited

U.S. PATENT DOCUMENTS

| | | | |
|---|---|---|---|
| 3,755,446 | A | 8/1973 | Scheuermann |
| 6,632,961 | B1 | 10/2003 | Kawai et al. |
| 2002/0128208 | A1 | 9/2002 | Snyder et al. |
| 2004/0048891 | A1 | 3/2004 | Kato et al. |
| 2004/0259877 | A1 | 12/2004 | Muto et al. |

FOREIGN PATENT DOCUMENTS

| | | | |
|---|---|---|---|
| CA | 2 488 974 | A1 | 12/2003 |
| WO | WO 93/23357 | A1 | 11/1993 |
| WO | 97/03967 | | 2/1997 |
| WO | WO 99/32433 | A1 | 7/1999 |
| WO | 0181311 | A1 * | 11/2001 |
| WO | WO 01/85671 | A2 | 11/2001 |
| WO | 02/064547 | A2 | 8/2002 |
| WO | WO 02-059080 | A2 | 8/2002 |
| WO | WO 03/103655 | A1 | 12/2003 |

OTHER PUBLICATIONS

Heesemann, J. Ame. Chem. soc. (1980), vol. 102(7), pp. 2167-2176.*
Matsumura, Nippon Kagaku Zasshi (1961), vol. 82, pp. 623-626.*

* cited by examiner

*Primary Examiner*—Taofiq A Solola
(74) *Attorney, Agent, or Firm*—Browdy and Neimark, PLLC

(57) ABSTRACT

To provide compounds which have high angiogenesis inhibiting activity, and are useful as agents for effective treatment and prevention of diseases involving pathologic angiogenesis, for example, cancer and cancer metastasis, methods for producing the compounds, intermediate compounds useful for their production, and pharmaceutical compositions containing these compounds.

The present invention provides compounds of formula (II), or prodrugs thereof, or pharmaceutically acceptable salts of the compounds or the prodrugs, and pharmaceuticals, and pharmaceutical compositions containing these compounds:

[Formula 1]

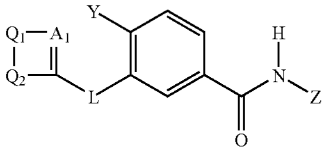

(II)

where $A_1$ is C—$X_1$ or N; $Q_1$ is —$A_2$═$A_3$—, or a heteroatom selected from —O—, —S—, and —N($R_{10}$)—; $Q_2$ is —$A_4$═$A_5$—, or a heteroatom selected from —O—, —S—, and —N($R_{10}$)—; provided that $Q_1$ and $Q_2$ are not heteroatoms at the same time; $A_2$ is C—$X_2$ or N, $A_3$ is C—$X_3$ or N, $A_4$ is C—$X_4$ or N, and $A_5$ is C—$X_5$ or N; Y is $C_{1-6}$alkyl, $C_{3-9}$cycloalkyl, $C_{2-7}$alkenyl, $C_{2-7}$alkynyl, $C_{1-6}$alkoxy, $C_{2-7}$alkenyloxy, $C_{2-7}$alkynyloxy, or $C_{1-6}$alkylthio; Z is a hydrogen atom, hydroxy, $C_{1-6}$alkyl, $C_{3-9}$cycloalkyl, or —$NR_1R_2$; and L is selected from the formula:

[Formula 2]

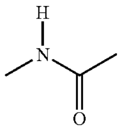

and

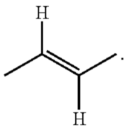

.

8 Claims, 1 Drawing Sheet

BENZAMIDE DERIVATIVE

TECHNICAL FIELD

This invention relates to novel benzamide derivatives, pharmaceuticals containing them as active ingredients, and particularly, angiogenesis inhibitors useful as agents for treatment of diseases, such as malignant tumors, in which angiogenesis partakes.

BACKGROUND ART

In healthy adults, angiogenesis is only observed as a physiological phenomenon, such as endometrial maturation associated with the menstrual cycle, or placentation, and is observed during the process of wound healing. In pathologic states, however, angiogenesis is noted in inflammation, rheumatoid arthritis, arteriosclerosis, diabetic retinopathy, or solid carcinoma, sand may often lead to the progression or aggravation of these diseases. In solid carcinoma, in particular, cancer tissue grows to a diameter of more than 1 to 2 mm, thus necessitating the formation of nutrient vessels (see non-patent document 1). Furthermore, blood vessels which have infiltrated cancer tissue are deeply involved in cancer metastasis and the prognosis of cancer patients (see non-patent document 2 and non-patent document 3).

Thus, an angiogenesis inhibitor is expected as an anticancer drug with minimal injury to normal tissue, unlike an antineoplastic drug showing cytotoxicity, and is also expected as a postoperative adjuvant therapy because of its effect of suppressing the infiltration and metastasis of cancer cells.

The process of angiogenesis comprises multiple steps, i.e., destruction of the vascular basement membrane by the dysfunction of vascular endothelial cells forming the lining of the blood vessel, spouting and migration of vascular endothelial cells, their proliferation, and tube formation (see non-patent document 4). Vascular endothelial cells involved in angiogenesis are also recruited from vascular endothelial precursor cells existent in the peripheral blood, etc. (see non-patent document 5).

These processes are activated by various angiogenic factors, and many reports have suggested the relationship between VEGF (vascular endothelial growth factor), which is one of the angiogenic factors, and cancer. In recent years, drugs targeting VEGF, or the tyrosine kinase activity of the receptor of VEGF, have been under development (see non-patent document 6 and non-patent document 7).

Many factors to partake in angiogenesis, other than VEGF, are known. An earnest demand for the development of inhibitors, which specifically act on vascular endothelial cells playing a central role in angiogenesis and inhibit their proliferation and function, has been uttered, with the expectation that such inhibitors will be promising as agents for treatment of angiogenic diseases such as cancer.

There have been no reports so far that benzamide derivatives have a specific growth inhibitor action on vascular endothelial cells.

As compounds similar in chemical structure to the benzamide derivatives of the present invention, or their salts, those described in the following documents are named:

Japanese Patent Application Laid-Open No. 2001-526255 (patent document 1, Warner Lambert), Japanese Patent Application Laid-Open No. 2002-249473 (patent document 2, Ishihara Sangyo Kaisha), International Publication No. 02/47679 pamphlet (patent document 3, Emory Univ.), International Publication No. 02/059080 pamphlet (patent document 4, Guilford Pharmaceuticals), and International Publication No. 93/23357 pamphlet (patent document 5, Res. Corporation Tech. Inc.).

However, none of the compounds disclosed in these documents are described or suggested as having an angiogenesis suppressing effect. International Publication No. 02/49632 pamphlet (patent document 6, Institute of Medicinal Molecular Design) discloses compounds, which are similar in chemical structure to the benzamide derivatives of the present invention or their salts, as NFkB activity inhibitors, concretely as IKK inhibitors, and suggests cancer, cancer metastasis, and vascular hyperplastic disease as applications for which such inhibitors are targeted. However, this document does not disclose concrete facts.

KDR tyrosine kinase inhibitors are named as compounds which act specifically on vascular endothelial cells and inhibit their proliferation (see non-patent document 8, non-patent document 9, and non-patent document 10 for outlines). Of these compounds, SU11248 (Sugen/Pfizer, a compound having a 3-(pyrrol-2-ylmethylidene)-2-indolinone skeleton, see patent document 7), PTK787 (Novartis, a compound having a 1-anilino-(4-pyridylmethyl)-phthalazine skeleton, see patent document 8), ZD6474 (AstraZeneca, a compound having a quinazoline skeleton, see patent document 9), and CP-547.632 (Pfizer, a compound having an isothiazole skeleton, see patent document 10), for example, are at the stage of clinical development as anticancer drugs. However, all of these compounds are different from the present invention in chemical structure and the mechanism of action.

[Patent document 1] Japanese Patent Application Laid-Open No. 2001-526255

[Patent document 2] Japanese Patent Application Laid-Open No. 2002-249473

[Patent document 3] International Publication No. 02/47679 pamphlet

[Patent document 4] International Publication No. 02/59080 pamphlet

[Patent document 5] International Publication No. 93/23357 pamphlet

[Patent document 6] International Publication No. 02/49632 pamphlet

[Patent document 7] International Publication No. 01/37820 pamphlet

[Patent document 8] U.S. Pat. No. 6,258,812

[Patent document 9] International Publication No. 01/32651 pamphlet

[Patent document 10] International Publication No. 99/62890 pamphlet

[Non-patent document 1] Folkmann, J., J. Natul. Cancer Inst., Vol. 82, pages 4-6, 1990

[Non-patent document 2] Weidner, N. et al. N. Engl. J. Med., Vol. 324, pages 1-8, 1991

[Non-patent document 3] Bochner, B. H. et al., J. Natl. Cancer Inst., Vol. 87, pages 1603-1612, 1995

[Non-patent document 4] Klagsbrun, M. and Folkmann, J., Handbook of Experimental Pharmacology, Vol. 95 II, pp. 549-586, 1990

[Non-patent document 5] Asahara, T. et al., Science, Vol. 275, pp. 964-967, 1997

[Non-patent document 6] Kabbinavar, F. et al., J. Clinical Oncology, Vol. 21, pp. 60-65, 2003

[Non-patent document 7] Laird, A. D. and Cherrington, J. M., Expert Opinion Investigational Drugs, Vol. 12, pp. 51-64, 2003

[Non-patent document 8] Boyer, S. J., Current Topics in Medicinal Chemistry, Vol. 2, pp. 973-1000, 2002

[Non-patent document 9] Glade-Bender, J., Kandel, J. J. and Yamashiro, D. J., Expert Opinion on Biological Therapy, Vol. 3, No. 2, pp. 263-276, 2003

[Non-patent document 10] Laird, A. D. and J. M. Cherrington, Expert Opinion Investigational Drugs, Vol. 12, No. 1, pp. 51-64, 2003

DISCLOSURE OF THE INVENTION

Problems to be Solved by the Invention

An object of the present invention is to provide compounds which show strong anti-angiogenic activity and are useful as agents for treatment and prevention of diseases involving pathologic angiogenesis, for example, cancer and cancer metastasis, processes for producing the compounds, intermediate compounds useful for their production, and pharmaceutical compositions containing these compounds.

Means for Solving the Problems

The inventors diligently conducted studies with the aim of providing novel agents for treatment and prevention which are effective against diseases involving pathologic angiogenesis, for example, cancer and cancer metastasis. As a result, the inventor has found that the compounds of the present invention have selective and strong activity of inhibiting angiogenesis. Further, the inventors have discovered manufacturing methods capable of easily synthesizing these compounds, and have accomplished the present invention.

According to an aspect of the present invention, there is provided a compound of formula (II), or a prodrug thereof, or a pharmaceutically acceptable salt of the compound or the prodrug:

[Formula 1]

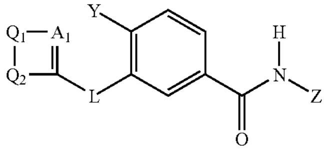

(II)

where $A_1$ is C—$X_1$ or N;

$Q_1$ is —$A_2$═$A_3$—, or a heteroatom selected from —O—, —S—, and —N($R_{10}$)—; $Q_2$ is —$A_4$═$A_5$—, or a heteroatom selected from —O—, —S—, and —N($R_{10}$)—; provided that $Q_1$ and $Q_2$ are not heteroatoms at the same time;

$A_2$ is C—$X_2$ or N, $A_3$ is C—$X_3$ or N, $A_4$ is C—$X_4$ or N, and $A_5$ is C—$X_5$ or N;

$R_{10}$ is a hydrogen atom, $C_{1-6}$alkyl, halo$C_{1-6}$alkyl, $C_{1-6}$alkylcarbonyl or aryl; the aryl being optionally substituted by one or more substituents selected from a halogen atom, $C_{1-6}$alkyl, and $C_{1-6}$alkoxy;

$X_1$, $X_2$, $X_3$, $X_4$ and $X_5$ are each independently selected from the group consisting of a hydrogen atom, hydroxy, a halogen atom, cyano, hydroxyaminocarbonyl, hydroxyamidino, nitro, amino, amidino, guanidino, $C_{1-6}$alkylamino, di$C_{1-6}$alkylamino; $C_{1-6}$alkylamidino, di$C_{1-6}$alkylamidino, $C_{1-6}$alkylguanidino, di$C_{1-6}$alkylguanidino, $C_{1-6}$alkylthio, $C_{1-6}$alkylsulfo, $C_{1-6}$alkylsulfonyl, $C_{1-6}$alkylphosphono, di$C_{1-6}$alkylphosphono, $C_{1-6}$alkyl, $C_{1-6}$alkoxy, $C_{3-9}$cycloalkyl, $C_{3-9}$cycloalkoxy, $C_{2-7}$alkenyl, $C_{2-7}$alkynyl, $C_{1-6}$alkylcarbonyl, $C_{1-6}$alkoxycarbonyl (the above 19 groups may be substituted by one or more substituents selected from a halogen atom, hydroxy, aryl, heteroaryl, and cyano), aryl, aryloxy, arylcarbonyl, heteroaryl, heteroaryloxy, heteroarylcarbonyl, and aryl$C_{1-6}$alkyloxy (the above 7 groups may be substituted by one or more substituents selected from a halogen atom, $C_{1-6}$alkyl, and $C_{1-6}$alkoxy); or $X_1$ and $X_2$, $X_2$ and $X_3$, $X_3$ and $X_4$, and $X_4$ and $X_5$, together with the carbon atoms to which they are bound, form a saturated or unsaturated 5- to 7-membered carbocyclic ring, or a saturated or unsaturated 5- to 7-membered heterocyclic ring containing one or more heteroatoms selected from an oxygen atom, a nitrogen atom, and a sulfur atom;

Y is selected from the group consisting of $C_{1-6}$alkyl, $C_{3-9}$cycloalkyl, $C_{2-7}$alkenyl, $C_{2-7}$alkynyl, $C_{1-6}$alkylcarbonyl, $C_{1-6}$alkoxycarbonyl, arylcarbonyl, heteroarylcarbonyl, aryloxycarbonyl, heteroaryloxycarbonyl, $C_{1-6}$alkoxy, $C_{2-7}$alkenyloxy; $C_{2-7}$alkynyloxy, $C_{1-6}$alkylthio, $C_{1-6}$alkylsulfonyl {the above 15 groups may be substituted by one or more substituents selected from a saturated or unsaturated 3- to 7-membered carbocyclyl, a saturated or unsaturated 3- to 7-membered heterocyclyl containing one or more heteroatoms selected from an oxygen atom, a nitrogen atom, and a sulfur atom, a halogen atom, hydroxy, $C_{1-6}$alkoxy, hydroxy$C_{1-6}$ alkoxy, $C_{1-6}$alkoxy$C_{1-6}$alkoxy, amino$C_{1-6}$alkoxy, N—$C_{1-6}$alkylamino$C_{1-6}$alkoxy, N,N-di$C_{1-6}$alkylamino$C_{1-6}$alkoxy, amino, $C_{1-6}$alkylamino, hydroxy$C_{1-6}$ alkylamino, $C_{1-6}$alkoxy$C_{1-6}$alkylamino, amino$C_{1-6}$ alkylamino, di$C_{1-6}$alkylamino, bis(hydroxy$C_{1-6}$alkyl) amino, bis($C_{1-6}$alkoxy$C_{1-6}$alkyl)amino, bis(amino$C_{1-6}$ alkyl) amino, amidino, $C_{1-6}$alkylamidino, di$C_{1-6}$alkylamidino, guanidino, $C_{1-6}$alkylguanidino, di$C_{1-6}$ alkylguanidino, cyano, carboxyl, $C_{1-6}$alkoxycarbonyl, $C_{1-6}$alkylthio, $C_{1-6}$alkylsulfonyl, $C_{1-6}$alkylphosphono, and di$C_{1-6}$alkylphosphono}, amino, $C_{1-6}$alkylamino, di$C_{1-6}$alkylamino (the above 2 groups may be substituted by one or more substituents selected from a saturated or unsaturated 3- to 7-membered carbocyclyl, a saturated or unsaturated 3- to 7-membered heterocyclyl containing one or more heteroatoms selected from an oxygen atom, a nitrogen atom, and a sulfur atom, a halogen atom, hydroxy, $C_{1-6}$alkoxy, hydroxy$C_{1-6}$ alkoxy, $C_{1-6}$alkoxy$C_{1-6}$alkoxy, amino$C_{1-6}$alkoxy, N-$C_{1-6}$ alkylamino$C_{1-6}$alkoxy, N,N-di$C_{1-6}$alkylamino$C_{1-6}$ alkoxy, amino, $C_{1-6}$alkylamino, hydroxy$C_{1-6}$ alkylamino, $C_{1-6}$alkoxy$C_{1-6}$alkylamino, amino$C_{1-6}$ alkylamino, di$C_{1-6}$alkylamino, bis(hydroxy$C_{1-6}$alkyl) amino, bis($C_{1-6}$alkoxy$C_{1-6}$alkyl)amino, bis(amino$C_{1-6}$ alkyl) amino, amidino, $C_{1-6}$alkylamidino, di$C_{1-6}$ alkylamidino, guanidino, $C_{1-6}$alkylguanidino, di$C_{1-6}$ alkylguanidino, cyano, carboxyl, $C_{1-6}$alkoxycarbonyl, $C_{1-6}$alkylthio, $C_{1-6}$alkylsulfonyl, $C_{1-6}$alkylphosphono, and di$C_{1-6}$alkylphosphono), a halogen atom, nitro, cyano, carboxyl, and a saturated or unsaturated 3- to 7-membered heterocyclyl containing one or more heteroatoms selected from an oxygen atom, a nitrogen atom, and a sulfur atom (the heterocyclyl may be substituted by one or more substituents selected from hydroxy, $C_{1-6}$alkyl, halo$C_{1-6}$alkyl, hydroxy$C_{1-6}$alkyl, $C_{1-6}$alkoxy$C_{1-6}$alkyl, and oxo);

Z is selected from the group consisting of a hydrogen atom, hydroxy, $C_{1-6}$alkyl, $C_{3-9}$cycloalkyl {the above 2 groups may be substituted by one or more substituents selected from a saturated or unsaturated 3- to 7-membered carbocyclyl (the carbocyclyl group may be substituted by one or more substituents selected from $C_{1-6}$alkyl, hydroxy$C_{1-6}$alkyl, and $C_{1-6}$alkoxy$C_{1-6}$alkyl), a saturated or unsaturated 3- to 7-membered heterocyclyl containing one or more heteroatoms selected from an oxygen atom, a nitrogen atom, and a sulfur atom (the heterocyclyl group may be substituted by one or more substituents selected from $C_{1-6}$alkyl, hydroxy$C_{1-6}$alkyl, and $C_{1-6}$alkoxy$C_{1-6}$alkyl), a halogen atom, hydroxy, $C_{1-6}$alkoxy, hydroxy$C_{1-6}$alkoxy, $C_{1-6}$alkoxy$C_{1-6}$alkoxy, hydroxy$C_{1-6}$alkoxy$C_{1-6}$alkoxy, amino$C_{1-6}$alkoxy, N-$C_{1-6}$alkylamino$C_{1-6}$alkoxy, N,N-di$C_{1-6}$alkylamino$C_{1-6}$alkoxy, amino, $C_{1-6}$alkylamino, hydroxy$C_{1-6}$ alkylamino, $C_{1-6}$alkoxy$C_{1-6}$alkylamino, amino$C_{1-6}$ alkylamino, di$C_{1-6}$alkylamino, bis(hydroxy$C_{1-6}$alkyl) amino, bis($C_{1-6}$alkoxy$C_{1-6}$alkyl) amino, bis(amino$C_{1-6}$ alkyl)amino, cyano, carboxyl, $C_{1-6}$alkoxycarbonyl, aryloxycarbonyl, carbamoyl, $C_{1-6}$alkylcarbamoyl, di$C_{1-6}$ alkylcarbamoyl{the above 2 groups may be substituted by one or more substituents selected from a halogen atom, hydroxy, cyano and amino), phosphono, $C_{1-6}$alkylphosphono, di$C_{1-6}$alkylphosphono, sulfonic acid, and $C_{1-6}$alkylsulfo}, and —$OR_1$ and —$NR_1R_2$;

$R_1$ and $R_2$ are each dependently selected from the group consisting of a hydrogen atom, $C_{1-6}$alkyl, $C_{1-6}$alkylcarbonyl, and a saturated or unsaturated 3- to 7-membered heterocyclyl containing one or more heteroatoms selected from an oxygen atom, a nitrogen atom, and a sulfur atom (the above 3 groups may be substituted by one or more substituents selected from a saturated or unsaturated 3- to 7-membered carbocyclyl, a saturated or unsaturated 3- to 7-membered heterocyclyl containing one or more heteroatoms selected from an oxygen atom, a nitrogen atom, and a sulfur atom, a halogen atom, hydroxy, $C_{1-6}$alkoxy, hydroxy$C_{1-6}$alkoxy, $C_{1-6}$alkoxy$C_{1-6}$alkoxy, amino$C_{1-6}$alkoxy, N-$C_{1-6}$alkylamino$C_{1-6}$alkoxy, N,N-di$C_{1-6}$alkylamino$C_{1-6}$alkoxy, amino, $C_{1-6}$alkylamino, hydroxy$C_{1-6}$alkylamino, $C_{1-6}$alkoxy$C_{1-6}$alkylamino, amino$C_{1-6}$alkylamino, di$C_{1-6}$alkylamino, bis(hydroxy$C_{1-6}$alkyl)amino, bis ($C_{1-6}$ alkoxy$C_{1-6}$alkyl)amino, bis(amino$C_{1-6}$alkyl) amino, cyano, carboxyl, $C_{1-6}$alkoxycarbonyl, aryloxycarbonyl, phosphono, $C_{1-6}$alkylphosphono, di$C_{1-6}$ alkylphosphono, sulfonic acid, and $C_{1-6}$alkylsulfo); or $R_1$ and $R_2$, together with the nitrogen atoms to which they are bound, form a saturated or unsaturated 5- to 7-membered heterocyclic ring containing one nitrogen atom and optionally further containing one or more heteroatoms selected from a oxygen atom, a nitrogen atom, and a sulfur atom; and L is selected from the formula:

[Formula 2]

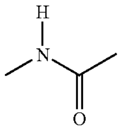

and

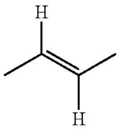

In the formula (II), if $Q_1$ is $A_2$═$A_3$—, $A_2$ binds to $A_1$ to form $A_1$-$A_2$═$A_3$—. If $Q_2$ is —$A_4$═$A_5$—, $A_4$ binds to $Q_1$ to form $Q_1$—$A_4$═$A_5$—.

Further, if L is —NHC(═O)—, the carbon atom of the carbonyl group binds to the benzene ring, while the nitrogen atom binds to the following moiety:

[Formula 3]

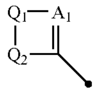

According to another aspect of the present invention, there is provided the compound of the formula (II), or the prodrug thereof, or the pharmaceutically acceptable salt of the compound or the prodrug, the compound being represented by the formula (I):

[Formula 4]

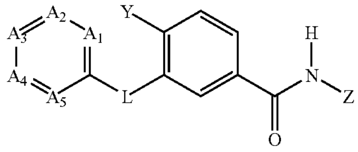

(I)

where $A_1$, $A_2$, $A_3$, $A_4$, $A_5$, L, Y, and Z are as defined above.

According to still another aspect of the present invention, there is provided the compound of the formula (II) or (I), or the prodrug thereof, or the pharmaceutically acceptable salt of the compound or the prodrug, wherein Z is a hydrogen atom, $C_{1-6}$alkyl, $C_{3-9}$cycloalkyl, hydroxy$C_{1-6}$alkyl, hydroxy$C_{1-6}$alkoxy$C_{1-6}$alkyl, $C_{1-6}$alkoxy$C_{1-6}$alkyl, cyano$C_{1-6}$alkyl, pyridyl$C_{1-6}$alkyl, dihydroxy$C_{1-6}$alkyl, trihydroxy$C_{1-6}$alkyl, morpholino$C_{1-6}$alkyl, (N,N-di$C_{1-6}$alkylamino)$C_{1-6}$alkyl, or (N,N-bis(hydroxy$C_{1-6}$alkyl)amino)$C_{1-6}$ alkyl. Examples of Z in these formulas include a hydrogen atom, methyl, ethyl, cyclopropyl, cyclopentyl, 2-hydroxyethyl, 2-(2-hydroxyethoxy)ethyl, 2-methoxyethyl, 2-cyanoethyl, 4-pyridylmethyl, 1-methoxybut-2-yl, 2,3-dihydroxyprop-1-yl, 1,3-dihydroxyprop-2-yl, 1,3-dihydroxy-2-hydroxymethylprop-2-yl, 2-morpholinoethyl, 1-hydroxyprop-2-yl, 1-hydroxy-3-methylbut-2-yl, 2-(N,N-dimethylamino)ethyl, 2-(N,N-bis(2-hydroxyethyl)amino) ethyl, 2,4-dihydroxylbutyl, 2,3,4-trihydroxybutyl, 2,3,4,5-tetrahydroxypentyl, and 2,3,4,5,6-pentahydroxyhexyl.

According to a further aspect of the present invention, there is provided the compound of the formula (II) or (I), or the prodrug thereof, or the pharmaceutically acceptable salt of the compound or the prodrug, wherein Y is a halogen atom, cyano, $C_{1-6}$alkyl, halo$C_{1-6}$alkyl, $C_{2-7}$alkenyl, $C_{2-7}$alkynyl, $C_{1-6}$alkoxy, $C_{3-9}$cycloalkyl$C_{1-6}$alkoxy, $C_{2-7}$alkynyloxy, or halo$C_{1-6}$alkoxy. Examples of Y in these formulas include chloro, bromo, cyano, methyl, trifluoromethyl, ethyl, n-propyl, i-propyl, ethynyl, methoxy, trifluoromethoxy, cyclopropylmethoxy, 2-butyn-1-yloxy, and 2-chloroethoxy.

According to a still further aspect of the present invention, there is provided the compound of the formula (II) or (I), or the prodrug thereof, or the pharmaceutically acceptable salt of the compound or the prodrug, wherein $A_1$ is C—$X_1$ or N, $A_2$ is C—$X_2$ or N, $A_3$ is C—$X_3$ or N, $A_4$ is C—$X_4$ or N, and $A_5$ is C—$X_5$ or N;

$X_1$, $X_2$, $X_3$, $X_4$ and $X_5$ are each independently selected from a hydrogen atom, a halogen atom, $C_{1-6}$alkyl, $C_{1-6}$alkoxy, halo$C_{1-6}$alkyl, halo$C_{1-6}$alkoxy, $C_{1-6}$alkylthio, and halo$C_{1-6}$alkylthio; or $X_1$ and $X_2$, $X_2$ and $X_3$, $X_3$ and $X_4$, and $X_4$ and $X_5$, together with the carbon atoms to which they are bound, form a cyclohexane ring, a cyclopentane ring, a benzene ring, a pyridine ring, a pyrimidine ring, a 1,4-dioxane ring, a 1,3-dioxolane ring, a pyrrole ring, an imidazole ring, a thiazole ring, or a furan ring. Examples of $X_1$, $X_2$, $X_3$, $X_4$ and $X_5$ in these formulas include a hydrogen atom, fluoro, chloro, bromo, methyl, ethyl, t-butyl, i-propyl, methoxy, i-propoxy, trifluoromethyl, trifluoromethoxy, methylthio, and trifluoromethylthio. Alternatively, $X_1$ and $X_2$, together with the carbon atoms to which they are bound, form a cyclohexane ring; $X_1$ and $X_2$, together with the carbon atoms to which they are bound, form a pyridine ring; $X_2$ and $X_3$, together with the carbon atoms to which they are bound, form a 1,4-dioxane ring; or $X_2$ and $X_3$, together with the carbon atoms to which they are bound, form a cyclopentane ring.

According to an additional aspect of the present invention, there is provided the compound of the aforementioned formulas, or the prodrug thereof, or the pharmaceutically acceptable salt of the compound or the prodrug, wherein $A_1$ is C—$X_1$ or N, $A_2$ is C—$X_2$ or N, $A_3$ is C—$X_3$ or N, $A_4$ is C—$X_4$, and $A_5$ is C—$X_5$; and two or more of $A_1$, $A_2$ and $A_3$ are not N at the same time.

According to a still additional aspect of the present invention, there are provided a pharmaceutical composition, an angiogenesis inhibitor, an agent for treatment and prevention of a disease involving angiogenesis, such as a cancerous disease including solid tumor, and an agent for treatment and prevention of metastasis of solid tumor, each of the pharmaceutical composition, the angiogenesis inhibitor, and the two agents containing the above-described compound, or the prodrug thereof, or the pharmaceutically acceptable salt of the compound or the prodrug, as an active ingredient.

In the present invention, the "halogen atom" refers to a fluorine atom, a chlorine atom, a bromine atom, or an iodine atom. If the halogen atom is the substituent for the aromatic carbon ring or the aromatic heterocycle in the present invention, a chlorine atom and a bromine atom are named as examples of the preferred halogen atom. If the halogen atom is the substituent for the alkyl group, or the group containing alkyl in its part (i.e., alkoxy, alkenyl, unsaturated carbon ring, or unsaturated heterocycle) in the present invention, a fluorine atom is named as an example of the preferred halogen atom.

In the present invention, the "$C_{1-6}$alkyl" refers to a straight chain or branched chain alkyl group having 1 to 6 carbon atoms, including, for example, methyl, ethyl, n-propyl, i-propyl, n-butyl, s-butyl, i-butyl, t-butyl, n-pentyl, 3-methylbutyl, 2-methylbutyl, 1-methylbutyl, 1-ethylpropyl, n-hexyl, 4-methylpentyl, 3-methylpentyl, 2-methylpentyl, 1-methylpentyl, 3-ethylbutyl, and 2-ethylbutyl.

In the present invention, the "$C_{3-9}$cycloalkyl" refers to a cyclic or partially cyclic alkyl group having 3 to 9 carbon atoms, including, for example, cyclopropyl, cyclobutyl, cyclopentyl, cyclohexyl, cycloheptyl, cyclooctyl, cyclononyl, cyclopropylmethyl, cyclohexylmethyl, cyclopropyl substituted by a $C_{1-6}$alkyl group, cyclopentyl substituted by a $C_{1-4}$alkyl group, and cyclohexyl substituted by a $C_{1-3}$alkyl group.

In the present invention, the "$C_{2-7}$alkenyl" refers to a straight chain or branched chain alkenyl group having 2 to 7 carbon atoms, including, for example, ethenyl (vinyl), 1-propenyl, 2-propenyl (allyl), propen-2-yl, and 3-butenyl (homoallyl).

In the present invention, the "$C_{2-7}$alkynyl" refers to a straight chain or branched chain alkynyl group having 2 to 7 carbon atoms, including, for example, ethynyl, 1-propynyl, 2-propynyl, 1-butynyl, 2-butynyl, and 3-butynyl.

In the present invention, the "$C_{1-6}$alkoxy" refers to an alkyloxy group having the straight chain or branched chain alkyl group having 1 to 6 carbon atoms which has already been defined as the alkyl portion, including, for example, methoxy, ethoxy, n-propoxy, i-propoxy, n-butoxy, s-butoxy, i-butoxy, t-butoxy, n-pentoxy, 3-methylbutoxy, 2-methylbutoxy, 1-methylbutoxy, 1-ethylpropoxy, n-hexyloxy, 4-methylpentoxy, 3-methylpentoxy, 2-methylpentoxy, 1-methylpentoxy, 3-ethylbutoxy, and 2-ethylbutoxy.

In the present invention, the "aryl" refers to a $C_{6-10}$ aromatic hydrocarbon group, including, for example, phenyl, 1-naphthyl, and 2-naphthyl.

In the present invention, the "heteroaryl" refers to a 5- to 10-membered aromatic heterocyclic group containing one or more heteroatoms selected from an oxygen atom, a nitrogen atom and a sulfur atom, including, for example, furyl, thienyl, pyrrolyl, imidazolyl, pyrazolyl, oxazolyl, isooxazolyl, thiazolyl, isothiazolyl, oxadiazolyl, thiadiazolyl, triazolyl, tetrazolyl, pyridinyl, pyrimidinyl, pyrazinyl, pyridazinyl, indolyl, and quinolinyl.

In the present invention, the "$C_{1-6}$alkylcarbonyl" refers to an alkylcarbonyl group having the straight chain or branched chain alkyl group having 1 to 6 carbon atoms which has already been defined as the alkyl portion, including, for example, acetyl, propionyl, methylpropionyl, and pivaloyl.

In the present invention, the "$C_{1-6}$alkoxycarbonyl" refers to an alkylcarbonyl group having the straight chain or branched chain alkyl group having 1 to 6carbon atoms which has already been defined as the alkoxy portion, including, for example, methoxycarbonyl, ethoxycarbonyl, n-propoxycarbonyl, i-propoxycarbonyl, n-butoxycarbonyl, s-butoxycarbonyl, i-butoxycarbonyl, t-butoxycarbonyl, n-pentoxycarbonyl, 3-methylbutoxycarbonyl, 2-methylbutoxycarbonyl, 1-methylbutoxycarbonyl, 1-ethylpropoxycarbonyl, n-hexyloxycarbonyl, 4-methylpentoxycarbonyl, 3-methylpentoxycarbonyl, 2-methylpentoxycarbonyl, 1-methylpentoxycarbonyl, 3-ethylbutoxycarbonyl, and 2-ethylbutoxycarbonyl.

In the present invention, the "$C_{1-6}$alkylthio" refers to an alkylthio group having the straight chain or branched chain alkyl group having 1 to 6 carbon atoms which has already been defined as the alkyl portion, including, for example, methylthio, ethylthio, n-propylthio, i-propylthio, n-butylthio, s-butylthio, i-butylthio, t-butylthio, n-pentylthio, 3-methylbutylthio, 2-methylbutylthio, 1-methylbutylthio, 1-ethylpropylthio, n-hexylthio, 4-methylpentylthio, 3-methylpentylthio, 2-methylpentylthio, 1-methylpentylthio, 3-ethylbutylthio, and 2-ethylbutylthio.

In the present invention, the "$C_{1-6}$alkylsulfonyl" refers to an alkylsulfonyl group having the straight chain or branched chain alkyl group having 1 to 6 carbon atoms which has already been defined as the alkyl portion, including, for example, methylsulfonyl, ethylsulfonyl, n-propylsulfonyl, i-propylsulfonyl, n-butylsulfonyl, s-butylsulfonyl, i-butylsulfonyl, t-butylsulfonyl, n-pentylsulfonyl, 3-methylbutylsulfonyl, 2-methylbutylsulfonyl, 1-methylbutylsulfonyl, 1-ethylpropylsulfonyl, n-hexylsulfonyl, 4-methylpentylsulfonyl, 3-methylpentylsulfonyl, 2-methylpentylsulfonyl, 1-methylpentylsulfonyl, 3-ethylbutylsulfonyl, and 2-ethylbutylsulfonyl.

In the present invention; the "$C_{1-6}$alkylamino" refers to an alkylamino group having the straight chain or branched chain alkyl group having 1 to 6 carbon atoms which has already been defined as the alkyl portion, including, for example, methylamino, ethylamino, n-propylamino, i-propylamino, n-butylamino, s-butylamino, i-butylamino, t-butylamino, n-pentylamino, 3-methylbutylamino, 2-methylbutylamino, 1-methylbutylamino, 1-ethylpropylamino, n-hexylamino, 4-methylpentylamino, 3-methylpentylamino, 2-methylpentylamino, 1-methylpentylamino, 3-ethylbutylamino, and 2-ethylbutylamino.

In the present invention, the "di$C_{1-6}$alkylamino" refers to a dialkylamino group having two of the straight chain or branched chain alkyl groups having 1 to 6 carbon atoms which have already been defined as the alkyl portions, and these two alkyl portions may be the same or different. The "di$C_{1-6}$alkylamino" includes, for example, dimethylamino, diethylamino, di-n-propylamino, di-i-propylamino, di-n-butylamino, methyl-n-butylamino, methyl-s-butylamino, methyl-i-butylamino, methyl-t-butylamino, ethyl-n-butylamino, ethyl-s-butylamino, ethyl-i-butylamino, and ethyl-t-butylamino.

In the present invention, the "saturated or unsaturated 3- to 7-membered carbocyclic ring" refers to a saturated, or an unsaturated bond-containing hydrocarbon ring having 3 to 7 carbon atoms contained in the ring, and also includes an aromatic hydrocarbon ring. The "saturated or unsaturated 3- to 7-membered carbocyclic ring" includes, for example, cyclopropane, cyclobutane, cyclopentane, cyclohexane, cycloheptane, cyclopentene, cyclohexene, and benzene.

In the present invention, the "saturated or unsaturated 5- to 7-membered carbocyclic ring" refers to a saturated, or an unsaturated bond-containing hydrocarbon ring having 5 to 7 carbon atoms contained in the ring, and also includes an aromatic hydrocarbon ring. The "saturated or unsaturated 5- to 7-membered carbocyclic ring" includes, for example, cyclopentane, cyclohexane, cycloheptane, cyclopentene, cyclohexene, and benzene.

In the present invention, the "saturated or unsaturated 3- to 7-membered heterocyclic ring" refers to a saturated, or an unsaturated bond-containing heterocycle, which has 3 to 7 carbon atoms contained in the ring and contains one or more heteroatoms selected from an oxygen atom, a nitrogen atom and a sulfur atom, and also includes an aromatic heterocycle. The "saturated or unsaturated 3- to 7-membered heterocyclic ring" includes, for example, oxirane, aziridine, azetidine, pyrrolidine, piperidine, piperazine, furan, thiophene, pyrrole, imidazole, pyrazole, oxazole, thiazole, thiadiazole, triazole, tetrazole, pyridine, pyrimidine, pyrazine, tetrahydrofuran, tetrahydropyran, 1,4-dioxane, morpholine, and thiomorpholine.

If, in the present invention, the "saturated or unsaturated 3- to 7-membered heterocyclyl" binds, as a substituent, to an aromatic carbon ring such as a benzene ring, the heterocyclyl includes a saturated or unsaturated 5- to 7-membered heterocyclyl binding to the aromatic carbon ring at the nitrogen atom in the ring. The "saturated or unsaturated 3- to 7-membered heterocyclyl" includes, for example, pyrrolidin-1-yl, piperidin-1-yl, morpholin-4-yl, piperazin-1-yl, thiomorpholin-4-yl, pyrrol-1-yl, pyrazol-1-yl, and imidazol-1-yl. The preferred heterocycles are pyrrolidin-1-yl, piperidin-1-yl, morpholin-4-yl, and piperazin-1-yl.

In the present invention, the "saturated or, unsaturated 5- to 7-membered heterocyclic ring" refers to a saturated, or an unsaturated bond-containing heterocycle, which has 5 to 7 carbon atoms contained in the ring and contains one or more heteroatoms selected from an oxygen atom, a nitrogen atom and a sulfur atom, and also includes an aromatic heterocycle. The "saturated or unsaturated 5- to 7-membered heterocyclyl" includes, for example, pyrrolidine, piperidine, piperazine, furan, thiophene, pyrrole, imidazole, pyrazole, oxazole, isoxazole, thiazole, isothiazole, oxadiazole, thiadiazole, triazole, tetrazole, pyridine, pyrimidine, pyrazine, pyridazine, tetrahydrofuran, tetrahydropyran, 1,4-dioxane, morpholine, and thiomorpholine.

In the present invention, the "$C_2$-$_7$alkenyloxy" refers to an alkenyloxy group having the straight chain or branched chain alkenyl group having 2 to 7 carbon atoms which has already been defined as the alkenyl portion.

In the present invention, the "$C_{2-7}$alkynyloxy" refers to an alkynyloxy group having the straight chain or branched chain alkynyl group having 2 to 7 carbon atoms which has already been defined as the alkynyl portion.

In the present invention, the alkyl portion, the alkynyl portion, and the alkoxy portion contained in the "$C_{1-6}$alkylcarbamoyl", the "di$C_{1-6}$alkylcarbamoyl", the "hydroxy$C_{1-6}$ alkoxy", the "$C_{1-6}$alkoxy$C_{1-6}$alkoxy", the "amino$C_{1-6}$ alkoxy", the "N—$C_{1-6}$alkylamino$C_{1-6}$alkoxy", the "N,N-di$C_{1-6}$alkylamino$C_{1-6}$alkoxy", the "hydroxy$C_{1-6}$ alkylamino", the "$C_{1-6}$alkoxy$C_{1-6}$alkylamino", the "amino$C_{1-6}$ alkylamino", the "bis(hydroxy$C_{1-6}$alkyl)amino", the "bis($C_{1-6}$ alkoxy$C_{1-6}$alkyl)amino", the "bis(amino$C_{1-6}$ alkyl) amino", the "$C_{1-6}$alkylamidino", the "di$C_{1-6}$alkylamidino", the "cyano$C_{1-6}$alkyl", the "pyridyl$C_{1-6}$alkyl", the "$C_{1-6}$ alkoxy$C_{2-7}$alkyl", the "hydroxy$C_{1-6}$alkyl", the "hydroxy$C_{1-6}$ alkoxy$C_{1-6}$alkyl", the "dihydroxy$C_{1-6}$alkyl", the "trihydroxy$C_{1-6}$alkyl", the "morpholino$C_{1-6}$alkyl", the "(N,N-di$C_{1-6}$alkylamino)$C_{1-6}$alkyl", or the "(N,N-bis(hydroxy$C_{1-6}$ alkyl)amino)$C_{1-6}$alkyl" refer to the alkyl group having 1 to 6 carbon atoms, the alkoxy group having 1 to 6 carbon atoms, and the alkynyl group having 2 to 7 carbon atoms which have already been defined.

In the present invention, no limitation is imposed on the substitution position of the alkyl group on the pyridine ring or the morpholine ring in the "pyridyl$C_{1-6}$alkyl" and the "morpholino$C_{1-6}$alkyl".

In the present invention, the "halo$C_{1-6}$alkyl" refers to an alkyl group formed by substituting a halogen atom for the straight chain or branched chain alkyl group having 1 to 6 carbon atoms which has already been defined as the alkyl portion, the halogen atom being as already defined. The number of the halogen atoms that the halo$C_{1-6}$alkyl has as substituents may be 1 or more, and the halo$C_{1-6}$alkyl includes, for example, monohalo$C_{1-6}$alkyl, dihalo$C_{1-6}$alkyl, trihalo$C_{1-6}$ alkyl, and perhalo$C_{1-6}$alkyl.

In the present invention, the "halo$C_{1-6}$alkoxy" refers to an alkoxy group formed by substituting a halogen atom for the straight chain or branched chain alkoxy group having 1 to 6 carbon atoms which has already been defined as the alkoxy portion, the halogen atom being as already defined. The number of the halogen atoms that the halo$C_{1-6}$alkoxy has as substituents may be 1 or more, and the halo$C_{1-6}$alkoxy includes, for example, monohalo$C_{1-6}$alkoxy, dihalo$C_{1-6}$alkoxy, trihalo$C_{1-6}$alkoxy, and perhalo$C_{1-6}$alkoxy.

In the present invention, the "halo$C_{1-6}$alkylthio" refers to an alkylthio group formed by substituting a halogen atom for the straight chain or branched chain alkyl group having 1 to 6 carbon atoms which has already been defined as the alkyl portion, the halogen atom being as already defined. The number of the halogen atoms that the halo$C_{1-6}$alkyl has as substituents may be 1 or more, and the halo$C_{1-6}$alkylthio includes, for example, monohalo$C_{1-6}$alkylthio, dihalo$C_{1-6}$ alkylthio, trihalo$C_{1-6}$alkylthio, and perhalo$C_{1-6}$alkylthio.

In the present invention, the "aryloxycarbonyl" refers to aryloxycarbonyl having the already defined $C_{6-10}$aromatic hydrocarbon group as the aryl portion, and includes, for example, phenoxycarbonyl, 1-naphthoxycarbonyl, and 2-naphthoxycarbonyl.

In the present invention, the "$C_{1-6}$alkylguanidino" refers to a guanidino group (—NHC(NH)$NH_2$) in which one of the three nitrogen atoms contained has been substituted by a $C_{1-6}$alkyl group. The "$C_{1-6}$alkylguanidino" includes, for example, —NHC(NH)NH($C_{1-6}$alky).

In the present invention, the "di$C_{1-6}$alkylguanidino" refers to a guanidino group (—NHC(NH)$NH_2$) which has been substituted by $C_{1-6}$alkyl groups at two sites on the nitrogen atom. The "di$C_{1-6}$alkylguanidino" includes, for example, —NHC(NH)N($C_{1-6}$alky)$_2$.

In the present invention, the "di$C_{1-6}$alkylamidino" refers to an amidino group (—C(NH)$NH_2$) which has been substituted by $C_{1-6}$alkyl groups at two sites on the nitrogen atom. The "di$C_{1-6}$alkylamidino" includes, for example, —C(NH)N($C_{1-6}$ alky)$_2$.

In the present invention, the "hydroxyaminocarbonyl" refers to "—C(O)NH—OH". In the present invention, the "hydroxyamidino" refers to "—C(NH)NH—OH" or its tautomer.

In the present invention, the "phosphono" refers to "—PO(OH)$_2$". In the present invention, the "$C_{1-6}$alkylphosphono" refers to "—PO(OH) (O—$C_{1-6}$alkyl)" having the already defined $C_{1-6}$alkyl as the alkyl portion. The "di$C_{1-6}$alkylphosphono" refers to "—PO(O—$C_{1-6}$alkyl)$_2$" having the already defined $C_{1-6}$alkyls as the two alkyl portions.

In the present invention, the "sulfonic acid" refers to "—$SO_2$OH". In the present invention, the "$C_{1-6}$alkylsulfo" refers to "—$SO_2$O—$C_{1-6}$alkyl" having the already defined $C_{1-6}$alkyl as the alkyl portion.

Herein, the "oxo" refers to "═O". For example, a methylene group substituted by an oxo group forms a carbonyl group "—C(═O)—".

In the present invention, the "$C_{1-6}$alkylamino", the "di$C_{1-6}$ alkylamino", the "$C_{1-6}$alkylamidino", the "di$C_{1-6}$alkylamidino", the "$C_{1-6}$alkylguanidino", the "di$C_{1-6}$alkylguanidino", the "$C_{1-6}$alkylthio", the "$C_{1-6}$alkylsulfo", the "$C_{1-6}$alkylsulfonyl", the "$C_{1-6}$alkylphosphono", the "di$C_{1-6}$alkylphosphono", the "$C_{1-6}$alkyl", the "$C_{1-6}$alkoxy", the "$C_{3-9}$cycloalkyl", the "$C_{3-9}$cycloalkoxy", the "$C_{2-7}$alkenyl", the "$C_{2-7}$ alkynyl", the "$C_{1-6}$alkylcarbonyl", and "$C_{1-6}$ alkoxycarbonyl" may, in some cases, be substituted by one or more substituents selected from a halogen atom, hydroxy, aryl, heteroaryl, and cyano. The number of the substituents may be 1 to the largest number that can be taken in terms of chemical structure. The number of the substituents is, for example, 1 to 5, preferably 1 to 3.

In the present invention, the "aryl", the "aryloxy", the "arylcarbonyl", the "heteroaryl", the "heteroaryloxy", and the "heteroarylcarbonyl" may, in some cases, be substituted by one or more halogen atoms, $C_{1-6}$alkyls, or $C_{1-6}$alkoxys. The number of the substituents may be 1 to the largest number that can be taken in terms of chemical structure. The number of the substituents is, for example, 1 to 5, preferably 1 to 3.

In the present invention, the "$C_{1-6}$alkyl", the "$C_{3-9}$cycloalkyl", the "$C_{2-7}$alkenyl", the "$C_{2-7}$alkynyl", the "$C_{1-6}$ alkylcarbonyl", "$C_{1-6}$alkoxycarbonyl", the "arylcarbonyl", the "heteroarylcarbonyl", the "aryloxycarbonyl", the "heteroaryloxycarbonyl", the "$C_{1-6}$alkoxy", the "$C_{2-7}$alkenyloxy", the "$C_{2-7}$alkynyloxy", the "$C_{1-6}$alkylthio", and the "$C_{1-6}$alkylsulfonyl" may, in some cases, be substituted by one or more substituents selected from a saturated or unsaturated 3- to 7-membered carbocyclyl, a saturated or unsaturated 3- to 7-membered heterocyclyl containing one or more heteroatoms selected from an oxygen atom, a nitrogen atom, and a sulfur atom, a halogen atom, hydroxy, $C_{1-6}$alkoxy, hydroxy$C_{1-6}$alkoxy, $C_{1-6}$alkoxy$C_{1-6}$alkoxy, amino$C_{1-6}$ alkoxy, N—$C_{1-6}$alkylamino$C_{1-6}$alkoxy, N,N-di$C_{1-6}$alkylamino$C_{1-6}$alkoxy, amino, $C_{1-6}$alkylamino, hydroxy$C_{1-6}$ alkylamino, $C_{1-6}$alkoxy$C_{1-6}$alkylamino, amino$C_{1-6}$ alkylamino, di$C_{1-6}$alkylamino, bis(hydroxy$C_{1-6}$alkyl)amino, bis ($C_{1-6}$alkoxy$C_{1-6}$alkyl)amino, bis(amino$C_{1-6}$alkyl)amino, amidino, $C_{1-6}$alkylamidino, di$C_{1-6}$alkylamidino, guanidino, $C_{1-6}$alkylguanidino, di$C_{1-6}$alkylguanidino, cyano, carboxyl, $C_{1-6}$alkylthio, $C_{1-6}$alkylsulfonyl, $C_{1-6}$alkylphosphono, and di$C_{1-6}$alkylphosphono. The number of the substituents may be 1 to the largest number that can be taken in terms of chemical structure. The number of the substituents is, for example, 1 to 5, preferably 1 to 3.

In the present invention, the "$C_{1-6}$alkyl" and the "$C_{3-9}$cycloalkyl" may, in some cases, be substituted by one or more substituents selected from a saturated or unsaturated 3- to 7-membered carbocyclyl (the carbocyclyl group may be substituted by one or more substituents selected from $C_{1-6}$alkyl, hydroxy$C_{1-6}$alkyl, and $C_{1-6}$alkoxy$C_{1-6}$alkyl), a saturated or unsaturated 3- to 7-membered heterocyclyl containing one or more heteroatoms selected from an oxygen atom, a nitrogen atom, and a sulfur atom (the heterocyclyl group may be substituted by one or more substituents selected from $C_{1-6}$alkyl, hydroxy$C_{1-6}$alkyl, and $C_{1-6}$alkoxy$C_{1-6}$alkyl), a halogen atom, hydroxy, $C_{1-6}$alkoxy, hydroxy$C_{1-6}$alkoxy, $C_{1-6}$alkoxy$C_{1-6}$alkoxy, amino$C_{1-6}$alkoxy, N—$C_{1-6}$alkylamino$C_{1-6}$alkoxy, N,N-di$C_{1-6}$alkylamino$C_{1-6}$alkoxy, amino, $C_{1-6}$alkylamino, hydroxy$C_{1-6}$alkylamino, $C_{1-6}$alkoxy$C_{1-6}$ alkylamino, amino$C_{1-6}$alkylamino, di$C_{1-6}$alkylamino, bis (hydroxy$C_{1-6}$alkyl)amino, bis($C_{1-6}$alkoxy$C_{1-6}$alkyl)amino, bis(amino$C_{1-6}$alkyl)amino, cyano, carboxyl, $C_{1-6}$alkoxycarbonyl, aryloxycarbonyl, phosphono, $C_{1-6}$alkylphosphono, di$C_{1-6}$alkylphosphono, sulfonic acid, or $C_{1-6}$alkylsulfonyl. The number of the substituents may be 1 to the largest number that can be taken in terms of chemical structure. The number of the substituents is, for example, 1 to 5, preferably 1 to 3.

In the present invention, the "$C_{1-6}$alkyl", the "$C_{1-6}$alkylcarbonyl", and the "saturated or unsaturated 3- to 7-membered heterocyclyl containing one or more heteroatoms selected from an oxygen atom, a nitrogen atom, and a sulfur atom" may, in some cases, be substituted by one or more substituents selected from a saturated or unsaturated 3- to 7-membered carbocyclyl, a saturated or unsaturated 3- to 7-membered heterocyclyl containing one or more heteroatoms selected from an oxygen atom, a nitrogen atom, and a sulfur atom, a halogen atom, hydroxy, $C_{1-6}$alkoxy, hydroxy$C_{1-6}$alkoxy, $C_{1-6}$alkoxy$C_{1-6}$alkoxy, amino$C_{1-6}$ alkoxy, N—$C_{1-6}$alkylamino$C_{1-6}$alkoxy, N,N-di$C_{1-6}$alkylamino$C_{1-6}$alkoxy, amino, $C_{1-6}$alkylamino, hydroxy$C_{1-6}$ alkylamino, $C_{1-6}$alkoxy$C_{1-6}$alkylamino, amino$C_{1-6}$ alkylamino, di$C_{1-6}$alkylamino, bis (hydroxy$C_6$alkyl) amino, bis ($C_{1-6}$alkoxy$C_{1-6}$alkyl)amino, bis(amino$C_{1-6}$alkyl)amino, cyano, carboxyl, $C_{1-6}$alkoxycarbonyl, aryloxycarbonyl, phosphono, $C_{1-6}$alkylphosphono, di$C_{1-6}$alkylphosphono, sulfonic acid, or $C_{1-6}$alkylsulfo. The number of the substituents may be 1 to the largest number that can be taken in terms of chemical structure. The number of the substituents is, for example, 1 to 5, preferably 1 to 3.

Herein, if the arbitrary group is-substituted by one or more substituents, these substituents may be the same or different, and the number of the substituents is 1 to the largest number that can substituent in terms of, chemical structure. The number of the substituents is, for example, 1 to 7, typically 1 to 5, preferably 1 to 3.

The group

[Formula 5]

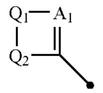

which the compound of the present invention represented by the formula (II) has, includes, for example, the following aromatic carbon ring groups or aromatic heterocyclic groups:

[Formula 6]

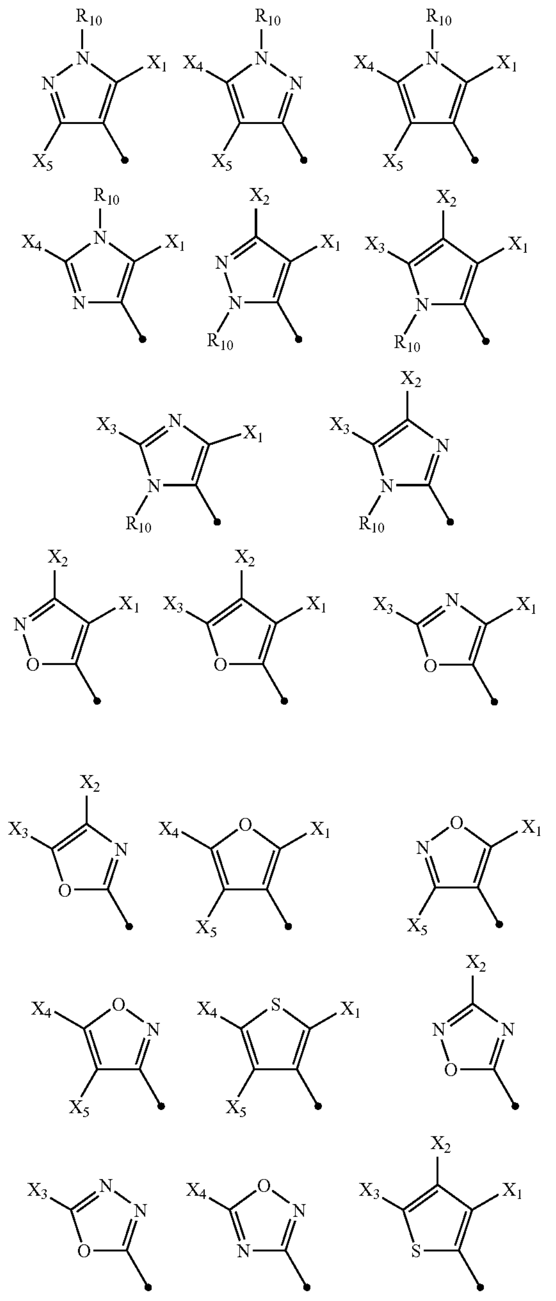

[Formula 7]

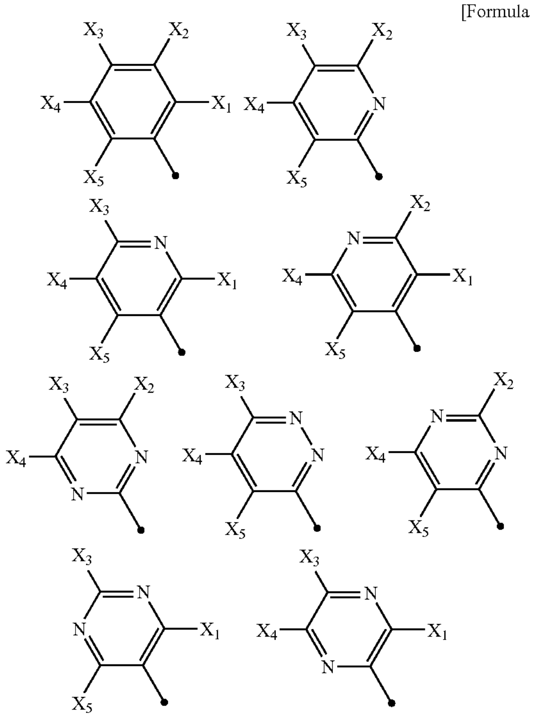

The present invention includes salts of the compounds represented by the formula (I) or the formula (II), and pharmaceutically acceptable salts of prodrugs of the compounds. These salts are produced by bringing the compounds or the prodrugs of the compounds into contact with acids or bases which can be used in the production of medicines. These salts include, for example, hydrochlorides, hydrobromides, hydriodides, sulfates, sulfonates, phosphates, phosphonates, carboxylates such as acetates, citrates, malates and salicylates, or alkali metal salts such as sodium salts and potassium salts; alkaline earth metal salts such as magnesium salts and calcium salts; and ammonium salts such as ammonium salts, alkylammonium salts, dialkylammonium salts, trialkylammonium salts, and tetraalkylammonium salts.

The "prodrugs" in the present invention refer to derivatives of the compounds of the formula (I) or (II) which are converted into the compounds of the formula (I) or (II) or their pharmaceutically acceptable salts by enzymatic or non-enzymatic decomposition under physiological conditions. The prodrugs are those which may be inert when administered to patients, but in vivo, are present in active forms converted into the compounds of the formula (I) or (II).

The prodrugs are those which may be inert when administered to patients, but in vivo, are present in active forms converted into the compounds of the formula (I).

Next, the methods of producing the compounds of the present invention will be described. If, in the manufacturing methods shown below, the defined groups undergo undesirable chemical conversion under the conditions of the methods practiced, the production can be performed by using means such as protection or deprotection of functional groups. Operations for selecting and detaching the protective groups can be performed, for example, by the methods described in "Greene and Wuts, "Protective Groups in Organic Synthesis" (2nd Ed., John Wiley & Sons, 1991)". These methods may be employed, as appropriate, according to the reaction conditions. Where necessary, the sequence of the reaction steps such as the introduction of substituents can be changed. Various method are conceivable as the manufacturing methods for the compounds of the present invention represented by formula (I), and these compounds can be synthesized by use of ordinary means for organic synthesis. Representative methods which can produce the compounds are as shown below.

Representative Methods for Manufacture

Manufacturing Method 1

The compounds of the formula (II) where L denotes —NH—C(O)— can be produced, for example, by the method shown as the manufacturing method 1-1, 1-2, 1-3 or 1-4.

Manufacturing Method 1-1

[Formula 8]

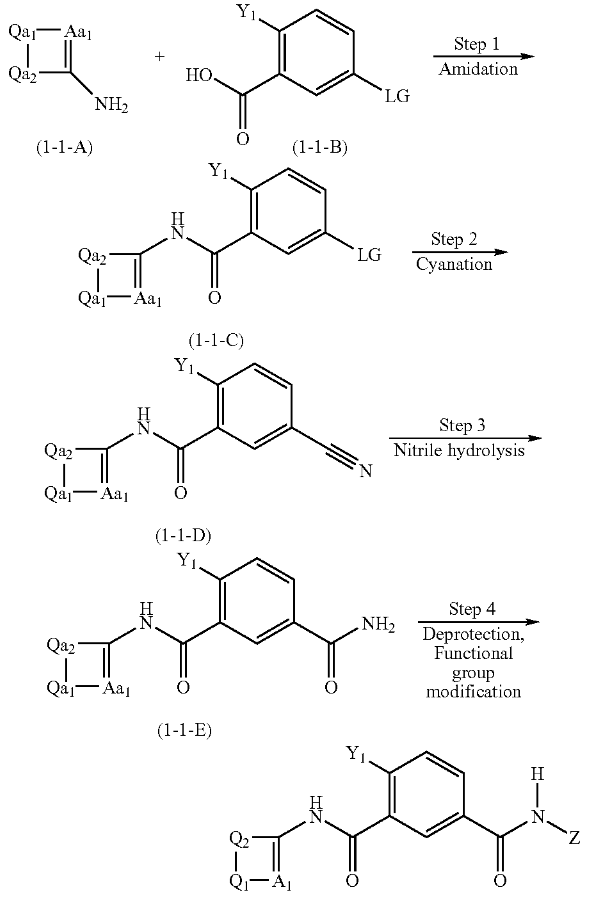

(1-1-A) (1-1-B) (1-1-C) (1-1-D) (1-1-E) (1-1-F)

In the formulas, $A_1$, $Q_1$, $Q_2$, Y and Z are as defined in the formula (II), and $Aa_1$, $Qa_1$, $Qa_2$, $Y_1$, and $Z_1$, respectively, have the same definitions as for $A_1$, $Q_1$, $Q_2$, Y and Z in the definitions of the formula (II), or represent groups which can be converted into $A_1$, $Q_1$, $Q_2$, Y and Z by functional group modification or deprotection. LG denotes a leaving group applicable to the reaction concerned, such as halogen or sulfonate.

Step 1 (Amidation)

An amine derivative (1-1-A) and a benzoic acid derivative (1-1-B) are subjected to dehydration condensation, whereby an amide (1-1-C) can be prepared. This reaction is carried out under reaction conditions at 0° C. to 180° C. in an aprotic solvent in the presence of an acid halogenating agent or a dehydration condensation agent, in the presence or absence of an active esterifying agent, or in the presence or absence of a base.

Examples of the acid halogenating agent are oxalyl chloride and thionyl chloride. Examples of the dehydration condensation agent are carbodiimide compounds carried on polymers (for example, N-cyclohexylcarbodiimide-N'-propyloxymethylpolystyrene (PS-carbodiimide), 1,3-dicyclohexylcarbodiimide (DCC), 2-ethoxy-1-ethoxycarbonyl-1,2-dihydroquinoline (EEDQ), bromo-tris(pyrrolidino)-phosphonium=hexafluorophosphate (PyBrOP), 1-ethyl-3-(3'-dimethylaminopropyl)carbodiimide (EDC), and (benzotriazolyloxy)tripyrrolidino-phosphonium hexafluorophosphate (PyBOP)). Examples of the active esterifying agent are N-hydroxybenzotriazole (HOBt), di(N-succinimidyl) carbonate, and carbonyldiimidazole. Examples of the base are triethylamine, N,N-diisopropylethylamine, and 1,8-diazabicyclo[5.4.0]-7-undecene (DBU). Examples of the aprotic solvent are carboxylic acid amides such as formamide or N,N-dimethylformamide, halogenated hydrocarbons such as dichloromethane, carbon tetrachloride or chlorobenzene, ketones such as acetone, cyclic ethers such as tetrahydrofuran or dioxane, esters such as ethyl acetate, nitrites such as acetonitrile, and their mixtures.

Step 2 (Cyanation)

In the formulas, LG denotes a leaving group applicable to the reaction concerned, such as a halogen atom or sulfonate. Cyanation of a compound having a leaving group on the benzene ring can be performed, for example, by applying, as appropriate, the method described in Synthetic Communication, 887-90, 24(6), (1994). Concretely, the compound (1-1-C) is reacted with a metal cyanide, for example, zinc cyanide, in a solvent inert to the reaction, for example, N,N-dimethylformamide, in the presence of a catalytic amount of a palladium complex, for example, tetrakistriphenylphosphine palladium, whereby a corresponding cyanation product (1-1-D) can be obtained.

Step 3 (Nitrile Hydrolysis)

The hydrolysis of the nitrile group to an amide can be performed, for example, by applying, as appropriate, a method using hydrogen peroxide and an inorganic base (for example, Org. Syn. Coll. vol. 2, 586-588 (1943), and J. Med. Chem., 43, 873-882 (2000)), a method performed in an aliphatic alcohol or dimethy sulfoxide in the presence of an inorganic base (for example, Japanese Patent Application Laid-Open No. 2000-86610 or Japanese Patent Application Laid-Open No. 2001-39936), or a method involving hydrolysis in the presence of an acid (Japanese Patent Application Laid-Open No. 1994-239810). The preferred method is the conversion of the nitrile group into an amide (1-1-E) performed using an aqueous solution of hydrogen peroxide in the presence of an inorganic base, for example, potassium carbonate. Dimethyl sulfoxide or the like can be used as the reaction solvent. The reaction time is about 10 minutes to about 30 hours. The reaction temperature is in a temperature range of from about 10° C. to about 100° C.

Step 4 (Deprotection, Functional Group Modification)

If the amide (1-1-E) has a protective group and/or a substituent capable of functional group modification (for example, a hydroxyl group, an amino group, halogen, a carboxyl group, a carbonyl group, a nitro group, a cyano group, or carbon-carbon unsaturated bond), a deprotection reaction and/or functional group modification is performed during this step, whereby a compound (1-1-F), the desired final product, can be produced. Various publicly known methods are available for this reaction, and selection and detachment of the protective group are performed, for example, by the method described in "Greene and Wuts, "Protective Groups in Organic Synthesis" (2nd Ed., John Wiley & Sons, 1991)". The functional group modification reaction is performed, for example, by the method described in "Smith and March, "March's Advanced Organic Chemistry" (5th Ed., John Wiley & Sons, 2001)" or "Richard C. Larock, Comprehensive Organic Transformations (VCH Publishers, Inc. 1989)".

Manufacturing Method 1-2

[Formula 9]

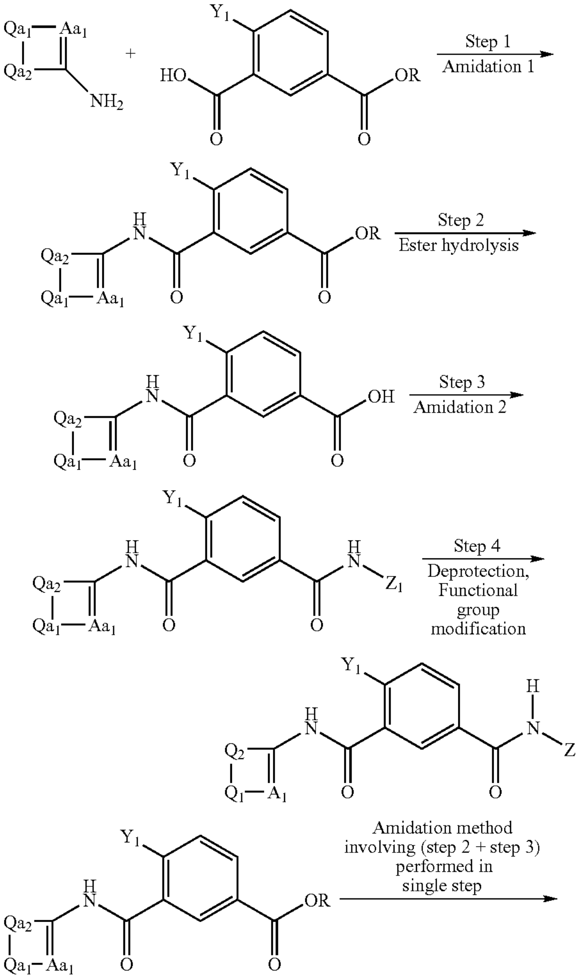

-continued

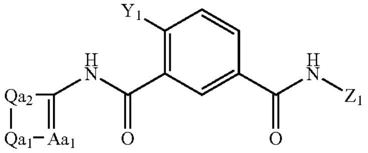

In the formulas, $A_1$, $Q_1$, $Q_2$, Y and Z are as defined in the formula (II), and $Aa_1$, $Qa_1$, $Qa_2$, $Y_1$, and $Z_1$, respectively, have the same definitions as for $A_1$, $Q_1$, $Q_2$, Y and Z in the definitions of the formula (II), or represent groups which can be converted into $A_1$, $Q_1$, $Q_2$, Y and Z by functional group modification or deprotection. R represents a $C_{1-6}$ alkyl group such as methyl, ethyl, propyl, butyl, pentyl, isopropyl, or tert-butyl. In the amidation of step 3, an optically active amine is used as the starting material, whereby the compound of the present invention having optical activity can be obtained.

Manufacturing Method 1-3

[Formula 10]

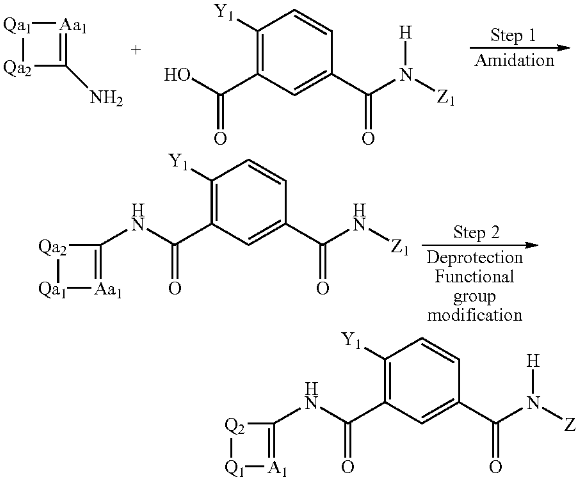

In the formulas, $A_1$, $Q_1$, $Q_2$, Y and Z are as defined in the formula (II), and $Aa_1$, $Qa_1$, $Qa_2$, $Y_1$, and $Z_1$, respectively, have the same definitions as for $A_1$, $Q_1$, $Q_2$, Y and Z in the definitions of the formula (II), or represent groups which can be converted into $A_1$, $Q_1$, $Q_2$, Y and Z by functional group modification or deprotection.

Manufacturing Method 1-4

[Formula 11]

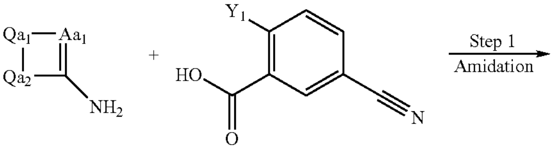

-continued

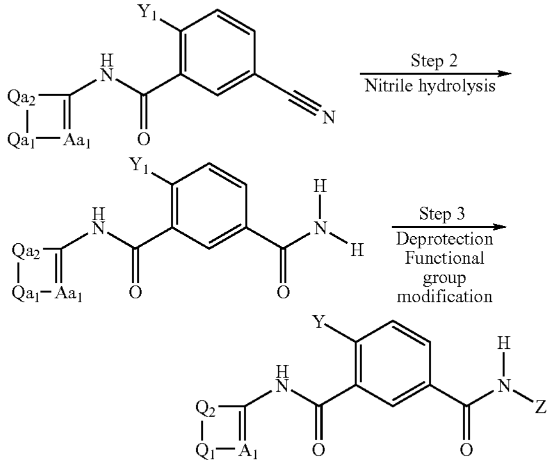

In the formulas, $A_1$, $Q_1$, $Q_2$, Y and Z are as defined in the formula (II), and $Aa_1$, $Qa_1$, $Qa_2$, $Y_1$, and $Z_1$, respectively, have the same definitions as for $A_1$, $Q_1$, $Q_2$, Y and Z in the definitions of the formula (II), or represent groups which can be converted into $A_1$, $Q_1$, $Q_2$, Y and Z by functional group modification or deprotection.

Step 1 (Amidation 1)

The same conditions as those for the amidation of Step 1 in the manufacturing method 1-1 can be applied.

Step 2 (Nitrile Hydrolysis)

The same conditions as those for the nitrile hydrolysis of Step 3 in the manufacturing method 1-1 can be applied.

Step 3 (Deprotection, Functional Group Modification)

The same conditions as those for the deprotection and functional group modification of Step 4 in the manufacturing method 1-1 can be applied.

Manufacturing Method 2

The compounds of the formula (II) where L denotes —CH═CH— can be produced, for example, by the method shown as the manufacturing method 2-1, 2-2, 2-3 or 2-4.

Manufacturing Method 2-1

[Formula 12]

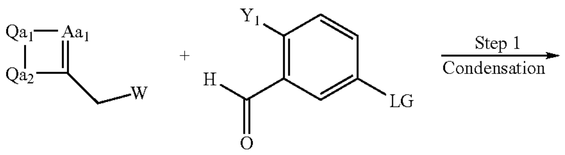

-continued

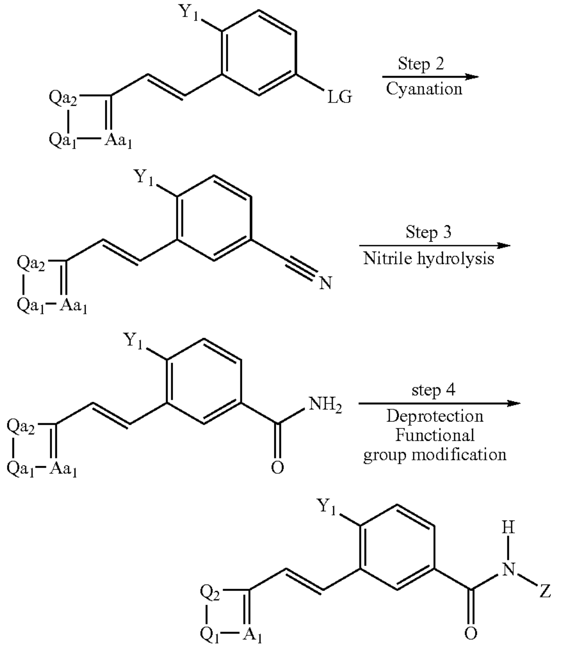

In the formulas, $A_1$, $Q_1$, $Q_2$, Y and Z are as defined in the formula (II), and $Aa_1$, $Qa_1$, $Qa_2$, $Y_1$, and $Z_1$, respectively, have the same definitions as for $A_1$, $Q_1$, $Q_2$, Y and Z in the definitions of the formula (II), or represent groups which can be converted into $A_1$, $Q_1$, $Q_2$, Y and Z by functional group modification or deprotection. LG denotes a leaving group applicable to the reaction concerned, such as halogen or sulfonate. W represents an O,O'-di-hydrocarbon-phosphono group, or a triarylphosphonium group. If W represents a triarylphosphonium group, a part of the phenyl group of the phosphonium portion may be polymerized.

Manufacturing Method 2-2

[Formula 13]

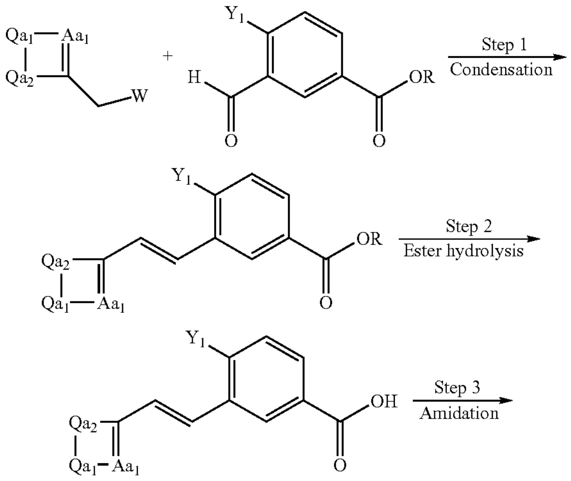

-continued

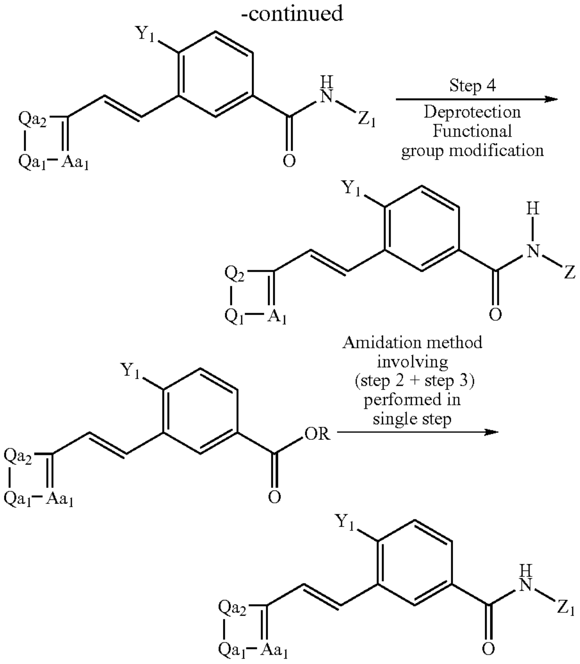

In the formulas, $A_1$, $Q_1$, $Q_2$, Y and Z are as defined in the formula (II), and $Aa_1$, $Qa_1$, $Qa_2$, $Y_1$, and $Z_1$, respectively, have the same definitions as for $A_1$, $Q_1$, $Q_2$, Y and Z in the definitions of the formula (II), or represent groups which can be converted into $A_1$, $Q_1$, $Q_2$, Y and Z by functional group modification or deprotection. R represents a $C_{1-6}$ alkyl group such as methyl, ethyl, propyl, butyl, pentyl, isopropyl, or tert-butyl. W represents an O,O'-di-hydrocarbon-phosphono group, or a triarylphosphonium group. If W represents a triarylphosphonium group, a part of the phenyl group of the phosphonium portion may be polymerized. In the amidation of step 3, an optically active amine is used as the starting material, whereby the compound of the present invention having optical activity can be obtained.

Manufacturing Method 2-3

[Formula 14]

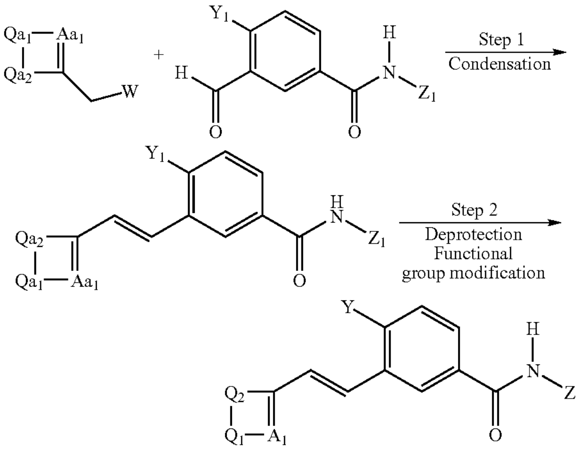

In the formulas, $A_1$, $Q_1$, $Q_2$, Y and Z are as defined in the formula (II), and $Aa_1$, $Qa_1$, $Qa_2$, $Y_1$, and $Z_1$, respectively, have the same definitions as for $A_1$, $Q_1$, $Q_2$, Y and Z in the definitions of the formula (II), or represent groups which can be converted into $A_1$, $Q_1$, $Q_2$, Y and Z by functional group modification or deprotection. W represents an O,O'-di-hydrocarbon-phosphono group, or a triarylphosphonium group. If W represents a triarylphosphonium group, a part of the phenyl group of the phosphonium portion may be polymerized.

Manufacturing Method 2-4

[Formula 15]

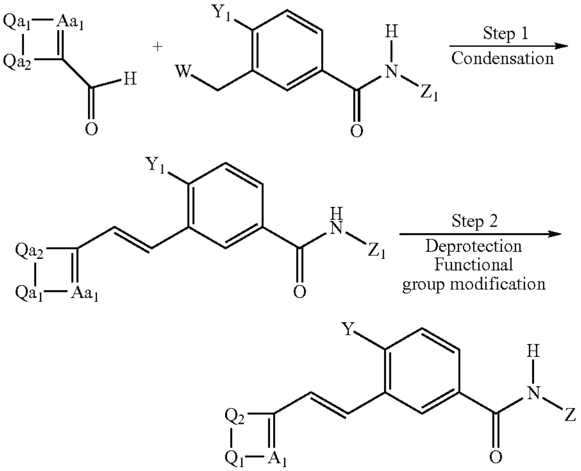

In the formulas, $A_1$, $Q_1$, $Q_2$, Y and Z are as defined in the formula (II), and $Aa_1$, $Qa_1$, $Qa_2$, $Y_1$, and $Z_1$, respectively, have the same definitions as for $A_1$, $Q_1$, $Q_2$, Y and Z in the definitions of the formula (II), or represent groups which can be converted into $A_1$, $Q_1$, $Q_2$, Y and Z by functional group modification or deprotection. W represents an O,O'-di-hydrocarbon-phosphono group, or a triarylphosphonium group. If W represents a triarylphosphonium group, a part of the phenyl group of the phosphonium portion may be polymerized.

Manufacturing Method 2-5

[Formula 16]

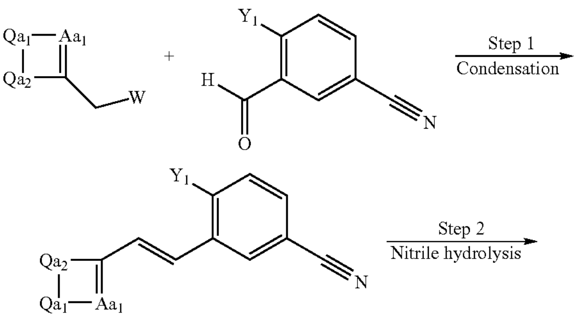

-continued

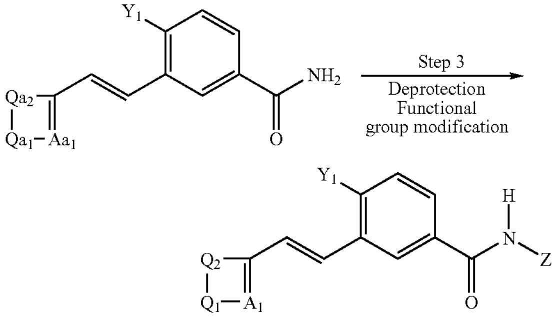

In the formulas, $A_1$, $Q_1$, $Q_2$, Y and Z are as defined in the formula (II), and $Aa_1$, $Qa_1$, $Qa_2$, $Y_1$, and $Z_1$, respectively, have the same definitions as for $A_1$, $Q_1$, $Q_2$, Y and Z in the definitions of the formula (II), or represent groups which can be converted into $A_1$, $Q_1$, $Q_2$, Y and Z by functional group modification or deprotection. W represents an O,O'-di-hydrocarbon-phosphono group, or a triarylphosphonium group. If W represents a triarylphosphonium group, a part of the phenyl group of the phosphonium portion may be polymerized.

Manufacturing Method 3

The compounds of the formula (I) where L denotes —NH—C(O)— can be produced, for example, by the method shown as the manufacturing method 3-1, 3-2 or 3-3.

Manufacturing Method 3-1

[Formula 17]

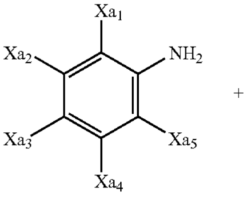

(3-1-A)

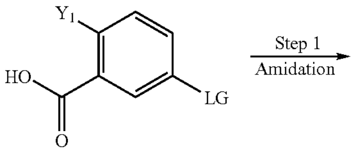

(3-1-B)

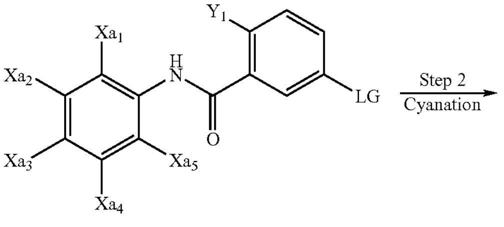

(3-1-C)

-continued

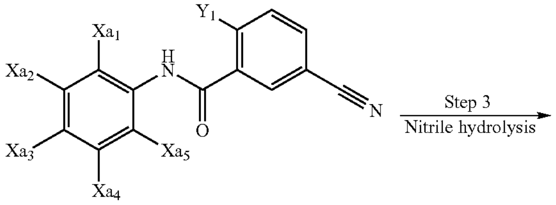

(3-1-D)

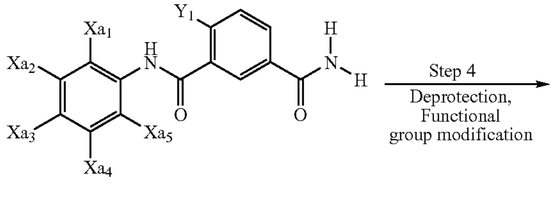

(3-1-E)

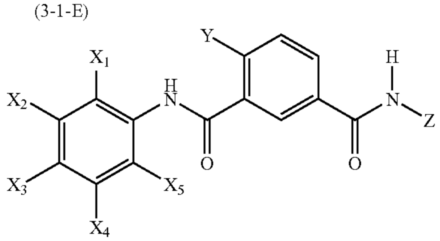

(3-1-F)

In the formulas, $X_1$, $X_2$, $X_3$, $X_4$, $X_5$, Y and Z are as defined in the formula (I), and $Xa_1$, $Xa_2$, $Xa_3$, $Xa_4$, $Xa_5$, $Y_1$, and $Z_1$, respectively, have the same definitions as for $X_1$, $X_2$, $X_3$, $X_4$, $X_5$, Y and Z in the definitions of the formula (I), or represent groups which can be converted into $X_1$, $X_2$, $X_3$, $X_4$, $X_5$, Y and Z by functional group modification or deprotection. LG denotes a leaving group applicable to the reaction concerned, such as halogen or sulfonate.

Step 1 (Amidation)

An aniline derivative (3-1-A) and a benzoic acid derivative (3-1-B) are subjected to dehydration condensation, whereby an amide (3-1-C) can be prepared. This reaction is carried out under reaction conditions at 0° C. to 180° C. in an aprotic solvent in the presence of an acid halogenating agent or a dehydration condensation agent, in the presence or absence of an active esterifying agent, or in the presence or absence of a base.

Examples of the acid halogenating agent are oxalyl chloride and thionyl chloride. Examples of the dehydration condensation agent are carbodiimide compounds carried on polymers (for example, N-cyclohexylcarbodiimide-N'-propyloxymethylpolystyrene-(PS-carbodiimide), 1,3-dicyclohexylcarbodiimide (DCC), 2-ethoxy-1-ethoxycarbonyl-1,2-dihydroquinoline (EEDQ), bromo-tris(pyrrolidino)-phosphonium hexafluorophosphate (PyBrOP), 1-ethyl-3-(3'-dimethylaminopropyl)carbodiimide (EDC), and (benzotriazolyloxy)tripyrrolidino-phosphonium hexafluorophosphate (PyBOP)). Examples of the active esterifying agent are N-hydroxybenzotriazole (HOBt), di(N-succinimidyl) carbonate, and carbonyldiimidazole. Examples of the base are triethylamine, N,N-diisopropylethylamine, and 1,8-diazabicyclo[5.4.0]-7-undecene (DBU). Examples of the aprotic solvent are carboxylic acid amides such as formamide or N,N-dimethylformamide, halogenated hydrocarbons such as dichloromethane, carbon tetrachloride or chlorobenzene, ketones such as acetone, cyclic ethers such as tetrahydrofuran or dioxane, esters such as ethyl acetate, nitriles such as acetonitrile, and their mixtures.

Step 2 (Cyanation)

In the formulas, LG denotes a leaving group applicable to the reaction concerned, such as a halogen atom or sulfonate. Cyanation of a compound having a leaving group on the benzene ring can be performed, for example, by applying, as appropriate., the method described in Synthetic Communication, 887-90, 24(6), (1994). Concretely, the compound (3-1-C) is reacted with a metal cyanide, for example, zinc cyanide, in a solvent inert to the reaction, for example, N,N-dimethylformamide, in the presence of a catalytic amount of a palladium complex, for example, tetrakistriphenylphosphine palladium, whereby a corresponding cyanation product (3-1-D) can be obtained.

Step 3 (Nitrile Hydrolysis)

The hydrolysis of the nitrile group to an amide can be performed, for example, by applying, as appropriate, a method using hydrogen peroxide and an inorganic base (for example, Org. Syn. Coll. vol. 2, 586-588 (1943), and J. Med. Chem., 43, 873-882 (2000)), a method performed in an aliphatic alcohol or dimethy sulfoxide in the presence of an inorganic base (for example, Japanese Patent Application Laid-Open No. 2000-86610 or Japanese Patent Application Laid-Open No. 2001-39936), or a method involving hydrolysis in the presence of an acid (Japanese Patent Application Laid-Open No. 1994-239810). The preferred method is the conversion of the nitrile group into an amide (3-1-E) performed using an aqueous solution of hydrogen peroxide in the presence of an inorganic base, for example, potassium carbonate. Dimethyl sulfoxide or the like can be used as the reaction solvent. The reaction time is about 10 minutes to about 30 hours. The reaction temperature is in a temperature range of from about 100° C. to about 100° C.

Step 4 (Deprotection, Functional Group Modification)

If the amide (3-1-E) has a protective group and/or a substituent capable of functional group modification (for example, a hydroxyl group, an amino group, halogen, a carboxyl group, a carbonyl group, a nitro group, a cyano group, or carbon-carbon unsaturated bond), a deprotection reaction and/or functional group modification is performed during this step, whereby a compound (3-1-F), the desired final product, can be produced. Various publicly known methods are available for this reaction, and selection and detachment of the protective group are performed, for example, by the method described in "Greene and Wuts, "Protective Groups in Organic Synthesis" (2nd Ed., John Wiley & Sons, 1991)". The functional group modification reaction is performed, for example, by the method described in "Smith and March, "March's Advanced Organic Chemistry" (5th Ed., John Wiley & Sons, 2001)" or "Richard C. Larock, Comprehensive Organic Transformations (VCH Publishers, Inc. 1989)".

Manufacturing Method 3-2

[Formula 18]

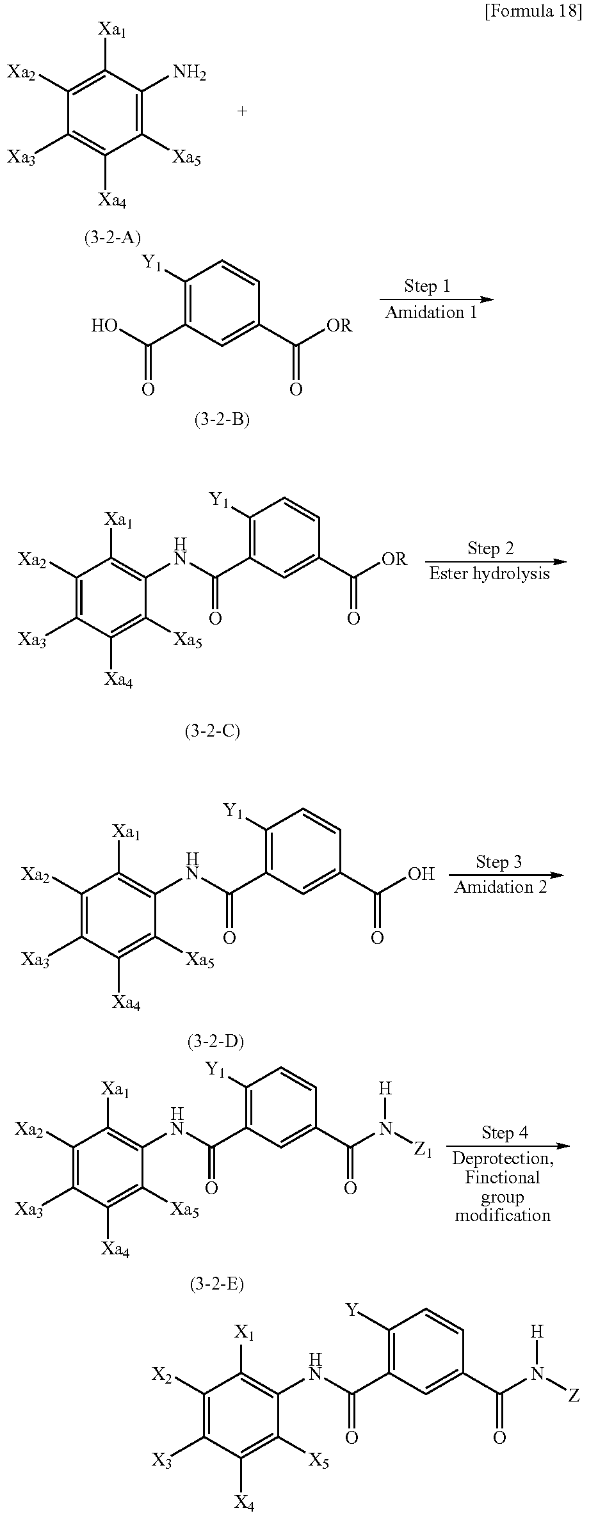

(3-2-A) (3-2-B) (3-2-C) (3-2-D) (3-2-E) (3-2-F)

-continued

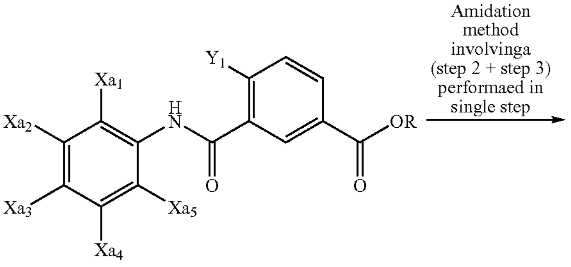

(3-2-C)

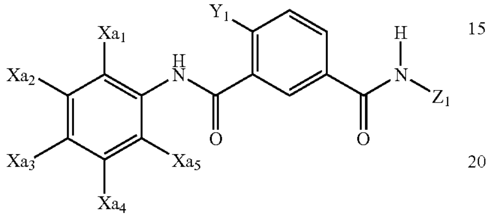

(3-2-E)

In the formulas, $X_1$, $X_2$, $X_3$, $X_4$, $X_5$, Y and Z are as defined in the formula (I), and $Xa_1$, $Xa_2$, $Xa_3$, $Xa_4$, $Xa_5$, $Y_1$, and $Z_1$, respectively, have the same definitions as for $X_1$, $X_2$, $X_3$, $X_4$, $X_5$, Y and Z in the definitions of the formula (I), or represent groups which can be converted into $X_1$, $X_2$, $X_3$, $X_4$, $X_5$, Y and Z by functional group modification or deprotection. R represents a $C_{1-6}$ alkyl group such as methyl, ethyl, propyl, butyl, pentyl, isopropyl, or tert-butyl.

Step 1 (Amidation 1)

The same conditions as those for the amidation of Step 1 in the manufacturing method 3-1 can be applied.

Step 2 (Ester Hydrolysis)

For the hydrolysis of the ester group, there are named, for example, a method involving hydrolysis performed in an aqueous solvent, for example, an alcohol-based solvent, in the presence of an inorganic base (for example, Corey, E. J.; Szekely, I.; Shiner, C. S. Tetrahedron Lett. 3529, 1977), and a method of hydrolysis in the presence of an acid (for example, Bryan, D. B.; Hall, R. F.; Holden, K. G.; Fuffman, W. F.; Gleason, J. G. J. Am. Chem. Soc., 1977, 99, 2353). The methods described there can be applied, as appropriate, for the hydrolysis. The preferred method is the hydrolysis of the ester group performed using an aqueous solution of potassium hydroxide or sodium hydroxide in an alcohol solvent such as ethanol. The reaction time is about 10 minutes to about 30 hours, preferably about 30 minutes to about 3 hours. The reaction temperature is in a temperature range of from about 0° C. to the boiling point of the solvent, preferably about 80° C. to about 100° C.

Step 3 (Amidation 2)

Various amines, for example, ammonia, hydrazine, mono-substituted amines, substituted hydrazines, and a benzoic acid derivative (3-2-D) are subjected to dehydration condensation, whereby an amide (3-2-E) can be prepared. This reaction is carried out under reaction conditions at 0° C. to 180° C. in an aprotic solvent in the presence of an acid halogenating agent or a dehydration condensation agent, in the presence or absence of an active esterifying agent, or in the presence or absence of a base. By using an optically active amine as the starting material, the compound of the present invention having optical activity can be obtained.

Examples of the acid halogenating agent are oxalyl chloride and thionyl chloride. Examples of the dehydration condensation agent are carbodiimide compounds carried on polymers (for example, N-cyclohexylcarbodiimide-N'-propyloxymethylpolystyrene (PS-carbodiimide), 1,3-dicyclohexylcarbodiimide (DCC), 2-ethoxy-1-ethoxycarbonyl-1,2-dihydroquinoline (EEDQ), bromo-tris(pyrrolidino)-phosphonium hexafluorophosphate (PyBrOP), 1-ethyl-3-(3'-dimethylaminopropyl)carbodiimide (EDC), and (benzotriazolyloxy)tripyrrolidino-phosphonium=hexafluorophosphate (PyBOP)). Examples of the active esterifying agent are N-hydroxybenzotriazole (HOBt), di(N-succinimidyl) carbonate, and carbonyldiimidazole. Examples of the base are triethylamine, N,N-diisopropylethylamine, and 1,8-diazabicyclo[5.4.0]-7-undecene (DBU). Examples of the aprotic solvent are carboxylic acid amides such as formamide or N,N-dimethylformamide, halogenated hydrocarbons such as dichloromethane, carbon tetrachloride or chlorobenzene, ketones such as acetone, cyclic ethers such as tetrahydrofuran or dioxane, esters such as ethyl acetate, nitrites such as acetonitrile, and their mixtures.

Method of Amidation Involving (Step 2+Step 3) Performed in Single Step

The benzoic acid-derived ester derivative (3-2-C) obtained in step 1 can be converted into the amide (3-2-E) without undergoing the ester hydrolysis of step 2. That is, this reaction is carried out by reacting the benzoic acid-derived ester derivative with various amines, such as ammonia or aliphatic amine, at atmospheric pressure or under pressure under reaction conditions at 0° C. to 180° C. in an aprotic or protonic solvent in the presence or absence of an activator such as a Lewis acid.

Step 4 (Deprotection, Functional Group Modification)

The same conditions as those for the deprotection and functional group modification of Step 4 in the manufacturing method 3-1 can be applied.

Manufacturing Method 3-3

[Formula 19]

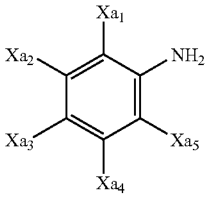

+

(3-3-A)

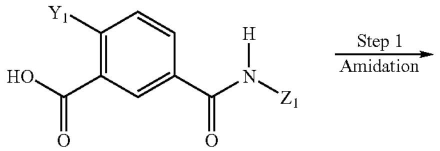

(3-3-B)

-continued

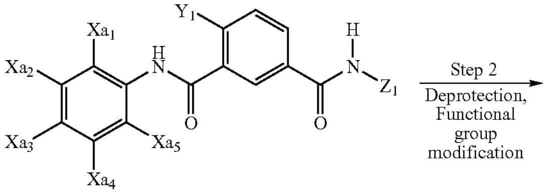

(3-3-C)

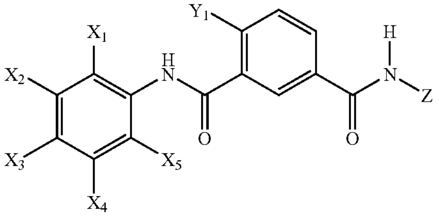

(3-3-D)

In the formulas, $X_1$, $X_2$, $X_3$, $X_4$, $X_5$, Y and Z are as defined in the formula (I), and $Xa_1$, $Xa_2$, $Xa_3$, $Xa_4$, $Xa_5$, $Y_1$, and $Z_1$, respectively, have the same definitions as for $X_1$, $X_2$, $X_3$, $X_4$, $X_5$, Y and Z in the definitions of the formula (I), or represent groups which can be converted into $X_1$, $X_2$, $X_3$, $X_4$, $X_5$, Y and Z by functional group modification or deprotection.

Step 1 (Amidation 1)

The same conditions as those for the amidation of Step 1 in the manufacturing method 3-1 can be applied.

Step 2 (Deprotection, Functional Group Modification)

The same conditions as those for the deprotection and functional group modification of Step 4 in the manufacturing method 3-1 can be applied.

Manufacturing Method 4

The compounds of the formula (I) where L denotes —CH═CH— can be produced, for example, by the method shown as the manufacturing method 4-1, 4-2, or 4-3.

Manufacturing Method 4-1

[Formula 20]

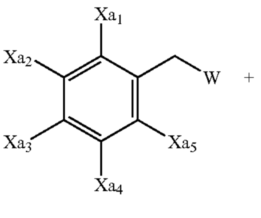

(4-1-A)

-continued

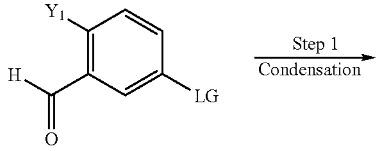

(4-1-B)

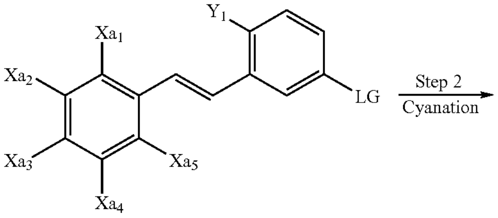

(4-1-C)

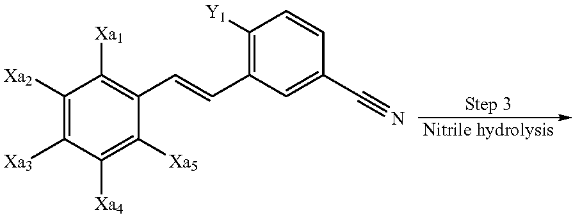

(4-1-D)

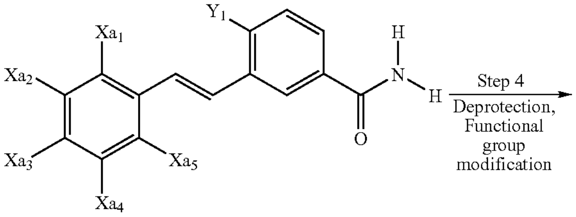

(4-1-E)

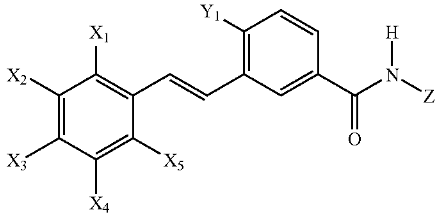

(4-1-F)

In the formulas, $X_1$, $X_2$, $X_3$, $X_4$, $X_5$, Y and Z are as defined in the formula (I), and $Xa_1$, $Xa_2$, $Xa_3$, $Xa_4$, $Xa_5$, $Y_1$, and $Z_1$, respectively, have the same definitions as for $X_1$, $X_2$, $X_3$, $X_4$, $X_5$, Y and Z in the definitions of the formula (I), or represent groups which can be converted into $X_1$, $X_2$, $X_3$, $X_4$, $X_5$, Y and Z by functional group modification or deprotection. LG denotes a leaving group applicable to the reaction concerned, such as halogen or sulfonate. W represents an O,O'-di-hydrocarbon-phosphono group, or a triarylphosphonium group. If W represents a triarylphosphonium group, a part of the phenyl group of the phosphonium portion may be polymerized.

Step 1 (Condensation)

A phosphorus compound (4-1-A) and an aldehyde (4-1-B) are subjected to dehydration condensation, whereby the desired stilbene derivative (4-1-C) can be produced. This reaction is performed in a solvent in the presence of a base at a reaction temperature of −78° C. to the boiling point of the solvent. Examples of the base are inorganic bases such as sodium carbonate, potassium carbonate, sodium hydride, potassium hydride, or calcium hydride, and organic bases such as pyridine, triethylamine, N,N-diisopropylethylamine, lithium diisopropylamide, lithium hexamethyldisilazide, n-butyl lithium, and sodium amide. Preferably, sodium hydride, lithium diisopropylamide, or lithium hexamethyldisilazide can be named. Examples of the solvent are non-reactive solvents, including tetrahydrofuran, diethyl ether, dioxane, methanol, ethanol, toluene, n-hexane, and dimethylformamide. The preferred examples are tetrahydrofuran, and diethyl ether.

Step 2 (Cyanation)

The same conditions as those for the cyanation of Step 2 in the manufacturing method 3-1 can be applied.

Step 3 (Nitrile Hydrolysis)

The same conditions as those for the nitrile hydrolysis of Step 3 in the manufacturing method 3-1 can be applied.

Step 4 (Deprotection, Functional Group Modification)

The same conditions as those for the deprotection and functional group modification of Step 4 in the manufacturing method 3-1 can be applied.

Manufacturing Method 4-2

[Formula 21]

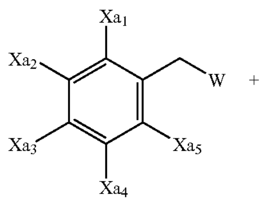

(4-2-A)

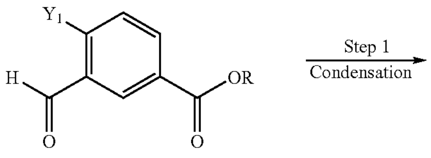

(4-2-B)

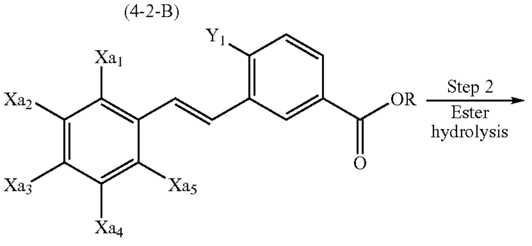

(4-2-C)

-continued

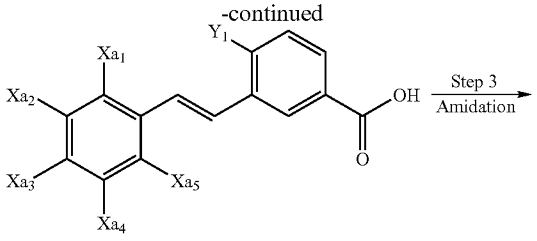

(4-2-D)

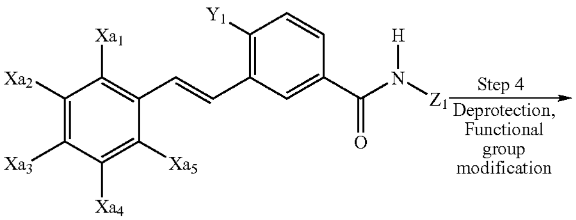

(4-2-E)

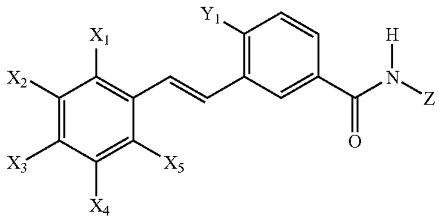

(4-2-F)

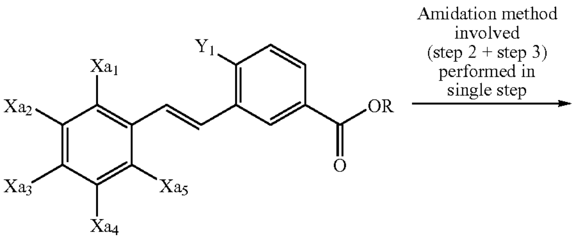

(4-2-C)

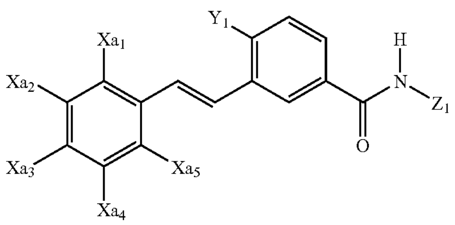

(4-2-E)

In the formulas, $X_1$, $X_2$, $X_3$, $X_4$, $X_5$, Y and Z are as defined in the formula (I), and $Xa_1$, $Xa_2$, $Xa_3$, $Xa_4$, $Xa_5$, $Y_1$, and $Z_1$, respectively, have the same definitions as for $X_1$, $X_2$, $X_3$, $X_4$, $X_5$, Y and Z in the definitions of the formula (I), or represent groups which can be converted into $X_1$, $X_2$, $X_3$, $X_4$, $X_5$, Y and Z by functional group modification or deprotection. R represents a $C_{1-6}$ alkyl group such as methyl, ethyl, propyl, butyl, pentyl, isopropyl, or tert-butyl. W represents an O,O'-di-hydrocarbon-phosphono group, or a triarylphosphonium group.

If W represents a triarylphosphonium group, a part of the phenyl group of the phosphonium portion may be polymerized.

Step 1 (Condensation)

The same conditions as those for the condensation of Step 1 in the manufacturing method 4-1 can be applied.

Step 2 (Ester Hydrolysis)

The same conditions as those for the ester hydrolysis of Step 2 in the manufacturing method 3-2 can be applied.

Step 3 (Amidation)

The same conditions as those for the amidation 2 of Step 3 in the manufacturing method 3-2 can be applied. By using optically active amines as starting materials, the compounds of the present invention, which are optically active, can be obtained.

Amidation Method Involving (Step 2+Step 3) Performed in Single Step

The benzoic acid-derived ester derivative obtained in step 1 can be converted into the amide without undergoing the ester hydrolysis of step 2. That is, this reaction is carried out by reacting the benzoic acid-derived ester derivative with various amines, such as ammonia or aliphatic amine, at atmospheric pressure or under pressure under reaction conditions at 0° C. to 180° C. in an aprotic or protonic solvent in the presence or absence of an activator such as a Lewis acid.

Step 4 (Deprotection, Functional Group Modification)

The same conditions as those for the deprotection and functional group modification of Step 4 in the manufacturing method 3-1 can be applied.

Manufacturing Method 4-3

[Formula 22]

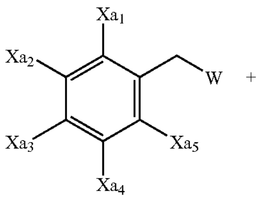

(4-3-A)

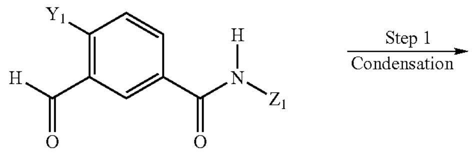

(4-3-B)

-continued

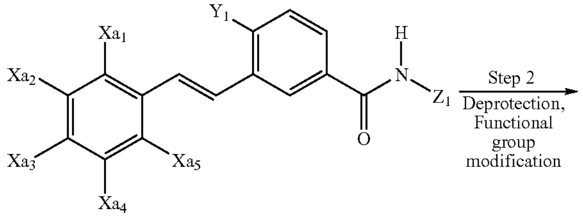

(4-3-C)

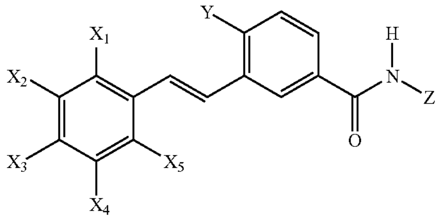

(4-3-D)

In the formulas, $X_1$, $X_2$, $X_3$, $X_4$, $X_5$, Y and Z are as defined in the formula (I), and $Xa_1$, $Xa_2$, $Xa_3$, $Xa_4$, $Xa_5$, $Y_1$, and $Z_1$, respectively, have the same definitions as for $X_1$, $X_2$, $X_3$, $X_4$, $X_5$, Y and Z in the definitions of the formula (I), or represent groups which can be converted into $X_1$, $X_2$, $X_3$, $X_4$, $X_5$, Y and Z by functional group modification or deprotection. W represents an O,O'-di-hydrocarbon-phosphono group, or a triarylphosphonium group. If W represents a triarylphosphonium group, a part of the phenyl group of the phosphonium portion may be polymerized.

Step 1 (Condensation)

The same conditions as those for the condensation of Step 1 in the manufacturing method 4-1 can be applied.

Step 2 (Deprotection, Functional Group Modification)

The same conditions as those for the deprotection and functional group modification of Step 4 in the manufacturing method 3-1 can be applied.

Synthesis of Starting Compounds

Some of the starting compounds for the compounds of the present invention are novel compounds, and these compounds can be synthesized easily in the same manner as for the publicly known starting compounds, or by use of methods publicly known to people skilled in the art.

Examples of the amine usable as the starting material in the amidation step in the manufacturing methods 1-2, 2-2, 3-2 and 4-2 are optically active forms of amines selected from 2,4-dihydroxybutylamine, 2,3,4-trihydroxybutylamine, 2,3-dihydroxypropylamine, 2-hydroxy-1-methylethylamine and 1-methoxymethylpropylamine, and amino acids such as serine, homoserine, threonine, tyrosine, lysine, glutamic acid and aspartic acid. When an amino acid is used in the amidation step, the carboxy group and/or a functional group contained in the amino acid residue of the amino acid may be protected by a protective group. Further, the compound obtained by the amidation step may be subjected to deprotection and/or functional group modification, for example amidation of the carboxy group. These chemical conversions can be carried out in accordance with a procedure well known to those skilled in the art or a procedure as described in Examples hereinafter.

An example of the manufacturing method for the compounds of the formula (I) and the formula (II) according to the present invention has been described above. The isolation and purification of the desired compounds in the above-described reaction steps can be performed by applying ordinary chemical procedures, such as extraction, concentration, removal by distillation, crystallization, filtration, recrystallization, and various chromatographic techniques.

The compounds of the present invention, and their pharmaceutically acceptable salts include all stereoisomers (for example, enantiomers and diastereomers (cis-geometric isomers and trans-geometric isomers)) of the compounds represented by the formula (I) and the formula (II), racemic bodies of these isomers, and other mixtures thereof. For example, the compounds of the present invention may be those of the formulas (I) and (II) in which Z has one or more asymmetric points. The present invention includes racemic mixtures, diastereomer mixtures, and enantiomers of such compounds.

The compounds of the present invention, and their pharmaceutically acceptable salts can be present in several tautomeric forms, for example, enol and imine forms, keto and enamine forms, and as mixtures thereof. The tautomers exist in solutions as mixtures of tautomeric sets. In the solid form, one of the tautomers is usually predominant. One of the tautomers may be described herein, but in the present invention, all tautomers of the compounds of the present invention are included.

If the compounds according to the present invention are obtained as free compounds, they can be converted into salts, their hydrates, or their solvates, which the compounds may form, in accordance with the conventional methods.

If the compounds according to the present invention are obtained as salts, hydrates, or solvates of the compounds, they can be converted into the free forms of the compounds in accordance with the conventional methods.

The compounds of the present invention, and their pharmaceutically acceptable salts have an excellent angiogenesis inhibiting action, are excellent in stability in the body and solubility in water, and are useful as prophylactic or therapeutic agents (especially, therapeutic agents) for proliferative diseases. Also, the compounds of the present invention, and their pharmaceutically acceptable salts are useful as prophylactic or therapeutic agents (especially, therapeutic agents) for diseases, such as various cancers, for example, breast cancer, colon cancer, rectal cancer, ovarian cancer, pulmonary cancer, pancreatic cancer, hepatic cancer, uterine cancer, brain cancer, prostatic cancer, acute leukemia, and gastric cancer. Further, the compounds of the present invention are useful as prophylactic or therapeutic agents (especially, therapeutic agents) for the infiltration and metastasis of solid cancer. Additionally, the compounds of the present invention are effective as prophylactic or therapeutic agents for other diseases related to angiogenesis, for example, Alzheimer disease and HIV infection.

These methods include the step of administering medically effective amounts of pharmaceutical compositions containing the compounds of the present invention and their pharmaceutically acceptable salts, which have been disclosed above, to patients requiring such therapies or suffering from such diseases or states.

If the pharmaceutical composition of the present invention is used as an angiogenesis inhibitor, or an agent for treatment or prevention of proliferative disease, the method of its administration includes, for example, oral, rectal, parenteral (intravenous, intramuscular, subcutaneous), intracisternal, intravaginal, intraperitoneal, intravesical, and local (drip infusion, powder, ointment, gel or cream) administration and inhalation (intraoral or nasal spray). The dosage forms are, for example, tablets, capsules, granules, powders, pills, aqueous and nonaqueous oral solutions and suspensions, and parenteral solutions charged into containers suitable for dispensing into individual doses. The dosage forms can also be adapted for various modes of administration including controlled release prescriptions, such as subcutaneous implantation.

The above-mentioned preparations can be produced by well-known methods using additives, such as vehicles, tablet lubricants (coating agents), binders, disintegrants, stabilizers, taste and odor correctives, and diluents.

Examples of the vehicles are starches such as starch, potato starch, and corn starch, lactose, microcrystalline cellulose, and calcium hydrogen phosphate.

Examples of the coating agents are ethylcellulose hydroxypropylcellulose, hydroxypropyl methylcellulose, shellac, talc, carnauba wax, and paraffin.

Examples of the binders are polyvinylpyrrolidone, macrogol, and the same compounds as the above-mentioned vehicles.

Examples of the disintegrants are the same compounds as the above-mentioned vehicles, and chemically modified starch-celluloses such as croscarmellose sodium, sodium carboxymethylstarch, and crosslinked polyvinylpyrrolidone.

Examples of the stabilizers are parahydroxybenzoate esters such as methylparaben and propylparaben; alcohols such as chlorobutanol, benzyl alcohol, and phenylethyl alcohol; benzalkonium chloride; phenols such as phenol and cresol; thimerosal; dehydroacetic acid; and sorbic acid.

As the taste and odor correctives, there can be named sweeteners, sour agents, and flavors which are usually used.

As the solvents for producing liquid and solution preparations, ethanol, phenol, chlorocresol, purified water, and distilled water can be used.

As surfactants and emulsifiers, polysorbate 80, polyoxyl 40 stearate, and lauromacrogol, for example, can be named.

In using the pharmaceutical composition of the present invention as an inhibitor of angiogenesis, or an agent for treatment or prevention of proliferative disease, the amount of the compound of the present invention or its pharmaceutically acceptable salt used differs according to symptoms, age, body weight, and relative health condition of the patient, the presence of other drug administered, and the mode of administration. In the patient (warm-blooded animal, especially human), for example, the generally effective dose, as the active ingredient (the compound of the present invention represented by the formula (I) or the formula (II)), is preferably 0.1 to 1000 mg per kg of body weight per day, more preferably 1 to 300 mg per kg of body weight, in the case of an oral preparation. The daily dose in an adult patient of normal body weight is preferably in the range of 10 to 800 mg. In the case of a parenteral preparation, the dose is preferably 0.1 to 1000 mg per kg of body weight per day, more preferably 10 to 800 mg per kg of body weight. This dose is desirably administered once daily or in several portions daily according to symptoms.

Effects of the Invention

The present invention provides benzamide compounds having high angiogenesis inhibiting activity which results from the mechanism of action different from that of the existing NF-kB inhibitory effect and KDR tyrosine kinase activity inhibition. The present invention also provides compounds which are useful as agents for treatment and prevention of diseases involving pathologic angiogenesis, for example, cancer and cancer metastasis, methods for producing the compounds, intermediate compounds useful for their production, and pharmaceutical compositions containing these compounds.

EXAMPLES

Figure 1:
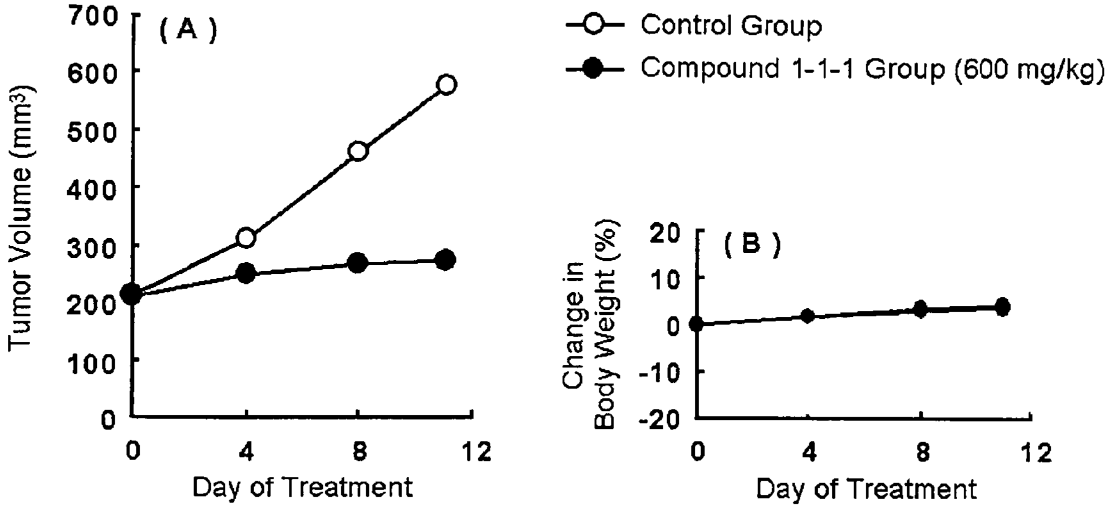
[FIG. 1] An example of the results of antitumor test, showing changes in the tumor volume (A), and changes in the body weight (B), following treatment with 600 mg/kg of compound 1-1-1 of the present invention in mice.

The present invention will now be described in greater detail by examples, but is in no way limited to these examples.

NMR analysis was made using JNM-EX270 (270 MHz) or JNM-GSX400 (400 MHz) produced by JEOL. NMR data were shown in ppm (parts per million) (δ), and referred to deuterium lock signals from sample solvents. Mass spectrum data were obtained using JMS-DX303 or JMS-SX/SX102A produced by JEOL. Mass spectrum data from high-performance liquid chromatography-mass spectrometry were obtained using a micromass spectrometer (ZMD produced by Micromass) equipped with a gradient high-performance liquid chromatograph 996-600E produced by Waters, or a micromass spectrometer (Navigator produced by Finnigan) equipped with a gradient high-performance liquid chromatograph Agilent 1100 produced by Agilent Technologies. The conditions used for high-performance liquid chromatography were any of the following:

Condition 1 for High-performance Liquid Chromatography

Device: 996-600E produced by Waters;

Column: Combi ODS (ODS, 5 μm, 4.6 mm I.D.×50 mm, produced by Wako Pure Chemical Industries), COSMOSIL (ODS, 5 μm, 4.6 mm I.D.×50 mm, produced by Nacalai Tesque), or Inertsil C18 (ODS, 5 μm, 4.6 mm I.D.×50 mm, produced by GL Sciences);

Mobile phase: Water (A) containing 0.05% trifluoroacetic acid and acetonitrile (B) containing 0.05% trifluoroacetic acid;

Elution method: Stepwise solvent gradient elution with from 10% B to 95% B (3.5 min), from 95% B to 10% B (1 min), and kept with 10% B (0.5 min); and Flow rate: 4.0 mL/min.

Condition 2 for High-performance Liquid Chromatography

Device: 996-600E produced by Waters;

Column: Combi ODS (ODS, 5 μm, 4.6 mm I.D.×50 mm, produced by Wako Pure Chemical Industries), COSMOSIL (ODS, 5 μm, 4.6 mm I.D.×50 mm, produced by Nacalai Tesque), or Inertsil C18 (ODS, 5 μm, 4.6 mm I.D.×50 mm, produced by GL Sciences);

Mobile phase: Water (A) containing 0.05% trifluoroacetic acid and acetonitrile (B) containing 0.05% trifluoroacetic acid;

Elution method: Stepwise solvent gradient elution with from 30% B to 35% B (0.2 min), from 35% B to 98% B (3.3 min), from 98% B to 30% B (1 min), and kept with 30% B (0.5 min); and Flow rate: 4.0 mL/min.

Condition 3 for High-performance Liquid Chromatography

Device: Agilent 1100 produced by Agilent Technologies;

Column: Combi ODS (ODS, 5 μm, 4.6 mm I.D.×50 mm, produced by Wako Pure Chemical Industries), COSMOSIL (ODS, 5 Wm, 4.6 mm I.D.×50 mm, produced by Nacalai Tesque), or Inertsil C18 (ODS, 5 μm, 4.6 mm I.D.×50 mm, produced by GL Sciences);

Mobile phase: Water (A) containing 0.05% trifluoroacetic acid and acetonitrile (B) containing 0.05% trifluoroacetic acid;

Elution method: Stepwise solvent gradient elution with from 10% B to 95% B (3.5 min), kept with 95% B (1 min), and from 95% B to 10% B (0.5 min); and Flow rate: 2.0 mL/min.

Condition 4 for High-performance Liquid Chromatography

Device: Agilent 1100 produced by Agilent Technologies;

Column: Combi ODS (ODS, 5 μm, 4.6 mm I.D.×50 mm, produced by Wako Pure Chemical Industries), COSMOSIL (ODS, 5 μm, 4.6 mm I.D.×50 mm, produced by Nacalai Tesque), or Inertsil C18 (ODS, 5 μm, 4.6 mm I.D.×50 mm, produced by GL Sciences);

Mobile phase: Water (A) containing 0.05% trifluoroacetic acid and acetonitrile (B) containing 0.05% trifluoroacetic acid;

Elution method: Stepwise solvent gradient elution with from 10% B to 30% B (0.5 min), from 30% B to 98% B (3.5 min), kept with 98% B (1 min), and from 98% B to 10% B (1 min); and Flow rate: 2.0 mL/min.

Condition 5 for High-performance Liquid Chromatography

Device: 996-600E produced by Waters;

Column: Combi ODS (ODS, 5 μm, 4.6 mm I.D.×50 mm, produced by Wako Pure Chemical Industries), COSMOSIL (ODS, 5 μm, 4.6 mm I.D.×50 mm, produced by Nacalai Tesque), or Inertsil C18 (ODS, 5 μm, 4.6 mm I.D.×50 mm, produced by GL Sciences);

Mobile phase: Water (A) containing 0.05% trifluoroacetic acid and acetonitrile (B) containing 0.05% trifluoroacetic acid;

Elution method: Stepwise solvent gradient elution with from 1% B to 95% B (3.5 min), from 95% B to 1% B (1 min), and kept with 1% B (0.5 min); and Flow rate: 4.0 mL/min.

Purification of the compound by a micromass spectrometer (ZMD produced by Micromass) equipped with a gradient high-performance liquid chromatograph 996-600E produced by Waters was performed based on the detection of signals from a mass spectrometer under the following conditions:

Column: Combi ODS (ODS, 5 μm, 28 mm I.D.×50 mm, produced by Wako Pure Chemical Industries);

Mobile phase: Water (A) containing 0.05% trifluoroacetic acid and acetonitrile (B) containing 0.05% trifluoroacetic acid;

Elution method: Stepwise solvent gradient elution, kept with 10% B (0.5 min), from 10% B to 95% B (7.5 min), kept with 95% B (0.5 min), and from 95% B to 10% B (1.5 min); and Flow rate: 35 mL/min.

Commercially available reagents were used without further purification. Room temperature refers to a range of from 20 to 25° C. All nonaqueous reactions were carried out under a nitrogen or argon atmosphere. Concentration or solvent distilling-off under reduced pressure refers to the use of a rotary evaporator.

In the preparation of compounds, functional groups were protected by protective groups, where necessary, and after preparation of target molecules, these protective groups were removed. Operations for selection and detachment of the protective groups were performed by the methods described in "Greene and Wuts, "Protective Groups in Organic Synthesis" (2nd Ed., John Wiley & Sons, 1991)".

Kaiser test conducted in the Examples to confirm the presence of amino groups in the product was performed in accordance with the procedure described in J. M. Stewart, J. D. Young, Solid Phase Peptide Synthesis, 2nd Ed., page 105 (Pierce Chemical Company, 1984).

Example 1-1-1

Production of 3-N'-(4-chlorophenyl)-4-methoxy-isophthalamide (Compound 1-1-1)

[Formula 23]

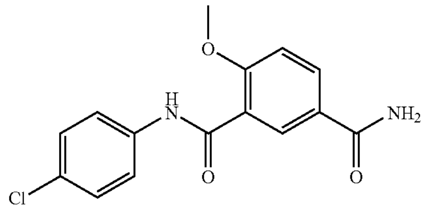

Step A

Preparation of methyl 5-bromo-2-methoxybenzoate (CAS Registry Number: 7120-41-4)

[Formula 24]

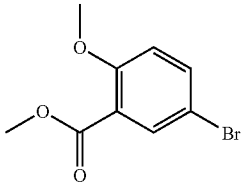

5-Bromo-2-hydroxybenzoic acid (25 g) and 40 g of potassium carbonate were suspended in 300 mL of acetone. Dimethyl sulfate (28 mL) was added to the suspension, and the mixture was stirred for 19 hours under reflux with heating. The reaction mixture was cooled to room temperature, whereafter the insolubles were separated by filtration, and washed with ethyl acetate. The filtrate and the washings were combined, and acetone and ethyl acetate were distilled off under reduced pressure. The resulting residue was dissolved in 300 mL of ethyl acetate. Water (300 mL) was added to the solution, and the organic layer was separated; followed by extracting the aqueous layer with 200 mL of ethyl acetate. After the respective organic layers were combined, the combined organic layer was washed with a saturated aqueous solution of sodium chloride, and dried over anhydrous sodium sulfate. The anhydrous sodium sulfate was separated by filtration, and then washed with ethyl acetate. The filtrate and the washings were combined, and ethyl acetate was distilled off under reduced pressure to obtain 30 g of methyl 5-bromo-2-methoxybenzoate.

$^1$H-NMR (400 MHz, $CDCl_3$) δ 3.89 (3H, s), 6.87 (1H, d, J=8.8 Hz), 7.55 (1H, dd, J=8.8 Hz, 2.9 Hz), 7.90 (1H, d, J=2.9 Hz).

ESI (LC/MS positive mode) m/z 245, 247 ($M+H^+$); retention time 3.18 min (Condition 1 for high-performance liquid chromatography).

Step B

Preparation of 5-bromo-2-methoxybenzoic acid (CAS Registry Number: 2476-35-9)

[Formula 25]

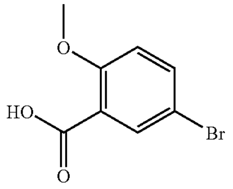

Methyl 5-bromo-2-methoxybenzoate (14.7 g) obtained in step A was dissolved in 100 mL of methanol. To the solution, 40 mL of a 20% aqueous solution of potassium hydroxide was added, and the mixture was stirred for 2 hours at 80° C. The reaction solution was cooled to 0° C., and then adjusted to pH of about 3 with the use of 11 mL of concentrated hydrochloric acid. The precipitate was separated by filtration, washed with water, and then dried over diphosphorus pentoxide under reduced pressure to obtain 10.9 g (85%) of 5-bromo-2-methoxybenzoic acid.

$^1$H-NMR (400 MHz, DMSO-$d_6$) δ 3.81 (3H, s), 7.11 (1H, d, J=9.0 Hz), 7.67 (1H, dd, J=9.0 Hz, 2.6 Hz), 7.72 (1H, d, J=2.6 Hz), 12.94 (1H, bs).

ESI (LC/MS positive mode) m/z 231, 233 ($M+H^+$); retention time 2.66 min (Condition 1 for high-performance liquid chromatography).

Step C

Preparation of 5-bromo-N-(4-chlorophenyl)-2-methoxybenzamide

[Formula 26]

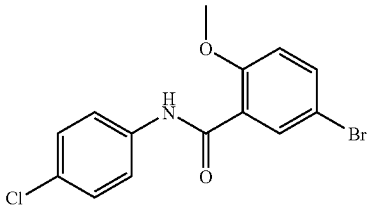

5-Bromo-2-methoxybenzoic acid (20 g) obtained in step B and 0.34 mL of N,N-dimethylformamide were dissolved in 380 mL of dichloromrethane, and the solution was cooled to 0° C. This solution was stirred for 30 minutes at 0° C., with oxalyl chloride (11.3 mL) being added little by little thereto, and then the mixture was stirred for 3 hours at room temperature. The reaction mixture was distilled under reduced pressure and dried to obtain a light yellow solid. This solid was added, with the use of 120 mL of dichloromethane, to a solution of 11.1 g of 4-chloroaniline and 45 mL of N,N-diisopropylethylamine dissolved in 380 mL of dichloromethane. The mixture was stirred for 2 hours and a half at room temperature, and then 300 mL of water was added. The organic layer was separated, and the aqueous layer was extracted twice with 100 mL of dichloromethane. After the respective organic layers were combined, the combined organic layer was washed with 200 mL of a saturated aqueous solution of sodium bicarbonate, and dried over anhydrous sodium sulfate. The anhydrous sodium sulfate was separated by filtration, and then washed with dichloromethane. The filtrate and the washings were combined, dichloromethane was distilled off under reduced pressure, and the resulting residue was washed with methanol. The resulting solid was dried under reduced -pressure to obtain 23.6 g (80%) of 5-bromo-N-(4-chlorophenyl)-2-methoxybenzamide.

$^1$H-NMR (400 MHz, $CDCl_3$) δ 4.06 (3H, s), 6.93 (1H, d, J=8.8 Hz), 7.33 (2H, d, J=8.8 Hz), 7.59 (1H, dd, J=8.8 Hz, 2.9 Hz), 7.61 (2H, d, J=8.8 Hz), 8.39 (1H, d, J=2.9 Hz), 9.70 (1H, bs).

ESI (LC/MS positive mode) m/z 340, 342 $(M+H^+)$; retention time 3.49 min (Condition 2 for high-performance liquid chromatography).

Step D

Preparation of 5-cyano-N-(4-chlorophenyl)-2-methoxybenzamide

[Formula 27]

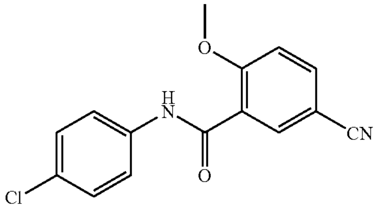

5-Bromo-N-(4-chlorophenyl)-2-methoxybenzamide (9.0 g) obtained in step C, and 7.8 g of zinc cyanide were dissolved in 100 mL of N,N-dimethylformamide. The N,N-dimethylformamide was degassed under reduced pressure, and then the interior of the reactor was purged with nitrogen. After 2.3 g of tetrakistriphenylphosphine palladium was added, the N,N-dimethylformamide was degassed again under reduced pressure, and then the interior of the reactor was purged with argon. This solution was stirred for 2 hours and a half at 100° C., whereafter the solvent was distilled off under reduced pressure, and the residue was dissolved in ethyl acetate. The insolubles were removed by filtration, and washed with ethyl acetate. The filtrate and the washings were combined, 100 mL of water was added, and then the organic layer was separated. The aqueous layer was extracted twice with ethyl acetate. After the respective organic layers were combined, the combined organic layer was washed with a saturated aqueous solution of sodium chloride, and dried over anhydrous sodium sulfate. The anhydrous sodium sulfate was separated by filtration, and then washed with ethyl acetate. The filtrate and the washings were combined, and ethyl acetate was distilled off under reduced pressure. The resulting residue was washed with methanol. The resulting solid was dried under reduced pressure to obtain 4.9 g (64%) of 5-cyano-N-(4-chlorophenyl)-2-methoxybenzamide.

$^1$H-NMR (400 MHz, $CDCl_3$) δ 4.15 (3H, s), 7.14 (1H, d, J=8.8 Hz), 7.34 (2H, d, J=8.8 Hz), 7.60 (2H, d, J=8.8 Hz), 7.79 (1H, dd, J=8.8 Hz, 2.4 Hz), 8.58 (1H, d, J=2.4 Hz), 9.53 (1H, bs).

ESI (LC/MS positive mode) m/z 287, 289 $(M+H^+)$; retention time 3.54 min (Condition 1 for high-performance liquid chromatography).

Step E

Preparation of 3-N-(4-chlorophenyl)-4-methoxy-isophthalamide (Compound 1-1-1)

[Formula 28]

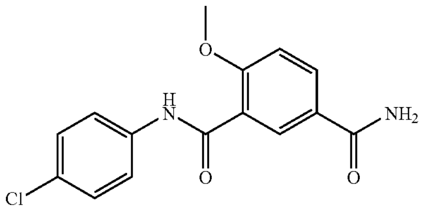

5-Cyano-N-(4-chlorophenyl)-2-methoxybenzamide (9.8 g) obtained in step D was dissolved in 80 mL of dimethyl sulfoxide, and the solution was cooled in a water bath. A solution prepared from 17.4 mL of a 30% aqueous solution of hydrogen peroxide and 9.5 g of potassium carbonate was added dropwise to the solution. After stirring for 1 hour, the mixture was poured into 800 mL of cold water. The precipitate formed was separated by filtration, washed with cold water, and then dried over diphosphorus pentoxide under reduced pressure to obtain 10.3 g (99%) of 3-N-(4-chlorophenyl)-4-methoxyisophthalamide.

$^1$H-NMR (400 MHz, DMSO-$d_6$) δ 3.92 (3H, s), 7.24 (1H, d, J=8.8 Hz), 7.29 (1H, bs), 7.40 (2H, d, J=8.8 Hz), 7.76 (2H, d, J=8.8 Hz), 7.97 (1H, bs), 8.03 (1H, dd, J=8.8 Hz, 2.2 Hz), 8.12 (1H, d, J=2.2 Hz), 10.31 (1H, s).

ESI (LC/MS positive mode) m/z 305, 307 $(M+H^+)$; retention time 2.91 min (Condition 1 for high-performance liquid chromatography).

Example 1-1-2

Production of 3-N-(4-chlorophenyl)-4-propoxy-isophthalamide (Compound 1-1-2)

[Formula 29]

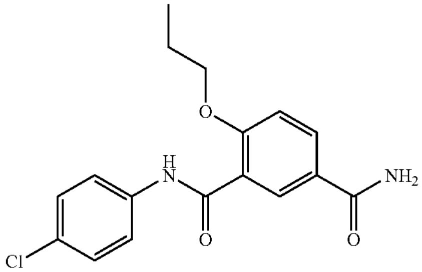

3-N-(4-Chlorophenyl)-4-methoxyisophthalamide (Compound 1-1-1) (50 mg) obtained in step E of Example 1-1-1 was suspended in 5 mL of dichloromethane. With the suspension being stirred, 1.0 mL of a 0.16 M solution of boron tribromide in dichloromethane was added dropwise at room temperature. After stirring for 1 hour, 0.7 mL of a 0.16 M solution of boron tribromide in dichloromethane was added dropwise at room temperature, and the mixture was further stirred for 30 minutes. The reaction solution was diluted with 50 mL of ethyl acetate, then the dilution was washed with 0.1 M hydrochloric acid and then with a saturated aqueous solution of sodium chloride, and dried over anhydrous sodium sulfate. Sodium sulfate was separated by filtration, and the filtrate was concentrated under reduced pressure. The residue was dried under reduced pressure to obtain 44 mg of a colorless solid. This solid (10 mg) and 9 mg of potassium carbonate were suspended in 1 mL of N,N-dimethylformamide. Propyl iodide (3 μL) was added to the suspension, and the mixture was stirred for 1 hour at 70° C. The reaction solution cooled to room temperature was diluted with 50 mL of ethyl acetate, washed with distilled water and then with a saturated aqueous solution of sodium chloride, and dried over anhydrous sodium sulfate. Sodium sulfate was separated by filtration, and the filtrate was concentrated under reduced pressure. The residue was purified using a micromass spectrometer (ZMD produced by Micromass) equipped with a gradient high-performance liquid chromatograph 996-600E produced by Waters, to obtain 6 mg (52%) of 3-N-(4-chlorophenyl)-4-propoxyisophthalamide as a white solid.

$^1$H-NMR (400 MHz, DMSO-$d_6$) δ 0.96 (3H, t, J=7.6 Hz), 1.74-1.80 (2H, m), 4.11 (2H, t, J=6.2 Hz), 7.22 (1H, d, J=8.8 Hz), 7.30 (1H, bs), 7.41 (2H, d, J=8.8 Hz), 7.76 (2H, d, J=8.8 Hz), 7.99 (1H, bs), 8.01 (1H, dd, J=8.8 Hz, 2.4 Hz), 8.14 (1H, d, J=2.4 Hz), 10.30 (1H, bs).

ESI (LC/MS positive mode) m/z 333, 335 (M+H$^+$); retention time 3.29 min (Condition 1 for high-performance liquid chromatography).

Example 1-1-3

Production of 4-aryloxy-3-N-(4-chlorophenyl)-isophthalamide (Compound 1-1-3)

[Formula 30]

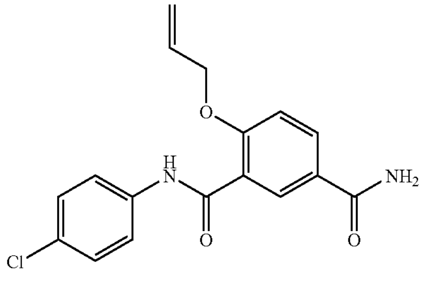

The captioned compound was synthesized from 3-N-(4-chlorophenyl)-4-methoxyisophthalamide and allyl bromide by the same procedure as in the manufacturing method described in Example 1-1-2.

$^1$H-NMR (400 MHz, DMSO-$d_6$) δ 4.74 (2H, d, J=4.8 Hz), 5.25 (1H, dd, J=10.8 Hz, 1.2 Hz), 5.41 (1H, dd, J=10.8 Hz, 1.2 Hz), 6.02-6.11 (1H, m), 7.23 (1H, d, J=8.8 Hz), 7.32 (1H, bs), 7.41 (2H, d, J=8.8 Hz), 7.75 (2H, d, J=8.8 Hz), 7.99-8.02 (2H, m), 8.11 (1H, d, J=2.0 Hz), 10.36 (1H, bs).

ESI (LC/MS positive mode) m/z 331, 333 (M+H$^+$); retention time 3.17 min (Condition 1 for high-performance liquid chromatography).

Example 1-1-4

Production of 3-N-(4-chlorophenyl)-4-(2-pentenyloxy)-isophthalamide (Compound 1-1-4)

[Formula 31]

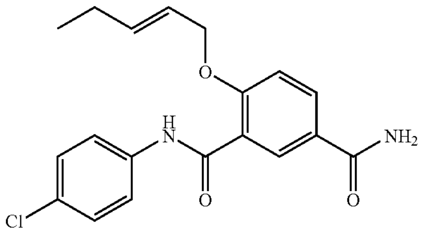

The captioned compound was synthesized from 3-N-(4-chlorophenyl)-4-methoxyisophthalamide and 1-bromo-2-pentene by the same procedure as in the manufacturing method described in Example 1-1-2.

$^1$H-NMR (270 MHz, DMSO-$d_6$) δ 0.93 (3H, t, J=7.6 Hz), 1.99-2.09 (2H, m), 4.68 (2H, d, J=5.3 Hz), 5.70 (1H, dt, J=15.5 Hz, 5.3 Hz), 5.93 (1H, dt, J=15.5 Hz, 6.3 Hz), 7.23 (1H d, J=8.9 Hz), 7.30 (1H, bs), 7.42 (2H, d, J=8.9 Hz), 7.75 (2H, d, J=8.9 Hz), 7.98-8.03 (2H, m), 8.14 (1H d, J=2.0 Hz), 10.34 (1H, bs).

ESI (LC/MS positive mode) m/z 291, 293 (M+H$^+$); retention time 3.70 min (Condition 1 for high-performance liquid chromatography).

Example 1-1-5

Production of 4-(2-butynyloxy)-3-N-(4-chlorophenyl)-isophthalamide (Compound 1-1-5)

[Formula 32]

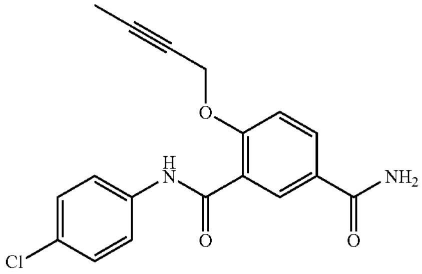

The captioned compound was synthesized from 3-N-(4-chlorophenyl)-4-methoxyisophthalamide and 1-bromo-2-butyne by the same procedure as in the manufacturing method described in Example 1-1-2.

$^1$H-NMR (270 MHz, DMSO-$d_6$) δ 1.84 (3H, d, J=2.3 Hz), 4.9.4 (2H, d, J=2.3 Hz), 7.27 (1H, d, J=8.9 Hz), 7.33 (1H bs), 7.41 (2H, d, J=8.9 Hz), 7.75 (2H, d, J=8.9 Hz), 7.98-8.11 (2H, m), 8.11 (1H, d, J=.2.3 Hz)., 10.36 (1H, bs).

ESI (LC/MS positive mode) m/z 343, 345 (M+H$^+$); retention time 3.32 min (Condition 1 for high-performance liquid chromatography).

Example 1-1-6

Production of 4-butoxy-3-N-(4-chlorophenyl)-isophthalamide (Compound 1-1-6)

[Formula 33]

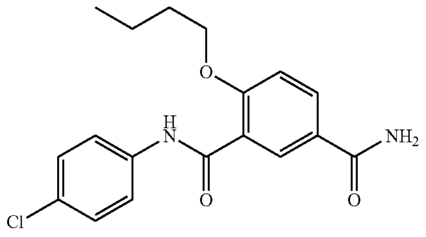

The captioned compound was synthesized from 3-N-(4-chlorophenyl)-4-methoxyisophthalamide and butyl bromide by the same procedure as in the manufacturing method described in Example 1-1-2.

$^1$H-NMR (270 MHz, DMSO-$d_6$) δ 0.89 (3H, t, J=7.4 Hz), 1.35-1.49 (2H, m), 1.68-1.79 (2H, m), 4.15 (2H, t, J=6.3 Hz), 7.24 (1H d, J=8.6 Hz), 7.30 (1H, bs), 7.42 (2H, d, J=8.9 Hz), 7.75 (2H, d, J=8.9 Hz), 7.98 (1H bs), 8.01 (1H, dd, J=8.6 Hz, 2.3 Hz), 8.14 (1H d, J=2.3 Hz), 10.28 (1.H, bs).

ESI (LC/MS positive mode) m/z 347, 349 (M+H$^+$); retention time 3.61 min (Condition 1 for high-performance liquid chromatography).

Example 1-1-7

Production of 4-(2-chloroethoxy)-3-N-(4-chlorophenyl)-isophthalamide (Compound 1-1-7)

[Formula 34]

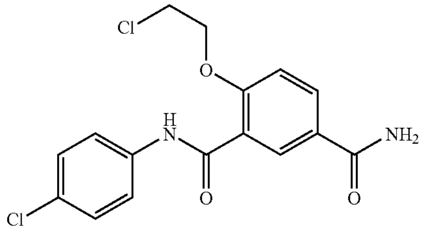

The captioned compound was synthesized from 3-N-(4-chlorophenyl)-4-methoxyisophthalamide and 1-bromo-2-chloroethane by the same procedure as in the manufacturing method described in Example 1-1-2.

$^1$H-NMR (270 MHz, DMSO-$d_6$) δ 4.04 (2H, t, J=5.1 Hz), 4.47 (2H, t, J=5.1 Hz), 7.28 (1H, d, J=8.9 Hz), 7.34 (1H, bs), 7.43 (2H, d, J=8.9 Hz), 7.78 (2H, d, J=8.9 Hz), 8.02-8.06 (2H, m), 8.25 (1H, d, J=2.0 Hz), 10.23 (1H, bs).

ESI (LC/MS positive mode) m/z 353-355 (M+H$^+$) retention time 3.25 min (Condition 1 for high-performance liquid chromatography).

Example 1-1-8

Production of 3-N-(4-chlorophenyl)-4-cyclopropylmethoxy-isophthalamide (Compound 1-1-8)

[Formula 35]

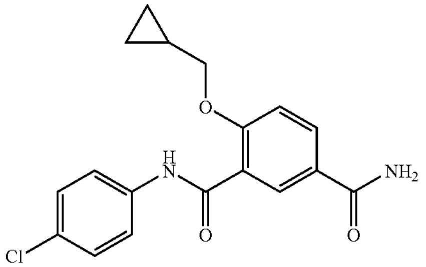

The captioned compound was synthesized from 3-N-(4-chlorophenyl)-4-methoxyisophthalamide and (bromomethyl)cyclopropane by the same procedure as in the manufacturing method described in Example 1-1-2.

$^1$H-NMR (270 MHz, DMSO-$d_6$) δ 0.41 (2H, dd, J=9.6 Hz, 4.6 Hz), 0.54-0.60 (2H, m), 1.24-1.40 (1H, m), 4.05 (2H, d, J=6.9 Hz), 7.21 (1H, d, J=8.9 Hz), 7.30 (1H bs), 7.43 (2HP d, J=8.9 Hz), 7.78 (2H, d, J=8.9 Hz), 8.00-8.03 (2H, m), 8.23 (1H, d, J=2.3 Hz), 10.35 (1H bs).

ESI (LC/MS positive mode) m/z 345, 347 (M+H$^+$); retention time 3.48 min (Condition 1 for high-performance liquid chromatography).

Example 1-1-9

Production of N-3-(4-chlorophenyl)-4-ethynyl-isophthalamide (Compound 1-1-9)

[Formula 36]

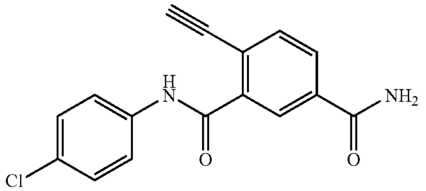

Step A

Preparation of trifluoromethanesulfonic acid 4-carbamoyl-2-(4-chlorophenylcarbamoyl)-phenyl ester (Compound 1-1-9-A)

[Formula 37]

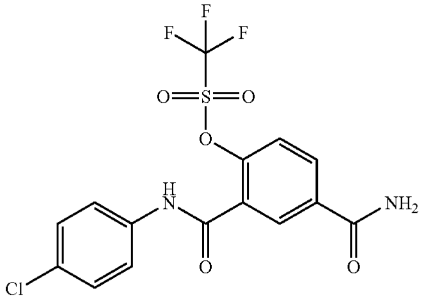

3-N-(4-Chlorophenyl)-4-methoxyisophthalamide (2.56 g) obtained in step E of Example 1-1-1 was suspended in 136 mL of dichloromethane. With the suspension being stirred, a 0.16 M solution of boron tribromide in dichloromethane was added dropwise at room temperature until the reaction was completed. The reaction solution was diluted with 500 mL of ethyl acetate, then the dilution was washed with 0.1 M hydrochloric acid and then with a saturated aqueous solution of sodium chloride, and dried over anhydrous sodium sulfate. Sodium sulfate was separated by filtration, and the filtrate was concentrated under reduced pressure. The residue was dried under reduced pressure to obtain 2.0 g of a white solid. This solid (50 mg) was dissolved in 2 mL of N,N-dimethylformamide. To this solution, there were added 72 μL of triethylamine and 92 mg of N-phenylbis (trifluoromethanesulfonimide), and the mixture was stirred for 1 hour at room temperature. The reaction solution was diluted with 50 mL of ethyl acetate, then the dilution was washed with saturated ammonium chloride, and dried over anhydrous sodium sulfate. Sodium sulfate was separated by filtration, and the filtrate was concentrated under reduced pressure. The residue was washed with 10 mL of dichloromethane, and dried under reduced pressure to obtain 38 mg (52%) of trifluoromethanesulfonic acid 4-carbamoyl-2-(4-chlorophenylcarbamoyl)-phenyl ester.

$^1$H-NMR (270 MHz, DMSO-$d_6$) δ 7.46 (2H, d, J=8.9 Hz), 7.70-7.75 (4H, m), 8.18 (1H, dd, J=8.6 Hz, 2.3 Hz), 8.25 (1H, bs), 8.32 (1H, d, J=2.3 Hz), 10.88 (1H bs).

ESI (LC/MS positive mode) m/z 423, 425 (M+H$^+$); retention time 3.40 min (Condition 1 for high-performance liquid chromatography).

Step B

Preparation of N-3-(4-chlorophenyl)-4-ethynyl-isophthalamide (Compound 1-1-9)

[Formula 38]

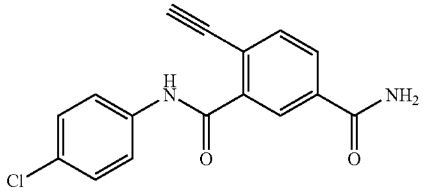

Trifluoromethanesulfonic acid 4-carbamoyl-2-(4-chlorophenylcarbamoyl)-phenyl ester (40 mg) obtained in step A was dissolved in 3 mL of N,N-dimethylformamide. To this solution, 0.5 ml of triethylamine, 6 mg of copper (I) iodide, 134 μl of TMS acetylene, and 33 mg of tetrakis(triphenylphosphine) palladium were added, followed by stirring the mixture for 3 hours at 75° C. The reaction solution was filtered through Celite, and the filtrate was diluted with 60 mL of ethyl acetate. This solution was washed with distilled water and then with a saturated aqueous solution of sodium chloride, and dried over anhydrous sodium sulfate. Sodium sulfate was separated by filtration, and the filtrate was concentrated under reduced pressure. The residue was dissolved in 3 mL of methanol, 20 mg of potassium carbonate was added to this solution, and the mixture was stirred for 1 hour at room temperature. The reaction solution was diluted with 50 mL of ethyl acetate, and then was washed with saturated ammonium chloride, and dried over anhydrous sodium sulfate. Sodium sulfate was separated by filtration, and the filtrate was concentrated under reduced pressure. The residue was purified by thin layer chromatography (hexane:ethyl acetate=1:4) to obtain 5 mg (17%) of N-3-(4-chlorophenyl)-4-ethynyl -isophthalamide.

ESI (LC/MS positive mode) m/z 299, 301 (M+H$^+$); 340 (M+$CH_3CN$+H$^+$); retention time 2.59 min (Condition 3 for high-performance liquid chromatography).

Example 1-1-10

Production of [4-carbamoyl-2-(4-trifluoromethoxy-phenylcarbamoyl)-phenoxy]-acetic acid ethyl ester

[Formula 39]

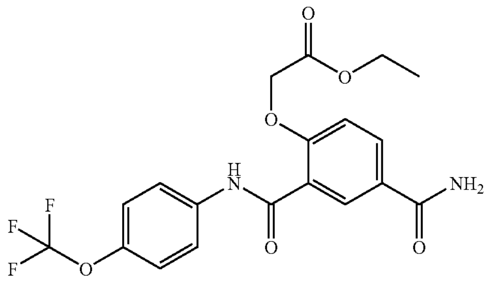

The captioned compound was synthesized from 3-N-(4-trifluoromethoxyphenyl)-4-methoxyisophthalamide and ethyl bromoacetate by the same procedure as in the manufacturing method described in Example 1-1-2.

$^1$H-NMR (400 MHz, DMSO-$d_6$) δ 1.22 (3H, t, J=6.8 Hz), 4.23 (2H, q, J=6.8 Hz), 5.04 (2H, s), 7.25 (1H, d, J =8.8 Hz), 7.36 (1H, bs), 7.40 (2H, d, J=8.8 Hz), 7.92 (2H, d, J=9.3 Hz), 8.03 (2H, dd, J=8.8 Hz, 2.0 Hz), 8.36 (1H, d, J=2.0 Hz), 10.53 (1H bs).

ESI (LC/MS positive mode) m/z 427 (M+H$^+$); retention time 2.78 min (Condition 2 for high-performance liquid chromatography).

Example 1-2-1

Preparation of 3-N-(4-trifluoromethoxyphenyl)-4-methoxyisophthalamide (Compound 1-2-1)

[Formula 40]

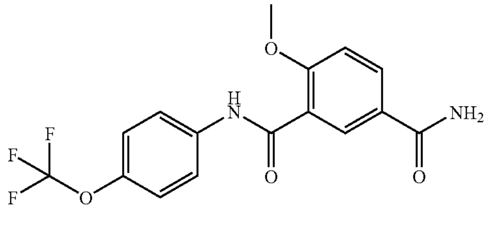

Step A

Preparation of ethyl 3-chloromethyl-4-methoxybenzoate

[Formula 41]

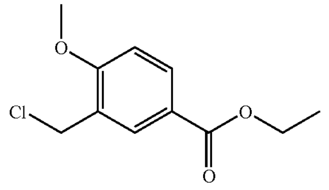

Ethyl 4-methoxybenzoate (28.0 mL) and 26.0 mL of methoxymethyl chloride were dissolved in 500 mL of dichloromethane, and the solution was cooled to 0° C. To this solution, 10.0 mL of tin (IV) chloride was added dropwise over 15 minutes, and then the mixture was stirred for 5 hours. The reaction mixture was poured into 1 L of water, and the organic layer was separated, whereafter the aqueous layer was extracted twice with dichloromethane. The organic layer was washed with a saturated aqueous solution of sodium chloride, and dried over anhydrous sodium sulfate. The anhydrous sodium sulfate was separated by filtration, and washed with dichloromethane. The filtrate and the washings were combined, and dichloromethane was distilled off under reduced pressure. The resulting residue was recrystallized from a mixture of n-hexane and ethyl acetate. The resulting crystals were separated by filtration, then washed with n-hexane, and dried under reduced pressure to obtain 23.8 g (60%) of ethyl 3-chloromethyl-4-methoxybenzoate.

$^1$H-NMR (400 MHz, $CDCl_3$) δ 1.39 (3H, t, J=7.0 Hz), 3.95 (3H, s), 4.36 (2H, q, J=7.0 Hz), 4.66 (2H, s), 6.92 (1H d, J=8.3 Hz), 8.03 (1H, dd, J=8.3 Hz, 2.1 Hz), 8.05 (1H d, J=2.1 Hz).

ESI (LC/MS positive mode) m/z 229, 231 ($M+H^+$); retention time 2.85 min (Condition 2 for high-performance liquid chromatography).

Step B

Preparation of 5-ethoxycarbonyl-2-methoxybenzyl-hexamethylenetetraminium chloride

[Formula 42]

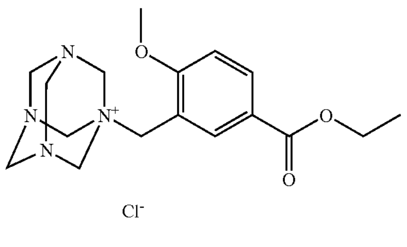

Ethyl 3-chloromethyl-4-methoxybenzoate (8.2 g) obtained in step A and 5.3 g of hexamethylenetetramine were dissolved in 30 mL of toluene, and stirred for 6 hours at 100° C., followed by cooling the solution to 0° C. The precipitate was separated by filtration, then washed with ethyl acetate, and dried under reduced pressure to obtain 12.0 g (91%) of 5-ethoxycarbonyl-2-methoxybenzylhexamethylenetetraminium chloride.

ESI (LC/MS positive mode) m/z 333 ($M^+$–Cl); retention time 1.88 min (Condition 1 for high-performance liquid chromatography).

Step C

Preparation of ethyl 3-formyl-4-methoxybenzoate (CAS Registry Number: 122136-03-2)

[Formula 43]

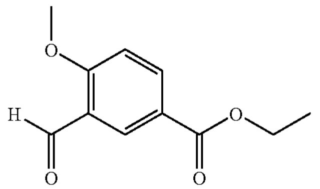

5-Ethoxycarbonyl-2-methoxybenzylhexamethylenetetraminium chloride (12.0 g) obtained in step B was dissolved in 24 mL of a 50% aqueous solution of acetic acid, and the solution was stirred for 4.5 hours at 100° C. The reaction mixture was cooled to about 40° C., 48 mL of water was added, and the mixture was stirred for 67 hours at room temperature. The precipitate was separated by filtration, washed with water, and then dried over diphosphorus pentoxide under reduced pressure to obtain 3.5 g (52%) of ethyl 3-formyl-4-methoxybenzoate.

$^1$H-NMR (400 MHz, $CDCl_3$) δ 1.40 (3H, t, J=7.1 Hz), 4.01 (3H, s), 4.37 (2H, q, J=7.1 Hz), 7.05 (1H, d, J=8.8 Hz), 8.26 (1H, dd, J=8.8 Hz, 2.1 Hz), 8.51 (1H d, J=2.1 Hz), 10.46 (1H s).

ESI (LC/MS positive mode) m/z 209 ($M+H^+$); retention time 3.08 min (Condition 1 for high-performance liquid chromatography).

Step D

Preparation of 1-ethyl 4-methoxyisophthalate

[Formula 44]

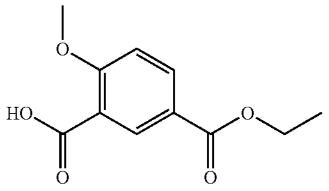

Ethyl 3-formyl-4-methoxybenzoate (5.0 g) obtained in step C, 20 mL of 2-methyl-2-butene, and 2.9 g of sodium dihydrogenphosphate were dissolved in a mixed solution of 20 mL of water and 50 mL of t-butyl alcohol, whereafter the solution was cooled to 0° C. To this solution, 7.4 g of sodium chlorite was added little by little, and then the mixture was stirred for 1 hour and a half at room temperature. The reaction mixture was cooled to 0° C., and then 23 mL of 1 M hydrochloric acid was added for acidification, followed by extracting the mixture 3 times with ethyl acetate. The organic layer was washed with a saturated aqueous solution of sodium chloride, and dried over anhydrous sodium sulfate. The anhydrous sodium sulfate was separated by filtration, and then washed with ethyl acetate. The filtrate and the washings were combined, and ethyl acetate was distilled off under reduced pressure. The resulting residue was washed with an n-hexane solution containing a small amount of diethyl ether, and dried under reduced pressure to obtain 5.1 g (96%) of 1-ethyl 4-methoxyisophthalate.

$^1$H-NMR (400 MHz, $CDCl_3$) δ 1.40 (3H, t, J=7.0 Hz), 4.15 (3H, s), 4.39 (2H, q, J=7.0 Hz), 7.12 (1H, d, J=8.8 Hz), 8.27 (1H, dd, J=8.8 Hz, 2.0 Hz), 8.84 (1H, d, J=2.0 Hz).

ESI (LC/MS positive mode) m/z 225 ($M+H^+$); retention time 2.54 min (Condition 1 for high-performance liquid chromatography).

Step E

Preparation of ethyl N-(4-trifluoromethoxyphenyl)-4-methoxyisophthalamate

[Formula 45]

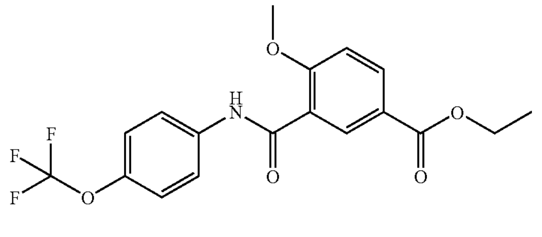

1-Ethyl 4-methoxyisophthalate (150 mg) obtained in step D, and 3 μL of N,N-dimethylformamide were dissolved in 10 mL of dichloromethane, and the solution was cooled to 0° C. To this solution, 88 μL of oxalyl chloride was added little by little, and the mixture was stirred for 20 minutes at 0° C., followed by stirring the mixture for. 16 hours at room temperature. The reaction mixture was distilled under reduced pressure, and dried to obtain a light yellow solid. This solid was dissolved in 9 mL of dichloromethane, and 3 mL of the solution was added to a solution of 42 mg of 4-trifluoromethoxyaniline and 123 μL of N,N-diisopropylethylamine-dissolved in 2 mL of dichloromethane. The mixture was stirred for 6 hours at room temperature, and then dichloromethane was distilled off under reduced pressure. The resulting residue was purified by column chromatography (5 g of silica gel) using a 1:1 mixture of dichloromethane and n-hexane as an elution solvent, thereby obtaining 79 mg (92%) of ethyl N-(4-trifluoromethoxyphenyl)-4-methoxyisophthalamate.

$^1$H-NMR (400 MHz, $CDCl_3$) δ 1.41 (3H, t, J=7.2 Hz), 4.14 (3H, s), 4.39 (2H, q, J=7.2 Hz), 7.10 (1H, d, J=8.8 Hz), 7.23 (2H, d, J=8.8 Hz), 7.71 (2H, d, J=8.8 Hz), 8.22 (1H, dd, J=8.8 Hz, 2.3 Hz), 8.94 (1H, d, J=2.3 Hz), 9.66 (1H, bs).

ESI (LC/MS positive mode) m/z 384 ($M+H^+$); retention time 3.42 min (Condition 2 for high-performance liquid chromatography).

Step F

Preparation of N-(4-trifluoromethoxyphenyl)-4-methoxyisophthalamate acid

[Formula 46]

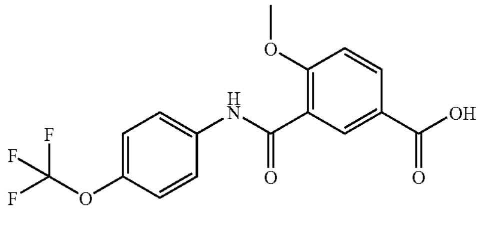

Ethyl N-(4-trifluoromethoxyphenyl)-4-methoxyisophthalamate (51 mg) obtained in step E was dissolved in 2 mL of methanol, and 0.8 mL of a 20% aqueous solution of potassium hydroxide was added. The resulting solution was stirred for 30 minutes at 80° C., and then cooled to room temperature. One M hydrochloric acid (3 mL) was used to adjust the solution to pH of about 3. Then, the resulting aqueous solution was extracted with ethyl acetate. The respective organic layers were combined, whereafter the combined organic layer was washed with a saturated aqueous solution of sodium chloride, and dried over anhydrous sodium sulfate. The anhydrous sodium sulfate was separated by filtration, and washed with ethyl acetate. The filtrate and the washings were combined, and ethyl acetate was distilled off under reduced pressure to obtain 48 mg (100%) of N-(4-trifluoromethoxyphenyl)-4-methoxyisophthalamic acid.

$^1$H-NMR (400 MHz, DMSO-$d_6$) δ 3.9.5 (3H, s), 7.29 (1H, d, J=8.8 Hz), 7.36 (2H, d, J=8.8 Hz), 7.84 (2H, d, J=8.8 Hz), 8.07 (1H, dd, J=8.8 Hz, 2.3 Hz), 8.12 (1H, d, J=2.3 Hz), 10.38 (1H, s), 12.91 (1H, s).

ESI (LC/MS positive mode) m/z 356 ($M+H^+$); retention time 3.36 min (Condition 1 for high-performance liquid chromatography).

Step G

Preparation of 3-N-(4-trifluoromethoxyphenyl)-4-methoxyisophthalamide (Compound 1-2-1)

[Formula 47]

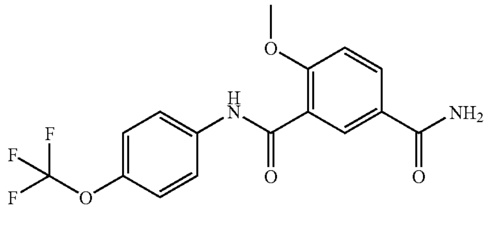

N-(4-Trifluoromethoxyphenyl)-4-methoxyisophthalamic acid (48 mg) obtained in step F, 11 mg of ammonium chloride, 25 mg of benzotriazol-1-ol monohydrate, and 31 mg of (3-dimethylaminopropyl)ethylcarbodiimide hydrochloride were dissolved in 2 mL of N,N-dimethylformamide, and 70 μL of N,N-diisopropylethylamine was added. This solution was stirred overnight at room temperature, and then the solvent was distilled off under reduced pressure. The resulting residue was purified by column chromatography (5 g of silica gel, 2 g of aminopropyl-modified silica gel) using a 100:1 mixture of dichloromethane and methanol as an elution solvent, thereby obtaining 45 mg (96%) of 3-N-(4-trifluoromethoxyphenyl)-4-methoxyisophthalamide.

$^1$H-NMR (400 MHz, DMSO-$d_6$) δ 3.92 (3H, s), 7.24 (1H, d, J=8.8 Hz), 7.31 (1H, bs), 7.37 (2H, d, J=9.0 Hz), 7.85 (2H, d, J=9.0 Hz), 7.99 (1H, bs), 8.04 (1H, dd, J=8.8 Hz, 2.0 Hz), 8.12 (1H, d, J=2.0 Hz), 10.39 (1H, s).

ESI (LC/MS positive mode) m/z 355 ($M+H^+$); retention time 3.07 min (Condition 1 for high-performance liquid chromatography).

Example 1-2-21

Production of 3-N-(4-tert-butylphenyl)-4-methoxy-isophthalamide (Compound 1-2-2)

[Formula 48]

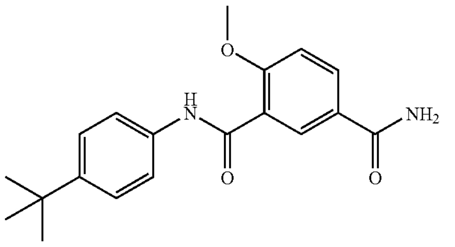

The captioned compound was synthesized using 4-tert-butylaniline instead of 4-chloroaniline in accordance with the methods described in steps E, F and G of Example 1-2-1.

ESI (LC/MS positive mode) m/z 327 ($M+H^+$); retention time 3.25 min (Condition 1 for high-performance liquid chromatography).

Example 1-2-31

Production of 3-N-(4-chlorophenyl)-1-N-cyclopentyl-4-methoxyisophthalamide (Compound 1-2-3)

[Formula 49]

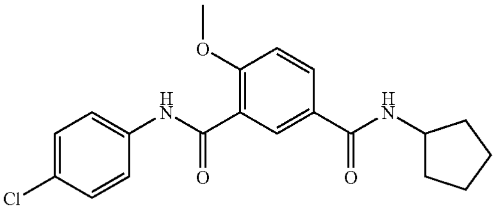

Step A

Preparation of ethyl N-(4-chlorophenyl)-4-methoxyisophthalamate

[Formula 50]

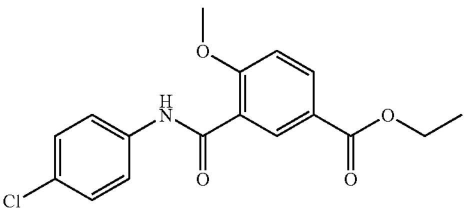

1-Ethyl 4-methoxyisophthalate (100 mg) obtained in step D of Example 1-2-1, and 2 μL of N,N-dimethylformamide were dissolved in 5 mL of dichloromethane, and the solution was cooled to 0° C. To this solution, 59 μL of oxalyl chloride was added little by little, and the mixture was stirred for 20 minutes at 0° C., followed by stirring the mixture for 16 hours at room temperature. The reaction mixture was distilled under reduced pressure, and dried to obtain a light yellow solid. This solid was dissolved, in 3 mL of dichloromethane, and the solution was added to a solution of 63 mg of 4-chloroaniline and 234 μL of N,N-diisopropylethylamine dissolved in 2 mL of dichloromethane. The mixture was stirred for 3 hours at room temperature, and then dichloromethane was distilled off under reduced pressure. The resulting residue was purified by column chromatography (5 g of silica gel) using a 1:1 mixture of dichloromethane and n-hexane as an elution solvent, thereby obtaining 134 mg (94%) of ethyl N-(4-chlorophenyl)-4-methoxyisophthalamate.

$^1$H-NMR (270 MHz, DMSO-$d_6$) δ1.32 (3H, t, J=7.3 Hz), 3.96 (3H, s), 4.31 (2H, q, J=7.3 Hz), 7.31 (1H, d, J=8.9 Hz), 7.40 (2H, d, J=8.8 Hz), 7.77 (2H, d, J=8.8 Hz), 8.09 (1H, .dd, J=8.9 Hz, 2.3 Hz), 8.15 (1H, d, J=2.3 Hz), 10.3 (1H, s).

ESI (LC/MS positive mode) m/z 334, 336($M+H^+$); retention time 3.28 min (Condition 2 for high-performance liquid chromatography).

Step B

Preparation of N-(4-chlorophenyl)-4-methoxyisophthalic acid

[Formula 51]

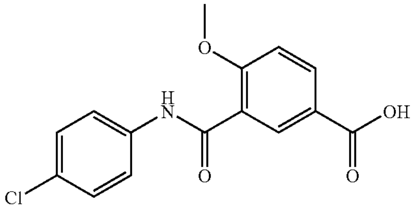

Ethyl N-(4-chlorophenyl)-4-methoxyisophthalamate (11.8 g) obtained in step A was dissolved in 200 mL of methanol and 60-mL of a 20% aqueous solution of potassium hydroxide. The resulting solution was stirred for 30 minutes at 80° C., and then cooled to room temperature. One M hydrochloric acid was used to adjust the solution to pH of about 3. Then, the resulting precipitate was separated by filtration, washed with water, and dried over calcium chloride under reduced pressure, thereby obtaining 10.7 g (99%) of N=(4-chlorophenyl)-4-methoxyisophthalic acid.

$^1$H-NMR (270 MHz; DMSO-$d_6$) δ 3.95 (3H, s), 7.28 (1H, d, J=8.6 Hz), 7.40 (2H, d, J=8.9 Hz), 7.76 (2H, d, J=8.9 Hz), 8.07 (1H, dd, J=8.6 Hz, 2.3 Hz), 8.12 (1H, d, J=2.3 Hz), 10.3 (1H, s), 12.9 (1H, s).

ESI (LC/MS positive mode) m/z 306, 308 ($M+H^+$); retention time 2.28 min (Condition 2 for high-performance liquid chromatography).

Step C

Preparation of 3-N-(4-chlorophenyl)-1-N-cyclopentyl-4-methoxyisophthalamide (Compound 1-2-3)

[Formula 52]

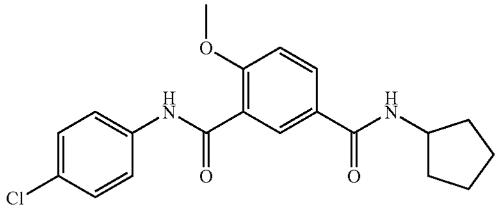

N-(4-Chlorophenyl)-4-methoxyisophthalic acid (140 mg) obtained in step B was dissolved in 20 μL of N,N-dimethylformamide and 4 mL of dichloromethane, and the solution was cooled to 0° C. To this solution, 60 μL of oxalyl chloride was added little by little, and the mixture was stirred for 20 minutes at 0° C., followed by stirring the mixture for 30 minutes at room temperature. The reaction mixture was distilled under reduced pressure, and dried to obtain a light yellow solid, which was dissolved in 3 mL of dichloromethane. To 500 μL of this solution, there was added 500

μL of a solution of 7.6 mg of cyclopentylamine and 20 μL of N,N-diisopropylethylamine dissolved in dichloromethane, followed by stirring the mixture for 30 minutes at room temperature. Water (1 mL) was added to separate the organic layer, and the organic layer was concentrated under reduced pressure. The resulting residue was purified by silica gel column chromatography to obtain 3.8 mg (13%) of N-3-(4-chlorophenyl)-N-1-cyclopentyl-4-methoxy-isophthalamide.

$^1$H-NMR (270 MHz, $CDCl_3$) δ 1.40-1.60 (2H, m), 1.60-1.85 (4H, m), 2.00-2.20 (2H, m), 4.13 (3H, s), 4.41 (1H, dd, J=14 Hz, 2.9 Hz), 6.24 (1H, bd, J=6.9 Hz), 7.13 (1H, d, J=8.9 Hz), 7.34 (2H, d, J=8.9 Hz), 7.63 (2H, d, J=8.9 Hz), 8.17 (1H, dd, J=8.9 Hz, 2.6 Hz), 8.50 (1H, d, J=2.6 Hz), 9.77 (1H, bs).

ESI (LC/MS-positive mode) m/z 373, 375 (M+H$^+$); retention time 3.24min (Condition 3 for high-performance liquid chromatography).

Example 1-2-4

Production of N-3-(4-chlorophenyl)-4-methoxy-N-1-methyl -isophthalamide (Compound 1-2-4)

[Formula 53]

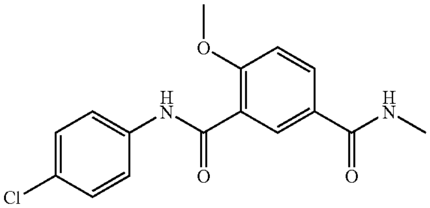

The captioned compound was synthesized using N-(4-chlorophenyl)-4-methoxyisophthalic acid and methylamine hydrochloride by the same procedure as in the manufacturing method described in step G of Example 1-2-1.

$^1$H-NMR (270 MHz, $CDCl_3$) δ 3.01 (3H, d, J=5.0 Hz), 4.12 (3H, s), 6.38 (1H, bs), 7.12 (1H, d, J=8.6 Hz), 7.33 (2H, d, J=8.9 Hz), 7.62 (2H, d, J=8.9 Hz), 8.15 (1H, dd, J=8.6 Hz, 2.7 Hz), 8.53 (1H, d, J=2.7 Hz), 9.75 (1H, bs).

ESI (LC/MS positive mode) 319, 321 (M+H$^+$); retention time 2.66 min (Condition 3 for high-performance liquid chromatography).

Example 1-2-5

Production of N-3-(4-chlorophenyl)-4-methoxy-N-1-ethyl-isophthalamide (Compound 1-2-5)

[Formula 54]

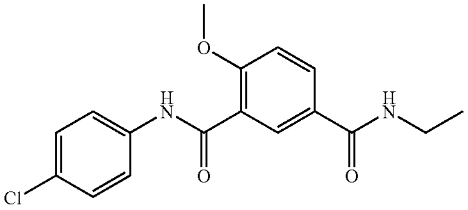

The captioned compound was synthesized using N-(4-chlorophenyl)-4-methoxyisophthalic acid and ethylamine hydrochloride by the same procedure as in the manufacturing method described in step C of Example 1-2-3.

$^1$H-NMR (270 MHz, $CDCl_3$) δ 1.26 (3H, t, J=4.5 Hz), 3.51 (2H, dd, J=7.3 Hz, 4.5 Hz), 4.13 (3H, s), 6.29 (1H, bs), 7.13 (1H, d, J=8.6 Hz), 7.34 (2H, d, J=9.0 Hz), 7.63 (2H, d, J=9.0 Hz), 8.17 (1H, dd, J=8.6 Hz, 2.5 Hz), 8.53 (1H, d, J=2.5 Hz), 9.77 (1H, bs).

ESI (LC/MS positive mode) m/z 333, 335 (M+H$^+$); retention time 2.66 min (Condition 4 for high-performance liquid chromatography).

Example 1-2-6

Production of N-3-(4-chlorophenyl)-N-1-cyclopropyl-4-methoxy-isophthalamide (Compound 1-2-6)

[Formula 55]

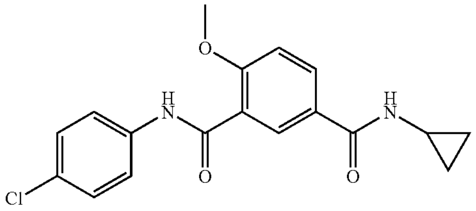

The captioned compound was synthesized using N-(4-chlorophenyl)-4-methoxyisophthalic acid and cyclopropylamine by the same procedure as in the manufacturing method described in step C of Example 1-2-3.

ESI (LC/MS positive mode) m/z 345, 347 (M+H$^+$); retention time 2.85 min (Condition 3 for high-performance liquid chromatography).

Example 1-2-7

Production of N-3-(4-chlorophenyl)-4-methoxy-N-1-(1-methoxymethyl-propyl)-isophthalamide

[Formula 56]

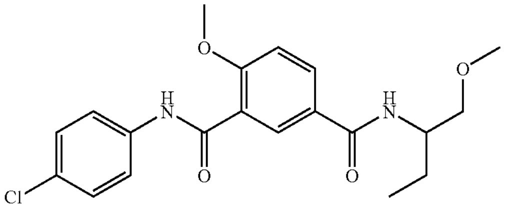

The captioned compound was synthesized using N-(4-chlorophenyl)-4-methoxyisophthalic acid and 2-amino-1-methoxybutane by the same procedure as in the manufacturing method described in step C of Example 1-2-3.

ESI XLC/MS positive mode) m/z 391, 393 (M+H$^+$); retention time 3.03 min (Condition 3 for high-performance liquid chromatography).

Example 1-2-8

Production of N-3-(4-chlorophenyl)-N-1-(2-cyanoethyl)-4-methoxy-isophthalamide (Compound 1-2-8)

[Formula 57]

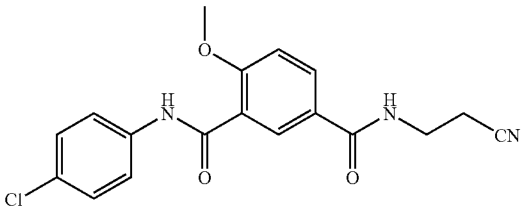

The captioned compound was synthesized using N-(4-chlorophenyl)-4-methoxyisophthalic acid and 2-aminopropionitrile by the same procedure as in the manufacturing method described in step C of Example 1-2-3.

$^1$H-NMR (270 MHz, $CDCl_3$) δ 2.76 (2H, t, J=6.2 Hz), 3.72 (2H, dd, J=12.5 Hz, 6.2 Hz), 4.13 (3H, s), 7.05 (1H, bs), 7.13 (1H, d, J=8.9 Hz), 7.33 (2H, d, J=8.9 Hz), 7.60 (2H, d, J=8.9 Hz), 8.13 (1H, dd, J=8.9 Hz, 2.3 Hz), 8.61 (1H, d, J=2.3 Hz), 9.71 (1H, bs).

ESI (LC/MS positive mode) m/z 358, 360 (M+H$^+$); retention time 2.58 min (Condition 4 for high-performance liquid chromatography).

Example 1-2-9

Production of N-3-(4-chlorophenyl)-N-1-isopropyl-4-methoxy-isophthalamide (Compound 1-2-9)

[Formula 58]

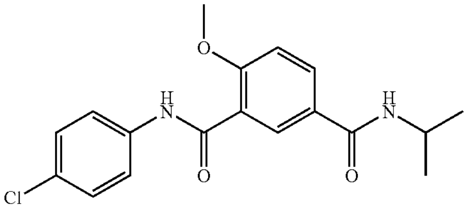

The captioned compound was synthesized using N-(4-chlorophenyl)-4-methoxyisophthalic acid and isopropylamine by the same procedure as in the manufacturing method described in step C of Example 1-2-3.

$^1$H-NMR (270 MHz, $CDCl_3$) δ 1.27 (6H, d, J=6.6 Hz), 3.66 (1H, brs), 4.13 (3H, s), 4.20-4.40 (1H, m), 6.16 (1H, brs), 7.13 (1H, d, J=8.9 Hz), 7.34 (2H, d, J=8.9 Hz), 7.63 (2H, d, J=8.9 Hz), 8.17 (1H, dd, J=8.9 Hz, 2.3 Hz), 8.51 (1H, d, J=2.3 Hz), 9.77 (1H, bs).

ESI (LC/MS positive mode) m/z 401, 403 (M+H$^+$); retention time 3.57 min (Condition 3 for high-performance liquid chromatography).

Example 1-2-10

Production of N-3-(4-chlorophenyl)-4-methoxy-N-1-(3-methyl-butyl)-isophthalamide (Compound 1-2-10)

[Formula 59]

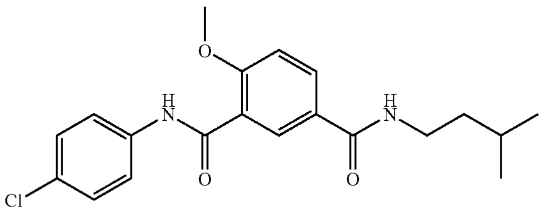

The captioned compound was synthesized using N-(4-chlorophenyl)-4-methoxyisophthalic acid and 3-methylbutylamine by the same procedure as in the manufacturing method described in step C of Example 1-2-3.

$^1$H-NMR (270 MHz, $CDCl_3$) δ 0.95 (6H, d, J=6.3 Hz), 1.51 (2H, dd, J=14.9 Hz, 7.0 Hz), 164-1.77 (1H, m), 3.47 (2H, dd, J=14.9 Hz, 5.9 Hz), 4.11 (3H, s), 6.30 (1H, bs), 7.11 (1H, d, J=8.6 Hz), 7.33 (2H, d, J=8.9 Hz), 7.62 (2H, d, J=8.9 Hz), 8.15 (1H, dd, J=8.6 Hz, 2.7 Hz), 8.51 (1H, d, J=2.7 Hz), 9.76 (1H, bs).

ESI (LC/MS positive mode) m/z 375, 377 (M+H$^+$); retention time 3.38 min (Condition 3 for high-performance liquid chromatography)

Example 1-2-11

Production of N-1-benzyl-N-3-(4-chlorophenyl)-4-methoxy-isophthalamide (Compound 1-2-11)

[Formula 60]

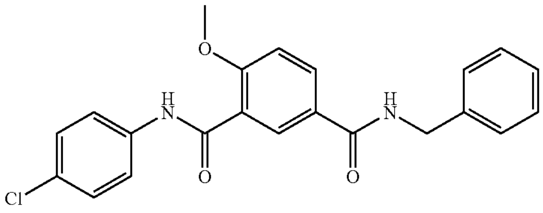

The captioned compound was synthesized using N-(4-chlorophenyl)-4-methoxyisophthalic acid and benzylamine by the same procedure as in the manufacturing method described in step C of Example 1-2-3.

$^1$H-NMR (270 MHz, $CDCl_3$) δ 4.12 (3H, s), 4.64 (2H, d, J=5.6 Hz), 6.63 (1H, bs), 7.13 (1H, d, J=2.3 Hz), 7.30-7.35 (7H, m), 7.60 (2H, d, J=8.9 Hz), 8.19 (1H, dd, J=8.6 Hz, 2.3 Hz), 8.55 (1H, d, J=2.3 Hz), 9.73 (1H, bs).

ESI (LC/MS positive mode) m/z 395, 397 (M+H$^+$); retention time 3.26 min (Condition 3 for high-performance liquid chromatography).

Example 1-2-12

Production of N-3-(4-chlorophenyl)-N-1-[2-(1H-imidazol-4-yl)-ethyl]-4-methoxy-isophthalamide (Compound 1-2-12)

[Formula 61]

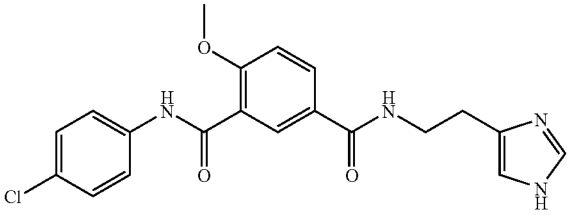

The captioned compound was synthesized using N-(4-chlorophenyl)-4-methoxyisophthalic acid and histamine by the same procedure as in the manufacturing method described in step C of Example 1-2-3.

$^1$H-NMR (270 MHz, $CDCl_3$) δ 2.89 (2H, t, J=6.2 Hz), 3.70 (2H, dd, J=12.2 Hz, 6.2 Hz), 4.08 (3H, s), 6.83 (1H, bs), 7.06 (1H, d, J=8.6 Hz), 7.30 (2H, d, J=8.9 Hz), 7.55-7.61 (4H, m), 8.07 (1H, dd, J=8.6 Hz, 2.6 Hz), 8.57 (1H, d, J=2.6 Hz), 9.71 (1H, bs).

ESI (LC/MS positive mode) m/z 399, 401 ($M+H^+$); retention time 2.14 min (Condition 3 for high-performance liquid chromatography).

Example 1-2-13

Production of N-3-(4-chlorophenyl)-4-methoxy-N-1-(2-methoxy-ethyl)-isophthalamide (Compound 1-2-13)

[Formula 62]

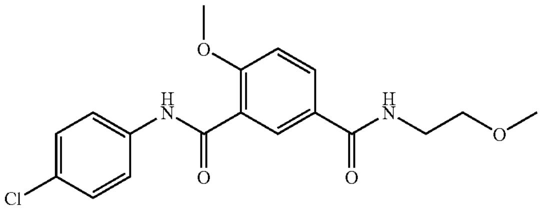

The captioned compound was synthesized using N-(4-chlorophenyl)-4-methoxyisophthalic acid and 2-methoxyethylamine by the same procedure as in the manufacturing method described in step C of Example 1-2-3.

$^1$H-NMR (270 MHz, $CDCl_3$) δ 3.39 (3H, s), 3.56 (2H, dd, J=9.3 Hz, 4.5 Hz), 3.66 (2H, dd, J=9.3 Hz, 4.5 Hz), 4.13 (3H, s), 6.65 (1H, bs), 7.13 (1H, d, J=8.8 Hz), 7.34 (2H, d, J=8.9 Hz), 7.63 (2H, d, J=8.9 Hz), 8.16 (1H, dd, J=8.6 Hz, 2.4 Hz), 8.58 (1H, d, J=2.3 Hz), 9.74 (1H, bs).

ESI (LC/MS positive mode) m/z 363, 365 ($M+H^+$); retention time 2.57 min (Condition 4 for high-performance liquid chromatography).

Example 1-2-14

Production of N-1-(2-chloroethyl)-N-3-(4-chlorophenyl)-4-methoxy-isophthalamide (Compound 1-2-14)

[Formula 63]

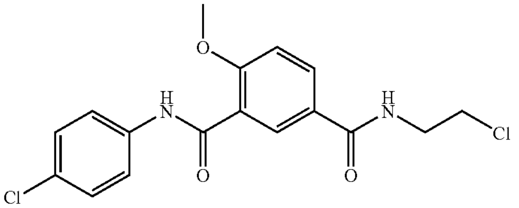

The captioned compound was synthesized using N-(4-chlorophenyl)-4-methoxyisophthalic acid and 2-chloro-ethylamine by the same procedure as in the manufacturing method described in step C of Example 1-2-3.

$^1$H-NMR (270 MHz, $CDCl_3$) δ 3.70-3.76 (2H, m), 3.77-3.86 (2H, m), 4.13 (3H, s), 7.12-7.15 (1H, m), 7.34 (2H, d, J=8.9 Hz), 7.63 (2H, d, J=8.9 Hz), 8.14 (1H, dd, J=8.6 Hz, 2.6 Hz), 8.60 (1H, d, J=2.6 Hz), 9.73 (1H, bs).

ESI (LC/MS positive mode) m/z 367, 369 ($M+H^+$); retention time 3.01 min (Condition 3 for high-performance liquid chromatography).

Example 1-2-15

Production of N-3-(4-chlorophenyl)-4-methoxy-N-1-(tetrahydrofuran-2-ylmethyl)-isophthalamide (Compound 1-2-15)

[Formula 64]

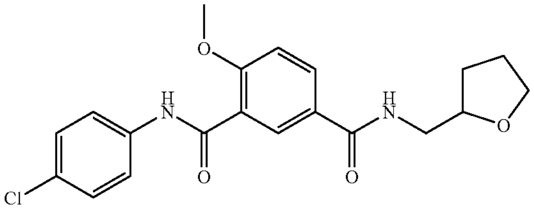

The captioned compound was synthesized using N-(4-chlorophenyl)-4-methoxyisophthalic acid and tetrahydrofurfurylamine by the same procedure as in the manufacturing method described in step C of Example 1-2-3.

ESI (LC/MS positive mode) m/z 389, 391 ($M+H^+$); retention time 2.84 min (Condition 3 for high-performance liquid chromatography).

Example 1-2-16

Production of N-3-(4-chlorophenyl)-N-1-cyclohexyl-methyl-4-methoxy-isophthalamide (Compound 1-2-16)

[Formula 65]

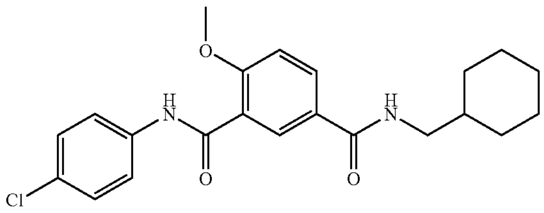

The captioned compound was synthesized using N-(4-chlorophenyl)-4-methoxyisophthalic acid and aminomethyl-cyclohexane by the same procedure as in the manufacturing method described in step C of Example 1-2-3.

$^{1}$H-NMR (270 MHz, $CDCl_3$) δ 90-1.10 (1H, m), 1.15-1.35 (2H, m), 1.50-1.88 (8H, m), 3.30 (2H, t, J=6.3 Hz), 4.13 (3H, s), 6.34 (1H, bs), 7.13 (2H, d, J=8.9 Hz), 7.34 (2H, d, J=8.9 Hz), 7.63 (2H, d, J=8.9 Hz), 8.17 (1H, dd, J=8.9 Hz, 2.6 Hz), 8.53 (1H, d, J=2.6 Hz), 9.77 (1H, bs).

ESI (LC/MS positive mode) m/z 347, 349 ($M+H^+$); retention time 3.01 min (Condition 3 for high-performance liquid chromatography).

Example 1-2-17

Production of N-3-(4-chlorophenyl)-N-1-furan-2-ylmethyl-4-methoxy-isophthalamide (Compound 1-2-17)

[Formula 66]

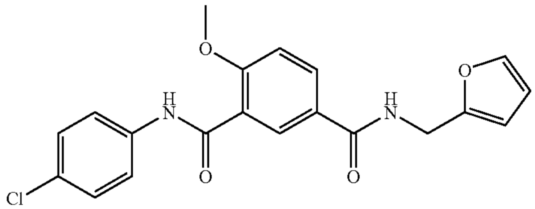

The captioned compound was synthesized using N-(4-chlorophenyl)-4-methoxyisophthalic acid and furfurylamine by the same procedure as in the manufacturing method described in step C of Example 1-2-3.

$^{1}$H-NMR (270 MHz, $CDCl_3$) δ 4.13 (3H, s), 4.64 (2H, d, J=5.3 Hz), 6.20-6.33 (1H, m), 6.38 (1H, dd, J=3.0 Hz, 2.0 Hz), 6.60 (1H, bs), 7.13 (1H, d, J =8.9 Hz), 7.33 (2H, d, J=8.9 Hz), 7.38 (1H, dd, J=1.8 Hz, 0.8 Hz), 7.61 (2H, d, J=8.9 Hz), 8.18 (1H, dd, J=8.9 Hz, 2.4 Hz), 8.55 (1H, d, J=2.4 Hz), 9.74 (1H, bs).

ESI (LC/MS positive mode) m/z 385, 387 ($M+H^+$); retention time 3.08 min (Condition 3 for high-performance liquid chromatography).

Example 1-2-18

Production of N-3-(4-chlorophenyl)-N-1-[2-(2-hydroxyethoxy)-ethyl]-4-methoxy-isophthalamide (Compound 1-2-18).

[Formula 67]

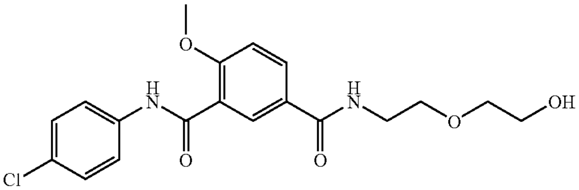

The captioned compound was synthesized using N-(4-chlorophenyl)-4-methoxyisophthalic acid and 2-(2-aminoethoxy)ethanol by the same procedure as in the manufacturing method described in step C of Example 1-2-3.

ESI (LC/MS positive mode) m/z 393, 395 ($M+H^+$); retention time 2.44 min (Condition 3 for high-performance liquid chromatography).

Example 1-2-19

Production of N-3-(4-chlorophenyl)-N-1-(2-dimethylaminoethyl)-4-methoxy-isophthalamide (Compound 1-2-19)

[Formula 68]

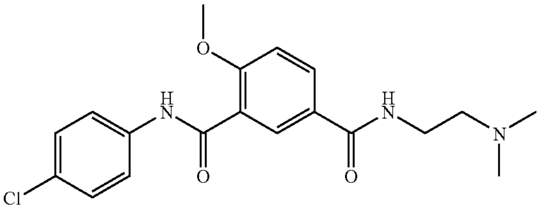

The captioned compound was synthesized using N-(4-chlorophenyl)-4-methoxyisophthalic acid and N,N-dimethylethylenediamine by the same procedure as in the manufacturing method described in step C of Example 1-2-3.

$^{1}$H-NMR (270 MHz, $CDCl_3$) δ 2.51 (2H, t, J=5.5 Hz), 3.53 (2H, dd, J=11.2 Hz, 5.5 Hz), 4.12 (3H, s), 6.89 (1H, bs), 7.12 (1H, d, J=8.6 Hz), 7.33 (2H, d, J=8.9 Hz), 7.63 (2H, d, J=8.9 Hz), 8.15 (1H, dd, J=8.6 Hz, 2.3 Hz), 8.58 (1H, d, J=2.3 Hz), 9.74 (1H, bs).

ESI (LC/MS positive mode) m/z 376, 378 ($M+H^+$); retention time 2.63 min (Condition 3 for high-performance liquid chromatography).

Example 1-2-20

Production of 4-nitro-3-N-(4-chlorophenyl)-isophthalamide (Compound 1-2-20)

[Formula 69]

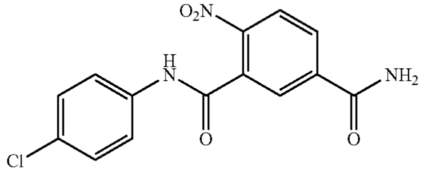

Step A

Preparation of methyl N-(4-chlorophenyl)-4-nitroisophthamate

[Formula 70]

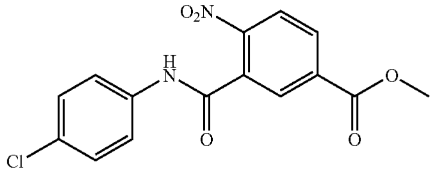

5-(Methoxycarbonyl)-2-nitrobenzoic acid (CAS registry number: 76143-33-4) (1.50 g) and 0.05 mL of N,N-dimethylformamide were dissolved in 150 mL of dichloromethane, and the solution was cooled to 0° C. To this solution, 0.87 mL of oxalyl chloride was added little by little, and the mixture was stirred for 30 minutes at 0° C., followed by stirring the mixture for 13 hours at room temperature. The reaction mixture was distilled under reduced pressure, and dried to obtain a light yellow solid, which was dissolved in 150 mL of dichloromethane. To this solution, a solution of 0.94 g of 4-chloroaniline and 3.57 mL of N,N-diisopropylethylamine dissolved in 25 mL of dichloromethane was added little by little. The mixture was stirred for 2 hours and a half at room temperature, whereafter 100 mL of a saturated aqueous solution of ammonium chloride was added to separate the organic layer. The aqueous layer was extracted twice with 50 mL of dichloromethane. The respective organic layers were combined, whereafter the combined organic layer was washed with 50 mL of a saturated aqueous solution of sodium chloride, and dried over anhydrous sodium sulfate. The anhydrous sodium sulfate was separated by filtration, and washed with dichloromethane. The filtrate and the washings were combined, and dichloromethane was distilled off under reduced pressure. The resulting residue was purified by silica gel column chromatography. The resulting solid was dried under reduced pressure to obtain 1.82 g (81%) of methyl N-(4-chlorophenyl)-4-nitroisophthalamate.

$^1$H-NMR (270 MHz, $CDCl_3$) δ 4.00 (3H, s), 7.36 (2H, d, J=8.9 Hz), 7.55 (2H, d, J=8.9 Hz), 7.66 (1H, bs), 8.14 (1H, d, J=8.6 Hz), 8.25-8.29 (2H, m).

ESI (positive mode) m/z 334 ($M^+$).

Step B

Preparation of 4-nitro-3-N-(4-chlorophenyl)-isophthalamide

[Formula 71]

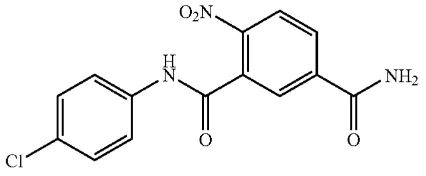

Methyl N-(4-chlorophenyl)-4-nitroisophthalamate (220 mg) obtained in step A was dissolved in 10 mL of a methanol solution of 7 mols of ammonia. After the reactor was sealed, the solution was heated for 36 hours at 80° C. with stirring. The reaction mixture was concentrated under reduced pressure, and the residue was purified by silica gel column chromatography. The resulting solid was dried under reduced pressure to obtain 48 mg (23%) of 4-nitro-3-N-(4-chlorophenyl)-isophthalamide.

$^1$H-NMR (270 MHz, DMSO-$d_6$) δ 7.45 (2H, d, J=8.9 Hz), 7.72 (2H, d, J =8.9 Hz), 7.83 (1H, bs), 8.16-8.26 (3H, m), 8.39 (1H, bs), 11.00 (1H, bs).

ESI (LC/MS positive mode) m/z 320, 322 ($M+H^+$); retention time 3.00 min (Condition 1 for high-performance liquid chromatography).

Example 1-2-21

Production of 4-amino-3-N-(4-chlorophenyl)-isophthalamide (Compound 1-2-21)

[Formula 72]

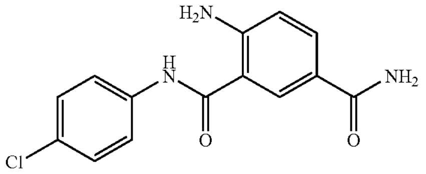

4-Nitro-3-N-(4-chlorophenyl)-isophthalamide (46 mg) obtained in Example 1-2-20 was dissolved in 7 mL of methanol, and 10 mg of platinum oxide was added to the solution, followed by stirring the mixture for 30 minutes at room temperature in an atmosphere of hydrogen. The reaction mixture was filtered to remove insolubles, and the filtrate was concentrated under reduced pressure. The resulting solid was dried under reduced pressure to obtain 41 mg (99%) of 4-amino-3-N-(4-chlorophenyl)-isophthalamide.

$^1$H-NMR (270 MHz, DMSO-$d_6$) δ 6.73-6.76 (3H, m), 7.07 (1H, bs), 7.41 (2H, d, J=8.9 Hz), 7.64 (1H, bs), 7.51-7.76 (3H, m), 8.17 (1H, d, J=2.0 Hz), 10.24 (1H, bs).

ESI (LC/MS positive mode) m/z 290, 292 ($M+H^+$); retention time 2.78 min (Condition 1 for high-performance liquid chromatography).

Example 1-2-22

Production of 4-chloro-3-N-(4-chlorophenyl)-isophthalamide (Compound 1-2-22)

[Formula 73]

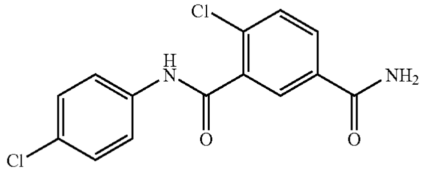

4-Amino-3-N-(4-chlorophenyl)-isophthalamide (25 mg) obtained in Example 1-2-21 was dissolved in a solvent mixture of 2 mL of tetrahydrofuran, 1.5 mL of , acetic acid, and 0.5 mL of purified water, and 12 mg of sodium nitrite was added to the solution. The reaction mixture was stirred for 30 minutes at room temperature, then 100 mg of cuprous chloride was added, and the mixture was further stirred for 15 hours at 70° C. A saturated aqueous solution of sodium bicarbonate (20 mL) was added, and the mixture was extracted twice with 50 mL of ethyl acetate. The respective organic layers were combined, whereafter the combined organic layer was washed with 20 mL of a saturated aqueous solution of sodium chloride, and dried over anhydrous sodium sulfate. The anhydrous sodium sulfate was separated by filtration, and washed with ethyl acetate. The filtrate and the washings were combined, and ethyl acetate was distilled off under reduced pressure. The resulting residue was purified using a micromass spectrometer (ZMD produced by Micromass) equipped with a gradient high-performance liquid chromatograph 996-600E produced by Waters. The resulting solid was dried under reduced pressure to obtain 11 mg (41%) of 4-chloro-3-N-(4-chlorophenyl)-isophthalamide.

$^1$H-NMR (270 MHz, $CD_3OD$) δ 7.37 (2H, d, J=8.9 Hz), 7.63 (1H, d, J=8.2 Hz), 7.69 (2H, d, J=8.9 Hz), 7.97 (1H, dd, J=8.2 Hz, 2.3 Hz), 8.07 (1H, d, J=2.3 Hz).

ESI (LC/MS positive mode) 309, 311 ($M+H^+$); retention time 3.04 min (Condition 1 for high-performance liquid chromatography).

Example 1-2-23

Production of 4-bromo-3-N-(4-chlorophenyl)-isophthalamide (Compound 1-2-23)

[Formula 74]

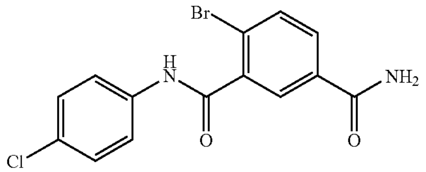

The captioned compound was synthesized from 4-amino-3-N-(4-chlorophenyl)-isophthalamide and cuprous bromide by the same procedure as in the manufacturing method described in Example 1-1-22.

$^1$H-NMR (270 MHz, $CD_3OD$) δ 7.37 (2H, d, J=8.8 Hz), 7.68 (2H, d, J=8.8 Hz), 7.80 (1H, d, J=8.2 Hz), 7.88 (1H, d, J=8.2 Hz), 8.02 (1H, bs).

ESI (LC/MS positive mode) m/z 353, 355 ($M+H^+$); retention time 3.00 min (Condition 1 for high-performance liquid chromatography).

Example 1-2-24

Production of $N^3$-(4-bromo-2-chloro-phenyl)-$N^1$-(2-hydroxy-1-methyl-ethyl)-4-methoxy-isophthalamide (Compound 1-2-24)

[Formula 75]

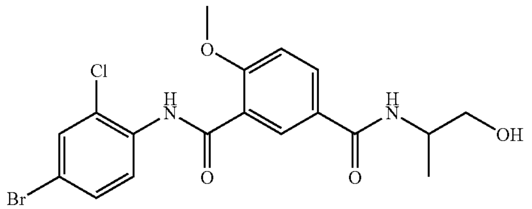

The captioned compound was synthesized using N-(2-chloro-4-bromophenyl)-4-methoxyisophthalic acid and (±)-2-amino-1-propanol by the same procedure as in the manufacturing method described in step C of Example 1-2-3.

ESI (LC/MS positive mode) m/z 441, 443, 445 ($M+H^+$); retention time 3.36 min. (Condition 1 for high-performance liquid chromatography).

Example 1-2-25

Production of $N^3$-(4-bromo-2-chloro-phenyl)-$N^1$-((S)-1-hydroxymethyl-2-methyl-propyl)-4-methoxy-isophthalamide (Compound 1-2-25)

[Formula 76]

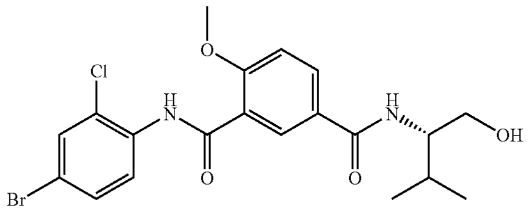

The captioned compound was synthesized using N-(2-chloro-4-bromophenyl)-4-methoxyisophthalic acid and (S)-(+)-2-amino-3-methylbutanol by the same procedure as in the manufacturing method described in step C of Example 1-2-3.

ESI (LC/MS positive mode) m/z 469, 471, 473 ($M+H^+$); retention time 3.67 min (Condition 1 for high-performance liquid chromatography).

Example 1-3-1

Production of 3-N-(4-bromo-2-fluorophenyl)-4-methoxy-isophthalamide (Compound 1-3-1)

[Formula 77]

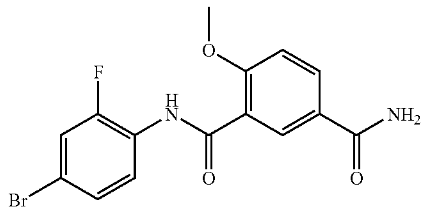

Step A

Preparation of methyl 5-cyano-2-methoxybenzoate (CAS Registry Number: 40757-12-8)

[Formula 78]

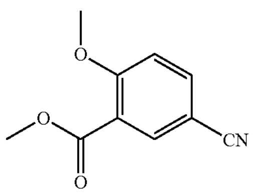

Methyl 5-bromo-2-methoxybenzoate (29.3 g) obtained in step A of Example 1-1-1, and 33.1 g of zinc cyanide were dissolved in 650 mL of N,N-dimethylformamide. N,N-Dimethylformamide was degassed under reduced pressure, and then the interior of the reactor was purged with nitrogen. After 9.8 g of tetrakistriphenylphosphine palladium was added, N,N-dimethylformamide was deaerated again under reduced pressure, and then the interior of the reactor was purged with argon. This solution was stirred for 2 hours at 100° C., whereafter the solvent was distilled off under reduced pressure, and the residue was dissolved in ethyl acetate. The insolubles were removed by filtration, and washed with ethyl acetate. The filtrate and the washings were combined, water was added, and then the organic layer was separated. The aqueous layer was extracted twice with ethyl acetate. After the respective organic layers were combined, the combined organic layer was washed with a saturated aqueous solution of sodium chloride, and dried over anhydrous sodium sulfate. The anhydrous sodium sulfate was separated by filtration, and then washed with ethyl acetate. The filtrate and the washings were combined, and ethyl acetate was distilled off under reduced pressure. The resulting residue was washed with diethyl ether. The resulting solid was dried under reduced pressure to obtain 13.5 g (42%) of methyl 5-cyano-2-methoxybenzoate. The mother liquor and the washings were combined, and concentrated, whereafter the residue was recrystallized from t-butyl methyl ether. The resulting crystals were separated by filtration, then washed with a 1:1 solvent mixture of n-hexane and diethyl ether, and then dried under reduced pressure to obtain 4.6 g (14%) of methyl 5-cyano-2-methoxybenzoate.

$^1$H-NMR (400 MHz, $CDCl_3$) δ 3.92 (3H, s), 3.98 (3H, s), 7.06 (1H, d, J=8.6 Hz), 7.76 (1H, dd, J=8.6 Hz, 2.3 Hz), 8.11 (1H, d, J=2.3 Hz).

ESI (LC/MS positive mode) m/z 192 (M+H$^+$); retention time 2.56 min (Condition 1 for high-performance liquid chromatography).

Step B

Preparation of 6-methoxyisophthalamic acid (CAS Registry Number: 89366-41-6)

[Formula 79]

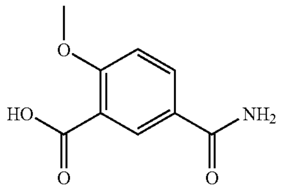

Methyl 5-cyano-2-methoxybenzoate (2 g) prepared in step A was dissolved in 24 mL of dimethyl sulfoxide, and 12 mL of a 1 M aqueous solution of sodium hydroxide was added. After stirring for 4 hours and a half at 80° C., the mixture was cooled in an ice bath, and adjusted to pH of about 4 with the use of 10 mL of 1 M hydrochloric acid. The resulting solution was diluted with 200 mL of water, and cooled for several hours in a refrigerator. The precipitate formed was separated by filtration, washed with cold water, and then dried over diphosphorus pentoxide under reduced-pressure to obtain 1.3 g (63%) of 6-methoxyisophthalamic acid.

$^1$H-NMR (400 MHz, DMSO-$d_6$) δ 3.89 (3H, s), 7.18 (1H, d, J=8.6 Hz), 7.28 (1H, bs), 7.97 (1H, bs), 8.02 (1H, dd, J=8.6 Hz, 2.3 Hz), 8.18 (1H, d, J =2.3 Hz), 12.80 (1H, s).

ESI (LC/MS positive mode) m/z 196 (M+H$^+$); retention time 0.55 min (Condition 1 for high-performance liquid chromatography).

Step C

Preparation of 3-N-(4-bromo-2-fluorophenyl)-4-methoxyisophthalamide (Compound 1-3-1)

[Formula 80]

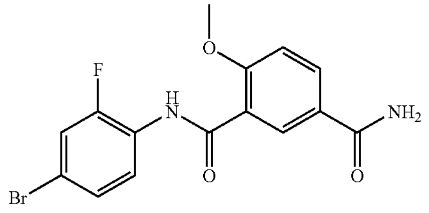

To 202 mg (1.24 mmols/g) of N-cyclohexylcarbodiimide-N'-propyloxymethylpolystyrene (PS-carbodiimide), there were added 0.5 mL (0.25 mol) of an N,N-dimethylformamide solution of 6-methoxyisophthalamic acid prepared in step B, 0.75 mL (0.25M) of an N,N-dimethylformamide solution of benzotriazol-1-ol monohydrate, and 20 mg of 4-bromo-2-fluoroaniline. This mixture was agitated for 16 hours at room temperature, and then agitated for 24 hours at 60° C. To the mixture, 213 mg (2.64 mmols/g) of macroporous triethylammonium methylpolystyrene carbonate (MP-carbonate) and 0.5 mL of N,N-dimethylformamide were added, followed by agitating the mixture for 12 hours at room temperature. The polystyrene solid phase-carried reagent was separated by filtration, and washed with N,N-dimethylformamide, tetrahydrofuran, and dichloromethane in this order. Then, the filtrate and the washings were combined, and concentrated. The resulting residue was purified using a micromass spectrometer (ZMD produced by Micromass) equipped with a gradient high-performance liquid chromatograph 996-600E produced by Waters, thereby obtaining 9 mg (22%) of 3-N-(4-bromo-2-fluorophenyl)-4-methoxyisophthalamide.

ESI (LC/MS positive mode) m/z 367, 369 ($M+H^+$); retention time 3.14 min (Condition 1 for high-performance liquid chromatography).

Example 1-3-2

Production of 3-N-(2,3-dichlorophenyl)-4-methoxyisophthalamide (Compound 1-3-2)

[Formula 81]

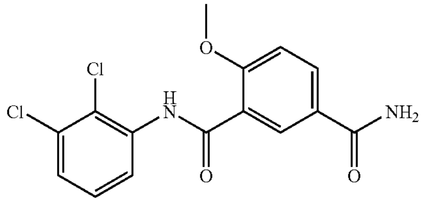

The captioned compound was synthesized from 6-methoxyisophthalamic acid and 2,3-dichloroaniline by the same procedure as in the manufacturing method described in step C of Example 1-3-1.

ESI (LC/MS positive mode) m/z 339, 341, 343 ($M+H^+$); retention time 3.24 min (Condition 1 for high-performance liquid chromatography).

Example 1-3-3

Production of 3-N-(4-chloro-2,5-dimethoxyphenyl)-4-methoxyisophthalamide (Compound 1-3-3)

[Formula 82]

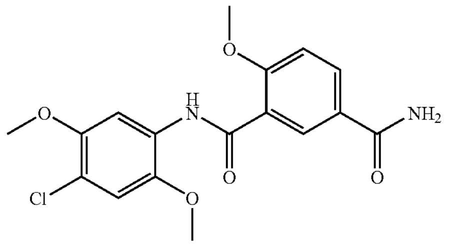

The captioned compound was synthesized from 6-methoxyisophthalamic acid and 4-chloro-2,5-dimethoxyaniline by the same procedure as in the manufacturing method described in step C of Example 1-3-1.

ESI (LC/MS positive mode) m/z 365, 367 ($M+H^+$); retention time 3.09 min (Condition 1 for high-performance liquid chromatography).

Example 1-3-4

Production of N-3-(2-chloro-4-methylphenyl)-4-methoxyisophthalamide (Compound 1-3-4)

[Formula 83]

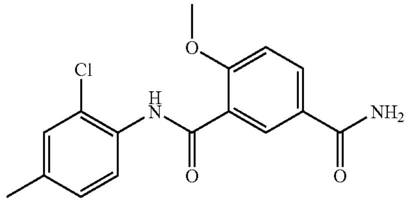

The captioned compound was synthesized from 6-methoxyisophthalamic acid and 2-chloro-4-methylaniline by the same procedure as in the manufacturing method described in step C of Example 1-3-1.

ESI (LC/MS positive mode) m/z 319, 321 ($M+H^+$); retention time 3.23 min (Condition 1 for high-performance liquid chromatography).

Example 1-3-5

Production of 4-methoxy-3-N-(2-trifluoromethoxyphenyl)-isophthalamide (Compound 1-3-5),

[Formula 84]

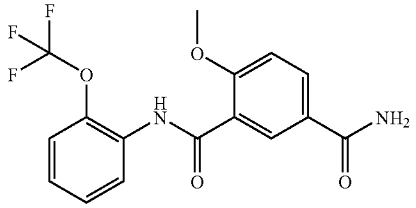

The captioned compound was synthesized from 6-methoxyisophthalamic acid and 2-trifluoromethoxyaniline by the same procedure as in the manufacturing method described in step C of Example 1-3-1.

ESI (LC/MS positive mode) m/z 355 ($M+H^+$); retention time 3.22 min (Condition 1 for high-performance liquid chromatography).

Example 1-3-6

Production of 4-methoxy-3-N-(5,6,7,8-tetrahydronaphthalen-1-yl)isophthalamide (Compound 1-3-6)

[Formula 85]

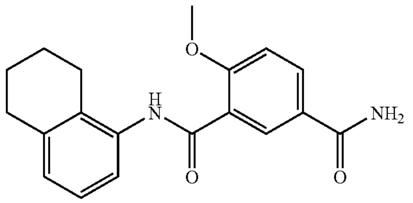

The captioned compound was synthesized from 6-methoxyisophthalamic acid and 1-amino-5,6,7,8-tetrahydronaphthalene by the same procedure as in the manufacturing method described in step C of Example 1-3-1.

ESI (LC/MS positive mode) m/z 325 (M+H$^+$); retention time 3.21 min (Condition 1 for high-performance liquid chromatography).

Example 1-3-7

Production of 3-N-(2-chlorophenyl)-4-methoxy-isophthalamide (Compound 1-3-7)

[Formula 86]

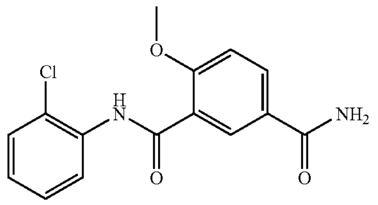

The captioned compound was synthesized from 6-methoxyisophthalamic acid and 2-chloroaniline by the same procedure as in the manufacturing method described in step C of Example 1-3-1.

ESI (LC/MS positive mode) m/z 305, 307 (M+H$^+$); retention time 2.95 min (Condition 1 for high-performance liquid chromatography).

Example 1-3-8

Production of 3-N-(2-fluoro-3-trifluoromethylphenyl)-4-methoxyisophthalamide (Compound 1-3-8)

[Formula 87]

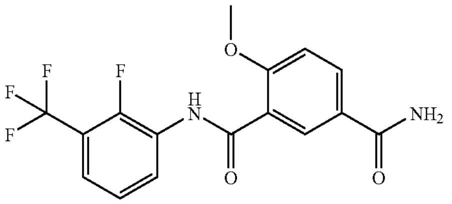

The captioned compound was synthesized from 6-methoxyisophthalamic acid and 2-fluoro-3-trifluoromethylaniline by the same procedure as in the manufacturing method described in step C of Example 1-3-1.

ESI (LC/MS positive mode) m/z 357 (M+H$^+$); retention time 3.19 min (Condition 1 for high-performance liquid chromatography).

Example 1-3-9

Production of 3-N-indan-5-yl-4-methoxyisophthalamide (Compound 1-3-9)

[Formula 88]

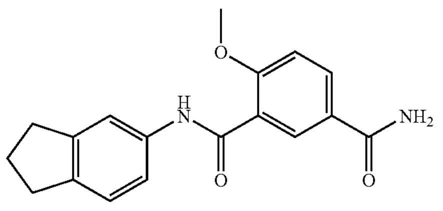

The captioned compound was synthesized from 6-methoxyisophthalamic acid and indan-4-yl-amine by the same procedure as in the manufacturing method described in step C of Example 1-3-1.

ESI (LC/MS positive mode) m/z 311 (M+H$^+$); retention time 3.10 min (Condition 1 for high-performance liquid chromatography).

Example 1-3-10

Production of 4-methoxy-3-N-(2-methoxyphenyl) isophthalamide (Compound 1-3-10)

[Formula 89]

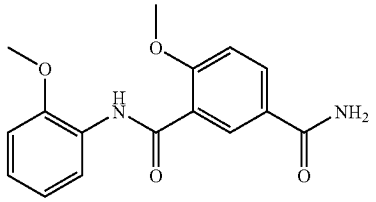

The captioned compound was synthesized from 6-methoxyisophthalamic acid and 2-methoxyaniline by the same procedure as in the manufacturing method described in step C of Example 1-3-1.

ESI (LC/MS positive mode) m/z 301 (M+H$^+$); retention time 3.53 min (Condition 1 for high-performance liquid chromatography).

Example 1-3-11

Production of 3-N-(3-chloro-4-methylphenyl)-4-methoxyisophthalamide (Compound 1-3-11)

[Formula 90]

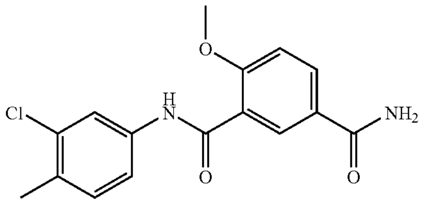

The captioned compound was synthesized from 6-methoxyisophthalamic acid and 3-chloro-4-methylaniline by the same procedure as in the manufacturing method described in step C of Example 1-3-1.

ESI (LC/MS positive mode) m/z 319, 321 (M+H$^+$); retention time 3.98 min (Condition 1 for high-performance liquid chromatography).

Example 1-3-12

Production of 3-N-(2-fluorophenyl)-4-methoxyisophthalamide (Compound 1-3-12)

[Formula 91]

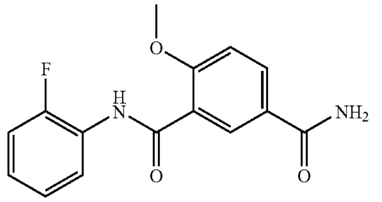

The captioned compound was synthesized from 6-methoxyisophthalamic acid and 2-fluoroaniline by the same procedure as in the manufacturing method described in step C of Example 1-3-1.

ESI (LC/MS positive mode) m/z 289 (M+$H^+$); retention time 2.73 min (Condition 1 for high-performance liquid chromatography).

Example 1-3-13

Production of 3-N-(2-acetylphenyl)-4-methoxyisophthalamide (Compound 1-3-13)

[Formula 92]

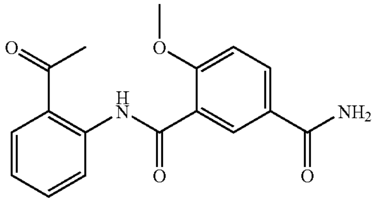

The captioned compound was synthesized from 6-methoxyisophthalamic acid and 2-acetylaniline by the same procedure as in the manufacturing method described in step C of Example 1-3-1.

ESI (LC/MS positive mode) m/z 313 (M+$H^+$); retention time 2.80 min (Condition 1 for high-performance liquid chromatography).

Example 1-3-14

Production of 3-N-(4-bromophenyl)-4-methoxyisophthalamide (Compound 1-3-14)

[Formula 93]

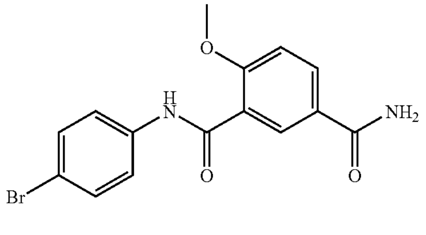

The captioned compound was synthesized from 6-methoxyisophthalamic acid and 4-bromoaniline by the same procedure as in the manufacturing method described in step C of Example 1-3-1.

ESI (LC/MS positive mode) m/z 349, 351 (M+$H^+$); retention time 2.95 min (Condition 1 for high-performance liquid chromatography).

Example 1-3-15

Production of 4-methoxy-3-N-(2-methylsulfanylphenyl)isophthalamide (Compound 1-3-15)

[Formula 94]

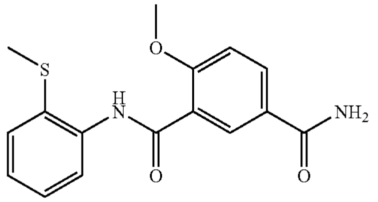

The captioned compound was synthesized from 6-methoxyisophthalamic acid and (2-amino)phenylmethylsulfide by the same procedure as in the manufacturing method described in step C of Example 1-3-1.

ESI (LC/MS positive mode) m/z 317 (M+$H^+$); retention time 3.02 min (Condition 1 for high-performance liquid chromatography).

Example 1-3-16

Production of 3-N-(2-chloro-5-trifluoromethylphenyl)-4-methoxyisophthalamide (Compound 1-3-16)

[Formula 95]

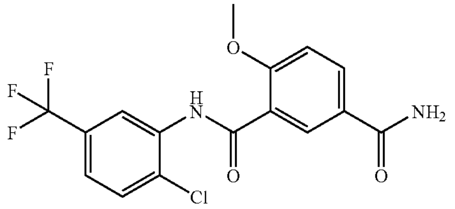

The captioned compound was synthesized from 6-methoxyisophthalamic acid and 2-chloro-5-trifluoromethylaniline by the same procedure as in the manufacturing method described in step C of Example 1-3-1.

ESI (LC/MS positive mode) m/z 373, 375 (M+$H^+$); retention time 3.30 min (Condition 1 for high-performance liquid chromatography).

Example 1-3-17

Production of 3-N-(2-chloro-4-fluoro-5-methylphenyl)-4-methoxyisophthalamide (Compound 1-3-17)

[Formula 96]

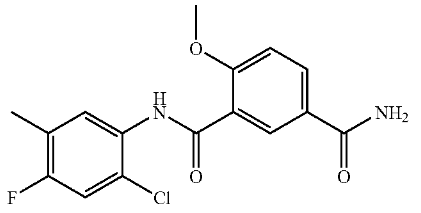

The captioned compound was synthesized from 6-methoxyisophthalamic acid and 2-chloro-4-fluoro-5-methylaniline by the same procedure as in the manufacturing method described in step C of Example 1-3-1.

ESI (LC/MS positive mode) m/z 337, 339 ($M+H^+$); retention time 3.21 min (Condition 1 for high-performance liquid chromatography).

Example 1-3-18

Production of 3-N-(3,5-dimethoxyphenyl)-4-methoxyisophthalamide (Compound 1-3-18)

[Formula 97]

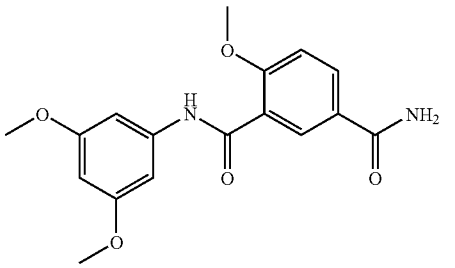

The captioned compound was synthesized from 6-methoxyisophthalamic acid and 3,5-dimethoxyaniline by the same procedure as in the manufacturing method described in step C of Example 1-3-1.

ESI (LC/MS positive mode) m/z 331 ($M+H^+$); retention time 3.43 min (Condition 1 for high-performance liquid chromatography).

Example 1-3-19

Production of 4-methoxy-3-N-(4-phenoxyphenyl)-isophthalamide (Compound 1-3-19)

[Formula 98]

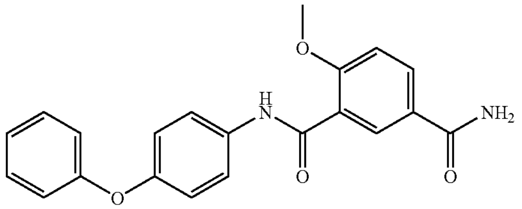

The captioned compound was synthesized from 6-methoxyisophthalamic acid and 4-phenoxyaniline by the same procedure as in the manufacturing method described in step C of Example 1-3-1.

ESI (LC/MS positive mode) m/z 363 ($M+H^+$); retention time 3.31 min (Condition 1 for high-performance liquid chromatography).

Example 1-3-20

Production of 3-N-(3,4-dimethylphenyl)-4-methoxy-isophthalamide (Compound 1-3-20)

[Formula 99]

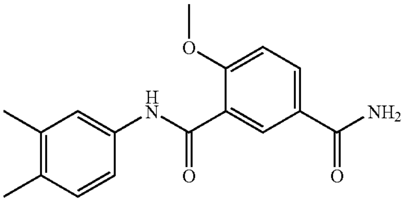

The captioned compound was synthesized from 6-methoxyisophthalamic acid and 3,4-dimethylaniline by the same procedure as in the manufacturing method described in step C of Example 1-3-1.

ESI (LC/MS positive mode) m/z 299 ($M+H^+$); retention time 3.01 min (Condition 1 for high-performance liquid chromatography).

Example 1-3-21

Production of 4-methoxy-3-N-(4-trifluoromethylphenyl)isophthalamide (Compound 1-3-21)

[Formula 100]

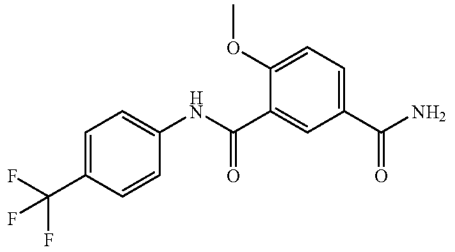

The captioned compound was synthesized from 6-methoxyisophthalamic acid and 4-trifluoromethylaniline by the same procedure as in the manufacturing method described in step C of Example 1-3-1.

ESI (LC/MS positive mode) m/z 339 ($M+H^+$); retention time 3.09 min (Condition 1 for high-performance liquid chromatography).

Example 1-3-22

Production of 3-N-(2,3-dihydrobenzo[1,4]dioxin-6-yl)-4-methoxyisophthalamide (Compound 1-3-22)

[Formula 101]

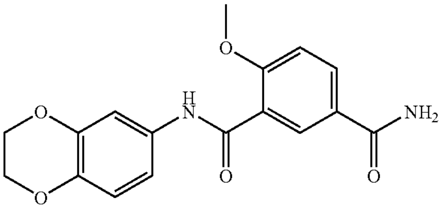

The captioned compound was synthesized from 6-methoxyisophthalamic acid and 2,3-dihydrobenzo[1,4]dioxin-6-ylamine by the same procedure as in the manufacturing method described in step C of Example 1-3-1.

ESI (LC/MS positive mode) m/z 329 ($M+H^+$); retention time 2.60 min (Condition 1 for high-performance liquid chromatography).

Example 1-3-23

Production of 4-methoxy3-N-o-tolylisophthalamide (Compound 1-3-23)

[Formula 102]

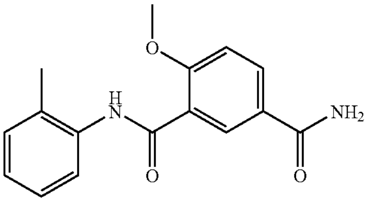

The captioned compound was synthesized from 6-methoxyisophthalamic acid and 2-methylaniline by the same procedure as in the manufacturing method described in step C of Example 1-3-1.

ESI (LC/MS positive mode) m/z 285 ($M+H^+$); retention time 3.49 min (Condition 1 for high-performance liquid chromatography).

Example 1-3-24

Production of 3-N-(2,4-difluorophenyl)-4-methoxy-isophthalamide (Compound 1-3-24)

[Formula 103]

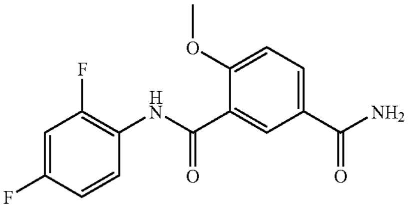

The captioned compound was synthesized from 6-methoxyisophthalamic acid and 2,4-difluoroaniline by the same procedure as in the manufacturing method described in step C of Example 1-3-1.

ESI (LC/MS positive mode) m/z 307 ($M+H^+$); retention time 2.79 min (Condition 1 for high-performance liquid chromatography).

Example 1-3-25

Production of 3-N-(3-ethynylphenyl)-4-methoxy-isophthalamide (Compound 1-3-25)

[Formula 104]

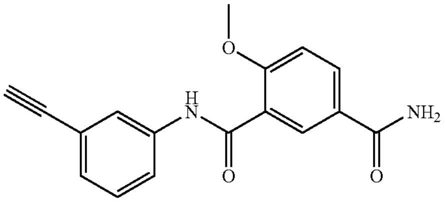

The captioned compound was synthesized from 6-methoxyisophthalamic acid and 3-ethynylaniline by the same procedure as in the manufacturing method described in step C of Example 1-3-1.

ESI (LC/MS positive mode) m/z 295 ($M+H^+$); retention time 2.89 min (Condition 1 for high-performance liquid chromatography).

Example 1-3-26

Production of 4-methoxy-3-N-(3-trifluoromethylphenyl)-isophthalamide (Compound 1-3-26)

[Formula 105]

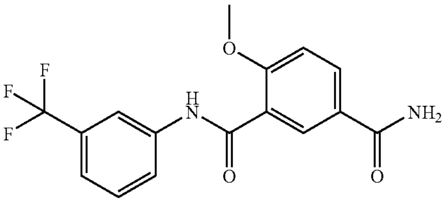

The captioned compound was synthesized from 6-methoxyisophthalamic acid and 3-trifluoromethylaniline by the same procedure as in the manufacturing method described in step C of Example 1-3-1.

ESI (LC/MS positive mode) m/z 339($M+H^+$), retention time 3.05 min (Condition 1 for high-performance liquid chromatography).

Example 1-3-27

Production of 3-N-(3-chlorophenyl)-4-methoxy-isophthalamide (Compound 1-3-27)

[Formula 106]

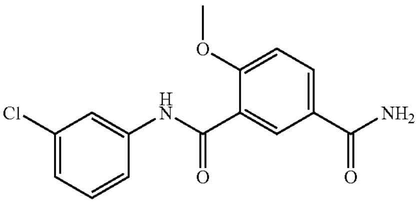

The captioned compound was synthesized from 6-methoxyisophthalamic acid and 3-chloroaniline by the same procedure as in the manufacturing method described in step C of Example 1-3-1.

ESI (LC/MS positive mode) m/z 305, 307 (M+H$^+$); retention time 2.90 min (Condition 1 for high-performance liquid chromatography).

Example 1-3-28

Production of 3-N-(2-fluoro-5-trifluoromethylphenyl)-4-methoxyisophthalamide (Compound 1-3-28)

[Formula 107]

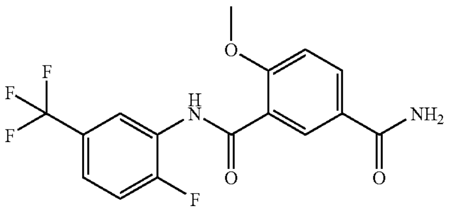

The captioned compound was synthesized from 6-methoxyisophthalamic acid and 2-fluoro-5-trifluoromethylaniline by the same procedure as in the manufacturing method described in step C of Example 1-3-1.

ESI (LC/MS positive mode) m/z 357 (M+H$^+$); retention time 3.19 min (Condition 1 for high-performance liquid chromatography).

Example 1-3-29

Production of 3-N-(2,5-dimethoxyphenyl)-4-methoxyisophthalamide (Compound 1-3-29)

[Formula 108]

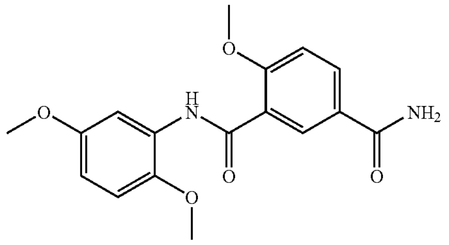

The captioned compound was synthesized from 6-methoxyisophthalamic acid and 2,5-dimethoxyaniline by the same procedure as in the manufacturing method described in step C of Example 1-3-1.

ESI (LC/MS positive mode) m/z 331 (M+H$^+$); retention time 2.89 min (Condition 1 for high-performance liquid chromatography).

Example 1-3-30

Production of 4-(5-carbamoyl-2-methoxybenzoylamino)benzoic acid ethyl ester (Compound 1-3-30)

[Formula 109]

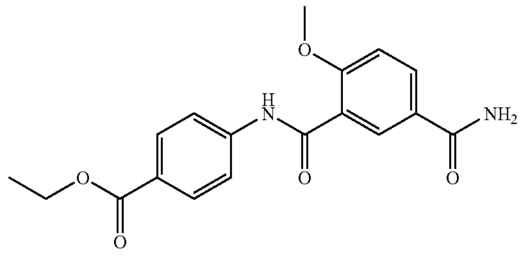

The captioned compound was synthesized from 6-methoxyisophthalamic acid and ethyl 4-amino-benzoate by the same procedure as in the manufacturing method described in step C of Example 1-3-1.

ESI (LC/MS positive mode) m/z 343 (M+H$^{30}$); retention time 2.92 min (Condition 1 for high-performance liquid chromatography).

Example 1-3-31

Production of 3-N-(5-chloro-pyridin-2-yl)-4-methoxyisophthalamide (Compound 1-3-31)

[Formula 110]

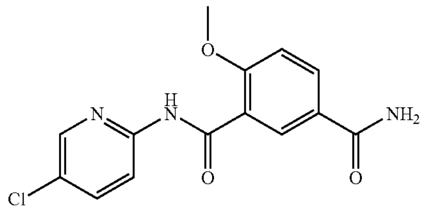

The captioned compound was synthesized from 6-methoxyisophthalamic acid and 2-amino-5-chloro-pyridine by the same procedure as in the manufacturing method described in step C of Example 1-3-1.

ESI (LC/MS positive mode) 306, 308 (M+H$^+$); retention time 2.77 min (Condition 1 for high-performance liquid chromatography).

Example 1-3-32

Production of 4-methoxy-3-N-(4-tolyl)isophthalamide (Compound 1-3-32)

[Formula 111]

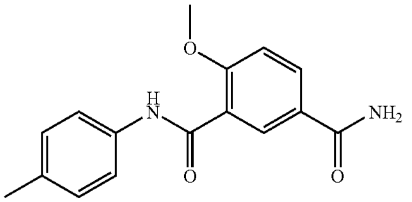

The captioned compound was synthesized from 6-methoxyisophthalamic acid and 4-methylaniline by the same procedure as in the manufacturing method described in step C of Example 1-3-1.

ESI (LC/MS positive mode) 285 ($M+H^+$); retention time 2.77 min (Condition 1 for high-performance liquid chromatography).

Example 1-3-33

Production of 4-methoxy-3-N-(5-methoxy-2-methylphenyl)isophthalamide (Compound 1-3-33)

[Formula 112]

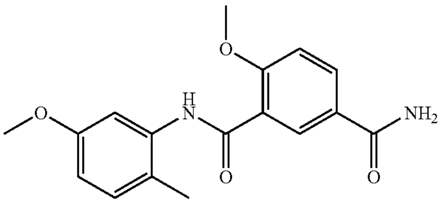

The captioned compound was synthesized from 6-methoxyisophthalamic acid and 5-methoxy-2-methylaniline by the same procedure as in the manufacturing method described in step C of Example 1-3-1.

ESI (LC/MS positive mode) 315 ($M+H^+$); retention time 2.79 min (Condition 1 for high-performance liquid chromatography).

Example 1-3-34

Production of 4-methoxy-3-N-(3-methoxy-5-trifluoromethylphenyl)isophthalamide (Compound 1-3-34)

[Formula 113]

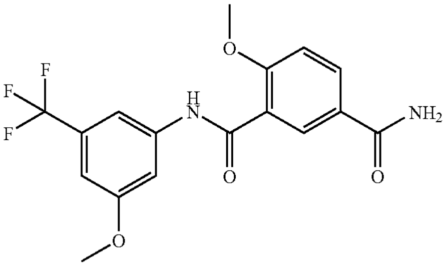

The captioned compound was synthesized from 6-methoxyisophthalamic acid and 3-methoxy-5-trifluoromethylaniline by the same procedure as in the manufacturing method described in step C of Example 1-3-1.

ESI (LC/MS positive mode) 369 ($M+H^+$); retention time 3.17 min (Condition 1 for high-performance liquid chromatography).

Example 1-3-35

Production of 3-N-(2,4-dimethoxyphenyl)-4-methoxyisophthalamide (Compound 1-3-35)

[Formula 114]

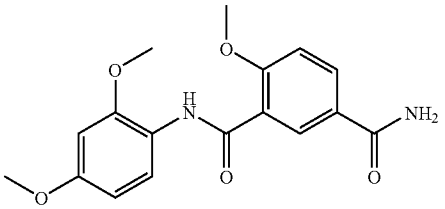

The captioned compound was synthesized from 6-methoxyisophthalamic acid and 2,4-dimethoxyaniline by the same procedure as in the manufacturing method described in step C of Example 1-3-1.

ESI (LC/MS positive mode) 331 ($M+H^+$); retention time 2.77 min (Condition 1 for high-performance liquid chromatography).

Example 1-3-36

Production of 3-N-(2-chloro-5-methylphenyl)-4-methoxyisophthalamide (Compound 1-3-36)

[Formula 115]

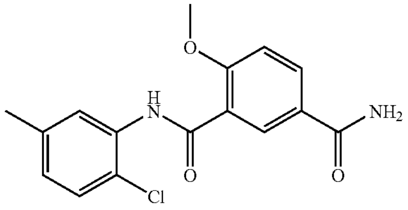

The captioned compound was synthesized from 6-methoxyisophthalamic acid and 2-chloro-5-methylaniline by the same procedure as in the manufacturing method described in step C of Example 1-3-1.

ESI (LC/MS positive mode) 319, 321 ($M+H^+$); retention time 3.18 min (Condition 1 for high-performance liquid chromatography).

Example 1-3-37

Production of 3-N-(2-chloro-5-methylphenyl)-4-methoxyisophthalamide (Compound 1-3-37)

[Formula 116]

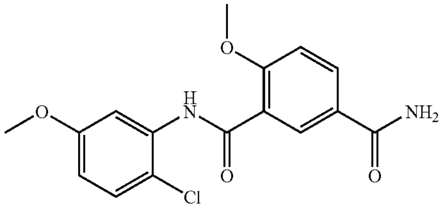

The captioned compound was synthesized from 6-methoxyisophthalamic acid and 2-chloro-5-methoxyaniline by the same procedure as in the manufacturing method described in step C of Example 1-3-1.

ESI (LC/MS positive mode) 335, 337 ($M+H^+$); retention time 3.06 min (Condition 1 for high-performance liquid chromatography).

Example 1-3-38

Production of 4-methoxy-3-N-naphthalen-1-yl-isophthalamide (Compound 1-3-38)

[Formula 117]

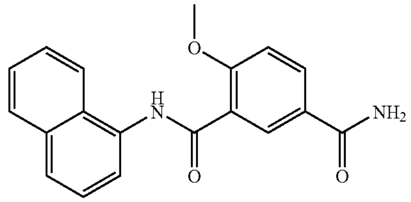

The captioned compound was synthesized from 6-methoxyisophthalamic acid and 1-naphthaleneamine by the same procedure as in the manufacturing method described in step C of Example 1-3-1.

ESI (LC/MS positive mode) 321 ($M+H^+$); retention time 2.90 min (Condition 1 for high-performance liquid chromatography).

Example 1-3-39

Production of 4-methoxy-3-N-quinolin-5-yl-isophthalamide (Compound 1-3-39)

[Formula 118]

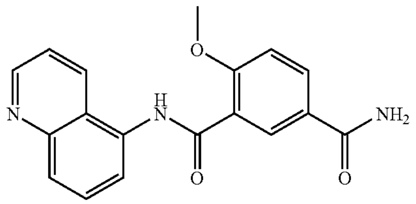

The captioned compound was synthesized from 6-methoxyisophthalamic acid and 5-aminoquinoline by the same procedure as in the manufacturing method described in step C of Example 1-3-1.

ESI (LC/MS positive mode) 322 ($M+H^+$); retention time 2.93 min (Condition 5 for high-performance liquid chromatography).

Example 1-3-40

Production of 3-N-(1H-indol-5-yl)-4-methoxyisophthalamide (Compound 1-3-40)

[Formula 119]

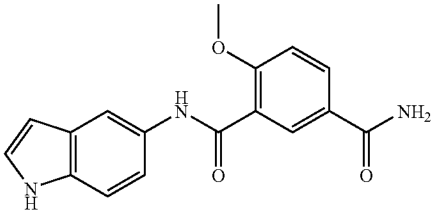

The captioned compound was synthesized from 6-methoxyisophthalamic acid and 5-aminoindole by the same procedure as in the manufacturing method described in step C of Example 1-3-1.

ESI (LC/MS positive mode) 310 ($M+H^+$); retention time 2.44 min (Condition 1 for high-performance liquid chromatography).

Example 1-3-41

Production of 3-N-(4-bromo-2-chlorophenyl)-4-methoxyisophthalamide (Compound 1-3-41)

[Formula 120]

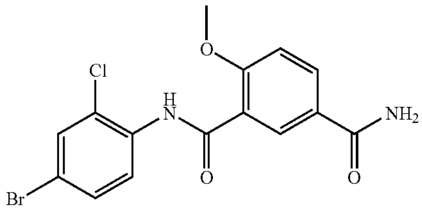

The captioned compound was synthesized from 6-methoxyisophthalamic acid and 4-bromo-2-chloroaniline by the same procedure as in the manufacturing method described in step C of Example 1-3-1.

ESI (LC/MS positive mode) 383, 385, 387 ($M+H^+$); retention time 3.39 min (Condition 1 for high-performance liquid chromatography).

Example 1-3-42

Production of 3-N-(2-bromo-4-chlorophenyl)-4-methoxyisophthalamide (Compound 1-3-42)

[Formula 121]

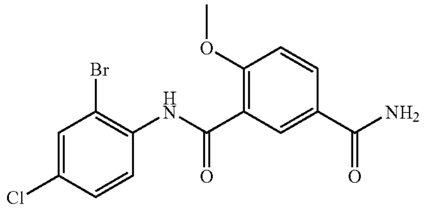

The captioned compound was synthesized from 6-methoxyisophthalamic acid and 2-bromo-4-chloroaniline by the same procedure as in the manufacturing method described in step C of Example 1-3-1.

ESI (LC/MS positive mode) 383, 385, 387 ($M+H^+$); retention time 3.36 min (Condition 1 for high-performance liquid chromatography).

Example 1-3-43

Production of 3-N-(2-chloro-4-trifluoromethylphenyl)-4-methoxyisophthalamide (Compound 1-3-43)

[Formula 122]

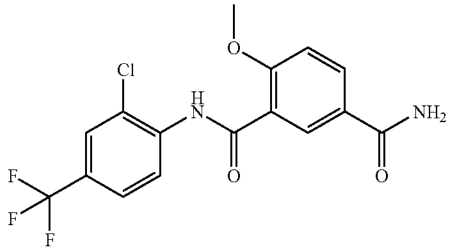

The captioned compound was synthesized from 6-methoxyisophthalamic acid and 2-chloro-4-trifluoromethylaniline by the same procedure as in the manufacturing method described in step C of Example 1-3-1.

ESI (LC/MS positive mode) 373, 375 ($M+H^+$); retention time 3.47 min (Condition 1 for high-performance liquid chromatography).

Example 1-3-44

Production of 3-N-(4-chloro-2-fluorophenyl)-4-methoxyisophthalamide (Compound 1-3-44)

[Formula 123]

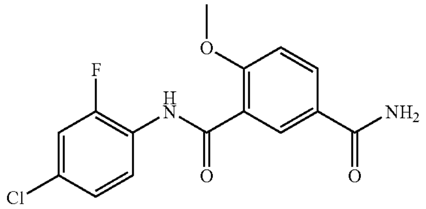

The captioned compound was synthesized from 6-methoxyisophthalamic acid and 4-chloro-2-fluoroaniline by the same procedure as in the manufacturing method described in step C of Example 1-3-1.

ESI (LC/MS positive mode) 323, 325 ($M+H^+$); retention time 3.09 min (Condition 1 for high-performance liquid chromatography).

Example 1-3-45

Production of 3-N-(2,4-dibromophenyl)-4-methoxyisophthalamide (Compound 1-3-45)

[Formula 124]

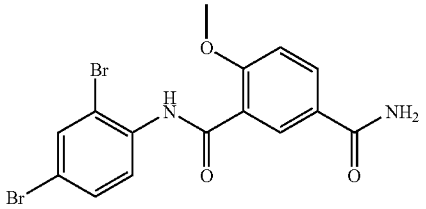

The captioned compound was synthesized from 6-methoxyisophthalamic acid and 2,4-dibromoaniline by the same procedure as in the manufacturing method described in step C of Example 1-3-1.

ESI (LC/MS positive mode) 427, 429, 431 ($M+H^+$); retention time 3.42 min (Condition 1 for high-performance liquid chromatography).

Example 1-3-46

Production of 3-N-(2,4-dichlorophenyl)-4-methoxyisophthalamide (Compound 1-3-46)

[Formula 125]

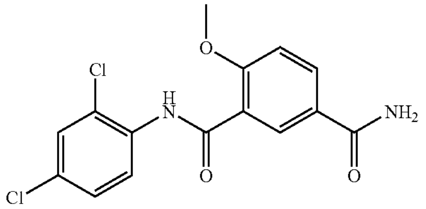

The captioned compound was synthesized from 6-methoxyisophthalamic acid and 2,4-dichloroaniline by the same procedure as in the manufacturing method described in step C of Example 1-3-1.

ESI (LC/MS positive mode) 339, 341, 343 ($M+H^+$); retention time 3.32 min (Condition 1 for high-performance liquid chromatography).

Example 1-3-47

Production of 4-methoxy-3-N-naphthalen-2-yl-isophthalamide (Compound 1-3-47)

[Formula 126]

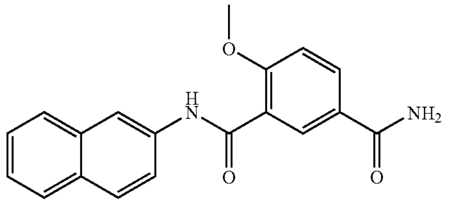

The captioned compound was synthesized from 6-methoxyisophthalamic acid and 2-naphthaleneamine by the same procedure as in the manufacturing method described in step C of Example 1-3-1.

ESI (LC/MS positive mode) 321 (M+H$^+$); retention time 3.10 min (Condition 1 for high-performance liquid chromatography).

Example 1-3-48

Production of 3-N-(2-bromo-4-trifluoromethoxyphenyl)-4-methoxyisophthalamide (Compound 1-3-48)

[Formula 127]

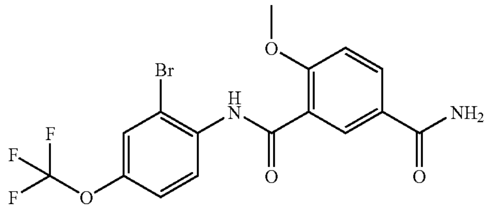

The captioned compound was synthesized from 6-methoxyisophthalamic acid and 2-bromo-4-trifluoromethoxyaniline by the same procedure as in the manufacturing method described in step C of Example 1-3-1.

ESI (LC/MS positive mode) 433, 435 (M+H$^+$); retention time 3.62 min (Condition 1 for high-performance liquid chromatography).

Example 1-3-49

Production of 3-N-(5-bromo-pyridin-2-yl)-4-methoxy-isophthalamide (Compound 1-3-49)

[Formula 128]

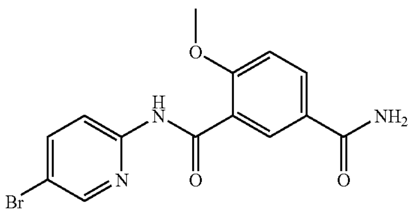

The-captioned compound was synthesized from 6-methoxyisophthalamic acid and 2-amino-5-bromopyridine by the same procedure as in the manufacturing method described in step C of Example 1-3-1.

ESI (LC/MS positive mode) 350, 352 (M+H$^+$); retention time 2.86 min (Condition 1 for high-performance liquid chromatography).

Example 1-3-50

Production of 4-methoxy-3-N-quinolin-2-yl-isophthalamide (Compound 1-3-50)

[Formula 129]

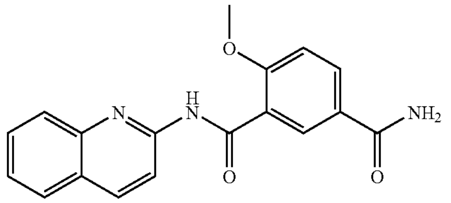

The captioned compound was synthesized from 6-methoxyisophthalamic acid and 2-aminoquinoline by the same procedure as in the manufacturing method described in step C of Example 1-3-1.

ESI (LC/MS positive mode) 322 (M+H$^+$); retention time 2.42 min (Condition 1 for high-performance liquid chromatography).

Example 1-4-1

Production of 3-N-(4-trifluoromethoxy-2-chlorophenyl)-4-methoxyisophthalamide (Compound 1-4-1)

[Formula 130]

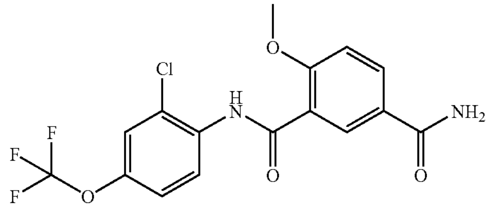

Step A

Preparation of 5-cyano-2-methoxybenzoic acid (CAS registry number: 84923-71-7)

[Formula 131]

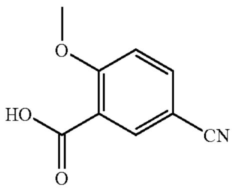

Methyl 5-cyano-2-methoxybenzoate (2 g) obtained in step A of Example 1-3-1 was dissolved in 28 mL of 1,4-dioxane, and 21 mL of an aqueous solution of 2.5 mols of sodium hydroxide was added. After stirring for 30 minutes at room temperature, the reaction mixture was cooled in an ice bath, and neutralized with the use of 50 mL of 1 M hydrochloric acid. The resulting aqueous solution was extracted 6 times with methylene chloride. The respective organic layers were combined, whereafter the combined organic layer was washed with a saturated aqueous solution of sodium chloride, and dried over anhydrous sodium sulfate. The anhydrous sodium sulfate was separated by filtration, and washed with methylene chloride. The filtrate and the. washings were combined, and methylene chloride was distilled off under reduced pressure. The resulting solid was dried under reduced pressure to obtain 1.6 g (87%) of 5-cyano-2-methoxybenzoic acid.

$^1$H-NMR (400 MHz, DMSO-$d_6$) δ 3.91 (3H, s), 7.32 (1H, d, J=8.8 Hz), 7.98 (1H, dd, J=8.8 Hz, 2.0 Hz), 8.02 (1H, d, J=2.0 Hz), 13.15 (1H, s).

ESI (LC/MS positive mode) m/z 178 (M+H$^+$); retention time 1.94 min (Condition 1 for high-performance liquid chromatography).

Step B

Preparation of 5-cyano-N-(4-trifluoromethoxy-2-chlorophenyl)-2-methoxybenzamide

[Formula 132]

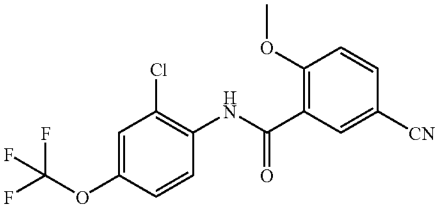

5-Cyano-2-methoxybenzoic-acid (0.73 g) obtained in step A, and 16 μL of N,N-dimethylformamide were dissolved in 18 mL of dichloromethane, and the solution was cooled to 0° C. To this solution, 0.54 mL of oxalyl chloride was added little by little, and the mixture was stirred for 2.7 hours at room temperature. The reaction mixture was distilled under reduced pressure, and dried to obtain a light yellow solid. This solid was added, with the use of 10 mL of tetrahydrofuran, to a solution of 0.95 g of 4-trifluoromethoxy-2-chloroaniline and 2.1 mL of N,N-diisopropylethylamine dissolved in 20 mL of tetrahydrofuran. The mixture was stirred overnight at room temperature, and then tetrahydrofuran was distilled off under reduced pressure. The resulting solid was purified by silica gel column chromatography using methylene chloride as an elution solvent, thereby obtaining 1.37 g (90%) of 5-cyano-N-(4-trifluoromethoxy-2-chlorophenyl)-2-methoxybenzamide.

$^1$H-NMR (400 MHz, DMSO-$d_6$) δ 4.13 (3H, s), 7.48 (2H, d, J=8.8 Hz), 7.75 (1H, d, J=2.1 Hz), 8.09 (1H, dd, J=8.8 Hz, 2.1 Hz), 8.30 (1H, s), 8.37 (1H, d, J=8.8 Hz), 10.41 (1H, s).

ESI (LC/MS positive mode) m/z 371, 373 (M+H$^+$); retention time 3.54 min (Condition 2 for high-performance liquid chromatography).

Step C

Preparation of 3-N-(4-trifluoromethoxy-2-chlorophenyl)-4-methoxyisophthalamide

[Formula 133]

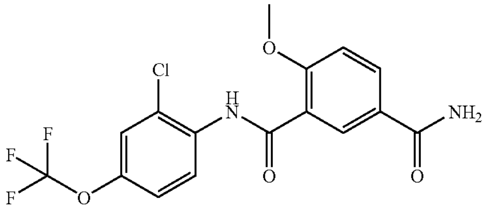

The captioned compound was synthesized from 5-cyano-N-(4-trifluoromethoxy-2-chlorophenyl)-2-methoxybenzamide obtained in step B by the same procedure as in step E of Example 1-1-1.

$^1$H-NMR (400 MHz, $CD_3OD$) δ 4.19 (3H, s), 7.33 (1H, d, J=8.8 Hz), 7.35 (1H, d, J=8.8 Hz), 7.50 (1H, s), 8.12 (1H, dd, J=8.8 Hz, 2.4 Hz), 8.64 (1H, d, J=8.8 Hz), 8.72 (1H, d, J=2.4 Hz).

ESI (LC/MS positive mode) m/z 389, 391 (M+H$^+$); retention time 3.46 min (Condition 1 for high-performance liquid chromatography).

Example 1-4-2

Production of 3-N-(2-bromo-4-trifluoromethyl-phenyl)-4-methoxy-isophthalamide (Compound 1-4-2)

[Formula 134]

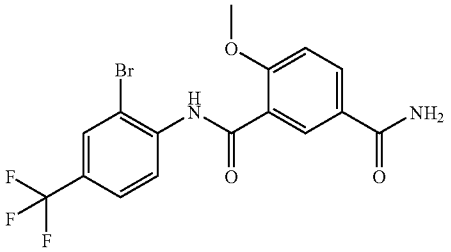

The captioned compound was synthesized from 5-cyano-2-methoxybenzoic acid and 2-bromo-4-trifluoromethylaniline by the same procedure as in the manufacturing method described in steps B and C of Example 1-4-1.

ESI (LC/MS positive mode) 417, 419 (M+H$^+$); retention time 3.52 min (Condition 1 for high-performance liquid chromatography).

Example 1-4-3

Production of 4-methoxy-3-N-(5-trifluoromethyl-pyridin-2-yl)-isophthalamide (Compound 1-4-3)

[Formula 135]

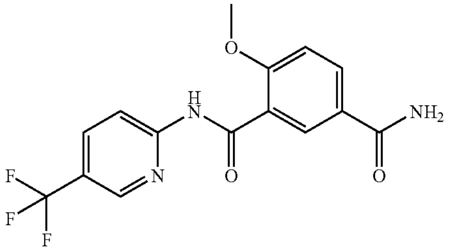

The captioned compound was synthesized from 5-cyano-2-methoxybenzoic acid and 2-amino-5-trifluoromethylpyridine by the same procedure as in the manufacturing method described in steps B and C of Example 1-4-1.

ESI (LC/MS positive mode) 340 (M+H$^+$); retention time 3.02 min (Condition 1 for high-performance liquid chromatography).

Example 1-4-4

Production of 3-N-(3-bromo-pyridin-4-yl)-4-methoxy-isophthalamide (Compound 1-4-4)

[Formula 136]

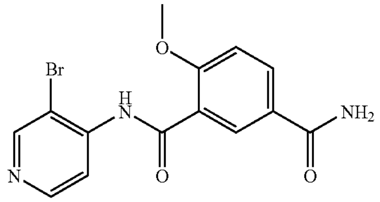

The captioned compound was synthesized from 5-cyano-2-methoxybenzoic acid and 4-amino-3-bromopyridine by the same procedure as in the manufacturing method described in steps B and C of Example 1-4-1.

ESI (LC/MS positive mode) 350, 352 (M+H$^+$); retention time 2.03 min (Condition 1 for high-performance liquid chromatography).

Example 1-4-5

Production of 3-N-(2,6-dimethoxy-pyridin-3-yl)-4-methoxyisophthalamide (Compound 1-4-5)

[Formula 137]

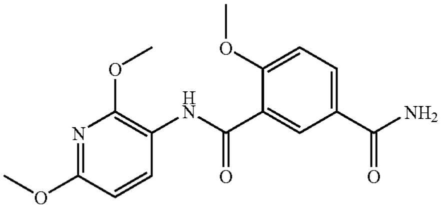

The captioned compound was synthesized from 5-cyano-2-methoxybenzoic acid and 3-amino-2,6-dimethoxypyridine by the same procedure as in the manufacturing method described in steps B and C of Example 1-4-1.

ESI (LC/MS positive mode) 332 (M+H$^+$); retention time 2.94 min (Condition 1 for high-performance liquid chromatography).

Example 1-4-6

Production of N-benzothiazol-2-yl-4-methoxyisophthalamide (Compound 1-4-6)

[Formula 138]

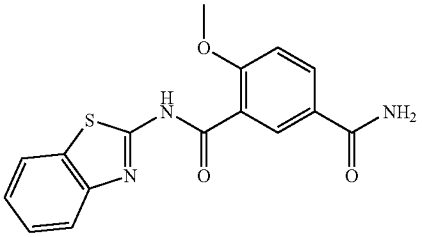

The captioned compound was synthesized from 5-cyano-2-methoxybenzoic acid and 2-aminobenzothiazole by the same procedure as in the manufacturing method described in steps B and C of Example 1-4-1.

ESI (LC/MS positive mode) m/z 328 (M+H$^+$); retention time 2.77 min (Condition 1 for high-performance liquid chromatography).

Example 1-4-7

Production of N-(2-acetylthiophen-3-yl)-4-methoxy-isophthalamide (Compound 1-4-7).

[Formula 139]

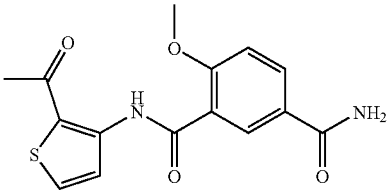

The captioned compound was synthesized from 5-cyano-2-methoxybenzoic acid and 2-acetyl-3-aminothiophene by the same procedure as in the manufacturing method described in steps B and C of Example 1-4-1.

ESI (LC/MS positive mode) m/z 319 (M+H$^+$); retention time 2.70 min (Condition 1 for high-performance liquid chromatography).

Example 2-1-1

Production of 4-methoxy-3-[(E)-2-(4-trifluoromethoxyphenyl)vinyl]benzamide (Compound 2-1-1)

[Formula 140]

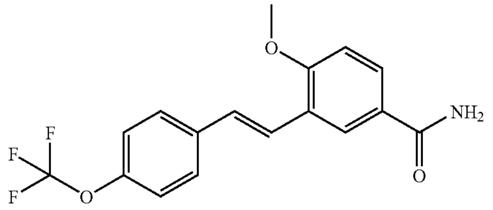

Step A

Preparation of 4-bromo-1-methoxy-2-[(E)-2-(4-trifluoromethoxyphenyl)vinyl]benzene

[Formula 141]

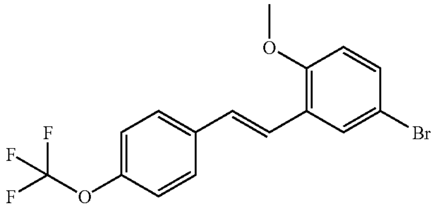

60% Oil-suspended sodium hydride (20.5 mg) was washed with n-hexane, and then suspended in 2 mL of tetrahydrofuran. To this suspension, 0.13 mL of diethyl (4-trifluoromethoxybenzyl)phosphonate was added in a stream of nitrogen while cooled with ice, and then the mixture was heated for 5 minutes under reflux. This mixture was cooled again in an ice bath, and 0.1 g of 5-bromo-2-methoxybenzaldehyde (CAS registry number: 25016-01-7) was added. The reaction mixture was stirred for 6 hours at room temperature, then poured into water, and extracted with ethyl acetate 3 times. The respective organic layers were combined, whereafter the combined organic layer was washed with a saturated aqueous solution of sodium chloride, and dried over anhydrous sodium sulfate. The anhydrous sodium sulfate was separated by filtration, and washed with ethyl acetate. The filtrate and the washings were combined, and ethyl acetate was distilled off under reduced pressure. The residue was purified by column chromatography (5 g silica gel) using a 1:10 mixture of ethyl acetate and n-hexane as an elution solvent, thereby obtaining 152 mg (88%) of 4-bromo-1-methoxy-2-[(E)-2-(4-trifluoromethoxyphenyl)vinyl]benzene.

$^1$H-NMR (400 MHz, $CDCl_3$) δ 3.87 (3H, s), 6.77 (1H, d, J=8.8 Hz), 7.05 (1H, d, J=16.1 Hz), 7.19 (2H, d, J=8.3 Hz), 7.34 (1H, d, J=16.1 Hz), 7.34 (1H, dd, J=8.6 Hz, 2.4 Hz), 7.52 (2H, d, J=8.8 Hz), 7.67 (1H, d, J=2.4 Hz).

EIMS m/z 372, 374 ($M^+$).

Step B

Preparation of 4-methoxy-3-[(E)-2-(4-trifluoromethoxy-phenyl)vinyl]benzonitrile

[Formula 142]

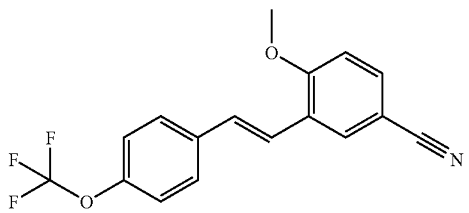

The captioned compound was synthesized from 4-bromo-1-methoxy-2-[(E)-2-(4-trifluoromethoxyphenyl)vinyl]benzene obtained in step A in accordance with the same procedure as in the methods described in step D of Example 1-1-1.

$^1$H-NMR (400 MHz, $CDCl_3$) δ 3.95 (3H, s), 6.94 (1H, d, J=8.8 Hz), 7.09 (1H, d, J=16.6 Hz), 7.21 (2H, d, J=8.8 Hz), 7.33 (1H, d, J=16.6 Hz), 7.54 (2H, d, J=8.8 Hz), 7.55 (1H, dd, J=8.8 Hz, 2.0 Hz), 7.83 (1H, d, J=2.0 Hz).

EIMS m/z 319 ($M^+$).

Step C

Preparation of 4-methoxy-3-[(E)-2-(4-trifluoromethoxy-phenyl)vinyl]benzamide (Compound 2-1-1)

[Formula 143]

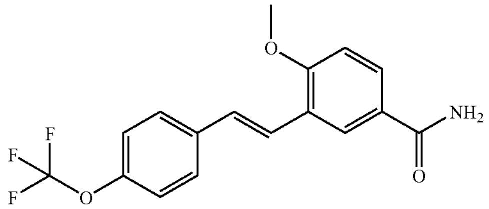

The captioned compound was synthesized from 4-methoxy-3-[(E)-2-(4-trifluoromethoxy-phenyl)vinyl]benzonitrile obtained in step B in accordance with the same procedure as in the methods described in step E of Example 1-1-1.

$^1$H-NMR (400 MHz, DMSO-$d_6$) δ 3.92 (3H, s), 6.93 (1H, d, J=8.8 Hz), 7.17 (1H, d, J=16.6 Hz), 7.20 (2H, d, J=8.5 Hz), 7.41 (1H, d, J=16.6 Hz), 7.55 (2H, d, J=8.8 Hz), 7.70 (1H, dd, J=8.8 Hz, 2.4 Hz), 8.09 (1H, d, J=2.4 Hz).

ESI (LC/MS positive mode) m/z. 338 ($M+H^+$); retention time 2.91 min (Condition 2 for high-performance liquid chromatography).

Example 2-2-1

Production of N-cyclopentyl-4-methoxy-3-[(E)-2-(4-trifluoromethoxy-phenyl)vinyl]benzamide (Compound 2-2-1)

[Formula 144]

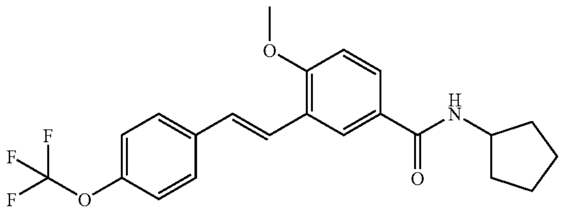

Step A

Preparation of ethyl 4-methoxy-3-[(E)-2-(4-trifluoromethoxyphenyl)vinyl]benzoate

[Formula 145]

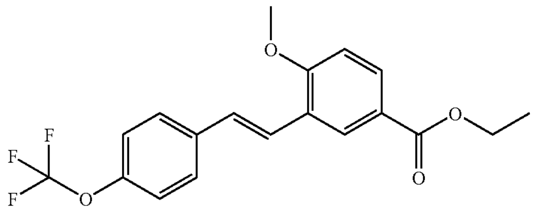

60% Oil-suspended sodium hydride (0.7 g) was washed with n-hexane, and then suspended in 48 mL of tetrahydrofuran. To this suspension, 5.78 g of diethyl (4-trifluoromethoxybenzyl)phosphonate was added in a stream of nitrogen while cooled with ice, and then the mixture was heated for 5 minutes under reflux. This mixture was cooled again in an ice bath, and 3.5 g of ethyl 3-formyl-4-methoxybenzoate obtained in Step C of Example 1-2-1 was added. The reaction mixture was stirred overnight at room temperature, then poured into water, and extracted with ethyl acetate 3 times. The respective organic layers were combined, whereafter the combined organic layer was washed with a saturated aqueous solution of sodium chloride, and dried over anhydrous sodium sulfate. The anhydrous sodium sulfate was separated by filtration, and washed with ethyl acetate. The filtrate and the washings were combined, and ethyl acetate was distilled off under reduced pressure. The residue was purified by column chromatography (100 g silica gel) using a 20:1 mixture of ethyl acetate and n-hexane as an elution solvent, thereby obtaining 5.5 g (90%) of ethyl 4-methoxy-3-[(E)-2-(4-trifluoromethoxyphenyl)vinyl]benzoate.

$^1$H-NMR (400 MHz, $CDCl_3$) δ 1.41 (3H, t, J=7.1 Hz), 3.95 (3H, s), 4.39 (2H, q, J=7.1 Hz), 6.79 (1H, d, J=8.6 Hz), 7.17 (1H, d, J=16.6 Hz), 7.20 (2H, d, J=8.8 Hz), 7.41 (1H, d, J=16.6 Hz), 7.56 (2H, d, J=8.8 Hz), 7.97 (1H, dd, J=8.6 Hz, 2.4 Hz), 8.27 (1H, d, J=2.4 Hz).

ESI (LC/MS positive mode) m/z 367 ($M+H^+$); retention time 4.21 min (Condition 2 for high-performance liquid chromatography).

Step B

Preparation of 4-methoxy-3-[(E)-2-(4-trifluoromethoxyphenyl)vinyl]benzoic acid

[Formula 146]

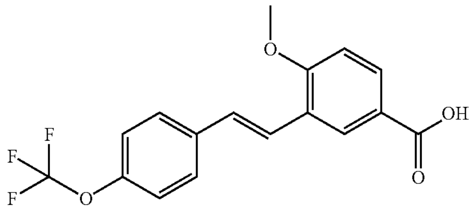

Ethyl 4-methoxy-3-[(E)-2-(4-trifluoromethoxyphenyl)vinyl]benzoate (4.5 g) obtained in step A was dissolved in 40 mL of methanol, and 16 mL of a 20% aqueous solution of potassium hydroxide was added. The resulting solution was stirred for 2 hours at 80° C., and then cooled to room temperature. The reaction mixture was adjusted to pH of about 3 with the use of 60 mL of 1 M hydrochloric acid. The resulting precipitate was separated by filtration, washed with water, and then dried over diphosphorus pentoxide under reduced pressure to obtain 4.1 g (99%) of 4-methoxy-3-[(E)-2-(4-trifluoromethoxyphenyl)vinyl]benzoic acid.

$^1$H-NMR (400 MHz, $CDCl_3$) δ 3.98 (3H, s), 6.97 (1H, d, J=8.8 Hz), 7.19 (1H, d, J=16.6 Hz), 7.21 (2H, d, J=8.3 Hz), 7.42 (1H, d, J=16.6 Hz), 7.57 (2H, d, J=8.3 Hz), 8.04 (1H, dd, J=8.8 Hz, 2.1 Hz), 8.34 (1H, d, J=2.1 Hz).

ESI (LC/MS positive mode) m/z 339 ($M+H^+$); retention time 3.88 min (Condition 1 for high-performance liquid chromatography).

Step C

Production of N-cyclopentyl-4-methoxy-3-[(E)-2-(4-trifluoromethoxy-phenyl)vinyl]benzamide (Compound 2-2-1)

[Formula 147]

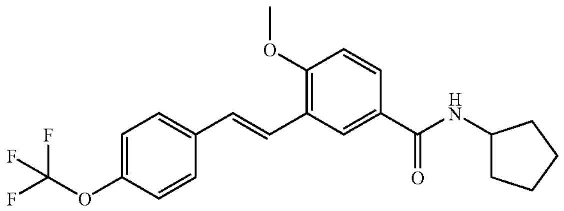

The captioned compound was synthesized from 4-methoxy-3-[(E)-2-(4-trifluoromethoxyphenyl)vinyl]benzoic acid obtained in step B of Example 2-2-1 and cyclopentylamine in accordance with the same procedure as in the methods described in step C of Example 1-2-3.

$^1$H-NMR (270 MHz, $CD_3OD$) δ 1.52-1.72 (4H, m), 1.72-1.88 (2H, m), 1.98-2.11 (2H, m), 3.95 (3H, s), 4.25-4.40 (1H, m), 7.06 (1H, d, J=8.6 Hz), 7.26 (2H, d, J=8.9 Hz), 7.28 (1H, d, J=16.9 Hz), 7.49 (1H, d, J=16.9 Hz), 7.64 (2H, d, J=8.9 Hz), 7.77 (1H, dd, J=8.6 Hz, 2.3 Hz), 8.13 (1H, d, J=2.3 Hz).

ESI: (LC/MS positive mode) m/z 406 ($M+H^+$); retention time 3.89 min (Condition 3 for high-performance liquid chromatography).

Example 2-2-2

Production of 4-methoxy-N-methyl-3-[(E)-2-(4-trifluoromethoxyphenyl)-vinyl]-benzamide (Compound 2-2-2)

[Formula 148]

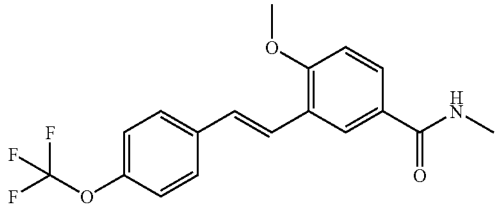

The captioned compound was synthesized from 4-methoxy-3-[(E)-2-(4-trifluoromethoxyphenyl)vinyl]benzoic acid obtained in step B of Example 2-2-1 and methylamine hydrochloride in accordance with the same procedure as in the methods described in step C of Example 1-2-3.

$^1$H-NMR (270 MHz, $CD_3OD$) δ 2.92 (3H, s), 3.96 (3H, s), 7.08 (1H, d, J=8.9 Hz), 7.26 (2H, d, J=8.5 Hz), 7.26 (1H, d, J=16.8 Hz), 7.49 (1H, d, J=16.8 Hz), 7.63 (2H, d, J=8.5 Hz), 7.76 (1H, dd, J=8.9 Hz, 2.3 Hz), 8.12 (1H, d, J=2.3 Hz).

ESI (LC/MS positive mode) m/z 352 ($M+H^+$); retention time 3.40 min (Condition 3 for high-performance liquid chromatography).

Example 2-2-3

Production of N-ethyl-4-methoxy-3-[(E)-2-(4-trifluoromethoxyphenyl)-vinyl]benzamide (Compound 2-2-3)

[Formula 149]

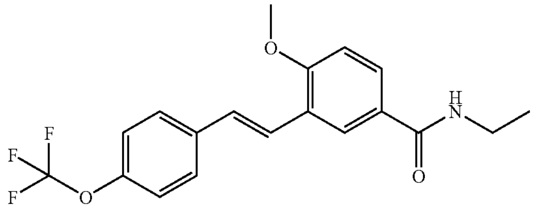

The captioned compound was synthesized from 4-methoxy-3-[(E)-2-(4-trifluoromethoxyphenyl)vinyl]benzoic acid and ethylamine hydrochloride in accordance with the same procedure-as in the methods described in step C of Example 1-2-3.

$^1$H-NMR (270 MHz, $CD_3OD$) δ 1.24 (3H, t, J=7.2 Hz), 3.42 (2H, q, J=7.2 Hz), 3.96 (3H, s), 7.07 (1H, d, J=8.6 Hz), 7.26 (2H, d, J=8.6 Hz), 7.27 (1H, d, J=16.5 Hz), 7.49 (1H, d, J=16.5 Hz), 7.64 (2H, d, J=8.6 Hz), 7.77 (1H, dd, J=8.6 Hz, 2.3 Hz), 8.13 (1H, d, J=2.3 Hz).

ESI (LC/MS positive mode) m/z 366 ($M+H^+$); retention time 3.55 min (Condition 3 for high-performance liquid chromatography).

Example 2-2-4

Production of N-cyclopropyl-4-methoxy-3-[(E)-2-(4-trifluoromethoxyphenyl)-vinyl]-benzamide (Compound 2-2-4)

[Formula 150]

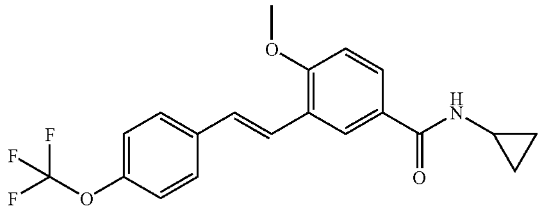

The captioned-compound was synthesized from 4-methoxy-3-[(E)-2-(4-trifluoromethoxyphenyl)vinyl]benzoic acid obtained in step B of Example 2-2-1 and cyclopropylamine in accordance with the same procedure as in the methods described in step C of Example 1-2-3.

$^1$H-NMR (270 MHz, $CD_3OD$) δ 0.59-0.70 (2H, m), 0.76-0.89 (2H, m), 2.78-2.90 (1H, m), 3.95 (3H, s), 7.06 (1H, d, J=8.6 Hz), 7.25 (2H, d, J=9.0 Hz), 7.26 (1H, d, J=16.5 Hz), 7.48 (1H, d, J=16.5 Hz), 7.64 (2H, d, J=9.0 Hz), 7.76 (1H, dd, J=8.6 Hz, 2.3 Hz), 8.11 (1H, d, J=2.3 Hz).

ESI (LC/MS positive mode) m/z 378 ($M+H^+$); retention time 3.55 min (Condition 3 for high-performance liquid chromatography).

Example 2-2-5

Production of 4-methoxy-N-(1-methoxymethyl-propyl)-3-[(E)-2-(4-trifluoromethoxyphenyl)-vinyl]-benzamide (Compound 2-2-5)

[Formula 151]

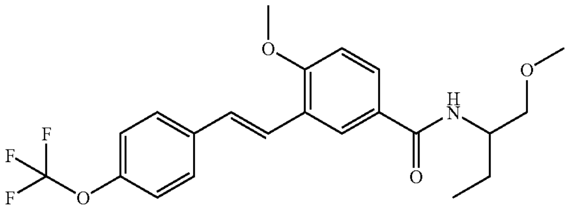

The captioned compound was synthesized from 4-methoxy-3-[(E)-2-(4-trifluoromethoxyphenyl)vinyl]benzoic acid obtained in step B of Example 2-2-1 and 2-amino-1-methoxybutane in accordance with the same procedure as in the methods described in step C of Example 1-2-3.

$^1$H-NMR (270 MHz, $CD_3OD$) δ 1.48-1.80 (2H, m), 3.38 (3H, s), 3.40-3.56 (2H, m), 3.96 (3H, s), 4.10-4.25 (1H, m), 7.08 (1H, d, J=8.8 Hz), 7.26 (2H, d, J=8.5 Hz), 7.28 (1H, d, J=16.9 Hz), 7.49 (1H, d, J=16.9 Hz), 7.64 (2H, d, J=8.5 Hz), 7.79 (1H, dd, J=8.8 Hz, 2.3 Hz), 8.15 (1H, d, J=2.3 Hz).

ESI (LC/MS positive mode) m/z 424 ($M+H^+$); retention time 3.72 min (Condition 3 for high-performance liquid chromatography).

Example 2-2-6

Production of N-[2-(2-hydroxyethoxy)-ethyl]-4-methoxy-3-[(E)-2-(4-chlorophenyl)-vinyl]-benzamide (Compound 2-2-6)

[Formula 152]

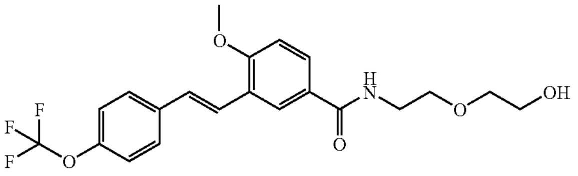

The captioned compound was synthesized from 4-methoxy-3-[(E)-2-(4-trifluoromethoxyphenyl)vinyl]benzoic acid obtained in step B of Example 2-2-1 and 2-(2-aminoethoxy)-ethanol in accordance with the same procedure as in the methods described in step C of Example 1-2-3.

ESI (LC/MS positive mode) m/z 426 ($M+H^+$); retention time 3.09 min (Condition 3 for high-performance liquid chromatography).

Example 2-2-7

Production of 3-[(E)-2-(4-chlorophenyl)vinyl]-4-methoxy-benzamide (Compound 2-2-7)

[Formula 153]

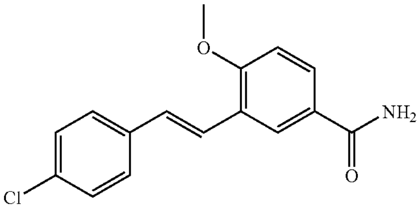

Step A

Preparation of ethyl 3-[(E)-2-(4-chlorophenyl)vinyl]-4-methoxy-benzoate

[Formula 154]

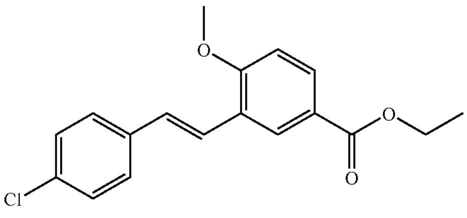

The captioned compound was synthesized from diethyl (4-chlorobenzyl)phosphonate and ethyl 3-formyl-4-methoxybenzoate obtained in step C of Example 1-2-1 in accordance with the same procedure as in the methods described in step A of Example 2-2-1.

$^1$H-NMR (400 MHz, $CDCl_3$) δ 1.41 (3H, t, J=7.2 Hz), 3.98 (3H, s), 4.38 (2H, q, J=7.2 Hz), 6.92 (1H, d, J=8.8 Hz), 7.15 (1H, d, J=16.4 Hz), 7.32 (2H, d, J=8.8 Hz), 7.41 (1H, d, J=16.4 Hz), 7.47 (2H, d, J=8.4 Hz), 7.95 (1H, dd, J=8.8 Hz, 2.4 Hz), 8.26 (1H, d, J=2.4 Hz).

Step B

Preparation of 3-[(E)-2-(4-chlorophenyl)vinyl]-4-methoxy-benzoic acid

[Formula 155]

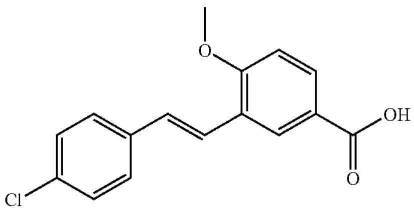

The captioned compound was synthesized using methyl 3-[(E)-2-(4-chlorophenyl)vinyl]-4-methoxy-benzoate obtained in step A in accordance with the same procedure as in the manufacturing method described in step B of Example 2-2-1.

$^1$H-NMR (400 MHz, DMSO-$d_6$) δ 3.94 (3H, s), 7.15 (1H, d, J=8.8 Hz), 7.30 (1H, d, J=16.6 Hz), 7.43 (2H, d, J=8.4 Hz), 7.43 (1H, d, J=16.6 Hz), 7.64 (2H, d, J=8.4 Hz), 7.88 (1H, dd, J=8.8 Hz, 2.1 Hz), 8.20 (1H, d, J=2.1 Hz), 12.8 (s, 1H).

ESI (LC/MS positive mode) m/z 289, 291 ($M+H^+$); retention time 4.00 min (Condition 1 for high-performance liquid chromatography).

Step C

Preparation of 3-[(E)-2-(4-chlorophenyl)vinyl]-4-methoxy-benzamide

[Formula 156]

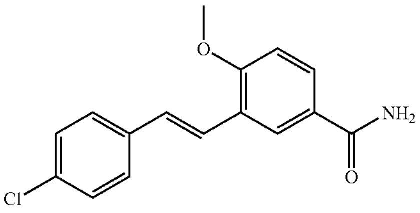

The captioned compound was synthesized from 3-[(E)-2-(4-chlorophenyl)vinyl]-4-methoxy-benzoic acid obtained in step B in accordance with the same procedure as in the manufacturing method described in step G of Example 1-2-1.

$^1$H-NMR (400 MHz, $CDCl_3$) δ 3.92 (3H, s), 7.10 (1H, d, J=8.8 Hz), 7.30 (1H, d, J=16.2 Hz), 7.43 (2H, d, J=8.6 Hz), 7.43 (1H, d, J=16.2 Hz), 7.61 (2H, d, J=8.6 Hz), 7.83 (1H, dd, J=8.8 Hz, 2.0 Hz), 7.93 (1H, brs), 8.21 (1H, d, J=2.0 Hz).

ESI (LC/MS positive mode) m/z 288, 290 (M+H$^+$); retention time 3.48 min (Condition 1 for high-performance liquid chromatography).

Example 2-2-8

Production of 3-[(E)-2-(4-chlorophenyl)-vinyl]-4-methoxy-N-methyl-benzamide (Compound 2-2-8)

[Formula 157]

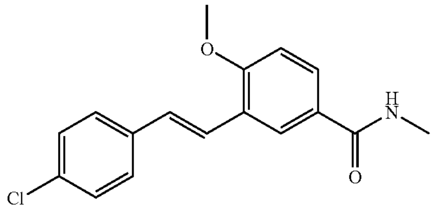

The captioned compound was synthesized from 3-[(E)-2-(4-chlorophenyl)vinyl]-4-methoxy-benzoic acid and methylamine hydrochloride in accordance with the same procedure as in the manufacturing method described in step G of Example 1-2-1.

$^1$H-NMR (270 MHz, $CDCl_3$) δ 3.02 (3H, d, J=4.6 Hz), 3.92 (3H, s), 6.16 (1H, bs), 6.90 (1H, d, J=8.6 Hz), 7.12 (1H, d, J=16.1 Hz), 7.32 (2H, d, J=8.6 Hz), 7.40 (1H, d, J=16.1 Hz), 7.45 (2H, d, J=8.6 Hz), 7.65 (1H, dd, J=8.6 Hz, 2.3 Hz), 8.01 (1H, d, J=2.3 Hz).

ESI (LC/MS positive mode) m/z 302 (M+H$^+$); retention time 3.31 min (Condition 3 for high-performance liquid chromatography).

Example 2-2-9

Production of 3-[(E)-2-(4-chlorophenyl)-vinyl]-N-ethyl-4-methoxy-benzamide (Compound 2-2-9)

[Formula 158]

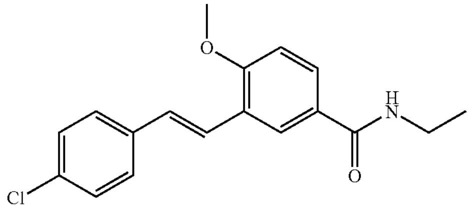

The captioned compound was synthesized from 3-[(E)-2-(4-chlorophenyl)vinyl]-4-methoxy-benzoic acid and ethylamine hydrochloride in accordance with the same procedure as in the manufacturing method described in step C of Example 1-2-3.

$^1$H-NMR (270 MHz, DMSO-$d_6$) δ 1.14 (3H, t, J=7.2 Hz), 3.30 (2H, dq, J=7.2 Hz, 6.9 Hz), 3.91 (3H, s), 7.11 (1H, d, J=8.6 Hz), 7.27 (1H, d, J=16.5 Hz), 7.43 (1H, d, J=8.6 Hz), 7.44 (1H, d, J=16.5 Hz), 7.44 (2H, d, J=8.6 Hz), 7.62 (2H, d, J=8.6 Hz), 7.80 (1H, dd, J=8.6 Hz, 2.3 Hz), 8.16 (1H, d, J=2.3 Hz), 8.42 (1H, bt, J=5.3 Hz).

ESI (LC/MS positive mode) m/z 316, 318 (M+H$^+$); retention time 3.81 min (Condition 3 for high-performance liquid chromatography).

Example 2-2-10

Production of 3-[(E)-2-(4-chlorophenyl)-vinyl]-N-cyclopentyl-4-methoxy-benzamide (Compound 2-2-10)

[Formula 159]

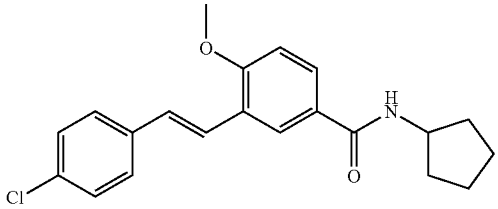

The captioned compound was synthesized from 3-[(E)-2-(4-chlorophenyl)vinyl]-4-methoxy-benzoic acid and cyclopentylamine in accordance with the same procedure as in the manufacturing method described in step C of Example 1-2-3.

$^1$H-NMR (270 MHz, DMSO-$d_6$) δ 1.42-1.61 (4H, m), 1.61-1.80 (2H, m), 1.80-1.95 (2H, m), 3.91 (3H, s), 4.21-4.26 (1H, m), 7.10 (1H, d, J=8.8 Hz), 7.28 (1H, d, J=16.5 Hz), 7.43 (2H, d, J=8.5 Hz), 7.43 (1H, d, J=16.5 Hz), 7.63 (2H, d, J=8.5 Hz), 7.81 (1H, dd, J=8.8 Hz, 2.0 Hz), 8.14 (1H, d, J=2.0 Hz), 8.21 (1H, bd, J=7.2 Hz).

ESI (LC/MS positive mode) m/z 356, 358 (M+H$^+$); retention time 4.20 min (Condition 3 for high-performance liquid chromatography).

Example 2-2-11

Production of 3-[(E)-2-(4-chlorophenyl)-vinyl]-N-cyclopropyl-4-methoxy-benzamide (Compound 2-2-11)

[Formula 160]

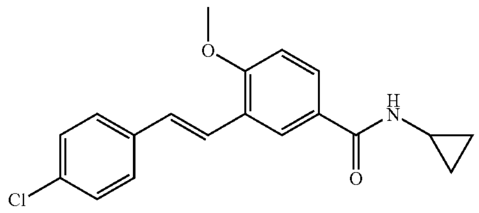

The captioned compound was synthesized from 3-[(E)-2-(4-chlorophenyl)vinyl]-4-methoxy-benzoic acid and cyclopropylamine in accordance with the same procedure as in the manufacturing method described in step C of Example 1-2-3.

$^1$H-NMR (270 MHz, DMSO-$d_6$) δ 0.50-0.62 (2H, m), 0.62-0.78 (2H, m), 2.74-2.92 (1H, m), 3.91 (3H, s), 7.10 (1H, d, J=8.7 Hz), 7.25 (1H, d, J=16.5 Hz), 7.43 (1H, d, J=16.5 Hz), 7.44 (2H, d, J=8.6 Hz), 7.62 (2H, d, J=8.6 Hz), 7.78 (1H, dd, J=8.7 Hz, 2.2 Hz), 8.12 (1H, d, J=2.2 Hz), 8.37 (1H, bd, J=4.0 Hz).

ESI (LC/MS positive mode) m/z 328, 330 (M+H$^+$); retention time 3.82 min (Condition 3 for high-performance liquid chromatography).

Example 2-2-12

Production of 3-[(E)-2-(4-chlorophenyl)-vinyl]-4-methoxy-N-(1-methoxymethyl-propyl)-benzamide (Compound 2-2-12)

[Formula 161]

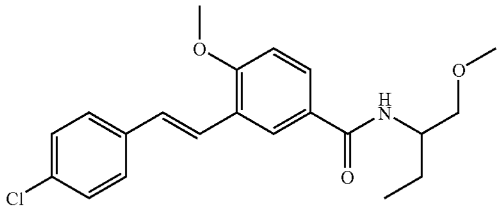

The captioned compound was synthesized from 3-[(E)-2-(4-chlorophenyl)vinyl]-4-methoxy-benzoic acid and 2-amino-1-methoxybutane in accordance with the same procedure as in the manufacturing method described in step C of Example 1-2-3.

$^1$H-NMR (270 MHz, $CD_3OD$) δ 0.98 (3H, t, J=6.6 Hz), 1.48-1.80 (2H, m), 3.37 (3H, s), 3.40-3.56 (2H, m), 3.94 (3H, s), 4.11-4.25 (1H, m), 7.05 (1H, d, J=8.6 Hz), 7.22 (1H, d, J=16.7 Hz), 7.33 (2H, d, J=8.5 Hz), 7.46 (1H, d, J=16.7 Hz), 7.51 (2H, d, J=8.5 Hz), 7.78 (1H, dd, J=8.6 Hz, 2.3 Hz), 8.13 (1H, d, J=2.3 Hz).

ESI (LC/MS positive mode) m/z 374, 376 (M+H$^+$); retention time 4.02 min (Condition 3 for high-performance liquid chromatography).

Example 2-2-13

Production of 3-[(E)-2-(4-chlorophenyl)-vinyl]-N-[2-(2-hydroxyethoxy)-ethyl]-4-methoxy-benzamide (Compound 2-2-13)

[Formula 162]

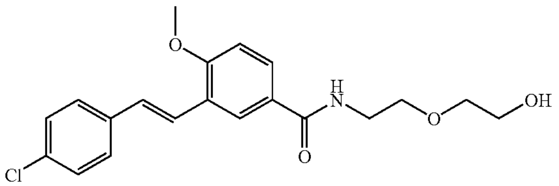

The captioned compound was synthesized from 3-[(E)-2-(4-chlorophenyl)vinyl]-4-methoxy-benzoic acid and 2-(2-aminoethoxy)-ethanol in accordance with the same procedure as in the manufacturing method described in step C of Example 1-2-3.

$^1$H-NMR (270 MHz, $CD_3OD$) δ 3.54-3.73 (8H, m), 3.95 (3H, s), 7.06 (1H, d, J=8.8 Hz), 7.23 (1H, d, J=16.8 Hz), 7.34 (2H, d, J=8.2 Hz), 7.46 (1H, d, J=16.8 Hz), 7.53 (2H, d, J=8.2 Hz), 7.78 (1H, dd, J=8.8 Hz, 2.1 Hz), 8.13 (1H, d, J=2.1 Hz).

ESI (LC/MS positive mode) m/z 376, 378 (M+H$^+$); retention time 3.37 min (Condition 3 for high-performance liquid chromatography).

Example 2-2-14

Production of 4-bromo-3-[(E)-2-(4-chlorophenyl)-vinyl]-benzamide (Compound 2-2-14)

[Formula 163]

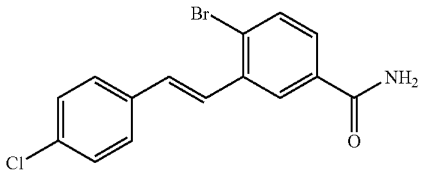

Step A

Preparation of methyl 4-bromo-3-[(E)-2-(4-chlorophenyl)-vinyl]-benzoate

[Formula 164]

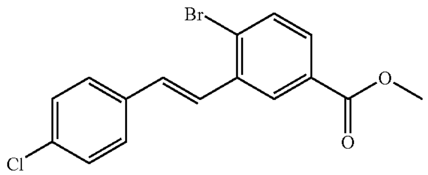

The captioned compound was synthesized from diethyl 4-chlorobenzylphosphonate and methyl 3-formyl-4-bromobenzoate in accordance with the same procedure as in the manufacturing method described in step A of Example 2-2-1.

ESI (LC/MS positive mode) m/z 351, 353 (M+H$^+$); retention time 4.77 min (Condition 1 for high-performance liquid chromatography).

Step B

Preparation of 4-bromo-3-[(E)-2-(4-chlorophenyl)-vinyl]-benzoic acid

[Formula 165]

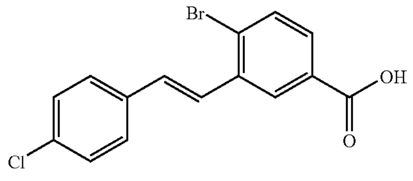

The captioned compound was synthesized from methyl 4-bromo-3-[(E)-2-(4-chlorophenyl)-vinyl]-benzoate obtained in step A in accordance with the same procedure as in the manufacturing method described in step B of Example 2-2-1.

$^1$H-NMR (270 MHz, DMSO-$d_6$) δ 7.37 (1H, d, J=16.2 Hz), 7.45 (1H, d, J=16.2 Hz), 7.48 (2H, d, J=8.6 Hz), 7.72 (2H, d, J=8.6 Hz), 7.76-7.84 (2H, m), 8.32 (1H, d, J=2.0 Hz), 13.32 (1H, bs).

Step C

Preparation of 4-bromo-3-[(E)-2-(4-chlorophenyl)-vinyl]-benzamide (Compound 2-2-14)

[Formula 166]

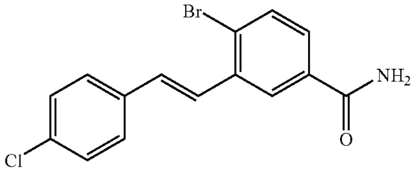

The captioned compound was synthesized from 4-bromo-3-[(E)-2-(4-chlorophenyl)-vinyl]-benzoic acid obtained in step B in accordance with the same procedure as in the manufacturing method described in step C of Example 2-2-1.

$^1$H-NMR (400 MHz, $CD_3OD$) δ 7.26 (1H, d, J=16.1 Hz), 7.39 (2H, d, J=8.8 Hz), 7.50 (1H, d, J=16.1 Hz), 7.59 (2H, d, J=8.8 Hz), 7.65 (1H, dd, J=8.3 Hz, 1.9 Hz), 7.72 (1H, d, J=8.3 Hz), 8.27 (1H, d, J=1.9 Hz).

ESI (LC/MS positive mode) 336, 338 ($M+H^+$); retention time 3.78 min (Condition 1 for high-performance liquid chromatography).

Example 2-2-15

Production of 3-[(E)-2-(4-chlorophenyl)-vinyl]-4-cyanobenzamide (Compound 2-2-15)

[Formula 167]

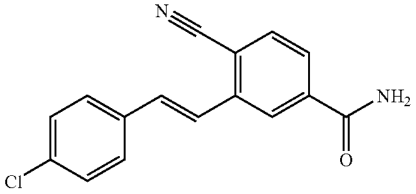

The captioned compound was synthesized from 4-bromo-3-[(E)-2-(4-chlorophenyl)-vinyl]-benzamide obtained in Example 2-2-14 in accordance with the same procedure as in the manufacturing method described in step D of Example 1-1-1.

$^1$H-NMR (270 MHz, DMSO-$d_6$) δ 7.42 (1H, d, J=16.4 Hz), 7.52 (2H, d, J=8.4 Hz), 7.64 (1H, d, J=16.4 Hz), 7.71 (2H, d, J=8.4 Hz), 7.76 (1H, bs), 7.89 (1H, dd, J=8.3 Hz, 1.3 Hz), 7.97 (1H, d, J=8.3 Hz), 8.28 (1H, bs), 8.45 (1H, d, J=1.3 Hz).

ESI (LC/MS positive mode) 324, 326 ($M+H^+$); retention time 3.44 min (Condition 1 for high-performance liquid chromatography).

Example 2-2-16

Production of 4-methoxy-N-[1,2,4]triazol-4-yl-3-[(E)-2-(4-trifluoromethoxyphenyl)-vinyl]benzamide (Compound 2-2-16)

[Formula 168]

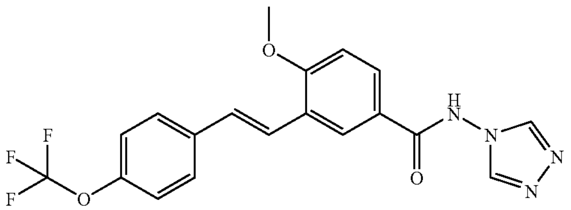

The captioned compound was synthesized from 4-methoxy-3-[(E)-2-(4-triflouromethoxyphenyl)vinyl]benzoic acid obtained in step B of Example 2-2-1 and 4-amino-1,2,4-triazole in accordance with the same procedure as in the methods described in step C of Example 1-2-3.

ESI (LC/MS positive mode) m/z 405 ($M+H^+$); retention time 2.75 min (Condition 2 for high-performance liquid chromatography).

Example 2-2-17

Production of 4-methoxy-N-pyrrolidin-1-yl-3-[(E)-2-(4-trifluoromethoxyphenyl)-vinyl]benzamide (Compound 2-2-17)

[Formula 169]

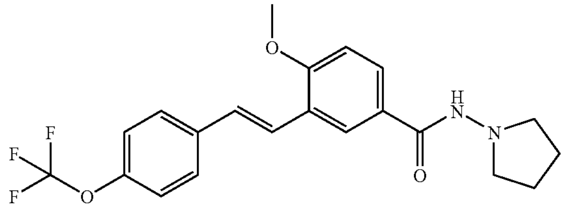

The captioned compound was synthesized from 4-methoxy-3-[(E)-2-(4-trifluormethoxyphenyl)vinyl]benzoic acid obtained in step B of Example 2-2-1 and 1-aminopyrrolidine hydrochloride in accordance with the same procedure as in the methods described in step C of Example 1-2-3.

ESI (LC/MS positive mode) m/z 407 ($M+H^+$); retention time 2.44 min (Condition 2 for high-performance liquid chromatography).

Example 2-2-18

Production of 4-methoxy-3-[(E)-2-(4-trifluoromethoxyphenyl)-vinyl]benzoic acid N'-benzylhydrazide (Compound 2-2-18)

[Formula 170]

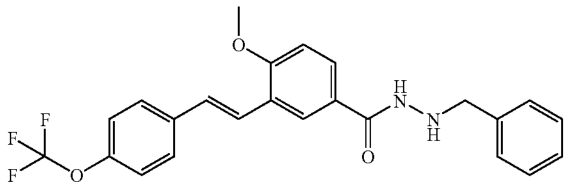

The captioned compound was synthesized from 4-methoxy-3-[(E)-2-(4-trifluoromethoxyphenyl)vinyl]benzoic acid obtained in step B of Example 2-2-1 and benzylhydrazine hydrochloride in accordance with the same procedure as in the methods described in step C of Example 1-2-3.

ESI (LC/MS positive mode) m/z 443 ($M+H^+$); retention time 3.57 min (Condition 2 for high-performance liquid chromatography).

Example 2-2-19

Production of 4-methoxy-3-[(E)-2-(4-trifluoromethoxyphenyl)-vinyl]benzoic acid N'-(2,2,2-trifluoroethyl)hydrazide (Compound 2-2-19)

[Formula 171]

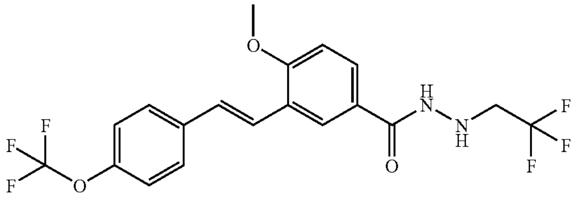

The captioned compound was synthesized from 4-methoxy-3-[(E)-2-(4-trifluoromethoxyphenyl)vinyl]benzoic acid obtained in step B of Example 2-2-1 and 2,2,2-trifluoroethylhydrazine in accordance with the same procedure as in the methods described in step C of Example 1-2-3.

ESI (LC/MS positive mode) m/z 435 ($M+H^+$); retention time 3.57 min (Condition 2 for high-performance liquid chromatography).

Example 2-2-20

Production of 4-methoxy-N-pyridin-4-ylmethyl-3-[(E)-2-(4-trifluoromethoxyphenyl)-vinyl]-benzamide (Compound 2-2-20)

[Formula 172]

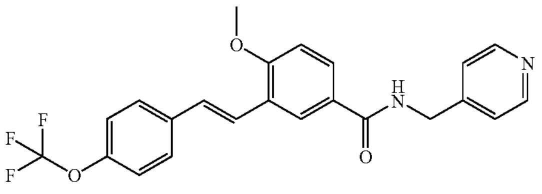

The captioned compound was synthesized from 4-methoxy-3-[(E)-2-(4-trifluoromethoxyphenyl)vinyl]benzoic acid obtained in step B of Example 2-2-1 and 4-(aminomethyl) pyridine in accordance with the same procedure as in the methods described in step C of Example 1-2-3.

ESI (LC/MS positive mode) m/z 429 ($M+H^+$); retention time 2.67 min (Condition 3 for high-performance liquid chromatography).

Example 2-2-21

Production of N-(2-cyanoethyl)-4-methoxy-3-[(E)-2-(4-trifluoromethoxyphenyl)-vinyl]-benzamide (Compound 2-2-21)

[Formula 173]

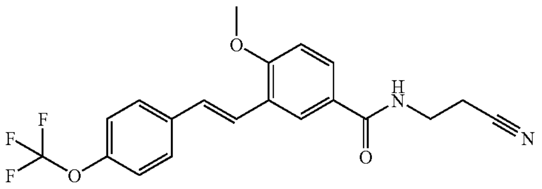

The captioned compound was synthesized from 4-methoxy-3-[(E)-2-(4-trifluoromethoxyphenyl)vinyl]benzoic acid obtained in step B of Example 2-2-1 and 3-aminopropionitrile in accordance with the same procedure as in the methods described in step C of Example 1-2-3.

$^1H$-NMR (270 MHz, $CDCl_3$) δ 2.70 (2H, t, J=6.0 Hz), 3.66 (2H, q, J=6.0 Hz), 3.87 (3H, s), 6.86 (1H, d, J=8.6 Hz), 7.09 (1H, d, J=16.5 Hz), 7.13 (2H, d, J=8.9 Hz), 7.33 (1H, d, J=16.5 Hz), 7.47 (2H, d, J=8.9 Hz), 7.60 (1H, dd, J=8.6 Hz, 2.3 Hz), 7.97 (1H, d, J=2.3 Hz).

ESI (LC/MS positive mode) m/z 391 ($M+H^+$); retention time 3.42 min (Condition 3 for high-performance liquid chromatography).

Example 2-2-22

Production of 4-methoxy-N-(2-methoxyethyl)-3-[(E)-2-(4-trifluoromethoxyphenyl)-vinyl]-benzamide (Compound 2-2-22)

[Formula 174]

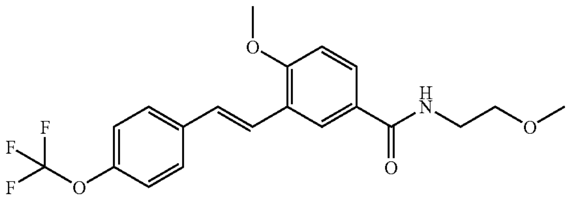

The captioned compound was synthesized from 4-methoxy-3-[(E)-2-(4-trifluoromethoxyphenyl)vinyl]benzoic acid obtained in step B of Example 2-2-1 and 2-methoxyethylamine in accordance with the same procedure as in the methods described in step C of Example 1-2-3.

ESI (LC/MS positive mode) m/z 396 ($M+H^+$); retention time 3.45 min (Condition 3 for high-performance liquid chromatography).

Example 2-2-23

Production of N-(2-hydroxyethyl)-4-methoxy-3-[(E)-2-(4-trifluoromethoxyphenyl)-vinyl]-benzamide (Compound 2-2-23)

[Formula 175]

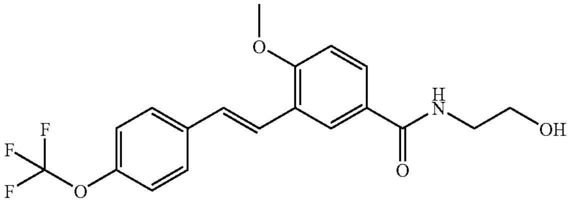

The captioned compound was synthesized from 4-methoxy-3-[(E)-2-(4-trifluoromethoxyphenyl)vinyl]benzoic acid obtained in step B of Example 2-2-1 and 2-aminoethanol in accordance with the same procedure as in the methods described in step C of Example 1-2-3.

ESI (LC/MS positive mode) m/z 382 ($M+H^+$); retention time 3.08 min (Condition 3 for high-performance liquid chromatography).

Example-2-2-24

Production of N-(2-hydroxy-1,1-bis-hydroxymethyl-ethyl)-4-methoxy-3-[(E)-2-(4-trifluoromethoxyphenyl)-vinyl]-benzamide

[Formula 176]

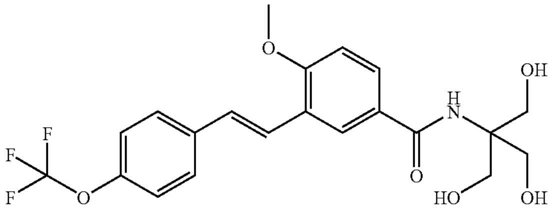

The captioned compound was synthesized from 4-methoxy-3-[(E)-2-(4-trifluoromethoxyphenyl)vinyl]benzoic acid obtained in step B of Example 2-2-1 and tris(hydroxymethyl) aminomethane in accordance with the same procedure as in the methods described in step C of Example 1-2-3.

ESI (LC/MS positive mode) m/z 442 ($M+H^+$); retention time 3.37 min (Condition 1 for high-performance liquid chromatography).

Example 2-2-25

Production of N-(2,3-dihydroxy-propyl)-4-methoxy-3-[(E)-2-(4-trifluoromethoxyphenyl)-vinyl]-benzamide (Compound 2-2-25)

[Formula 177]

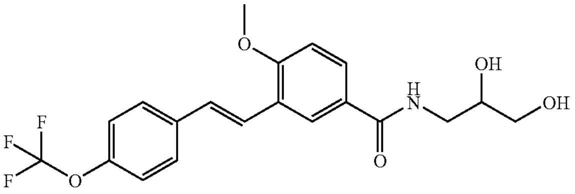

The captioned compound was synthesized from 4-methoxy-3-[(E)-2-(4-trifluoromethoxyphenyl)vinyl]benzoic acid obtained in step B of Example 2-2-1 and 3-amino-1,2-propanediol in accordance with the same procedure as in the methods described in step C of Example 1-2-3.

$^1H$-NMR (270 MHz, DMSO-$d_6$) δ 3.20-3.30 (1H, m), 3.30-3.50 (3H, m), 3.60-3.75 (1H, m), 3.92 (3H, s), 4.61 (1H, t, J=5.6 Hz), 4.85 (1H, d, J=4.6 Hz), 7.13 (1H, d, J=8.5 Hz), 7.30-7.50 (4H, m), 7.72 (2H, d, J=8.9 Hz), 7.82 (1H, dd, J=8.5 Hz, 2.0 Hz), 8.21 (1H, d, J=2.0 Hz), 8.41 (1H, bs).

ESI (LC/MS positive mode) m/z 412 ($M+H^+$); retention time 3.33 min (Condition 1 for high-performance liquid chromatography).

Example 2-2-26

Production of N-(2-hydroxy-1-hydroxymethyl-ethyl)-4-methoxy-3-[(E)-2-(4-trifluoromethoxyphenyl)-vinyl]-benzamide (Compound 2-2-26)

[Formula 178]

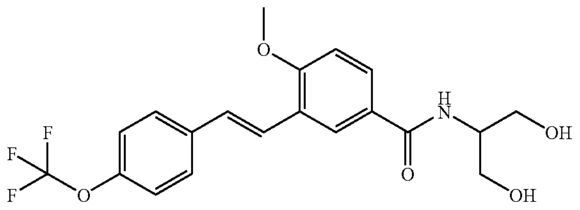

The captioned compound was synthesized from 4-methoxy-3-[(E)-2-(4-trifluoromethoxyphenyl)vinyl]benzoic acid obtained in step B of Example 2-2-1 and 2-amino-1,3-propanediol in accordance with the same procedure as in the methods described in step C of Example 1-2-3.

ESI (.LC/MS positive mode) m/z 412 (M+H$^+$); retention time 3.29 min (Condition 1 for high-performance liquid chromatography).

Example 2-2-27

Production of N-(2-hydroxy-1-methyl-ethyl)-4-methoxy-3-[(E)-2-(4-trifluoromethoxyphenyl)-vinyl]-benzamide (Compound 2-2-27)

[Formula 179]

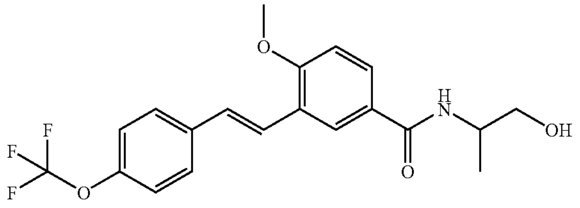

The captioned compound was synthesized from 4-methoxy-3-[(E)-2-(4-trifluoromethoxyphenyl)vinyl]benzoic acid obtained in step B of Example 2-2-1 and (±)-2-amino-1-propanol in accordance with the same procedure as in the methods described in step C of Example 1-2-3.

ESI (LC/MS positive mode) m/z 396 (M+H$^+$);. retention time 3.21 min (Condition 1 for high-performance liquid chromatography).

Example 2-2-28

Production of N-{2-[2-(2)-hydroxy-ethoxy)-ethoxy]-ethyl}-4-methoxy-3-[(E)-2-(4-trifluoromethoxyphenyl)-vinyl]-benzamide (Compound 2-2-28)

[Formula 180]

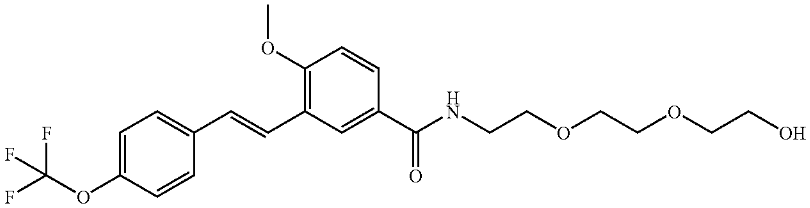

The captioned compound was synthesized from 4-methoxy-3-[(E)-2-(4-trifluoromethoxyphenyl)vinyl]-benzoic acid obtained in step B of Example 2-2-1 and 2-[2-(2-hydroxyethoxy)ethoxyl]ethylamine in accordance with the same procedure as in the methods described in step C of Example 1-2-3.

ESI (LC/MS positive mode) m/z 470 (M+H$^+$); retention time 3.43 min (Condition 1 for high-performance liquid chromatography).

Example 2-2-29

Production of N-(1-hydroxymethyl-cyclopropyl-methoxy)-4-methoxy-3-[(E)-2-(4-trifluoromethoxy-phenyl)-vinyl]-benzamide (Compound 2-2-29)

[Formula 181]

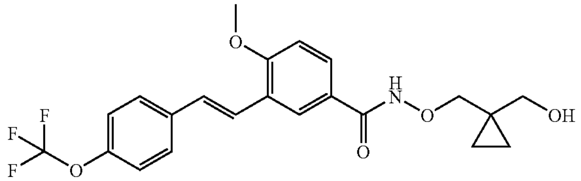

The captioned compound was synthesized from 4-methoxy-3-[(E)-2-(4-trifluoromethoxyphenyl)vinyl]-benzoic acid obtained-in step B of Example 2-2-1 and O-(3-hydroxy- 2-cyclopropylidene)propyl-hydroxylamine in accordance with the same procedure as in the methods described in step C of Example 1-2-3.

ESI (LC/MS positive mode) m/z 438 ($M+H^+$); retention time 3.64 min (Condition 1 for high-performance liquid chromatography).

Example 2-2-30

Production of 3-[(E)-2-(2-fluorophenyl)-vinyl]-4-methoxybenzamide (Compound 2-2-30)

[Formula 182]

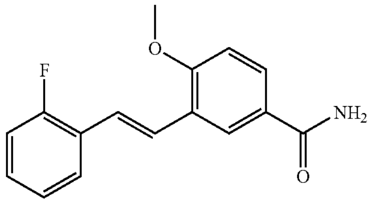

Step A

Preparation of ethyl 3-[2-(2-fluorophenyl)-vinyl]-4-methoxybenzoate

[Formula 183]

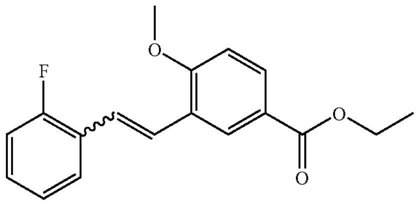

N,N-Dimethylformamide (5 mL) was added to 1.0 g of polymer-supported triphenylphosphine (produced by Fluka, CAS registry number 39319-11-4) and 1.1 g of 2-fluorobenzyl bromide, and the mixture was stirred for 10 hours at 80° C. The reaction mixture was filtered, and then washed with N,N-dimethylformamide, dichloromethane, and methanol. The residue was dried under reduced pressure to prepare polymer-supported (2-fluorobenzyl)triphenylphosphonium bromide. This product (144 mg) was added to a methanol solution (2 mL) of 30 mg of ethyl 3-formyl-4-methoxybenzoate obtained in step C of Example 1-2-1. After 80 μL of 28% sodium methoxide was added, the reactor was sealed, and the mixture was stirred for 4 hours at 70° C. The residue was diluted with ethyl acetate, washed with purified water, and dried over anhydrous sodium sulfate. The anhydrous sodium sulfate was separated by filtration, and then the filtrate was concentrated under reduced pressure. The residue was dried under reduced pressure to obtain 33 mg (80%) of ethyl 3-[2-(2-fluorophenyl)-vinyl]-4-methoxybenzoate.

ESI (LC/MS positive mode) m/z 287 ($M+H^+$); retention time 3.67 min (Condition 1 for high-performance liquid chromatography).

Step B

Preparation of 3-[(E)-2-(2-fluorophenyl)-vinyl]-4-methoxybenzamide

[Formula 184]

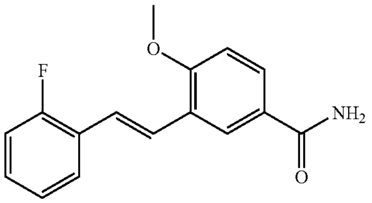

Ethyl 3-[2-(2-fluorophenyl)-vinyl]-4-methoxybenzoate (30 mg) obtained in step A was dissolved in 3 mL of carbon tetrachloride. Iodine (3 mg) was added to the solution, and the mixture was stirred for 7 days at room temperature. The reaction solution was diluted with ethyl acetate, washed with a saturated aqueous solution of sodium disulfite, and then with a saturated aqueous solution of sodium chloride, and dried over anhydrous sodium sulfate. The anhydrous sodium sulfate was separated by filtration, and the filtrate was concentrated under reduced pressure. The residue was dissolved in 2 mL of methanol, 100 μL of a 20% aqueous solution of potassium hydroxide was added to the solution, and the mixture was stirred for 3 hours at 60° C. To the reaction mixture, 0.1M hydrochloric acid was added little by little until the mixture became nearly pH 2. Then, the mixture was diluted with ethyl acetate, washed with purified water and a saturated aqueous solution of sodium chloride, and dried over anhydrous sodium sulfate. The anhydrous sodium sulfate was separated by filtration, and the filtrate was concentrated under reduced pressure. The residue was dissolved in 5 mL of N,N-dimethylformamide, and 11 mg of ammonium chloride, 24 mg of benzotriazol-1-ol monohydrate, 30 mg of (3-dimethylaminopropyl)ethylcarbodiimide hydrochloride, and 54 μL of N,N-diisopropylethylamine were added to the solution. The resulting solution was stirred for 15 hours at room temperature, and then 5 mL of 0.1M hydrochloric acid was added. This mixture was extracted with ethyl acetate twice, whereafter the organic layer combined was washed with a saturated aqueous solution of sodium chloride, and dried over anhydrous sodium sulfate. The residue was washed with ethanol, and then dried under reduced-pressure to obtain 14 mg (51%) of 3-[(E)-2-(2-fluorophenyl)-vinyl]-4-methoxybenzamide.

ESI (LC/MS positive mode) m/z 272 ($M+H^+$); retention time 2.84 min (Condition 3 for high-performance liquid chromatography).

Example 2-2-31

Production of N-(2,4-dihydroxybutyl)-4-methoxy-3-[(E)-2-(4-trifluoromethoxyphenyl)vinyl]benzamide (Compound 2-2-31)

[Formula 185]

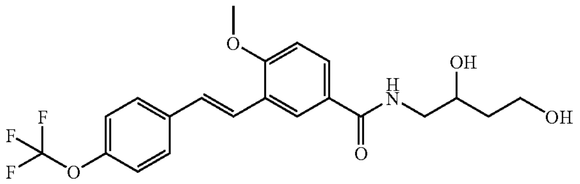

4-Methoxy-3-[(E)-2-(4-trifluoromethoxyphenyl)vinyl] benzoic acid (814 mg) obtained in step B of Example 2-2-1 was dissolved in 9 μL of N,N-dimethylformamide and 10 mL of dichloromethane. Oxalyl chloride (0.32 mL) was added little by little to the solution, and the mixture was stirred for 4 hours at room temperature. The reaction mixture was distilled under reduced pressure, and dried to obtain 850 mg of a light yellow solid. This solid (200 mg) and 100 mg of 4-amino-3-hydroxybutyric acid were dissolved in 2 mL of N,N-dimethylformamide. N,N-Diisopropylethylamine (293 μL) was added to this solution, and the mixture was stirred overnight at room temperature. The reaction mixture was purified by preparative high-performance liquid chromatography to obtain 55 mg (22%) of 3-hydroxy-4-{4-methoxy-3-[(E)-2-(4-trifluoromethoxyphenyl)vinyl]benzoylamino}butyric acid.

The obtained 3-hydroxy-4-{4-methoxy-3-[(E)-2-(4-trifluoromethoxyphenyl)vinyl]benzoylamino}butyric acid (27 mg) and 15 μL of N-methylmorpholine were dissolved in 3 mL of tetrahydrofuran under an atmosphere of nitrogen, and the solution was cooled to −15° C. Ethyl chloroformate (13 μL) was added to the solution, the mixture was stirred for 15 minutes, and then 18.4 mg of lithium boron hydride was added. After the mixture was stirred for 30 minutes at −15° C., 1 mL of water was added, and the reaction was quenched. The reaction mixture was purified by preparative high-performance liquid chromatography to obtain 21 mg (78%) of N-(2,4-dihydroxybutyl)-4-methoxy-3-[(E)-2-(4-trifluoromethoxyphenyl)vinyl]benzamide.

$^1$H-NMR (400 MHz, DMSO-$d_6$) δ 1.40-1.51 (1H, m), 1.56-1.68 (1H, m), 3.19-3.40 (4H, m), 3.45-3.60 (2H, m), 3.70-3.80 (1H, m), 3.92 (3H, s), 7.12 (1H, d, J=8.6 Hz), 7.33 (1H, d, J=16.6 Hz), 7.37 (2H, d, J=8.5 Hz), 7.45 (1H, d, J=16.6 Hz), 7.72 (2H, d, J=8.5 Hz), 7.83 (1H, dd, J=8.6 Hz, 2.1 Hz), 8.20 (1H, d, J=2.1 Hz), 8.36 (1H, bt, J=5.1 Hz).

ESI (LC/MS positive mode) 426 (M+H$^+$); retention time 3.27 min (Condition 1 for high-performance liquid chromatography).

Example 2-2-32

Production of 4-methoxy-3-[(E)-2-(4-trifluoromethoxyphenyl)-vinyl]-N-((2S,3S)-2,3,4-trihydroxy-butyl)benzamide (Compound 2-2-32)

[Formula 186]

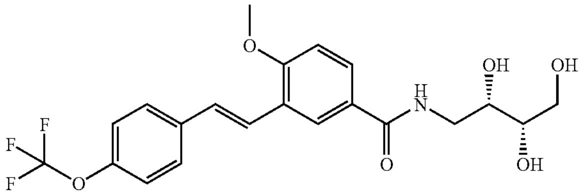

The captioned compound was synthesized from 4-methoxy-3-[(E)-2-(4-trifluoromethoxyphenyl)vinyl]-benzoic acid obtained in step B of Example 2-2-1 and (2S,3S)-4-amino-1,2,3-butantriol (CAS registry number: 168113-19-7) in accordance with the same procedure as in the methods described in step C of Example 1-2-3.

$^1$H-NMR (270 MHz, DMSO-$d_6$) δ 3.24-3.35 (1H, m), 3.38-3.47 (4H, m), 3.67-3.72 (1H, m), 3.91 (3H, s), 4.42-4.46 (2H, m), 4.54 (1H, d, J=5.9 Hz), 7.11 (1H, d, J=8.8 Hz), 7.30-7.37 (3H, m), 7.43 (1H, d, J=16.6 Hz), 7.71 (2H, d, J=8.8 Hz), 7.82 (1H, dd, J=8.8 Hz, 2.4 Hz), 8.19 (1H, d, J=2.4 Hz), 8.39 (1H, t, J=5.9 Hz).

ESI (LC/MS positive mode) m/z 442 (M+H$^+$); retention time 2.35 min (Condition 2 for high-performance liquid chromatography).

Example 2-2-33

Production of N-(2,3-dihydroxy-propyl)-4-methoxy-3-[(E)-2-(4-chlorophenyl)-vinyl]benzamide (Compound 2-2-33)

[Formula 187]

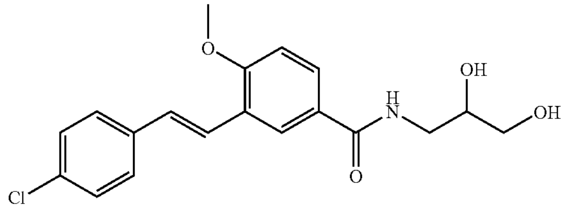

The captioned compound was synthesized from 4-methoxy-3-[(E)-2-(4-chlorophenyl)vinyl]benzoic acid obtained in step B of Example 2-2-7 and 3-amino-1,2-propanediol in accordance with the same procedure as in the methods described in step C of Example 1-2-3.

$^1$H-NMR (270 MHz, DMSO-$d_6$) δ 3.18-3.24 (1H, m), 3.30-3.44 (3H, m), 3.62-3.67 (1H, m), 3.91 (3H, s), 4.58 (1H, t, J=5.9 Hz), 4.83 (1H, d, J=4.9 Hz), 7.11 (1H, d, J=8.8 Hz), 7.29 (1H, d, J=16.6 Hz), 7.41-7.45 (3H, m), 7.61 (2H, d, J=8.8 Hz), 7.82 (1H, dd, J=8.8 Hz, 2.0 Hz), 8.19 (1H, d, J=2.0 Hz), 8.38 (1H, t, J=5.6 Hz).

ESI (LC/MS positive mode) m/z 362, 364 (M+H$^+$); retention time 3.10 min (Condition 1 for high-performance liquid chromatography).

Example 2-2-34

Production of N-(2-hydroxy-1-hydroxymethyl-ethyl)-4-methoxy-3-[(E)-2-(4-chlorophenyl)-vinyl] benzamide (Compound 2-2-34)

[Formula 188]

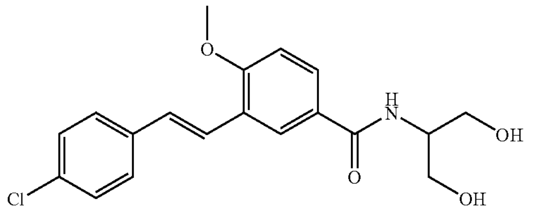

The captioned compound was synthesized from 4-methoxy-3-[(E)-2-(4-chlorophenyl)vinyl]benzoic acid obtained in step B of Example 2-2-7 and 2-amino-1,3-propanediol in accordance with the same procedure as in the methods described in step C of Example 1-2-3.

$^1$H-NMR (270 MHz, DMSO-$d_6$) δ 3.54 (4H, t, J=5.9 Hz), 3.92 (3H, s), 3.98 (1H, dt, J=8.1 Hz, 5.9 Hz), 4.66 (2H, t, J=5.9 Hz), 7.11 (1H, d, J=8.8 Hz), 7.29 (1H, d, J=16.6 Hz), 7.41-7.45 (3H, m), 7.62 (2H, d, J=8.3 Hz), 7.83 (1H, dd, J=8.8 Hz, 2.0 Hz), 7.91 (1H, d, J=8.1 Hz), 8.17 (1H, d, J=2.0 Hz).

ESI (LC/MS positive mode) m/z 362, 364 ($M+H^+$); retention time 3.07 min (Condition 1 for high-performance liquid chromatography).

Example 2-2-35

Production of N-(2-hydroxyethyl)-4-methoxy-3-[(E)-2-(4-chlorophenyl)-vinyl]benzamide (Compound 2-2-35)

[Formula 189]

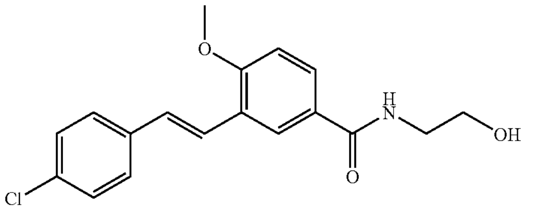

The captioned compound was synthesized from 4-methoxy-3-[(E)-2-(4-chlorophenyl)vinyl]benzoic acid obtained in step B of Example 2-2-7 and 2-aminoethanol in accordance with the same procedure as in the methods described in step C of Example 1-2-3.

$^1$H-NMR (270 MHz, DMSO-$d_6$) δ 3.31-3.37 (2H, m), 3.53 (2H, dt, J=6.3 Hz, 5.8 Hz), 3.91 (3H, s), 4.74 (1H, t, J=5.8 Hz), 7.11 (1H, d, J=8.8 Hz), 7.29 (1H, d, J=16.3 Hz), 7.41-7.45 (3H, m), 7.61 (2H, d, J=8.6 Hz), 7.82 (1H, dd, J=8.8 Hz, 2.4 Hz), 8.18 (1H, d, J=2.4 Hz), 8.39 (1H, t, J=5.4 Hz).

ESI (LC/MS positive mode) m/z 332, 334 ($M+H^+$); retention time 3.25 min (Condition 1 for high-performance liquid chromatography).

Example 2-2-36

Production of N-(2-hydroxyethyl-1-methyl-ethyl)-4-methoxy -3-[(E)-2-(4-chlorophenyl)-vinyl]benzamide (Compound 2-2-36)

[Formula 190]

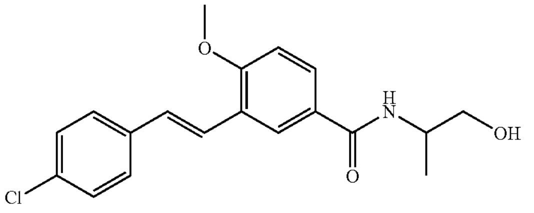

The captioned compound was synthesized from 4-methoxy-3-[(E)-2-(4-chlorophenyl)vinyl]benzoic acid obtained in step B of Example 2-2-7 and (±)-2-amino-1-propanol in accordance with the same procedure as in the methods described in step C of Example 1-2-3.

ESI (LC/MS positive mode) m/z 346, 348 ($M+H^+$); retention time 3.36 min (Condition 1 for high-performance liquid chromatography).

Example 2-2-37

Production of 3-[(E)-2-(4-chlorophenyl)-vinyl]-4-methoxy-N-((2S,3S)-2,3,4-trihydroxy-butyl)benzamide (Compound 2-2-37)

[Formula 191]

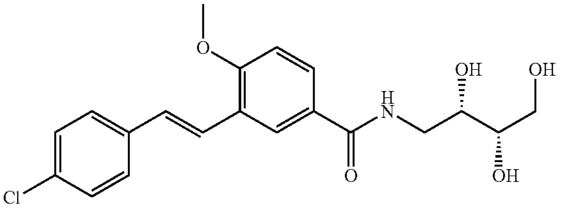

The captioned compound was synthesized from 4-methoxy-3-[(E)-2-(4-chlorophenyl)vinyl]benzoic acid obtained in step B of Example 2-2-7 and (2S,3S)-4-amino-1,2,3-butanetriol (CAS registry number: 168113-19-7) in accordance with the same procedure as in the methods described in step C of Example 1-2-3.

$^1$H-NMR (270 MHz, DMSO-$d_6$) δ 3.24-3.29 (1H, m), 3.38-3.47 (4H, m), 3.67-3.71 (1H, m), 3.90 (3H, s), 4.41-4.46 (2H, m), 4.53 (1H, d, J=5.4 Hz), 7.11 (1H, d, J=8.8 Hz), 7.28 (1H, d, J=16.6 Hz), 7.40-7.45 (3H, m), 7.61 (2H, d, J=8.8 Hz), 7.81 (1H, dd, J=8.8 Hz, 2.0 Hz), 8.18 (1H, d, J=2.0 Hz), 8.37 (1H, t, J=5.6 Hz).

ESI (LC/MS positive mode) m/z 392, 394 ($M+H^+$); retention time 2.11 min (Condition 2 for high-performance liquid chromatography).

Example 2-2-38

Production of N-(2,3-dihydroxy-propyl)-4-methoxy-3-[(E)-2-(4-trifluoromethylphenyl)vinyl]benzamide (Compound 2-2-38)

[Formula 192]

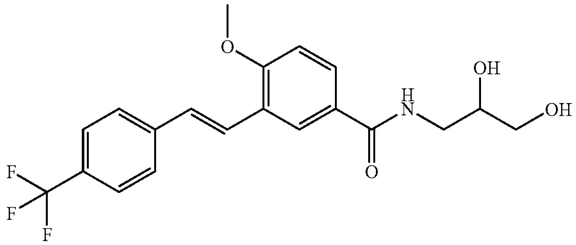

Step A

Preparation of 4-methoxy-3-[(E)-2-(4-trifluoromethylphenyl)vinyl]benzoic acid

[Formula 193]

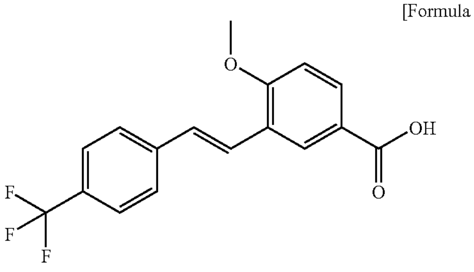

The captioned compound was synthesized from ethyl 4-methoxy-3-[(E)-2-(4-trifluoromethylphenyl)vinyl]-benzoate, which had been synthesized from diethyl (4-trifluoromethylbenzyl)phosphonate and ethyl 3-formyl-4-methoxybenzoate obtained in step C of Example 1-2-1, in accordance with the same procedure as in the methods described in step B of Example 2-2-1.

$^1$H-NMR (270 MHz, $CD_3OD$) δ 3.99 (3H, s), 7.10 (1H, d, J=8.6 Hz), 7.28 (1H, d, J=16.5 Hz), 7.60 (1H, d, J=16.5 Hz), 7.64 (2H, d, J=8.6 Hz), 7.73 (2H, d, J=8.8 Hz), 7.98 (1H, dd, J=2.3 Hz, 8.6 Hz), 8.30 (1H, d, J=2.3 Hz).

EI-MS (positive mode) m/z 322 ($M^+$).

Step B

Preparation of N-(2,3-dihydroxy-propyl)-4-methoxy-3-[(E)-2-(4-trifluoromethylphenyl)vinyl]benzamide

[Formula 194]

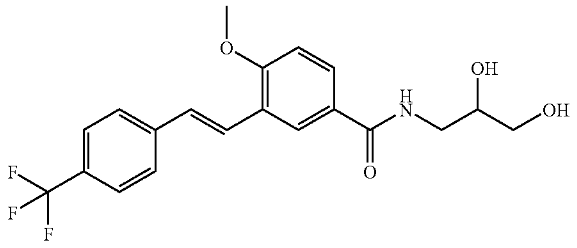

The captioned compound was synthesized from 4-methoxy-3-[(E)-2-(4-trifluoromethylphenyl)vinyl]benzoic acid obtained in step A of Example 2-2-38 and 3-amino-1,2-propanediol in accordance with the same procedure as in the methods described in step C of Example 1-2-3.

$^1$H-NMR (270 MHz, $CD_3OD$) δ 3.43 (1H, dd, J=6.9 Hz, 13.9 Hz), 3.51-3.63 (3H, m), 3.80-3.89 (1H, m), 3.97 (3H, s), 7.10 (1H, d, J=8.9 Hz), 7.33 (1H, d, J=16.5 Hz), 7.62 (1H, d, J=16.5 Hz), 7.64 (2H, d, J=8.6 Hz), 7.73 (2H, d, J=8.6 Hz), 7.82 (1H, dd, J=2.0 Hz, 8.9 Hz), 8.19 (1H, d, J=2.0 Hz).

ESI (LC/MS positive-mode) m/z 396 ($M+H^+$); retention time 2.87 min (Condition 3 for high-performance liquid chromatography).

Example 2-2-39

Production of N-(2-hydroxy-1-hydroxymethylethyl)-4-methoxy-3-[(E)-2-(4-trifluoromethylphenyl)vinyl]benzamide (Compound 2-2-39)

[Formula 195]

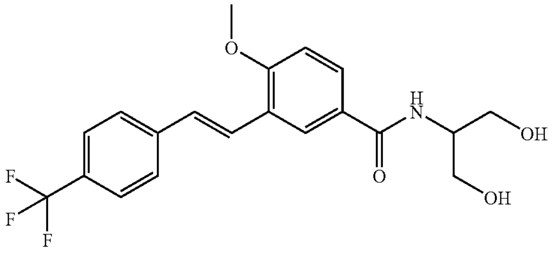

The captioned compound was synthesized from 4-methoxy-3-[(E)-2-(4-trifluoromethylphenyl)vinyl]benzoic acid obtained in step A of Example 2-2-38 and 2-amino-1,3-propanediol in accordance with the same procedure as in the methods described in step C of Example 1-2-3.

$^1$H-NMR (270 MHz, $CD_3OD$) δ 3.75 (4H, d, J=5.6 Hz), 3.93 (3H, s), 4.19 (1H, quint., J=5.6 Hz), 7.09 (1H, d, J=8.6 Hz), 7.34 (1H, d, J=16.5 Hz):, 7.57-7.66 (3H, m), 7.72 (2H, d, J=8.6 Hz), 7.84 (1H, dd, J=2.3 Hz, 8.6 Hz), 8.21 (1H, d, J=2.3 Hz).

ESI (LC/MS positive mode) m/z 396 ($M+H^+$); retention time 2.84 min (Condition 3 for high-performance liquid chromatography).

Example 2-2-40

Production of N-(2-hydroxyethyl)-4-methoxy-3-[(E)-2-(4-trifluoromethylphenyl)-vinyl]benzamide (Compound 2-2-40)

[Formula 196]

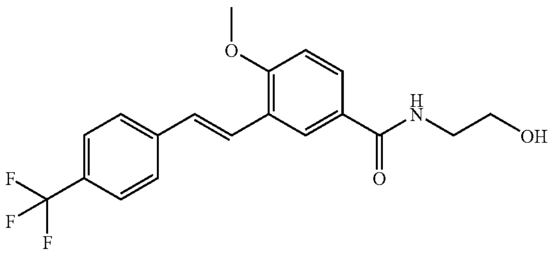

The captioned compound was synthesized from 4-methoxy-3-[(E)-2-(4-trifluoromethylphenyl)vinyl]benzoic acid obtained in step B of Example 2-2-38 and 2-aminoethanol in accordance with the same procedure as in the methods described in step C of Example 1-2-3.

ESI (LC/MS positive mode) m/z 366 ($M+H^+$); retention time 2.58 min (Condition 2 for high-performance liquid chromatography).

Example 2-2-41

Production of N-(2-hydroxy-1-methylethyl)-4-methoxy-3-[(E)-2-(4-trifluoromethylphenyl)-vinyl]benzamide (Compound 2-2-41)

[Formula 197]

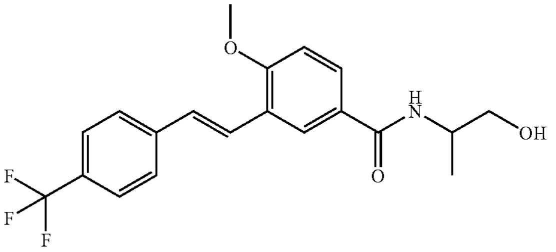

The captioned compound was synthesized from 4-methoxy-3-[(E)-2-(4-trifluoromethylphenyl)vinyl]benzoic acid obtained in step B of Example 2-2-38 and (±)-2-amino-1-propanol in accordance with the same procedure as in the methods described in step C of Example 1-2-3.

ESI (LC/MS positive mode) m/z 380 ($M+H^+$); retention time 2.73 min (Condition 2 for high-performance liquid chromatography).

Example 2-2-42

Production of N-[2-(2-hydroxyethoxy)-ethyl]-4-methoxy-3-[(E)-2-(4-trifluoromethylphenyl)-vinyl] benzamide (Compound 2-2-42)

[Formula 198]

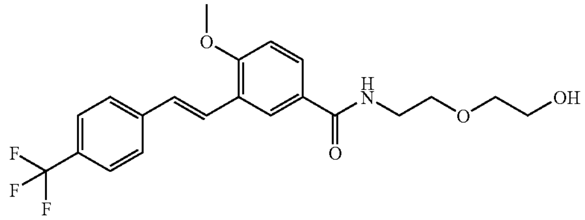

The captioned compound was synthesized from 4-methoxy-3-[(E)-2-(4-trifluoromethylphenyl)vinyl]benzoic acid obtained in step B of Example 2-2-38 and 2-(2-aminoethoxy) ethanol in accordance with the same procedure as in the methods described in step C of Example 1-2-3.

ESI (LC/MS positive mode) m/z 410 ($M+H^+$); retention time 2.59 min (Condition 2 for high-performance liquid chromatography).

Example 2-2-43

Production of N-(2,3-dihydroxypropyl)-4-methoxy-3-[(E)-2-(4-bromophenyl)vinyl]-4-benzamide (Compound 2-2-43)

[Formula 199]

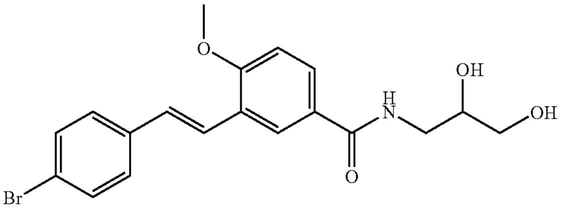

Step A

Preparation of ethyl 3-(E)-2-(4-bromo phenyl)vinyl]-4-methoxybenzoate

[Formula 200]

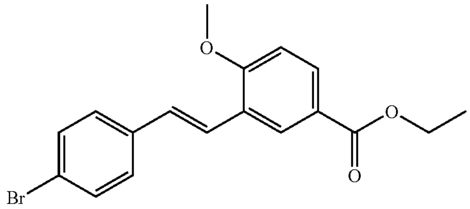

The captioned compound was synthesized from diethyl (4-bromobenzyl)phosphonate and ethyl 3-formyl-4-methoxybenzoate obtained in step C of Example 1-2-1 in accordance with the same procedure as in the methods described in step A of Example 2-2-1.

$^1$H-NMR (400 MHz, $CDCl_3$) δ 1.41 (3H, t, J=7.3 Hz), 3.95 (3H, s), 4.38 (2H, q, J=7.3 Hz), 6.92 (1H, d, J=8.6 Hz), 7.13 (1H, d, J=16.6 Hz), 7.41 (2H, d, J=8.5 Hz), 7.42 (1H, d, J=16.6 Hz), 7.48 (2H, d, J=8.5 Hz), 7.96 (1H, dd, J=8.6 Hz, 2.1 Hz), 8.26 (1H, d, J=2.1 Hz).

ESI (LC/MS positive mode) 361, 363 ($M+H^+$); retention time 4.12 min (Condition 2 for high-performance liquid chromatography).

Step B

Preparation of 3-[(E)-2-(4-bromophenyl)vinyl]-4-methoxybenzoic acid

[Formula 201]

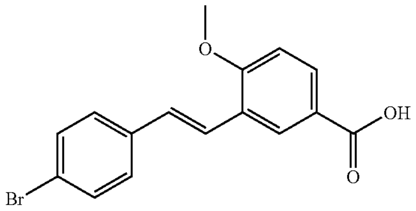

The captioned compound was synthesized from ethyl 3-[(E)-2-(4-bromophenyl)vinyl]-4-methoxybenzoate obtained, in step A in accordance with the same procedure as in the methods described in step B of Example 2-2-1.

$^1$H-NMR (400 MHz, DMSO-$d_6$) δ 3.94 (3H, s), 7.15 (1H, d, J=8.6 Hz), 7.29 (1H, d, J=16.6 Hz), 7.44 (1H, d, J=16.6 Hz), 7.56 (2H, d, J=9.8 Hz), 7.58 (2H, d, J=9.8 Hz), 7.88 (1H, dd, J=8.6 Hz, 2.0 Hz), 8.21 (1H, d, J=2.1 Hz), 12.75 (1H, bs).

ESI (LC/MS positive mode) 333, 335 (M+H$^+$); retention time 3.15 min (Condition 1 for high-performance liquid chromatography).

Step C

Preparation of N-(2,3-dihydroxypropyl)-4-methoxy-3-[(E)-2-(4-bromophenyl)vinyl]-4-benzamide

[Formula 202]

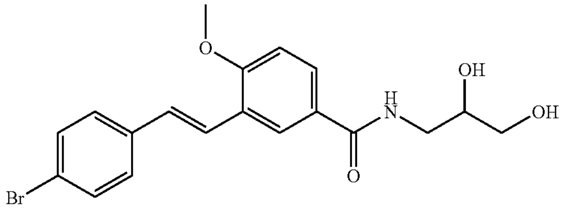

The captioned compound was synthesized from 4-methoxy-3-[(E)-2-(4-bromophenyl)vinyl]benzoic acid obtained in step B of Example 2-2-43 and 3-amino-1,2-propanediol in accordance with the same procedure as in the methods described in step C of Example 1-2-3.

$^1$H-NMR (400 MHz, DMSO-$d_6$) δ 3.17-3.24 (1H, m), 3.35 (2H, t, J=5.9 Hz), 3.38-3.44 (1H, m), 3.61-3.68 (1H, m), 3.92 (3H, s), 4.57 (1H, t, J=5.9 Hz), 4.82 (1H, d, J=4.9 Hz), 7.12 (1H, d, J=8.8 Hz), 7.28 (1H, d, J=16.4 Hz), 7.45 (1H, d, J=16.4 Hz), 7.55 (2H, d, J=8.8 Hz), 7.58 (2H, d, J=8.8 Hz), 7.82 (1H, dd, J=8.8 Hz, 2.0 Hz), 8.19 (1H, d, J=2.0 Hz), 8.38 (1H, t, J=5.9 Hz).

ESI (LC/MS positive mode) 406, 408 (M+H$^+$); retention time 3.17 min (Condition 1 for high-performance liquid chromatography).

Example 2-2-44

Production of 3-[(E)-2-(4-bromophenyl)vinyl]-N-(2-hydroxy-1-hydroxymethylethyl)-4-methoxybenzamide (Compound 2-2-44)

[Formula 203]

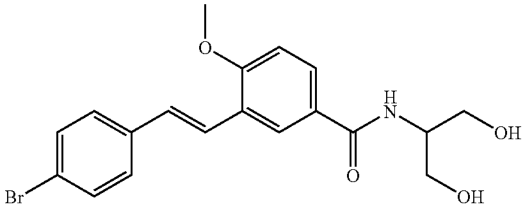

The captioned compound was synthesized from 4-methoxy-3-[(E)-2-(4-bromophenyl)vinyl]benzoic acid obtained in step B of Example 2-2-43 and 2-amino-1,3-propanediol in accordance with the same procedure as in the methods described in step C of Example 1-2-3.

$^1$H-NMR (400 MHz, DMSO-$d_6$) δ 3.54 (4H, t, J=5.9 Hz), 3.92 (3H, s), 3.94-4.02 (1H, m), 4.66 (2H, t, J=5.9 Hz), 7.12 (1H, d, J=8.8 Hz), 7.28 (1H, d, J=16.1 Hz), 7.45 (1H, d, J=16.1 Hz), 7.55 (2H, d, J=9.5 Hz), 7.58 (2H, d, J=9.5 Hz), 7.83 (1H, dd, J=8.8 Hz, 2.1 Hz), 7.92 (1H, d, J=7.8 Hz), 8.18 (1H, d, J=2.1 Hz).

ESI (LC/MS positive mode) 406, 408 (M+H$^+$); retention time 3.14 min (Condition 1 for high-performance liquid chromatography).

Example 2-2-45

Production of 3-[(E)-2-(4-bromophenyl)-vinyl]-N-(2-hydroxyethyl)-4-methoxybenzamide (Compound 2-2-45)

[Formula 204]

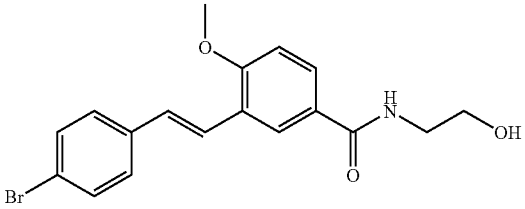

The captioned compound was synthesized from 4-methoxy-3-[(E)-2-(4-bromophenyl)vinyl]benzoic acid obtained in step B of Example 2-2-43 and 2-aminoethanol in accordance with the same procedure as in the methods described in step C of Example 1-2-3.

ESI (LC/MS positive mode) m/z 376, 378 (M+H$^+$); retention time 2.52 min (Condition 2 for high-performance liquid chromatography).

Example 2-2-46

Production of 3-[(E)-2-(4-bromophenyl)-vinyl]-N-(2-hydroxy-1-methylethyl)-4-methoxybenzamide (Compound 2-2-46)

[Formula 205]

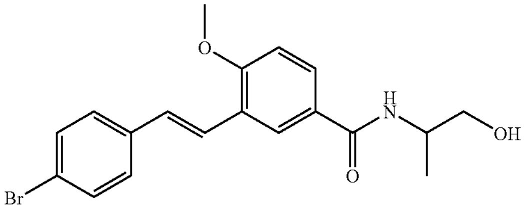

The captioned compound was synthesized from 4-methoxy-3-[(E)-2-(4-bromophenyl)vinyl]benzoic acid obtained in step B of Example 2-2-38 and (±)-2-amino-1-propanol in accordance with the same procedure as in the methods described in step C of Example 1-2-3.

ESI (LC/MS positive mode) m/z 390, 392 ($M+H^+$); retention time 2.70 min (Condition 2 for high-performance liquid chromatography).

Example 2-2-47

Production of 3-[(E)-2-(4-bromophenyl)-vinyl]-N-2-(2-hydroxyethoxy)-ethyl)-4-methoxybenzamide (Compound 2-2-47)

[Formula 206]

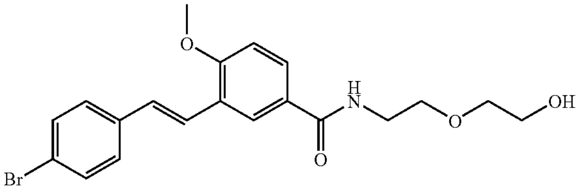

The captioned compound was synthesized from 4-methoxy-3-[(E)-2-(4-bromophenyl)vinyl]benzoic acid obtained in step B of Example 2-2-38 and 2-(2-aminoethoxy)ethanol in accordance with the same-procedure as in the methods described in step C of Example 1-2-3.

ESI (LC/MS positive mode) m/z 420, 422 ($M+H^+$); retention time 2.53 min (Condition 2 for high-performance liquid chromatography).

Example-2-2-48

Production of N-[(R)-2,3-dihydroxy-propyl)]-4-methoxy-3-[(E)-2-(4-chlorophenyl)-vinyl]benzamide (Compound 2-2-48)

[Formula 207]

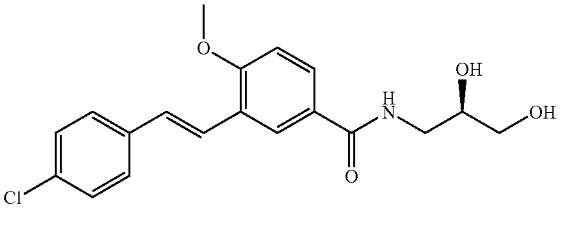

The captioned compound was synthesized from 4-methoxy-3-[(E)-2-(4-chlorophenyl)vinyl]benzoic acid obtained in step B of Example 2-2-7 and (R)-(+)-3-amino-1,2-propanediol (produced by Wako Pure Chemical Industries) in accordance with the same procedure as in the methods described in step C of Example 1-2-3.

$^1$H-NMR (270 MHz, DMSO-$d_6$) δ 3.18-3.24 (1H, m), 3.30-3.44 (3H, m), 3.62-3.67 (1H, m), 3.91 (3H, s), 4.58 (1H, t, J=5.9 Hz), 4.83 (1H, d, J=4.9 Hz), 7.11 (1H, d, J=8.8 Hz), 7.29 (1H, d, J=16.6 Hz), 7.41-7.45 (3H, m), 7.61 (2H, d, J=8.8 Hz), 7.82 (1H, dd, J=8.8 Hz, 2.0 Hz), 8.19 (1H, d, J=2.0 Hz), 8.38 (1H, t, J=5.6 Hz).

ESI (LC/MS positive mode) m/z 362, 364 ($M+H^+$); retention time 3.10 min (Condition 1 for high-performance liquid chromatography).

Example 2-2-49

Production of N-[(S)-2,3-dihydroxy-propyl)]-4-methoxy-3-[(E)-2-(4-chlorophenyl)-vinyl]benzamide (Compound 2-2-49)

[Formula 208]

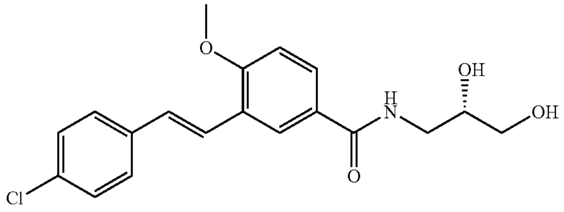

The captioned compound was synthesized from 4-methoxy-3-[(E)-2-(4-chlorophenyl)vinyl]benzoic acid obtained in step B of Example 2-2-7 and (S)-(−)-3-amino-1,2-propanediol (produced by Wako Pure Chemical Industries) in accordance with the same procedure as in the methods described in step C of Example 1-2-3.

$^1$H-NMR (270 MHz, DMSO-$d_6$) δ 3.18-3.24 (1H, m), 3.30-3.44 (3H, m), 3.62-3.67 (1H, m), 3.91 (3H, s), 4.58 (1H, t, J=5.9 Hz), 4.83 (1H, d, J=4.9 Hz), 7.11 (1H, d, J=8.8 Hz), 7.29 (1H, d, J=16.6 Hz), 7.41-7.45 (3H, m), 7.61 (2H, d, J=8.8 Hz), 7.82 (1H, dd, J=8.8 Hz, 2.0 Hz), 8.19 (1H, d, J=2.0 Hz), 8.38 (1H, t, J=5.6 Hz).

ESI (LC/MS positive mode) m/z 362, 364 ($M+H^+$); retention time 3.10 min (Condition 1 for high-performance liquid chromatography).

Example 2-2-50

Production of (R)-N-(2,3-dihydroxy-propyl)-4-methoxy-3-[(E)-2-(4-trifluoromethoxyphenyl)-vinyl]-benzamide (Compound 2-2-50)

[Formula 209]

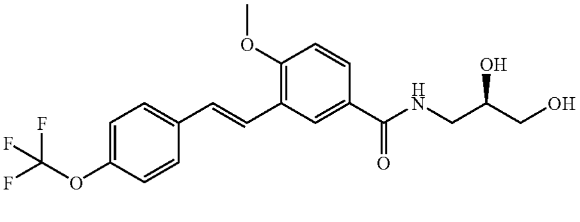

The captioned compound was synthesized from 4-methoxy-3-[(E)-2-(4-trifluoromethoxyphenyl)vinyl]-benzoic acid obtained in step B of Example 2-2-1 and (R)-3-amino-1,2-propanediol (produced by Wako Pure Chemical Industries) in accordance with the same procedure as in the methods described in step C of Example 1-2-3.

$^1$H-NMR (270 MHz, DMSO-$d_6$) δ 3.20-3.30 (1H, m), 3.30-3.50 (3H, m), 3.60-3.75 (1H, m), 3.92 (3H, s), 4.61 (1H, t, J=5.6 Hz), 4.85 (1H, d, J=4.6 Hz), 7.13, (1H, d, J=8.5 Hz), 7.30-7.50 (4H, m), 7.72 (2H, d, J=8.9 Hz), 7.82 (1H, dd, J=8.5 Hz, 2.0 Hz), 8.21 (1H, d, J=2.0 Hz), 8.41 (1H, bs).

ESI (LC/MS positive mode) m/z 412 (M+H$^+$); retention time 3.33 min (Condition 1 for high-performance liquid chromatography).

Example 2-2-51

Production of (S)-N-(2,3-dihydroxy-propyl)-4-methoxy-3-[(E)-2-(4-trifluoromethoxyphenyl)-vinyl]-benzamide (Compound 2-2-51)

[Formula 210]

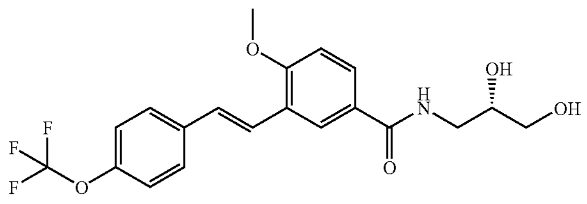

The captioned compound was synthesized from 4-methoxy-3-[(E)-2-(4-trifluoromethoxyphenyl)vinyl]-benzoic acid obtained in step B of Example 2-2-1 and (S)-3-amino-1,2-propanediol (produced by Wako Pure Chemical Industries) in accordance with the same procedure as in the methods described in step C of Example 1-2-3.

$^1$H-NMR (270 MHz, DMSO-$d_6$) δ 3.20-3.30 (1H, m), 3.30-3.50 (3H, m), 3.60-3.75 (1H, m), 3.92 (3H, s), 4.61 (1H, t, J=5.6 Hz), 4.85 (1H, d, J=4.6 Hz), 7.13 (1H, d, J=8.5 Hz), 7.30-7.50 (4H, m), 7.72 (2H, d, J=8.9 Hz), 7.82 (1H, dd, J=8.5 Hz, 2.0 Hz), 8.21 (1H, d, J=2.0 Hz), 8.41 (1H, bs).

ESI (LC/MS positive mode) m/z 412 (M+H$^+$); retention time 3.33 min (Condition 1 for high-performance liquid chromatography).

Example 2-2-52

Production of N-[(S)-2-hydroxy-1-(2-hydroxyethylcarbamoyl)ethyl]-4-methoxy-3-[(E)-2-(4-trifluoromethoxyphenyl)vinyl]benzamide (Compound 2-2-52)

[Formula 211]

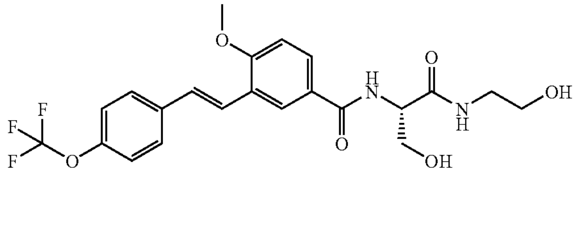

The (S)-3-t-butoxy-2-{4-methoxy-3-[(E)-2-(4-trifluoromethoxyphenyl)vinyl]benzoylamino}propionic acid was synthesized from 4-methoxy-3-[(E)-2-(4-trifluoromethoxyphenyl)vinyl]benzoic acid obtained in step B of Example 2-2-1 and O-t-butyl-L-serine in accordance with the same procedure as in the methods described in step C of Example 1-2-3.

(S)-3-t-butoxy-2-{4-methoxy-3-[(E)-2-(4-trifluoromethoxyphenyl)vinyl]benzoylamino}propionic acid (25 mg), 2-hydroxyethylamine (9 μL), benzotriazol-1-ol monohydrate (19 mg), and (3-dimethylaminopropyl)-ethylcarbodiimide hydrochloride (25 mg) were dissolved in 2 mL of N,N-dimethylformamide, and then, N,N-diisopropylethylamine (53 μL) was added to the solution. The solution was stirred overnight at room temperature. Then, 2-hydroxyethylamine (9 μL), benzotriazol-1-ol monohydrate (19 mg), and (3-dimethylaminopropyl)-ethylcarbodiimide hydrochloride (25 mg) were added again to the solution, and the solution was further stirred overnight. After removal of the solvent under reduced pressure, to the obtained residue was added water, and the mixture was extracted three times with dichloromethane. The respective organic layers were combined, whereafter the combined organic layer was washed with a saturated aqueous solution of sodium chloride, and dried over anhydrous sodium sulfate. The anhydrous sodium sulfate was separated by filtration, and washed with dichloromethane. The filtrate and the washings were combined, and dichloromethane was distilled off under reduced pressure. The obtained residue was purified by silica gel column chromatography to obtain 44 mg (76%) of N-[(S)-2-t-butoxy-1-(2-hydroxyethylcarbamoyl)ethyl]-4-methoxy-3-[(E)-2-(4-trifluoromethoxyphenyl)vinyl]-benzamide.

Trifluoroacetic acid (1 mL) was added to 20 mg of N-[(S)-2-t-butoxy-1-(2-hydroxyethylcarbamoyl)ethyl]-4-methoxy-3-[(E)-2-(4-trifluoromethoxyphenyl)vinyl]-benzamide and the mixture was stirred for 20 minutes at room temperature. After removal of the solvent, the resulting residue was purified using a micromass spectrometer (ZMD produced by Micromass) equipped with a gradient high-performance liquid chromatograph 996-600E produced by Waters. The resulting solid was dried under reduced pressure to obtain 9 mg (57%) of N-[(S)-2-hydroxy-1-(2-hydroxyethylcarbamoyl)ethyl]-4-methoxy-3-[(E)-2-(4-trifluoromethoxyphenyl)vinyl]benzamide.

ESI (LC/MS positive mode) m/z 469 (M+H$^+$); retention time 3.13 min (Condition 1 for high-performance liquid chromatography).

Example 2-3-1

Production of 3-[(E)-2-(3-fluorophenyl)-vinyl]-4-methoxybenzamide (Compound 2-3-1)

[Formula 212]

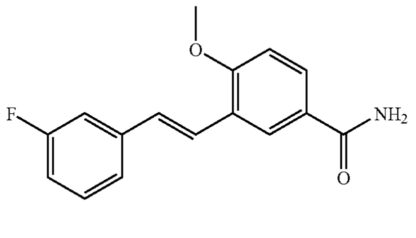

Step A

Preparation of ethyl 3-dimethoxymethyl-4-methoxybenzoate

[Formula 213]

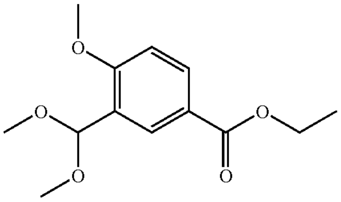

Ethyl 3-formyl-4-methoxybenzoate (500 mg) obtained in step C of Example 1-2-1 was dissolved in 10 mL of methanol. Trimethyl orthoformate (263 μL) and 41 mg of p-toluenesulfonic acid monohydrate were added to the solution, and then the mixture was heated for 2 hours under reflux. After the reaction solution was cooled, 5 mL of a saturated aqueous solution of sodium bicarbonate was added, and the resulting mixture was concentrated under reduced *pressure. The residue was diluted with ethyl acetate, washed with purified water and then with a saturated aqueous solution of sodium chloride, and dried over anhydrous sodium sulfate. The anhydrous sodium sulfate was separated by filtration, whereafter the filtrate was concentrated under reduced pressure. The residue was dried under reduced pressure to obtain 596 mg (97%) of ethyl 3-dimethoxymethyl-4-methoxybenzoate.

$^1$-NMR (270 MHz, $CDCl_3$) δ 1.38 (3H, t, J=7.3 Hz), 3.37 (6H, s), 3.91 (3H, s), 4.36 (2H, q, J=7.3 Hz), 5.67 (1H, s), 6.93 (1H, d, J=8.6 Hz), 8.04 (1H, dd, J=8.6 Hz, 2.3 Hz), 8.21 (1H, d, J=2.3 Hz).

Step B

Preparation of 3-dimethoxymethyl-4-methoxybenzoic acid

[Formula 214]

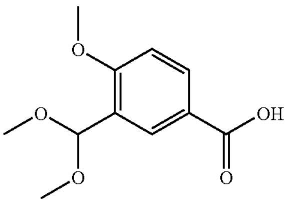

Ethyl 3-dimethoxymethyl-4-methoxybenzoate (3.67 g) obtained in step A was dissolved in 20 mL of methanol, 12 mL of a 20% aqueous solution of potassium hydroxide was added to the solution, and the mixture was stirred for 3 hours at 50° C. The reaction mixture was cooled to 0° C., and 1M hydrochloric acid was added little by little until the mixture became nearly pH 7, whereafter the mixture was concentrated under reduced pressure. The residue was diluted with ethyl acetate, washed with purified water and then with a saturated aqueous solution of sodium chloride, and dried over anhydrous sodium sulfate. The anhydrous sodium sulfate was separated by filtration, and the filtrate was concentrated under reduced pressure. The residue was dried under reduced pressure to obtain 1.82 g (55%) of 3-dimethoxymethyl-4-methoxybenzoic acid.

$^1$H-NMR (270 MHz, $CDC1_3$) δ 3.36 (6H, s), 3.94 (3H, s), 5.68 (1H, s), 6.96 (1H, d, J=8.6 Hz), 8.10 (1H, dd, J=8.6 Hz , 2.0 Hz), 8.29 (1H, d, J=2.0 Hz).

Step C

Preparation of 3-formyl-4-methoxybenzamide

[Formula 215]

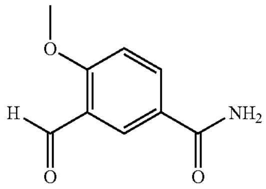

3-Dimethoxymethyl-4-methoxybenzoic acid (1.81 g) obtained in step B, 0.65 g of ammonium chloride, 1.48 g of benzotriazol-1-ol monohydrate, and 1.85 g of (3-dimethylaminopropyl)ethylcarbodiimide hydrochloride were dissolved in 50 mL of N,N-dimethylformamide, and 4.20 mL of N,N-diisopropylethylamine was added to the solution. The resulting solution was stirred for 13 hours at room temperature, and then 1M hydrochloric acid was added little by little until the mixture reached nearly pH 2. This mixture was extracted with ethyl acetate twice, whereafter the organic layer combined was washed with a saturated aqueous solution of sodium chloride, and dried over anhydrous sodium sulfate. The residue was washed with ethanol, and then dried under reduced pressure to obtain 1.03 g (71%) of 3-formyl-4-methoxybenzamide.

$^1$H-NMR (270 MHz, $CDCl_3$) δ 4.02 (3H, s), 7.11 (1H, d, J=8.6 Hz), 8.18-8.24 (2H, m), 10.48 (1H, s).

Step D

Preparation of 3-[(E)-2-(3-fluorophenyl)-vinyl]-4-methoxybenzamide

[Formula 216]

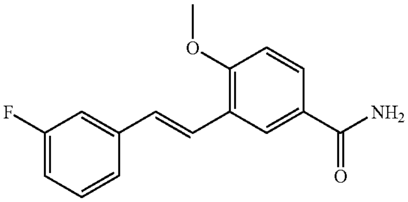

N,N-Dimethylformamide (5 mL) was added to 1.0 g of polymer-supported triphenylphosphine (produced by Fluka, CAS registry number 39319-11-4) and 1.1 g of 3-fluorobenzyl bromide, and the mixture was stirred for 10 hours at 80° C. The reaction mixture was filtered, and then washed with N,N-dimethylformamide, dichloromethane, and methanol. The residue was dried under reduced pressure to prepare polymer-supported (3-fluorobenzyl)triphenylphosphonium bromide. This product (111 mg), was added to a methanol solution (2 mL) of 20 mg of 3-formyl-4-methoxybenzamide obtained in step B. After 62 μL of 28% sodium methoxide was added, the reactor was sealed, and the mixture was stirred for 4 hours at 70° C. The reaction mixture was purified by thin-layer chromatography to obtain 4 mg (13%) of 3-[(E)-2-(3-fluorobrophenyl)-vinyl]-4-methoxybenzamide.

ESI (LC/MS positive mode) m/z 272 (M+H$^+$); retention time 3.29 min (Condition 1 for high-performance liquid chromatography).

Example 2-3-2

Production of 4-methoxy-3-[(E)-2-(2,4,6-trifluorophenyl)-vinyl]benzamide (Compound 2-3-2)

[Formula 217]

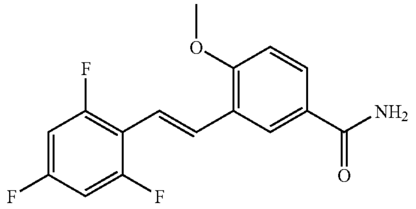

The captioned compound was synthesized from 2,4,6-trifluorobenzyl bromide by the same procedure as in step D of Example 2-3-1.

ESI (LC/MS positive mode) m/z 308 (M+H$^+$); retention time 3.33 min (Condition 1 for high-performance liquid chromatography).

Example 2-3-3

Production of 3-[(E)-2-(2,3-difluorophenyl)-vinyl]-4-methoxybenzamide (Compound 2-3-3)

[Formula 218]

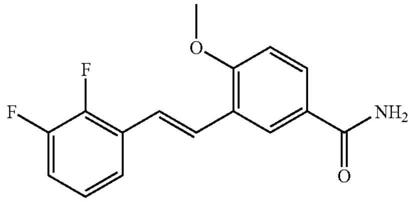

The captioned compound was synthesized from 2,3-difluorobenzyl bromide by the same procedure as in step D of Example 2-3-1.

ESI (LC/MS positive mode) m/z 290 (M+H$^+$); retention time 3.28 min (Condition 1 for high-performance liquid chromatography).

Example 2-3-4

Production of 3-[(E)-2-(3-chloro-2-fluorophenyl)-vinyl]-4-methoxybenzamide (Compound 2-3-4)

[Formula 219]

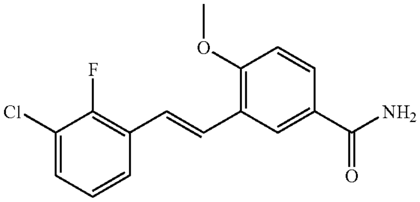

The captioned compound was synthesized from 3-chloro-2-fluorobenzyl bromide by the same procedure as in step D of Example 2-3-1.

ESI (LC/MS positive mode) m/z 306, 308 (M+H$^+$); retention time 3.46 min (Condition 1 for high-performance liquid chromatography).

Example 2-3-5

Production of 3-[(E)-2-(2-fluoro-4-methylphenyl)-vinyl]-4-methoxybenzamide (Compound 2-3-5)

[Formula 220]

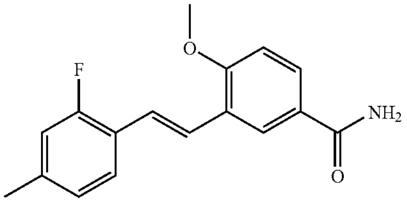

The captioned compound was synthesized from 2-fluoro-4-methylbenzyl bromide by the same procedure as in step D of Example 2-3-1.

ESI (LC/MS positive mode) m/z 286 (M+H$^+$); retention time 3.41 min (Condition 1 for high-performance liquid chromatography).

Example 2-3-6

Production of 4-methoxy-3-[(E)-2-(4-trifluoromethylsulfanil-phenyl)-vinyl]-benzamide (Compound 2-3-6)

[Formula 221]

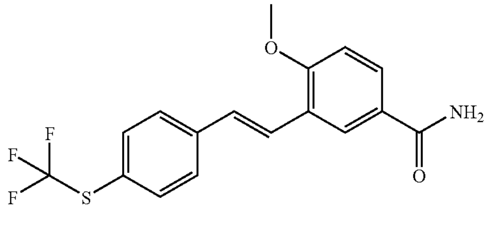

A mixture of 4-(trifluoromethylthio)benzyl bromide (50.4 mg) and triethyl phosphate (32 μL) was stirred for 16 hours at 160° C. After the reaction mixture was cooled to room temperature, 20 mg of 3-formyl-4-methoxybenzamide, 26 mg of 1,3,4,6,7,8-hexahydro-2H-pyrimido[1,2-a]pyrimidine, and 1 mL of tetrahydrofuran were added, and the mixture was stirred for 24 hours at room temperature and for 6 hours at 70° C. 3-Formyl-4-methoxybenzamide (20 mg) was further added, and the mixture was stirred for 24 hours at 70° C. This mixture was cooled to room temperature, then diluted with methanol, and passed through an SCX solid phase extraction column (1 g, produced by Varian). The eluate was concentrated to obtain 93 mg of a crude product. This product (46 mg) was purified using a micromass spectrometer, (ZMD produced by Micromass) equipped with a gradient high-performance liquid chromatograph 996-600E produced by Waters. The resulting solid was dried under reduced pressure to obtain 3.5 mg (6%) of 4-methoxy-3-[(E)-2-(4-trifluoromethylsulfanil-phenyl)-vinyl]-benzamide.

ESI (LC/MS positive mode) m/z 354 (M+H$^+$); retention time 3.77 min (Condition 1 for high-performance liquid chromatography).

Example 2-3-7

Production of 3-[(E)-2-(2-fluoro-4-trifluoromethyl-phenyl)-vinyl]-benzamide (Compound 2-3-7)

[Formula 222]

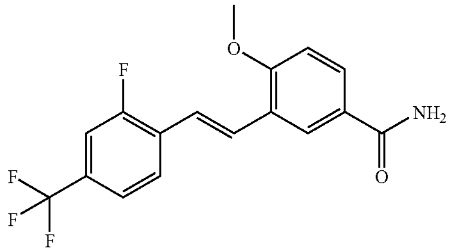

The captioned compound was synthesized from 2-fluoro-4-trifluoromethylbenzyl bromide and 3-formyl-4-methoxy-benzamide by the same procedure as in the manufacturing method described in Example 2-3-6.

ESI (LC/MS positive mode) m/z 340 (M+H$^+$); retention time 3.25 min (Condition 3 for high-performance liquid chromatography).

Example 2-3-8

Production of 3-[2-(4-cyano-phenyl)-vinyl]-4-methoxy-benzamide (Compound 2-3-8)

[Formula 223]

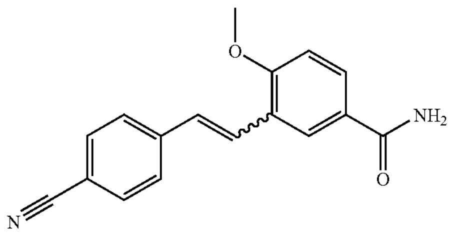

The captioned compound was synthesized from 4-cyanobenzyl bromide and 3-formyl-4-methoxybenzamide by the same procedure as in the manufacturing method described in Example 2-3-6.

ESI (LC/MS positive mode) m/z 279 (M+H$^+$); retention time-2.86 min for Z-form, 2.98 min for E-form (Condition 1 for high-performance liquid chromatography).

Example 2-4-1

Production of 3-[(E)-2-(4-fluorophenyl)-vinyl]-4-methoxybenzamide (Compound 2-4-1)

[Formula 224]

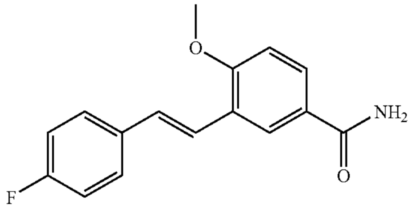

Step A

Preparation of 3-(diethoxyphosphonylmethyl)-4-methoxy-benzoic acid

[Formula 225]

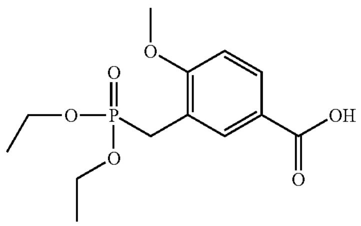

Ethyl 3-chloromethyl-4-methoxy-benzoate (10.00 g) obtained in step A of Example 1-2-1 was dissolved in 8.25 mL of triethyl phosphate, and the solution was stirred for 24 hours at 160° C. After cooling, the reaction mixture was dissolved in 200 mL of methanol, 36 mL of a 20% aqueous solution of potassium hydroxide was added to the solution, and the mixture was stirred for 1 hour at 60° C. The reaction mixture was concentrated under reduced pressure, and the residue was diluted with purified water, and washed with diethyl ether. With the addition of 1M hydrochloric acid, the aqueous layer was brought to nearly pH 2, and then extracted with ethyl acetate. The organic layer was washed with a saturated aqueous solution of sodium chloride, and dried over anhydrous sodium sulfate. The anhydrous sodium sulfate was separated by filtration, and the filtrate was concentrated under reduced pressure. The residue was dried under reduced pressure to obtain 12.78 g (98%) of 3-(diethoxyphosphonylmethyl)-4-methoxy-benzoic acid.

$^1$H-NMR (270 MHz, DMSO-d$_6$) δ 1.16 (6H, t, J=7.3 Hz), 3.22 (2H, d, J=21.4 Hz), 3.87 (3H, s), 3.94 (4H, quintet, J=7.3 Hz), 7.09 (1H, d, J=8.3 Hz), 7.82-7.87 (2H, m), 12.62 (1H, bs).

Step B

Preparation of polymer-Supported 3-(diethoxyphosphonylmethyl)-4-methoxy-benzamide A solvent mixture (1:4) (50 mL) of piperidine and N,N-dimethylformamide was added to 8.06 g of Rink resin (produced by Advanced Chemtech, 0.8 mmol/g), and the mixture was vigorously agitated for 3 hours at room temperature.

After the reaction mixture was filtered, the remaining resin was washed with dichloromethane and methanol, and dried under reduced pressure (results of Kaiser test: positive). To this resin, there were added 50 mL of N-methyl-2-pyrrolidinone, 5.85 g of 3-(diethoxyphosphonylmethyl)-4-methoxy-benzoic acid obtained in step A, 4.94 g of benzotriazol-1-ol monohydrate, and 4.99 mL of N,N-diisopropylcarbodiimide hydrochloride, and the mixture was stirred for 15 hours at room temperature. The reaction mixture was filtered, and washed with dichloromethane and methanol. The residue was dried under reduced pressure to prepare polymer-supported 3-(diethoxyphosphonylmethyl)-4-methoxy-benzamide.

Results of Kaiser test: Negative.

Step C

Preparation of 3-[(E)-2-(4-fluorophenyl)-vinyl]-4-methoxybenzamide

[Formula 226]

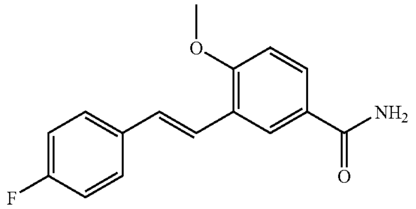

The resin (100 mg) obtained in step B was transferred into a reactor, where 54 μL of 4-fluorobenzaldehyde, 70 mg of 1,3,4,6,7,8-hexahydro-2H-pyrimido[1,2-a]pyrimidine, and 1.5 mL of N,N-dimethylformamide were added, and the mixture was stirred for 13 hours at 80° C. The reaction mixture was filtered, and then washed with methanol and dichloromethane. To the remaining resin, 2 mL of a 20% dichloromethane solution of trifluoroacetic acid was added, and the mixture was vigorously agitated for 30 seconds. The reaction mixture was filtered, and then washed with dichloromethane, followed by concentrating the filtrate under reduced pressure. The residue was purified-using a micromass spectrometer (ZMD produced by Micromass) equipped with a gradient high-performance liquid chromatograph 996-600E produced by Waters. The resulting solid was dried under reduced pressure to obtain 6 mg of 3-[(E)-2-(4-fluorophenyl)-vinyl]-4-methoxybenzamide.

ESI (LC/MS positive mode) m/z 272 ($M+H^+$); retention time 2.39 min (Condition 2 for high-performance liquid chromatography).

Example 2-4-2

Production of 4-methoxy-3-((E)-2-p-toluyl-vinyl)-benzamide (Compound 2-4-2)

[Formula 227]

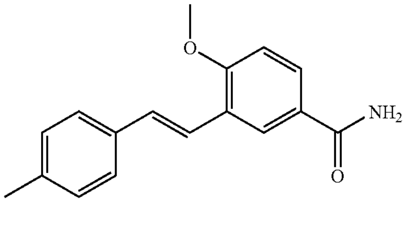

The captioned compound was synthesized from 4-methylbenzaldehyde by the same procedure as in step C of Example 2-4-1.

ESI (LC/MS positive mode) m/z 268 ($M+H^+$); retention time 2.59 min (Condition 2 for high-performance liquid chromatography).

Example 2-4-3

Production of 3-[(E)-2-(4-ethylphenyl)-vinyl)-4-methoxy-benzamide (Compound 2-4-3)

[Formula 228]

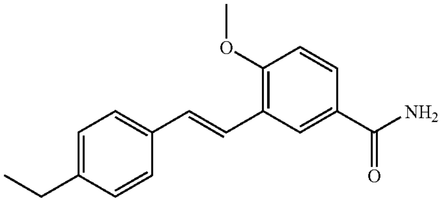

The captioned compound was synthesized from 4-ethylbenzaldehyde by the same procedure as in step C of Example 2-4-1.

ESI (LC/MS positive mode) m/z 282 ($M+H^+$); retention time 2.88 min (Condition 2 for high-performance liquid chromatography).

Example 2-4-4

Production of 4-methoxy-3-[(E)-2-(4-trifluoromethylphenyl)-vinyl)-benzamide (Compound 2-4-4)

[Formula 229]

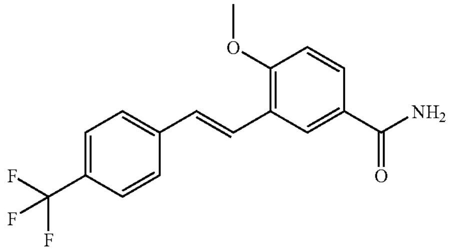

The captioned compound was synthesized from 4-trifluoromethylbenzaldehyde by the-same procedure as in step C of Example 2-4-1.

ESI (LC/MS positive mode) m/z 322 ($M+H^+$); retention time 2.86 min (Condition 2 for high-performance liquid chromatography).

Example 2-4-5

Production of 3-[(E)-2-(4-tert-butylphenyl)-vinyl)-4-methoxybenzamide (Compound 2-4-5)

[Formula 230]

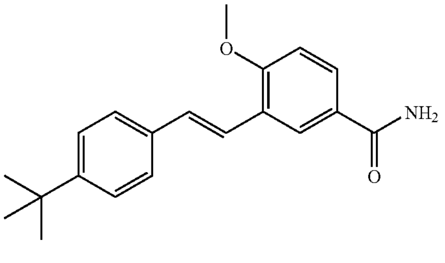

The captioned compound was synthesized from 4-(tert-butyl)benzaldehyde by the same procedure as in step C of Example 2-4-1.

ESI (LC/MS positive mode) m/z 310 ($M+H^+$); retention time 3.26 min (Condition 2 for high-performance liquid chromatography).

Example 2-4-6

Production of 3-((E)-2-biphenyl-4-yl-vinyl]-4-methoxybenzamide (Compound 2-4-6)

[Formula 231]

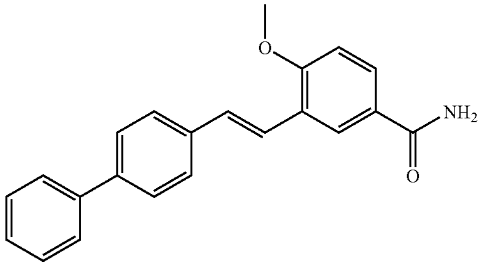

The captioned compound was synthesized from biphenyl-4-carbaldehyde by the same procedure as in step C of Example 2-4-1.

ESI (LC/MS positive mode) m/z 330 ($M+H^+$); retention time 3.13 min (Condition 2 for high-performance liquid chromatography).

Example 2-4-7

Production of 3-[(E)-2-(4-bromophenyl)-vinyl]-4-methoxybenzamide (Compound 2-4-7)

[Formula 232]

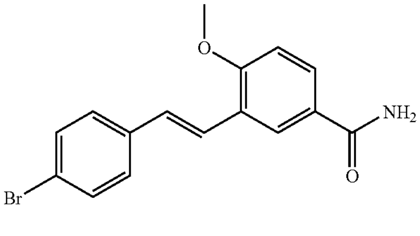

The captioned compound was synthesized from 4-bromobenzaldehyde by the same procedure as in step C of Example 2-4-1.

ESI (LC/MS positive mode) m/z 332, 334 ($M+H^+$); retention time 2.79 min (Condition 2 for high-performance liquid chromatography).

Example 2-4-8

Production of 3-[(E)-2-(4-bromo-2-fluorophenyl)-vinyl]-4-methoxybenzamide (Compound 2-4-8)

[Formula 233]

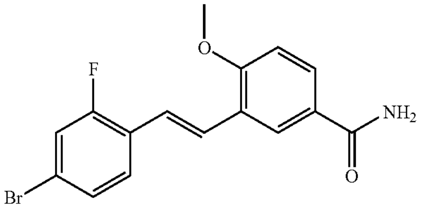

The captioned compound was synthesized from 4-bromo-2-fluorobenzaldehyde by the same procedure as in step C of Example 2-4-1.

ESI (LC/MS-positive mode) m/z 350, 352 ($M+H^+$); retention time 3.56 min (Condition 1 for high-performance liquid chromatography).

Example 2-4-9

Production of 3-[(E)-2-(2,4-dichlorophenyl)-vinyl]-4-methoxybenzamide (Compound 2-4-9)

[Formula 234]

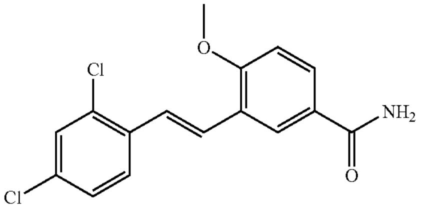

The captioned compound was synthesized from 2,4-dichlorobenzaldehyde by the same procedure as in step C of Example 2-4-1.

ESI (LC/MS positive mode) m/z 322, 324 ($M+H^+$); retention time 3.59 min (Condition 1 for high-performance liquid chromatography).

Example 2-4-10

Production of 3-{(E)-2-[4-(4-fluorobenzyloxy)-3-methoxyphenyl]-vinyl}-4-methoxybenzamide (Compound 2-4-10)

[Formula 235]

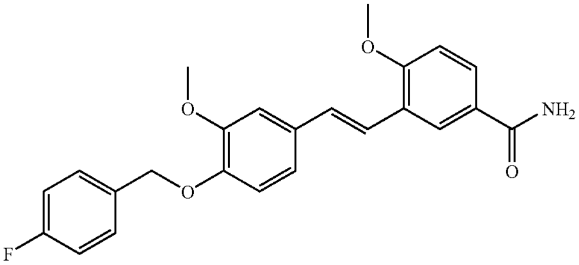

The captioned compound was synthesized from 4-(4-fluorobenzyloxy)-3-methoxybenzaldehyde by the same procedure as in step C of Example 2-4-1.

ESI (LC/MS positive mode) m/z 408 (M+H$^+$); retention time 3.54 min (Condition 1 for high-performance liquid chromatography).

Example 2-4-11

Production of 3-[(E)-2-(2,4-fluorophenyl)-vinyl]-4-methoxybenzamide (Compound 2-4-11)

[Formula 236]

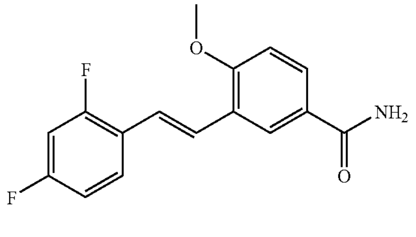

The captioned compound was synthesized from 2,4-difluorobenzaldehyde by the same procedure as in step C of Example 2-4-1.

ESI (LC/MS positive mode) m/z 290 (M+H$^+$); retention time 3.27 min (Condition 1 for high-performance liquid chromatography).

Example 2-4-12

Production of 4-methoxy-3-((E)-2-pyridin-3-yl-vinyl)benzamide (Compound 2-4-12)

[Formula 237]

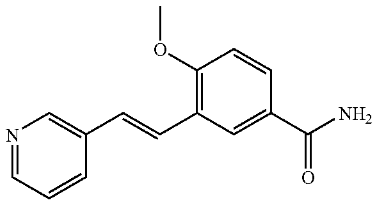

Step A

Preparation of 3-(diethoxyphosphonylmethyl)-4-methoxy-benzamide

[Formula 238]

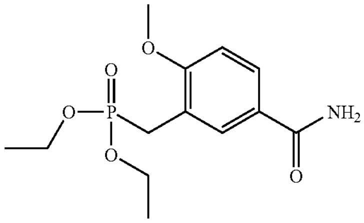

3-(Diethoxyphosphonylmethyl)-4-methoxy-benzoic acid (3.00 g) obtained in step A of Example 2-4-1, 1.06 g of ammonium chloride, 2.28 g of benzotriazol-1-ol monohydrate, and 2.85 g of (3-dimethylaminopropyl)ethylcarbodiimide hydrochloride were dissolved in 90 mL of N,N-dimethylformamide, and 5.18 mL of N,N-diisopropylethylamine was added. This solution was. stirred for 12 hours at room temperature, and then concentrated under reduced pressure. The residue was purified by silica gel chromatography to obtain 2.78 g (92%) of 3-(diethoxyphosphonylmethyl)-4-methoxy-benzamide.

$^1$H-NMR (270 MHz, DMSO-d$_6$) δ 1.16 (6H, t, J=6.9 Hz), 3.18 (2H, d, J=21.5 Hz), 3.85 (3H, s), 3.93 (4H, quintet, J=6.9 Hz), 7.03 (1H, d, J=9.2 Hz), 7.19 (1H, bs), 7.78-7.85 (3H, m).

Step B

Preparation of 4-methoxy-3-((E)-2-pyridin-3-yl-vinyl)benzamide

[Formula 239]

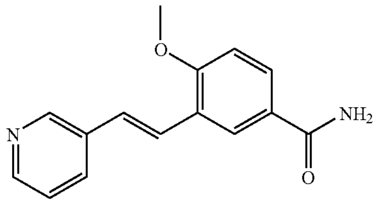

3-(Diethoxyphosphonylmethyl)-4-methoxy-benzamide (30 mg) obtained in step A, 28 μL of pyridine-3-carbaldehyde, 40 mg of 1,3,4,6,7,8-hexahydro-2H-pyrimido[1,2-a] pyrimidine, and 1.0 mL of N,N-dimethylformamide were added, and the mixture was stirred for 12 hours at 80° C. The reaction mixture was filtered, and then the filtrate was purified using a micromass spectrometer (ZMD produced by Micromass) equipped with a gradient high-performance liquid chromatograph 996-600E produced by Waters. The resulting solid was dried under reduced pressure to obtain 6 mg (24%) of 4-methoxy-3-((E)-2-pyridin-3-yl-vinyl)benzamide.

$^1$H-NMR (270 MHz, DMSO-d$_6$) δ 3.93 (3H, s), 7.12 (1H, d, J=8.8 Hz), 7.28 (1H, bs), 7.33 (1H, d, J=17.0 Hz), 7.41 (1H, dd, J=8.4 Hz, 4.4 Hz), 7.52 (1H, d, J=17.0 Hz), 7.85 (1H, dd, J=8.8 Hz, 2.4 Hz), 7.94 (1H, bs), 8.03-8.06 (1H, m), 8.23 (1H, d, J=2.4 Hz), 8.47 (1H, dd, 4.4 Hz, 1.6 Hz), 8.75 (1H, d, J=2.4 Hz).

ESI (LC/MS positive mode) m/z 255 (M+H$^+$); retention time 1.78 min (Condition 1 for high-performance liquid chromatography).

Example-2-5-1

Production of 4-bromo-3-[(E)-2-(4-trifluoromethoxy-phenyl)-vinyl]-benzamide (Compound 2-5-1)

[Formula 240]

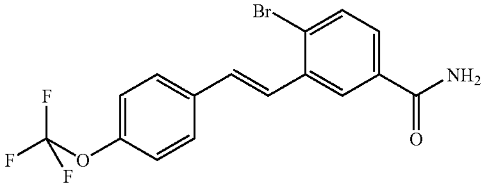

Diethyl (4-trifluoromethoxybenzyl)phosphonate (7.8 g) was dissolved in 100 mL of DMF, 5.0 g of 4-bromo-3-formylbenzonitrile was added, and the mixture was cooled to −25° C. Potassium tert-butoxide (6.4 g) was added, and the mixture was stirred for 2 hours at −25° C. To the reaction mixture, 100 mL of a saturated aqueous solution of ammonium chloride and 100 mL of water were added, and the mixture was extracted 3 times with ethyl acetate (100 mL). The respective organic layers were combined, whereafter the combined organic layer was washed with water and a saturated aqueous solution of sodium chloride, and dried over magnesium sulfate. The magnesium sulfate was separated by filtration, and the filtrate was concentrated under reduced pressure. The residue was subjected to 100 g silica gel column chromatography to obtain 3.9 g of 4-bromo-3-[2-(4-trifluoromethoxy-phenyl)-vinyl]-benzonitrile as a crude product with the use of an eluant (ethyl acetate and n-hexane, 1:10).

The crude product was dissolved in 100 mL of carbon tetrachloride, 0.4 g of iodine was added, and the mixture was stirred for 15.5 hours at room temperature under irradiation with a 500 W halogen lamp. A solution of 2.7 g of sodium dithionite dissolved in 157 mL of water was added to the reaction-mixture for washing, and the organic layer was washed with a saturated aqueous solution of sodium chloride, and dried over magnesium sulfate. The magnesium sulfate was separated by filtration, and then the filtrate was concentrated under reduced pressure to obtain 3.8 g of yellow crystals.

The crystals were dissolved in 35 mL of dimethyl sulfoxide, and a solution of 2.8 g of potassium carbonate dissolved in 5.2 mL of a 30% aqueous solution of hydrogen peroxide was slowly added at 0° C., followed by stirring the mixture for 1.5 hours at room temperature. Water was added to the reaction suspension, and the resulting precipitate was filtered, washed with water, and dried under reduced pressure to obtain crude crystals of 4-bromo-3-[(E)-2-(4-trifluoromethoxy-phenyl)-vinyl]-benzamide. The resulting crude crystals were recrystallized from methanol to obtain 1.1 g of 4-bromo-3-[(E)-2-(4-trifluoromethoxy-phenyl)-vinyl]-benzamide.

$^1$H-NMR (400 MHz, $CDCl_3$) δ 8.15 (1H, d, J=2.4 Hz), 7.68 (1H, d, J=8.3 Hz), 7.58 (2H, d, J=8.3 Hz), 7.50 (1H, dd, J=8.3 Hz, 2.4 Hz), 7.48 (1H, d, J=16.1 Hz), 7.24 (1H, d, J=8.3 Hz), 7.13 (1H, d, J=16.1 Hz).

ESI (LC/MS positive mode) m/z 386, 388 ($M+H^+$); retention time 3.20 min (Condition 2 for high-performance liquid chromatography).

Example 2-5-2

Production of 4-(2-hydroxy-ethylamino)-3-[(E)-2-(4-trifluoromethoxy-phenyl)-vinyl]-benzamide (Compound 2-5-2)

[Formula 241]

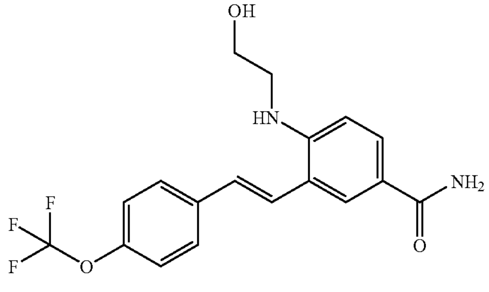

The interior of a container containing 4-bromo-3-[(E)-2-(4-trifluoromethoxy-phenyl)-vinyl]-benzamide (50.2 mg) obtained in Example 2-5-1, 2.8 mg of tris(dibenzylideneacetone) dipalladium(0), 10 μL of ethanolamine, and 2.6 mg of 2-(dicyclohexylphosphino)biphenyl was purged with argon. A 1.0M tetrahydrofuran solution (1 mL) of lithium bis(trimethylsilyl)amide was added into the container, and the mixture was stirred for 3.5 hours at 65° C. Then, 2.0 mg of tris(dibenzylideneacetone) dipalladium(0), and 10 μL of ethanolamine were further added, the interior of the container was purged with argon, and the mixture was stirred for 13.5 hours at 65° C. The reaction mixture was cooled to room temperature, and 2 mL of 1N hydrochloric acid was added for neutralization, followed by extracting the aqueous layer with ethyl acetate 4 times. After the respective organic layers were combined, the combined organic layer was filtered through Presep Dehydration Column (produced by Wako Pure Chemical Industries), and the filtrate was concentrated under reduced pressure. The resulting residue was subjected to 11 g silica gel column chromatography to obtain 5.6 mg of 4-(2-hydroxy-ethylamino)-3-[(E)-2-(4-trifluoromethoxy-phenyl)-vinyl]-benzamide with the use of an eluant (dichloromethane and methanol, 15:1).

$^1$H-NMR (400 MHz, $CD_3OD$) δ 7.91 (1H, d, J=2.4 Hz), 7.63 (1H, dd, J=8.8 Hz, 2.4 Hz), 7.60 (1H, d, J=8.8 Hz), 7.27 (1H, d, J=16.1 Hz), 7.16 (1H, d, J=8.8 Hz), 7.02 (1H, d, J=16.1 Hz), 6.64 (1H, d, J=8.8 Hz), 3.69 (2H, t, J=5.9 Hz), 3.30 (2H, t, J=5.9 Hz).

ESI (LC/MS positive mode) m/z 367 ($M+H^+$); retention time 2.96 min (Condition 1 for high-performance liquid chromatography).

Example 2-5-3

Production of 4-pyrrolidin-1-yl-3-[(E)-2-(4-trifluoromethoxy-phenyl)-vinyl]-benzamide (Compound 2-5-3)

[Formula 242]

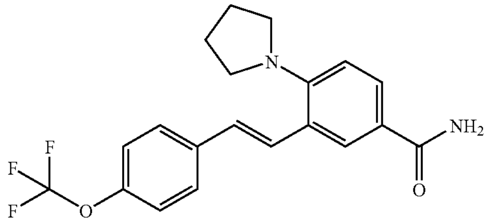

The captioned compound was synthesized from 4-bromo-3-[(E)-2-(4-trifluoromethoxy-phenyl)-vinyl]-benzamide and pyrrolidine by the same procedure as in Example 2-5-2.

ESI (LC/MS positive mode) m/z 407 ($M+H^+$); retention time 3.09 min (Condition 1 for high-performance liquid chromatography).

Example B-1

Cell Proliferation Assay

The test compound was serially diluted with DMSO, and then diluted 1:50 with a $Ca^{2+}$,$Mg^{2+}$-free phosphate-buffered physiological saline. The resulting dilution (10 μl) was dispensed into a 96-well plate. Human umbilical vein endothelial cells (HUVEC, purchased from Clonetics) were suspended in PRMI 1640 medium supplemented with 10% bovine fetal serum, 30 μg/mL vascular endothelial cell growth supplement, and 50 μg/mL heparin. Human lung carcinoma cell line Calu-6 was suspended in MEM medium supplemented with 10% bovine fetal serum, 0.1 mM nonessential amino acid, and 1 mM sodium pyruvate. Each cell suspension (190 μL) was dispensed into the plate containing the test compound such that the cell count per well was 3,000 cells. The plate was incubated in a $CO_2$ incubator (37° C., 5% $CO_2$). After 72 hours, 20 μL WST-1 (produced by Roche Diagnostics) was added to each well and, after 2 hours of incubation, the absorbance at 450 nm (reference wavelength: 650 nm) was measured. The 50% growth inhibition concentration ($IC_{50}$ value) of the test compound was calculated from the inhibition rate obtained when the test compound was added, in comparison with the reference value obtained when the test compound was not added.

The $IC_{50}$ values, for HUVEC and Calu-6, of representative examples of the compounds of the present invention are shown in Table 1.

[Table 1]

[Table 1-2]

TABLE 1

| | 50% growth inhibition concentration ($IC_{50}$ value)/μM | |
|---|---|---|
| Compound | HUVEC | Calu-6 |
| 1-1-1 | 2.27 | >100 |
| 1-2-1 | 2.40 | >100 |
| 1-3-1 | 0.19 | >50 |
| 1-3-2 | 0.15 | >50 |
| 1-3-5 | 0.14 | >50 |
| 1-3-6 | 0.24 | >50 |
| 1-3-7 | 0.28 | >50 |
| 1-3-8 | 0.35 | >50 |
| 1-3-10 | 0.76 | >50 |
| 1-3-12 | 2.54 | >50 |
| 1-3-16 | 4.60 | >50 |
| 1-3-17 | 1.20 | >25 |
| 1-3-18 | 1.25 | >50 |
| 1-3-21 | 5.10 | >50 |
| 1-3-23 | 2.85 | >50 |
| 1-3-24 | 5.19 | >50 |
| 1-3-39 | 2.36 | >25 |
| 1-3-41 | 0.04 | >50 |
| 1-3-45 | 0.05 | >50 |
| 2-1-1 | 0.17 | >100 |
| 2-2-1 | 3.35 | >50 |
| 2-2-2 | 2.27 | >50 |
| 2-2-9 | 1.41 | >25 |

As described in Table 1, the compounds of the present invention have more potent cell growth inhibiting activity against human umbilical vein endothelial cells (HUVEC) than against human lung carcinoma cell line Calu-6.

Example B-2

Tube Formation Assay

An angiogenesis measurement kit (produced by KURABO) was charged with the test compound at final concentration of 20 μM, and incubated in a $CO_2$ incubator (37° C., 5%). After 11 days of incubation, capillary-like tubes formed were fixed with 70% ethanol and visualized with a CD31 staining kit (produced by KURABO). Under a microscope, stain images of the wells were photographed, stored as an image file, and measured for the area of capillary-like tube formation by use of angiogenesis quantitative determination software of KURABO. The inhibition rates (%) of the test compound-charged wells were calculated, with the control taken as 100%.

The capillary-like tube formation inhibiting rates at 20 μM, against HUVEC, of representative examples of the compounds of the present invention are shown in Table 2.

[Table 2]

TABLE 2

| Capillary-like tube formation inhibiting activity | |
|---|---|
| Compound | capillary-like tube formation inhibition rates (%) |
| 1-1-1 | 43 |
| 1-2-1 | 68 |
| 1-3-5 | 91 |
| 1-3-6 | 46 |
| 1-3-7 | 67 |
| 1-3-10 | 46 |
| 1-3-12 | 27 |
| 1-3-16 | 80 |
| 1-3-17 | 80 |
| 1-3-18 | 29 |
| 1-3-21 | 71 |
| 1-3-23 | 27 |
| 1-3-24 | 28 |
| 1-3-39 | 20 |
| 1-3-41 | 82 |
| 1-3-45 | 31 |
| 2-1-1 | 93 |
| 2-2-1 | 60 |
| 2-2-2 | 77 |
| 2-2-9 | 79 |

As described above, the compounds concerned with the present invention inhibit the capillary-like tube formation of human-originated vascular endothelial cells.

Example B-3

Antitumor Test

A cell suspension of human lung carcinoma cell line Calu-6 was prepared using Hanks' balanced salt solution, and $5.0\times10^6$ of the cells were implanted subcutaneously in the flank region of female Balb/c nude mice. When the volume of the tumor reached 200 to 250 $mm^3$, the test compound was orally administered once daily for 11 days. The tumor volume was calculated from the equation $\pi/6\times$(long diameter$\times$short diameter$\times$thickness). The tumor growth inhibition rate was calculated from changes in the tumor volume in the test compound treatment group relative to changes in the tumor volume in the control group.

Figure 2:
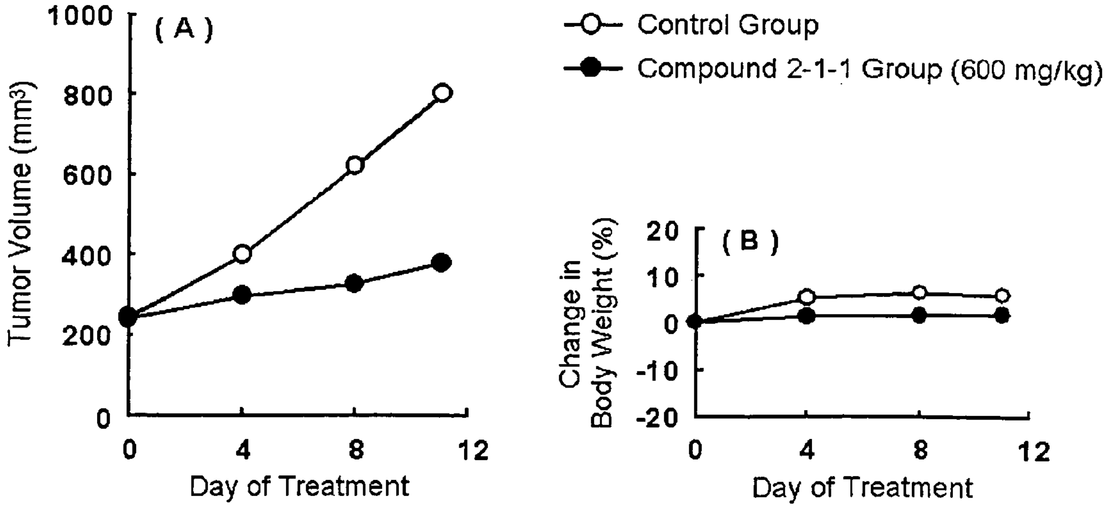
[FIG. 2] An example of the results of antitumor test, showing changes in the tumor volume (A), and changes in the body weight (B), following treatment with 600 mg/kg of compound 2-1-1 of the present invention in mice.

The results of the antitumor test of compound 1-1-1 and compound 2-1-1, as representative examples of the compounds of the present invention, are shown in FIGS. 1-(A) and 1-(B) and 2-(A) and 2-(B). As shown in FIGS. 1-(A) and 2-(A), the compounds according to the present invention had antitumor activity, and the tumor growth inhibition rates (TGI) by treatment with 600 mg/kg of compound 1-1-1 and compound 2-1-1 were 82% and 75%, respectively. As shown in FIG. 1-B and FIG. 2-B, moreover, no decreases in the body weights of the mice were observed, and no findings of toxicity observed, following treatment with the test compounds.

Example B-4

Measurement of the Number of Blood Vessels in the Tumor $5.0\times10^6$ Cells of human lung carcinoma cell line Calu-6 were implanted subcutaneously in the flank region of female Balb/c nude mice. When the volume of tumor reached 200 to 250 $mm^3$, the test compound was orally administered once daily for 11 days. Twenty-four hours after the final administration, xenograft tissue was removed from the mice, and a middle portion of the long diameter of the tumor was embedded, as a block 2 to 3 mm thick, in O.C.T. Compound, and preserved as a frozen tissue specimen. Frozen sections were prepared, and blood vessels in the tumor tissue were stained by an immunohistological method using anti-mouse CD31 antibody. The stained tissue was photographed under a microscope, and the images were stored as an image file. The number of the stained blood vessels was measured by Image Pro (Promega). The decrease rate of blood vessel density was calculated as a decrease rate relative to the blood vessel density in the control group.

The decrease rates of the blood vessel density in the tumor tissue following treatment with 600 mg/kg of compound 1-1-1 and compound 2-1-1, as representative examples of the compounds of the present invention, are shown in Table 3.

[Table 3]

TABLE 3

| Decrease rate of blood vessel density in tumor tissue | |
|---|---|
| Compound | Decrease (%) in intratumor blood vessel density |
| 1-1-1 | 44 |
| 2-1-1 | 37 |

As described above, the compounds according to the present invention have in vivo anti-angiogenic activity.

The invention claimed is:

1. A compound of formula (II) or a pharmaceutically acceptable salt thereof (II)

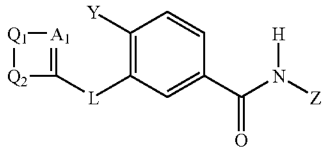

where $A_1$ is C—$X_1$;

$Q_1$ is —$A_2$=$A_3$—;

$Q_2$ is —$A_4$=$A_5$—;

$A_2$ is C—$X_2$, $A_3$ is C—$X_3$, $A_4$ is C—$X_4$, and $A_5$ is C—$X_5$;

$X_1$, $X_2$, $X_3$, $X_4$ and $X_5$ are each independently selected from the group consisting of a hydrogen atom, hydroxy, a halogen atom, cyano, hydroxyaminocarbonyl, hydroxyamidino, nitro, amino, amidino, guanidino, $C_{1-6}$alkylamino, di$C_{1-6}$alkylamino, $C_{1-6}$alkylamidino, di$C_{1-6}$alkylamidino, $C_{1-6}$alkylguanidino, di$C_{1-6}$alkylguanidino, $C_{1-6}$alkylthio, $C_{1-6}$alkylsulfo, $C_{1-6}$alkylsulfonyl, $C_{1-6}$alkylphosphono, di$C_{1-6}$alkylphosphono, $C_{1-6}$alkyl, $C_{1-6}$alkoxy, $C_{3-9}$cycloalkyl, $C_{3-9}$cycloalkoxy, $C_{2-7}$alkenyl, $C_{2-7}$alkynyl, $C_{1-6}$alkylcarbonyl, $C_{1-6}$alkoxycarbonyl (the above 19 groups may be substituted by one or more substituents selected from a halogen atom, hydroxy, aryl, heteroaryl, and cyano), aryl, aryloxy, arylcarbonyl, heteroaryl, heteroaryloxy, heteroarylcarbonyl, and aryl$C_{1-6}$alkyloxy (the above 7 groups may be substituted by one or more substituents selected from a halogen atom, $C_{1-6}$alkyl, and $C_{1-6}$alkoxy); or $X_1$ and $X_2$, $X_2$ and $X_3$, $X_3$ and $X_4$, and $X_4$ and $X_5$, together with the carbon atoms to which they are bound, form a saturated or unsaturated 5- to 7-membered carbocyclic ring, or a saturated or unsaturated 5- to 7-membered heterocyclic ring containing one or more heteroatoms selected from an oxygen atom, a nitrogen atom, and a sulfur atom;

Y is selected from the group consisting of $C_{3-9}$cycloalkyl, $C_{2-7}$alkenyl, $C_{2-7}$alkynyl, $C_{1-6}$alkylcarbonyl, $C_{1-6}$alkoxycarbonyl, arylcarbonyl, heteroarylcarbonyl, aryloxycarbonyl, heteroaryloxycarbonyl, $C_{1-6}$alkoxy, $C_{2-7}$alkenyloxy, $C_{2-7}$alkynyloxy, $C_{1-6}$alkylthio, $C_{1-6}$alkylsulfonyl {the above 15 groups may be substituted by one or more substituents selected from a saturated or unsaturated 3- to 7-membered carbocyclyl, a saturated or unsaturated 3- to 7-membered heterocyclyl containing one or more heteroatoms selected from an oxygen atom, a nitrogen atom, and a sulfur atom, a halogen atom, hydroxy, $C_{1-6}$alkoxy, hydroxy$C_{1-6}$alkoxy, $C_{1-6}$alkoxy$C_{1-6}$alkoxy, amino$C_{1-6}$alkoxy, N—$C_{1-6}$akylamino$C_{1-6}$alkoxy, N,N-di$C_{1-6}$alkyamino$C_{1-6}$alkoxy, amino, $C_{1-6}$alkylamino, hydroxy$C_{1-6}$alkylamino, $C_{1-6}$alkoxy$C_{1-6}$alkylamino, amino$C_{1-6}$alkylamino, di$C_{1-6}$alkylamino, bis(hydroxy$C_{1-6}$alkyl) amino, bis($C_{1-6}$alkoxy$C_{1-6}$alkyl) amino, bis(amino$C_{1-6}$alkyl) amino, amidino, $C_{1-6}$alkylamidino, di$C_{1-6}$alkylamidino, guanidino, $C_{1-6}$alkylguanidino, di$C_{1-6}$alkylguanidino, cyano, carboxyl, $C_{1-6}$alkoxycarbonyl, $C_{1-6}$alkylthio, $C_{1-6}$alkylsulfonyl, $C_{1-6}$alkylphosphono, and di$C_{1-6}$alkylphosphono}, amino, $C_{1-6}$alkylamino, di$C_{1-6}$alkylamino (the above 2 groups may be substituted by one or more substituents selected from a saturated or unsaturated 3- to 7-membered carbocyclyl, a saturated or unsaturated 3- to 7-membered heterocyclyl containing one or more heteroatoms selected from an oxygen atom, a nitrogen atom, and a sulfur atom, a halogen atom, hydroxy, $C_{1-6}$alkoxy, hydroxy$C_{1-6}$alkoxy, $C_{1-6}$alkoxy$C_{1-6}$alkoxy, amino$C_{1-6}$alkoxy, N—$C_{1-6}$alkylamino$C_{1-6}$alkoxy, N,N-di$C_{1-6}$alkylamino$C_{1-6}$alkoxy, amino, $C_{1-6}$alkylamino. hydroxy$C_{1-6}$alkylamino, $C_{1-6}$alkoxy$C_{1-6}$alkylamino, amino$C_{1-6}$alkylamino, di$C_{1-6}$alkylamino, bis(hydroxy$C_{1-6}$alkyl) amino, bis($C_{1-6}$alkoxy$C_{1-6}$alkyl)amino, bis(amino$C_{1-6}$alkyl) amino, amidino, $C_{1-6}$alkylamidino, di$C_{1-6}$ alkylamidino, guanidino, $C_{1-6}$alkylguanidino, di$C_{1-6}$ alkylguanidino, cyano, carboxyl, $C_{1-6}$alkoxycarbonyl, $C_{1-6}$alkylthio, $C_{1-6}$alkylsulfonyl, $C_{1-6}$alkylphosphono, and di$C_{1-6}$alkylphosphono), a halogen atom, nitro, cyano, carboxyl, and a saturated or unsaturated 3- to 7-membered heterocyclyl containing one or more heteroatoms selected from an oxygen atom, a nitrogen atom, and a sulfur atom (the heterocyclyl may be substituted by one or more substituents selected from hydroxy, $C_{1-6}$alkyl, halo$C_{1-6}$alkyl, hydroxy$C_{1-6}$alkyl, $C_{1-6}$alkoxy$C_{1-6}$alkyl, and oxo);

Z is selected from the group consisting of a hydrogen atom, hydroxy, $C_{1-6}$alkyl, $C_{3-9}$cycloalkyl {the above 2 groups may be substituted by one or more substituents selected from a saturated or unsaturated 3- to 7-membered carbocyclyl (the carbocyclyl group may be substituted by one or more substituents selected from $C_{1-6}$alkyl, hydroxy$C_{1-6}$alkyl, and $C_{1-6}$alkoxy$C_{1-6}$alkyl) , a saturated or unsaturated 3- to 7-membered heterocyclyl containing one or more heteroatoms selected from an oxygen atom, a nitrogen atom, and a sulfur atom (the heterocyclyl group may be substituted by one or more substituents selected from $C_{1-6}$alkyl, hydroxy$C_{1-6}$alkyl, and $C_{1-6}$alkoxy$C_{1-6}$alkyl), a halogen atom, hydroxy, $C_{1-6}$alkoxy, hydroxy$C_{1-6}$alkoxy, $C_{1-6}$alkoxy$C_{1-6}$alkoxy, hydroxy$C_{1-6}$alkoxy$C_{1-6}$alkoxy, amino$C_{1-6}$alkoxy, N—$C_{1-6}$alkylamino$C_{1-6}$alkoxy, N,N-di$C_{1-6}$alkylamino$C_{1-6}$alkoxy, amino, $C_{1-6}$alkylamino, hydroxy$C_{1-6}$ alkylamino, $C_{1-6}$alkoxy$C_{1-6}$alkylamino, amino$C_{1-6}$ alkylamino, di$C_{1-6}$alkylamino, bis(hydroxy$C_{1-6}$alkyl) amino, bis($C_{1-6}$alkoxy$C_{1-6}$alkyl)amino, bis(amino$C_{1-6}$ alkyl)amino, cyano, carboxyl, $C_{1-6}$alkoxycarbonyl, aryloxycarbonyl, carbamoyl, $C_{1-6}$alkylcarbamoyl, di$C_{1-6}$ alkylcarbamoyl (the above 2 groups may be substituted by one or more substituents selected from a halogen atom, hydroxy, cyano and amino), phosphono, $C_{1-6}$alkylphosphono, di$C_{1-6}$alkylphosphono, sulfonic acid, and $C_{1-6}$alkylsulfo}, and —$OR_1$ and —$NR_1R_2$;

$R_1$ and $R_2$ are each dependently selected from the group consisting of a hydrogen atom, $C_{1-6}$alkyl, $C_{1-6}$alkylcarbonyl, and a saturated or unsaturated 3 to 7-membered heterocyclyl containing one or more heteroatoms selected from an oxygen atom, a nitrogen atom, and a sulfur atom (the above 3 groups may be substituted by one or more substituents selected from a saturated or unsaturated 3- to 7-membered carbocyclyl, a saturated or unsaturated 3 to 7-membered heterocyclyl containing one or more heteroatoms selected from an oxygen atom, a nitrogen atom, and a sulfur atom, a halogen atom, hydroxy, $C_{1-6}$alkoxy, hydroxy$C_{1-6}$alkoxy, $C_{1-6}$alkoxy$C_{1-6}$alkoxy, amino$C_{1-6}$alkoxy, N—$C_{1-6}$alkylamino$C_{1-6}$alkoxy, N,N-di$C_{1-6}$alkylamino$C_{1-6}$alkoxy, amino, $C_{1-6}$alkylamino, hydroxy$C_{1-3}$alkylamino, $C_{1-6}$alkoxy$C_{1-6}$alkylamino, amino$C_{1-6}$alkylamino, di$C_{1-6}$alkylamino, bis(hydroxy$C_{1-6}$alkyl)amino, bis ($C_{1-6}$ alkoxy$C_{1-6}$alkyl)amino, bis(amino$C_{1-6}$alkyl) amino, cyano, carboxyl, $C_{1-6}$alkoxycarbonyl, aryloxycarbonyl, phosphono, $C_{1-6}$alkylphosphono, di$C_{1-6}$ alkylphosphono, sulfonic acid, and $C_{1-6}$alkylsulfo); or $R_1$ and $R_2$, together with the nitrogen atoms to which they are bound, form a saturated or unsaturated 5- to 7-membered heterocyclic ring containing one nitrogen atom and optionally further containing one or more heteroatoms selected from an oxygen atom, a nitrogen atom, and a sulfur atom; and L is:

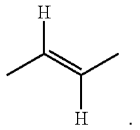

2. The compound or the pharmaceutically acceptable salt thereof according to claim 1, wherein Z is a hydrogen atom, $C_{1-6}$alkyl, $C_{3-9}$cycloalkyl, hydroxy$C_{1-6}$alkyl, hydroxy$C_{1-6}$ alkoxy$C_{1-6}$alkyl, $C_{1-6}$alkoxy$C_{1-6}$alkyl, cyano$C_{1-6}$alkyl, pyridyl$C_{1-6}$alkyl, dihydroxy$C_{1-6}$alkyl, trihydroxy$C_{1-6}$alkyl, morpholino$C_{1-6}$alkyl, (N,N-di$C_{1-6}$alkylamino) $C_{1-6}$alkyl, or (N,N-bis(hydroxy$C_{1-6}$alkyl)amino) $C_{1-6}$alkyl.

3. The compound or the pharmaceutically acceptable salt thereof according to claim 2, wherein Z is a hydrogen atom, methyl, ethyl, cyclopropyl, cyclopentyl, 2-hydroxyethyl, 2-(2-hydroxyethoxy)ethyl, 2-methoxyethyl, 2-cyanoethyl, 4-pyridylmethyl, 1-methoxybut-2-yl, 2,3-dihydroxyprop-1-yl, 1,3-dihydroxyprop-2-yl, 1,3-dihydroxy-2-hydroxymethylprop-2-yl, 2-morpholinoethyl, 1-hydroxyprop-2-yl, 1-hydroxy-3-methylbut-2-yl, 2-(N,N -dimethylamino)ethyl, 2-(N,N-bis(2-hydroxyethyl)amino) ethyl, 2,4-dihydroxylbutyl, 2,3,4-trihydroxybutyl, 2,3,4,5-tetrahydroxypentyl, or 2,3,4,5,6-pentahydroxyhexyl.

4. The compound or the pharmaceutically acceptable salt thereof according to claim 1, wherein Y is a halogen atom, cyano, $C_{2-7}$alkenyl, $C_{2-7}$alkynyl, $C_{1-6}$alkoxy, $C_{3-9}$cycloalkyl$C_{1-6}$alkoxy, $C_{2-7}$alkynyloxy, or halo$C_{1-6}$alkoxy.

5. The compound or the pharmaceutically acceptable salt thereof according to claim 4, wherein Y is chloro, bromo, cyano, ethynyl, methoxy, trifluoromethoxy, cyclopropylmethoxy, 2-butyn-1-yloxy, or 2-chloroethoxy.

6. The compound or the pharmaceutically acceptable salt thereof according to claim 1, wherein $X_1$, $X_2$, $X_3$, $X_4$ and $X_5$ are each independently selected from a hydrogen atom, a halogen atom, $C_{1-6}$alkyl, $C_{1-6}$alkoxy, halo$C_{1-6}$alkyl, halo$C_{1-6}$alkoxy, $C_{1-6}$alkylthio, and halo$C_{1-6}$alkylthio; or $X_1$ and $X_2$, $X_2$ and $X_3$, $X_3$ and $X_4$, and $X_4$ and $X_5$, together with the carbon atoms to which they are bound, form a cyclohexane ring, a cyclopentane ring, a benzene ring, a pyridine ring, a pyrimidine ring, a 1,4-dioxane ring, a 1,3-dioxolane ring, a pyrrole ring, an imidazole ring, a thiazole ring, or a furan ring.

7. The compound or the pharmaceutically acceptable salt thereof according to claim 6, wherein $X_1$, $X_2$, $X_3$, $X_4$ and $X_5$ are each independently selected from a hydrogen atom, fluoro, chloro, bromo, methyl, ethyl, t-butyl, i-propyl, methoxy, i-propoxy, trifluoromethyl, trifluoromethoxy, methylthio, and trifluoromethylthio; or $X_1$ and $X_2$, together with the carbon atoms to which they are bound, form a cyclohexane ring;

$X_1$ and $X_2$, together with the carbon atoms to which they are bound, form a pyridine ring;

$X_2$ and $X_3$, together with the carbon atoms to which they are bound, form a 1,4-dioxane ring; or $X_2$ and $X_3$, together with the carbon atoms to which they are bound, form a cyclopentane ring.

8. A pharmaceutical composition containing the compound, or the pharmaceutically acceptable salt thereof according to claim 1, as an active ingredient.

* * * * *